(12) United States Patent
Ricicova et al.

(10) Patent No.: US 10,725,024 B2
(45) Date of Patent: Jul. 28, 2020

(54) MICROFLUIDIC DEVICES AND METHODS FOR USE THEREOF IN MULTICELLULAR ASSAYS OF SECRETION

(71) Applicant: The University of British Columbia, Vancouver (CA)

(72) Inventors: Marketa Ricicova, Vancouver (CA); Kevin Albert Heyries, Vancouver (CA); Hans Zahn, Munich (DE); Oleh Petriv, Richmond (CA); Veronique Lecault, Vancouver (CA); Anupam Singhal, Mississauga (CA); Daniel J. Da Costa, Vancouver (CA); Carl L. G. Hansen, Vancouver (CA); Brad Nelson, Victoria (CA); Julie Nielsen, Victoria (CA); Kathleen Lisaingo, Port Moody (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 854 days.

(21) Appl. No.: 14/773,244

(22) PCT Filed: Mar. 28, 2014

(86) PCT No.: PCT/CA2014/000304
§ 371 (c)(1),
(2) Date: Sep. 4, 2015

(87) PCT Pub. No.: WO2014/153651
PCT Pub. Date: Oct. 2, 2014

(65) Prior Publication Data
US 2016/0252495 A1 Sep. 1, 2016

Related U.S. Application Data

(60) Provisional application No. 61/806,329, filed on Mar. 28, 2013.

(51) Int. Cl.
*G01N 33/50* (2006.01)
*G01N 33/543* (2006.01)
*G01N 33/68* (2006.01)
*B01L 3/00* (2006.01)
*C07K 16/40* (2006.01)
*C07K 16/10* (2006.01)
(Continued)

(52) U.S. Cl.
CPC ...... *G01N 33/5052* (2013.01); *B01L 3/50273* (2013.01); *B01L 3/502715* (2013.01); *B01L 3/502738* (2013.01); *B01L 3/502761* (2013.01); *C07K 16/00* (2013.01); *C07K 16/1018* (2013.01); *C07K 16/40* (2013.01); *C12N 5/0634* (2013.01); *C12N 5/0635* (2013.01); *C12Q 1/6888* (2013.01); *G01N 33/505* (2013.01); *G01N 33/5047* (2013.01); *G01N 33/54313* (2013.01); *G01N 33/6845* (2013.01); *G01N 33/6854* (2013.01); *G01N 35/0099* (2013.01); *B01L 2200/0647* (2013.01); *B01L 2200/12* (2013.01); *B01L 2300/04* (2013.01); *B01L 2300/0627* (2013.01); *B01L 2300/0838* (2013.01); *B01L 2300/0877* (2013.01); *B01L 2300/0887* (2013.01); *B01L 2300/14* (2013.01); *C07K 2317/14* (2013.01); *C07K 2317/21* (2013.01); *C07K 2317/70* (2013.01)

(58) Field of Classification Search
None
See application file for complete search history.

(56) References Cited

U.S. PATENT DOCUMENTS 8,030,095 B2 10/2011 Harriman
2002/0155487 A1* 10/2002 Greenberger .......... C12M 23/12
435/6.16

(Continued)

FOREIGN PATENT DOCUMENTS

WO 2009/111014 11/2009

OTHER PUBLICATIONS

Lecault et al. "High-throughput analysis of single hematopoietic stem cell proliferation in microfluidic cell culture arrays" Nat Methods. May 22, 2011;8(7):581-6, doi:10.1038/nmeth.1614, including accompanying online Supplemental Material (30 pages total) (Year: 2011).*

(Continued)

*Primary Examiner* — Christine Foster
(74) *Attorney, Agent, or Firm* — Potomac Law Group PLLC

(57) ABSTRACT

Methods and devices are provided herein for identifying a cell population comprising an effector cell that exerts an extracellular effect. In one embodiment the method comprises retaining in a microreactor a cell population comprising one or more effector cells, wherein the contents of the microreactor further comprise a readout particle population comprising one or more readout particles, incubating the cell population and the readout particle population within the microreactor, assaying the cell population for the presence of the extracellular effect, wherein the readout particle population or subpopulation thereof provides a direct or indirect readout of the extracellular effect, and determining, based on the results of the assaying step, whether one or more effector cells within the cell population exerts the extracellular effect on the readout particle. If an extracellular effect is measured, the cell population is recovered for further analysis to determine the cell or cells responsible for the effect.

10 Claims, 74 Drawing Sheets

Specification includes a Sequence Listing.

(51) Int. Cl.
| | | |
|---|---|---|
| *C07K 16/00* | (2006.01) | |
| *C12N 5/078* | (2010.01) | |
| *C12N 5/0781* | (2010.01) | |
| *C12Q 1/6888* | (2018.01) | |
| *G01N 35/00* | (2006.01) | |

(56) References Cited

U.S. PATENT DOCUMENTS

| | | | |
|---|---|---|---|
| 2006/0134109 | A1 | 6/2006 | Gaitanaris et al. |
| 2010/0249022 | A1* | 9/2010 | Clapham ............ C07K 14/705 514/3.8 |
| 2011/0262906 | A1 | 10/2011 | Dimov et al. |
| 2011/0275063 | A1* | 11/2011 | Weitz ................ G01N 33/5008 435/6.1 |
| 2012/0009671 | A1 | 1/2012 | Hansen et al. |
| 2012/0015347 | A1* | 1/2012 | Singhal ............ B01L 3/502738 435/5 |
| 2013/0005036 | A1 | 1/2013 | Song |
| 2015/0018226 | A1 | 1/2015 | Hansen et al. |
| 2016/0178502 | A1 | 6/2016 | Bocchi et al. |

OTHER PUBLICATIONS

TTP Labtech, "Automated dispensing for assay development", retrieved from https://www.ttplabtech.com/applications/drug-discovery/assay-development-drug-discovery/automated-assay-development/ on Oct. 22, 2019, 9 pages (Year: 2019).*

Czerkinsky et al., "A novel two colour ELISPOT assay: I. Simultaneous detection of distinct types of antibody-secreting cells", Journal of Immunological Methods, 115 (1988) 31-37, doi: 10.1016/0022-1759(88)90306-7 (Year: 1988).*

Arvilommi, "ELISPOT for detecting antibody-secreting cells in response to infections and vaccination", vol. 104, Jan. 1996, pp. 401-410, doi: 10.1111/j.1699-0463.1996.tb00734.x (Year: 1996).*

Bonsignori et al., "Simultaneous Detection of Antigen-Specific IgG- and IgM-Secreting Cells with a B Cell Fluorospot Assay" Cells 2012, 1, 15-26; doi:10.3390/cells1010015 (Year: 2012).*

Lecault et al. (2012) "Microfluidic Single Cell Analysis: from Promise to Practice" Current Opinion in Chemical Biology, 16:381-390, ISSN: 1879-0402.

Romanuik et al. (2011) "Microfluidic Trapping of Antibody-secreting Cells" Journal of Medical and Biological Engineering, 31(2):121-127, ISSN: 1609-0985.

Singahl et al. (2011) "A Microfluidic Platform for Screening and Selection of Monoclonal Antibodies from Single Cells" 15th International Conference on Miniature Systems for Chemistry and Life Sciences, 323-325.

Konry et al. (2011) "Droplet-based microlluidic platforms for single T cell secretion analysis of IL-10 cytokine" Biosensors and Bioelectronics, 26(5):2707-2710.

Lecault et al. (2011) "High-throughput analysis of single hematopoietic stem cell proliferation in microfluidic cell culture arrays" Nature Methods, 8(7):581-586.

Love et al. (2006) "A microengraving method for rapid selection of single cells producing antigen-specific antibodies" Nature Biotechnology, 24(6):703-707.

Story, Craig M., et al., (2009) "Profiling antibody responses by multiparametric analysis of primary B cells", Proc. Natl. Acad. Sci. U.S.A., 105(46):17902-17907.

Brouzes, Eric, et al, (2009) "Droplet microfluidic technology for single-cell high-throughput screening", Proc. Natl. Acad. Sci. U.S. A., 106(34):14195-14200.

Shim, Ann Hye-Ryong, et al., (2010). "Structures of a platelet-derived growth factor/ propeptide complex and a platelet-derived growth factor/receptor complex", Proc. Natl. Acad. Sci. U.S.A., 107(25):11307-11312.

Reichert, Janice M., (2009) "Probabilities of success for antibody therapeutics", Mabs, 1(4):387-389.

Hansen, Carl L., et al., (2004), "Systematic investigation of protein phase behavior with a microfluidic formulator", Proc. Natl. Acad. Sci. U.S.A., 101(40):14431-14436.

Ma, Chao, et al., (2011) "A clinical microchip for evaluation of single immune cells reveals high functional heterogeneity in phenotypically similar T cells", Nat Med, 17(6):738-743.

Jin, Aishun, et al., (2009) "A rapid and efficient single-cell manipulation method for screening antigen-specific antibody-secreting cells from human peripheral blood", Nat. Med., 15(9):1088-1092.

Tumarkin, Ethan, et al., (2011) "High-throughput combinatorial cell co-culture using microfluidics", Integr. Biol. 3 (6):653-662.

Nelson et al., (2010) "Development trends for human monoclonal antibody therapeutics", Nat. Rev. Drug Disc., 9 (10):767-774.

Maerkl and Quake, (2007) "A Systems Approach to Measuring the Binding Energy Landscapes of Transcription Factors", Science, 315:233-237.

Marcus, J.S. et al. (2006) "Microfluidic Single-Cell mRNA Isolation and Analysis", Anal. Chem, 78:3084-3089.

Singhal, Anupam, et al., (2010) "Microfluidic Measurement of Antibody-Antigen Binding Kinetics from Low-Abundance Samples and Single Cells", Anal. Chem., 82(20):8671-8679.

Hansen and Quake, (2003) "Microfluidics in structural biology: smaller, faster . . . better", Curr. Opin. Struc. Biol., 13:538-544.

* cited by examiner

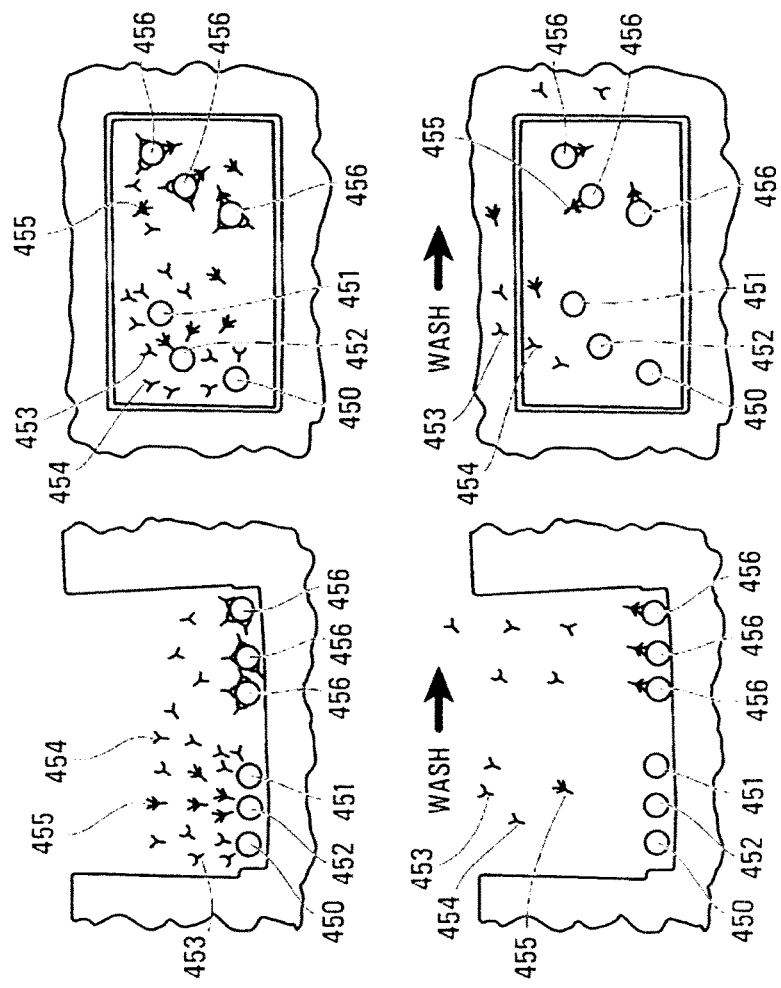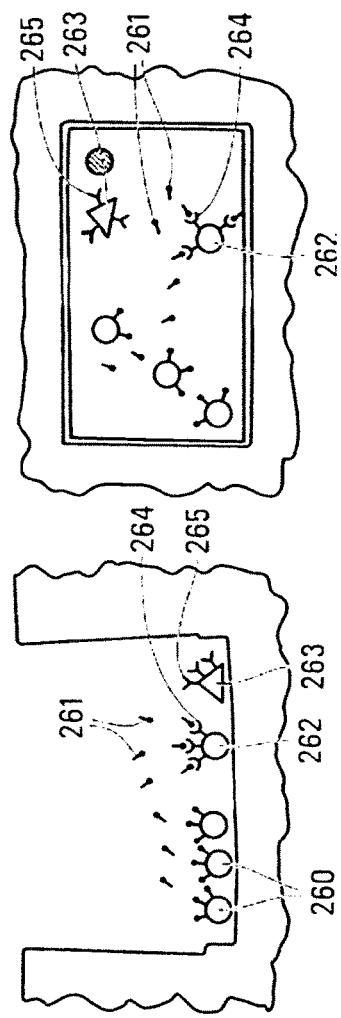
Figure 20
Figure 21

Figure 24

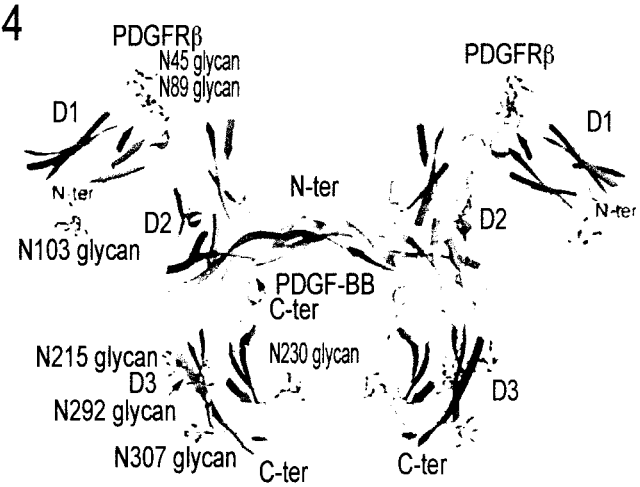

```
MGTSHPAFL--VLGCLLTGLSLILCQLSLPSILPNENEKVVQLNSSFSLRCFGESEVSWQ    58   PGFRA_HUMAN
MGTSHQVFL--VLSCLLTGPGLISCQLLLPSILPNENEKIVQLNSSFSLRCVGESEVSWQ    58   PGFRA_MOUSE
MGPSPPAFLVLVLGWLLAGPSLTRCQLPLPSISPGDSERVVPLNSSFTLRCSGESEVSWQ    60   PGFRA_RABBIT
MG-TSQAFL--VLSCLLTGPSLIVCQLLLPSILPNENEKIVPLSSSFSLRCFGESEVSWQ    57   PGFRA_RAT
          *  * *** **  **    *           *

YPMSEEESSDVEIRNEENNSGLFVTVLEVSSASAAHTGLYTCYYNHTQTEENELEGRHIY   118   PGFRA_HUMAN
HPMSEEDDPNVEIRSEENNSGLFVTVLEVVNASAAHTGWYTCYYNHTQTDESEIEGRHIY   118   PGFRA_MOUSE
YPVSEDEGPRVDVRSEENNTGYFVAVLEVGSATAAHTGLYTCYYNHTQTEDSDVEGSHVY   120   PGFRA_RABBIT
HPMSEEEDPNVEIRTEENNSSLFVTVLEVVNASAAHTGWYTCYYNHTQTEESEIEGRHIY   117   PGFRA_RAT
 *  *   *****  ** *   **      ****** ********** *   *  *

IYVPDPDVAFVPLGMTDYLVIVEDDDSAIIPCRTTDPETPVTLHNSEGVVPASYDSRQGF   178   PGFRA_HUMAN
IYVPDPDMAFVPLGMTDSLVIVEEDDSAIIPCRTTDPETQVTLHNNGRLVPASYDSRQGF   178   PGFRA_MOUSE
IYVPDPDVAFVPLGMTDYLVIVEDDDSAIIPCRTTDPETPVTLRNSQGLVPASYDSRHGF   180   PGFRA_RABBIT
IYVPDPDMAFVPLGMTDSLVIVEEDDSAIIPCLTTDPDTEVTLHNNGRLVPASYDSRQGF   177   PGFRA_RAT
        *         *    *            *  *  **** *

NGTFTVGPYICEATVKGKKFQTIPFNVYALKATSELDLEMEALKTVYKSGETIVVTCAVF   238   PGFRA_HUMAN
NGTFSVGPYICEATVKGRTFKTSEFNVYALKATSELNLEMDARQTVYKAGETIVVTCAVF   238   PGFRA_MOUSE
NGTFTMGPYVCEATVRGKTVQTIPFNIYALKATSELDLEMEALQTVYKAGETIVVTCAVF   240   PGFRA_RABBIT
NGTFSVGPYICEATVRGRTFKTSEFNVYALKATSELNLEMDTRQTVYKAGETIVVTCAVF   237   PGFRA_RAT
   ** *  * ****  *     ****  **** *    *    ****  *******

NNEVVDLQWTYPGEVKGKGITMLEEIKVPSIKLVYTLTVPEATVKDSGDYECAARQATRE   298   PGFRA_HUMAN
NNEVVDLQWTYPGEVRNKGITMLEEIKLPSIKLVYTLTVPKATVKDSGEYECAARQATKE   298   PGFRA_MOUSE
NNEVVDLQWTYPGEMKGKGVTMLEEIKVPTLKLVYTLTVPRATVKDSGDYECAARQAT-E   299   PGFRA_RABBIT
NNEVVDLQWTYPGEVRNKGITMLEEIKLPSIKLVYTLTVPKATVKDSGDYECAARQATKE   297   PGFRA_RAT
  ***           * **        *   *******   ******** *

VKEMKKVTISVHEKGFIEIKPTFSQLEAVNLHEVKHFVVEVRAYPPPRISWLKNNLTLIE   358   PGFRA_HUMAN
VKEMKRVTISVHEKGFVEIEPTFGQLEAVNLHEVREFVVEVQAYPTPRISWLKDNLTLIE   358   PGFRA_MOUSE
VKEMKKVTIAVHEKGFVEIKPTFNQSEAVNLHEVKHFVVEVRAYPPPRISWLKDSRTLIE   359   PGFRA_RABBIT
VKEMKTVTISVHEKGFVQIRPTFGHLETVNLHQVREFVVEVQAYPTPRISWLKDNLTLIE   357   PGFRA_RAT
 *     *  *   ** *  ***    *  **      *        *       ***

NLTEITTDVEKIQEIRYRSKLKLIRAKEEDSGHYTIV---AQNEDAVKSYTFELLTQVPS   415   PGFRA_HUMAN
NLTEITTDVQKSQETRYQSKLKLIRAKEEDSGHYTII---VQNEDDVKSYTFELSTLVPA   415   PGFRA_MOUSE
NLTEITTDVEQVQETRLSSMCN----RSAACGKWNFLTSVEQGWQIVQCSAWKAPLAVPA   415   PGFRA_RABBIT
NLTEITTDVQRSQETRYQSKLKLIRAKEEDSGHYTII---VQNDDDMKSYTFELSTLVPA   414   PGFRA_RAT
 *   *  ** *      ************ ********* ****************  *

SILDLVDDHHGSTGGQTVRCTAEGTPLPDIEWMICKDIKKCNNETSWTILANNVSNIITE   475   PGFRA_HUMAN
SILDLVDDHHGSGGGQTVRCTAEGTPLPEIDWMICKHIKKCNNDTSWTVLASNVSNIITE   475   PGFRA_MOUSE
TILDLVDDHHP-PGEKRVRCTAAGTP-PDVEWMICKDIKRCNNETSWTLLANNVSNIVTE   473   PGFRA_RABBIT
SILELVDDHHGSGGGQTVRCTAEGTPLPNIEWMICKDIKKCNNDTSWTVLASNVSNIITE   474   PGFRA_RAT
 *  *******    * *** *** **   ****   *  *** ****   *  ***  *

IHSRDRSTVEGRVTFAKVEETIAVRCLAKNLLGAENRELKLVAPTLRSELTVA        535   PGFRA_HUMAN
LPRRGRSTVEGRVSFAKVEETIAVRCLAKNNLSVVARELKLVAPTLRSELTVA        535   PGFRA_MOUSE
THPRGGGAVEGRVTFAKVEETLAVRCLARNPLGTENRELKLVAPTLRSELTVA        533   PGFRA_RABBIT
FHQRGRSTVEGRVSFAKVEETIAVRCLAKNDLGIGNRELKLVAPSLRSELTVA        534   PGFRA_RAT
 ***  ****    *   * ****    *    **** *  *
```

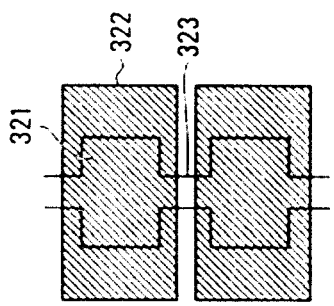
Figure 53
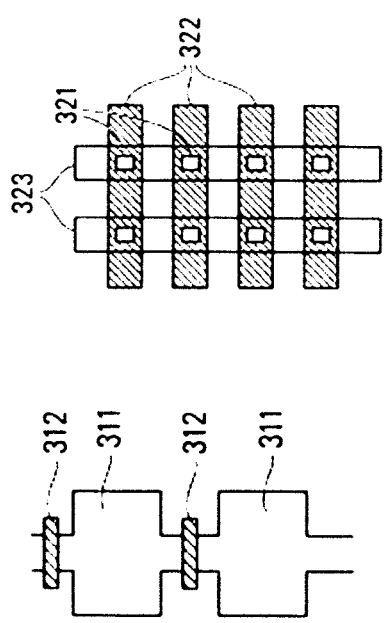
Figure 52
Figure 55
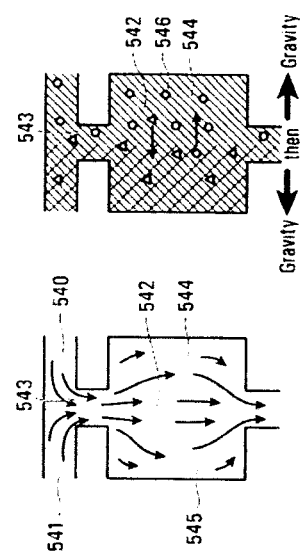
Figure 51
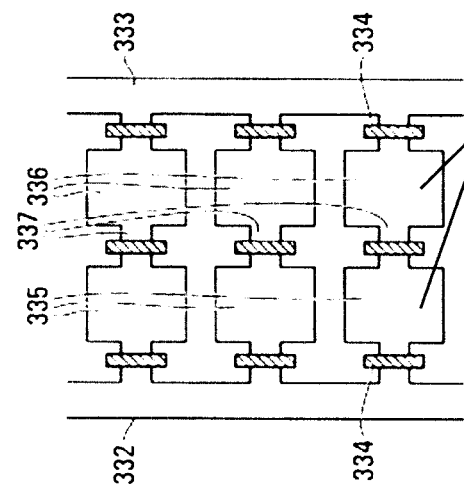
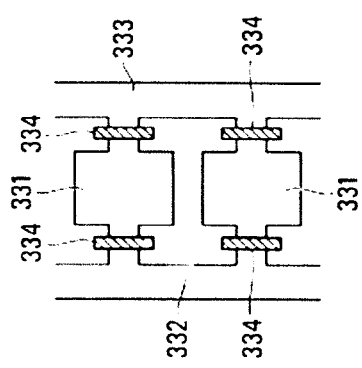
Figure 54

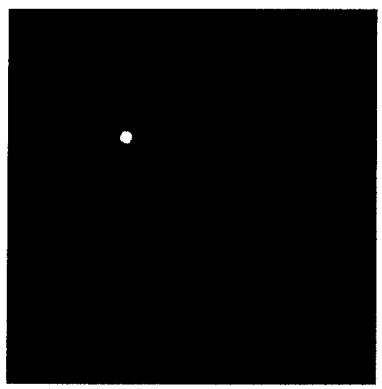
Figure 70D
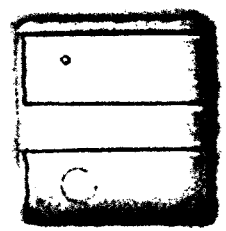
Figure 70C
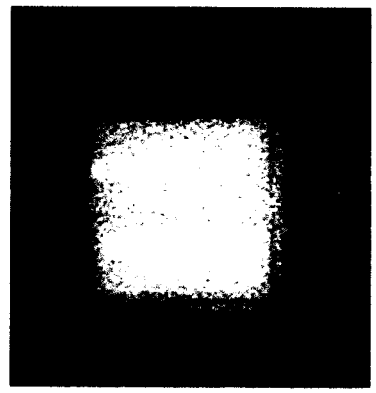
Figure 70F
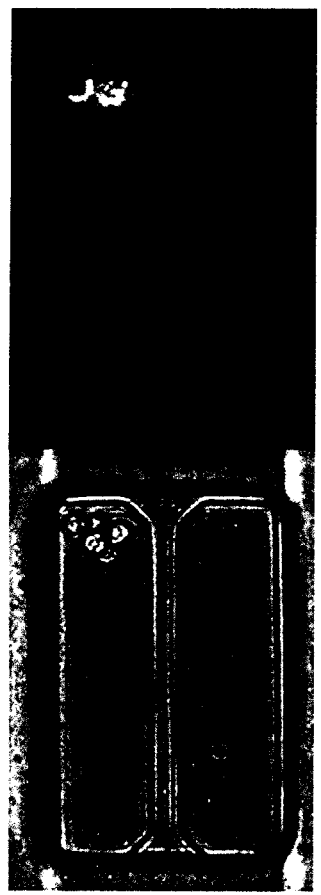
Figure 70B
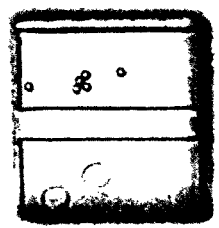
Figure 70E
Figure 70A

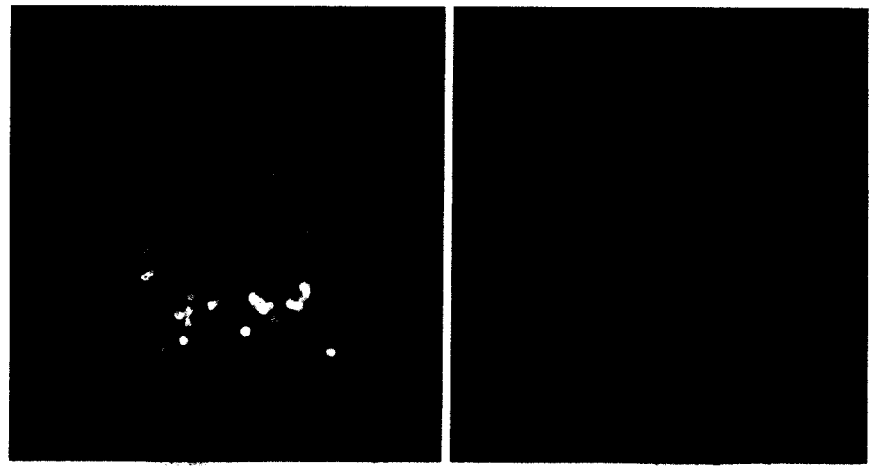
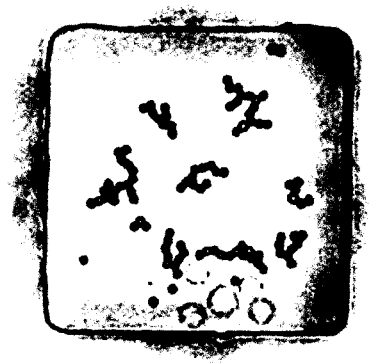
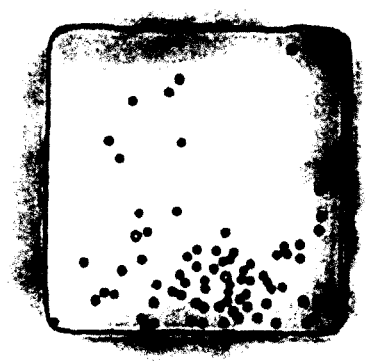
Figure 82
Figure 83

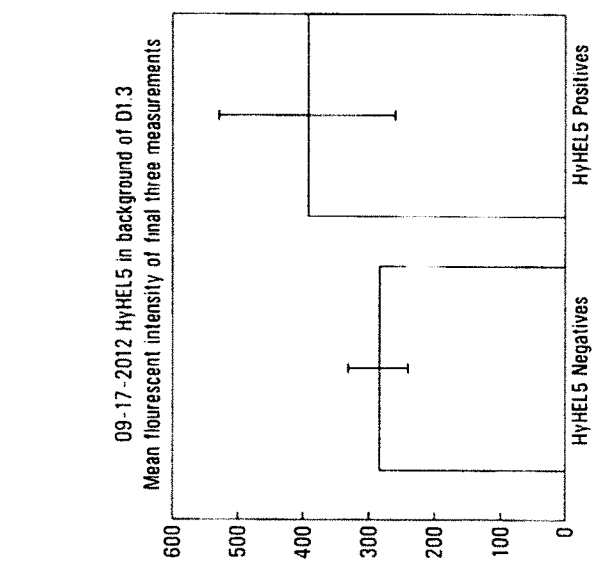
Figure 88
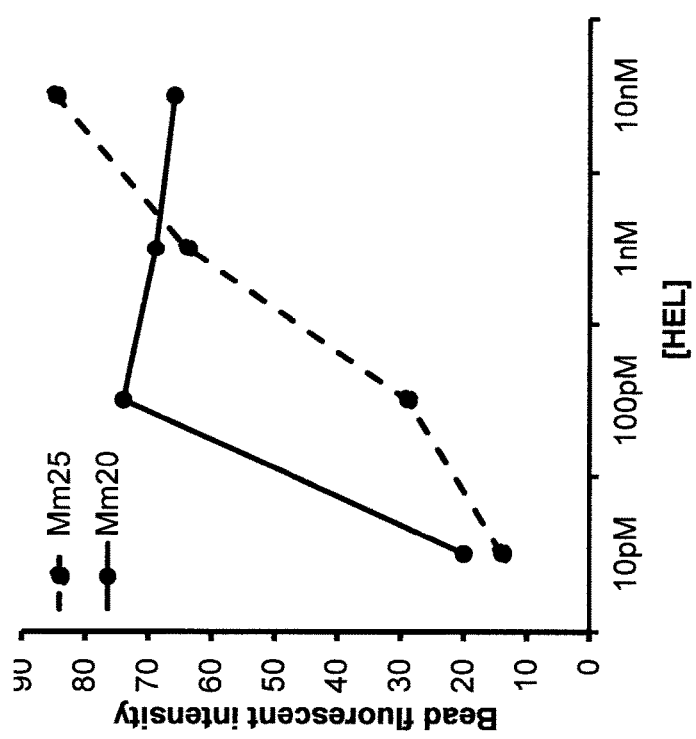
Figure 87
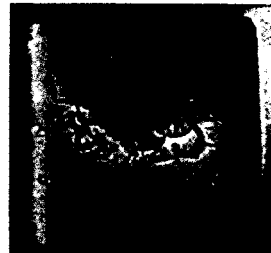
Figure 89F
Figure 89E
Figure 89D
Figure 89C
Figure 89B
Figure 89A

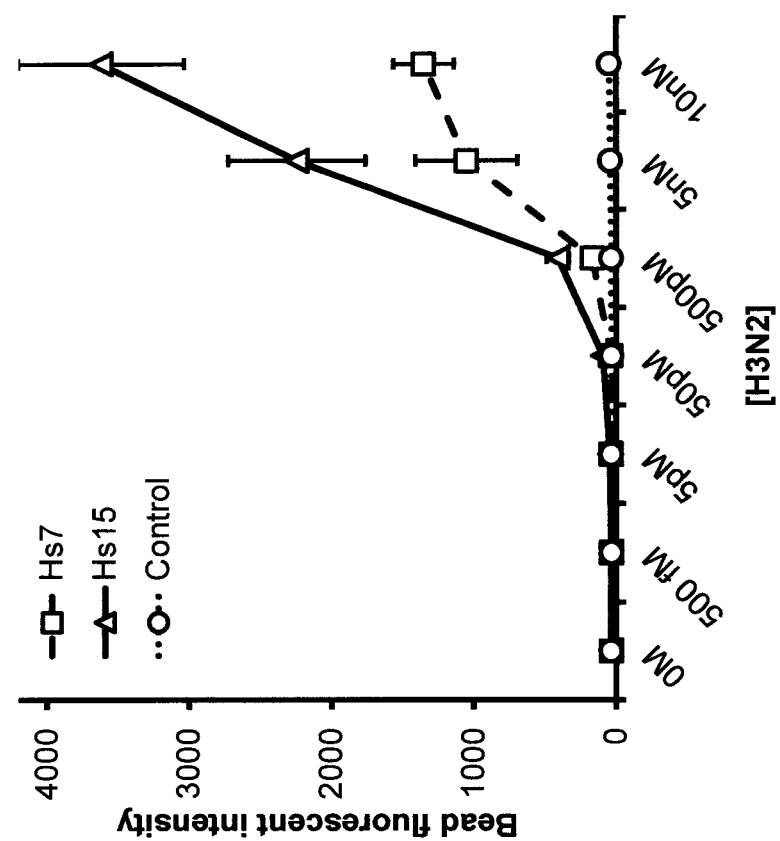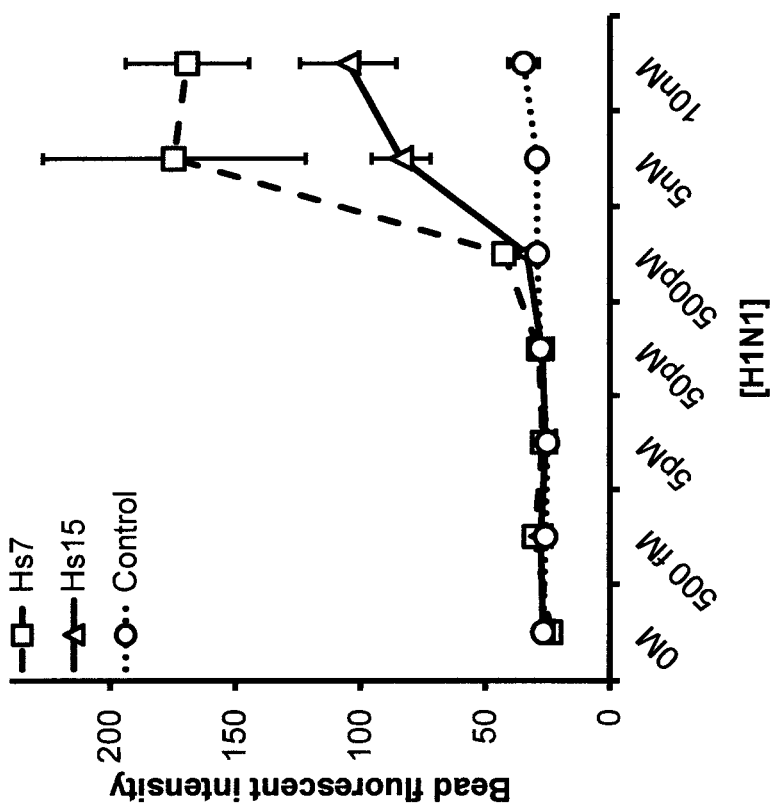
Figure 95C

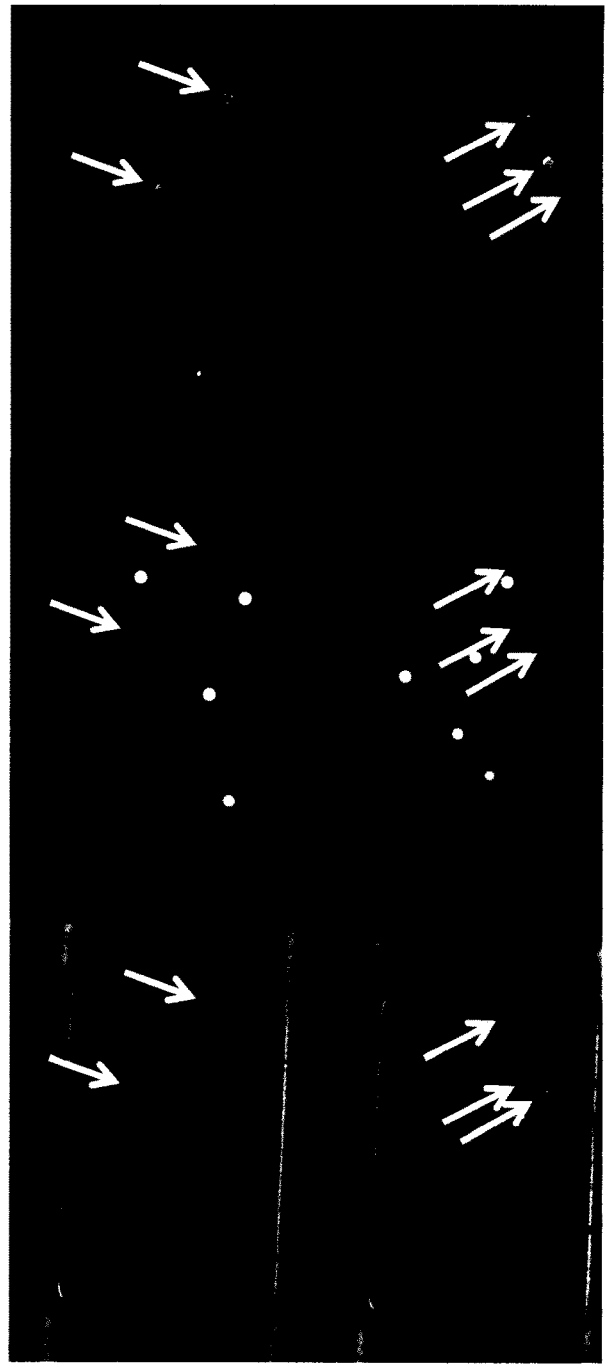
Figure 105A
Figure 105B  Figure 105C  Figure 105D

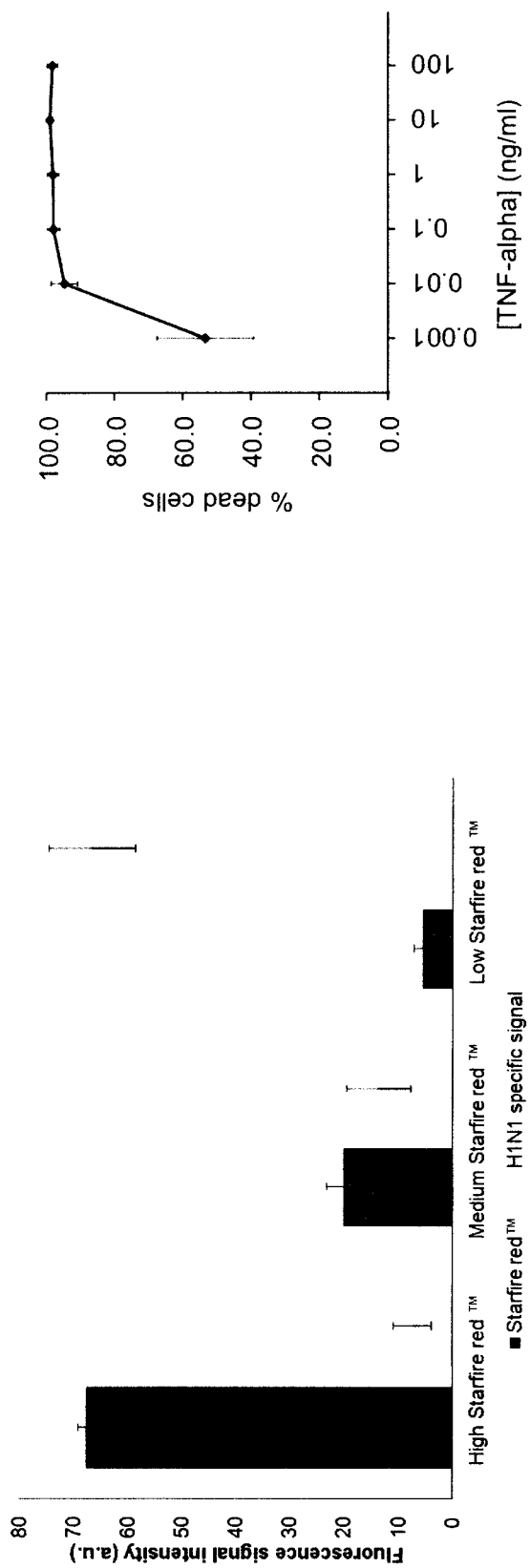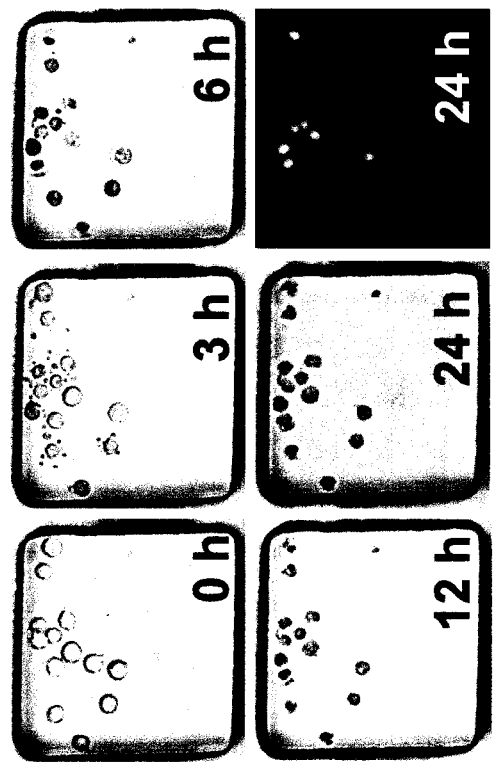

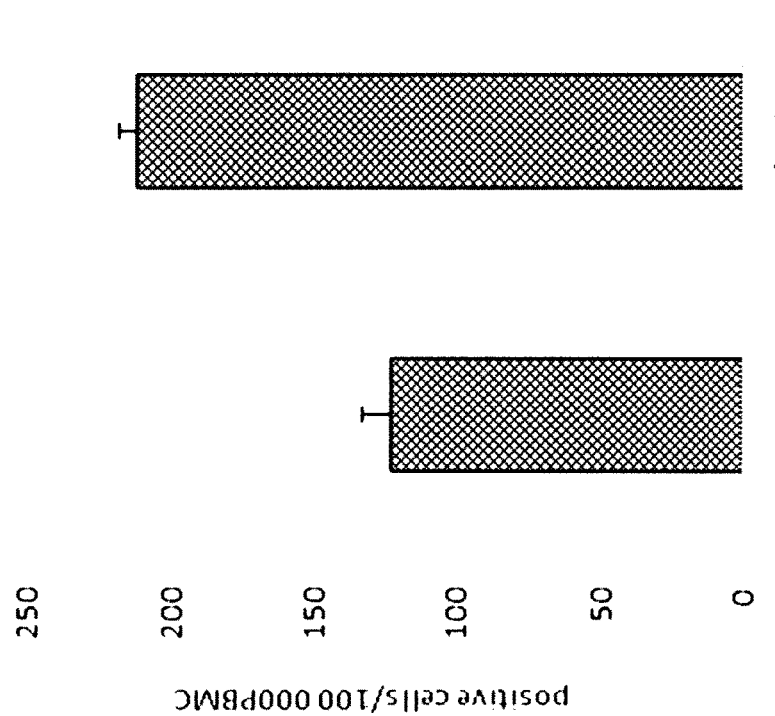
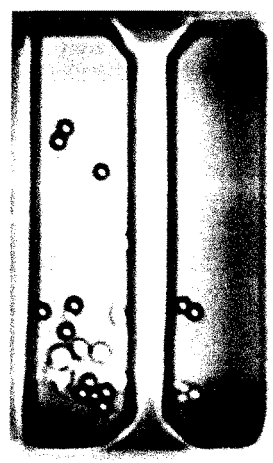
Figure 109A
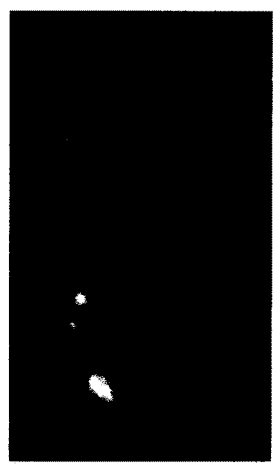
Figure 109B
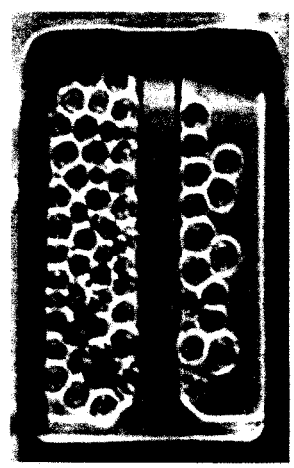
Figure 109C

MICROFLUIDIC DEVICES AND METHODS FOR USE THEREOF IN MULTICELLULAR ASSAYS OF SECRETION

CROSS REFERENCE TO RELATED APPLICATION

This application is the national stage entry of PCT/CA2014/000304, filed Mar. 28, 2014, which claims priority from U.S. Provisional Application Ser. No. 61/806,329, filed Mar. 28, 2013, the disclosure of each of which is incorporated by reference in their entirety for all purposes.

BACKGROUND OF THE INVENTION

The cell is the fundamental unit of life and no two cells are identical. For example, differences in genotype, phenotype and/or morphological property can contribute to cellular heterogeneity. Indeed, "seemingly identical" clonal populations of cells have been shown to display phenotypic differences among cells within the population. Cellular differences exist across all levels of life, ranging from bacterial cells to partially differentiated cells (for example, adult stem and progenitor cells) to highly differentiated mammalian cells (for example, immune cells). Differences in cellular state, function and responses can arise from a variety of mechanisms including different histories, different differentiation states, epigenetic variations, cell cycle effects, stochastic variations, differences in genomic sequence, gene expression, protein expression and differing cell interaction effects.

Conventional bulk cellular analyses, including measurements of expressed proteins or RNA, are performed by averaging very large numbers of cells, typically greater than 1000 cells per individual assay). This averaging of a cellular population masks the heterogeneity that exists within a cell population and obscures the underlying biological features of the individual cells within the population. There are many examples where such averaged measurements are inadequate. For example, measuring a cellular process in a cell population may be complicated by the responses of individual cells, which may be asynchronous, thus blurring the dynamics of the process. For example, the presence of dominant, yet phenotypically distinct subpopulations of cells can result in a population measurement that poorly reflects the internal states of the majority of cells in the population. See, e.g., Altschuler and Wu. (2010). *Cell* 141, pp. 559-563.

Existing methods for isolating populations of unique cell types are often limited in the purity of the population that is achievable. For example, enriched populations of primary multipotent stem cells rarely achieve better than 50% functional purity and are often well below 10% pure, so that the molecular signatures of these cells are obscured by large, and often overwhelming contamination from other cell types. Many cell types interact with each other, both through direct contact and through secreted factors, to promote survival, death, differentiation or some other function, and these interactions are difficult to isolate and study in a mixture comprising a large number of cells. Additionally, cells may have differences in their genomic sequences and/or cellular state that result in different levels or types of expressed mRNA or proteins. If analyzed in a bulk population, the particular cell with a unique cellular state or having the expressed mRNA or protein of interest, although of high value for industrial purposes, is very difficult or impossible to isolate from the population.

To overcome the deficiencies of bulk population cell analysis, single cell assay platforms have been developed. For example, microfluidic devices have been used to study single cells in the past (Lecault et al. (2012). *Curr. Opin. Chem. Biol.* 16, pp. 381-390). Ma et al. (Nat Med, 17, pp. 738-743 (2011)) applied a single cell barcode chip to simultaneously measure multiple cytokines (e.g., IL-10, TNF-β, IFN-γ) from human macrophages and cytotoxic T lymphocytes (CTLs) obtained from both healthy donors and a metastatic melanoma patient. Microfabricated chamber arrays have also been used to screen and select B cells secreting antigen-specific antibodies from both immunized humans and mice (Story et al. (2009). *Proc. Natl. Acad. Sci. U.S.A.* 105, pp. 17902-17907; Jin et al. (2009). *Nat. Med.* 15, pp. 1088-1092). In this approach, single B cells were arrayed on a surface containing tens of thousands of microfabricated wells (~10-100 μm deep), where the well surfaces were functionalized with capture antibodies. After incubation of cells on the well surfaces for less than 3 hours, the surfaces were washed with fluorescently labeled antigen and scanned in order to identify antigen-specific B cells. These cells were then manually recovered from the arrays by a microcapillary in order to amplify, sequence, and clone the antibody-encoding genes from these cells.

Two-phase microfluidic devices have also been applied to the analysis of secreted proteins from single immune cells by encapsulating them in sub-nanoliter aqueous droplets separated by a stream of oil (Konry et al. (2011). *Biosens. Bioelectron.* 26, pp. 2702-2710). These droplets can be analyzed in a flow-through format similar to FACS, and thus provide an opportunity for ultra-high throughput detection of secreted proteins from single cells. Water-in-oil emulsions have also been used to study cellular paracrine signaling by co-encapsulating cells in microfluidic-generated agarose beads (Tumarkin et al. (2011). *Integr. Biol.* 3, pp. 653-662). Microfluidic droplet generation also has been used for drug screening and development by enabling viability analysis of encapsulated single cells exposed to different compositions (Brouzes et al. (2009). *Proc. Natl. Acad. Sci. U.S.A.* 106, pp. 14195-14200).

Antibodies are molecules naturally produced by the immune system of humans or animals to fight off infection and disease. This is achieved by the unique ability of the immune system to generate an immense diversity of antibodies, each with the ability to recognize and bind a specific target (e.g., protein, virus, bacteria). This unmatched specificity is also what makes antibodies extremely potent and low side-effect drugs with clinically approved therapies for a wide array of conditions including cancer, autoimmune disorders, inflammation, neurology, and infection. In comparison to conventional small molecule drugs, antibodies offer several advantages including superior pharmacokinetics, fewer side effects, improved tolerability, and much higher success rates in clinical trials (27% vs. 7% for small molecules). (Reichert (2009). *Mabs* 1, pp. 387-389.) It is for this reason that antibodies are also by far the fastest growing class of drugs, with a total global market that was $50B in 2012 and that is growing at a rate of 9% per year. (Nelson et al. (2010). *Nat. Rev. Drug Disc.* 9(10), pp. 767-774.)

The discovery of antibodies with optimal therapeutic properties, and in particular antibodies that target surface receptors, remains a serious bottleneck in drug development. In response to immunization, an animal can make millions of different monoclonal antibodies (mAbs). Each mAb is produced by a single cell called an antibody-secreting cell (ASC), and each ASC makes only one type of mAb. Accordingly, antibody analysis, for example, for drug discovery purposes lends itself to single cell analyses. However, even if an ASC is analyzed individually, and not within a bulk population of cells, because a single ASC generates only a minute amount of antibody, when analyzed in the volume of conventional assay formats, the antibody is too dilute, making it completely undetectable. Accordingly, new methods for studying individual ASCs and their secreted antibodies are needed. The present invention addresses this and other needs.

SUMMARY OF THE INVENTION

The present invention provides a microfluidic platform for the analysis of an extracellular effect attributable to single effector cell. The effector cell, in one embodiment, is a cell that secretes a biological factor, for example, an antibody (an ASC). In a further embodiment, microfluidic analysis of the effector cell is an extracellular effect assay carried out on a cell population comprising the single effector cell.

In one aspect, a method of identifying a cell population comprising an effector cell having an extracellular effect is provided. In one embodiment, the method comprises retaining in a microreactor a cell population comprising one or more effector cells, wherein the contents of the microreactor further comprise a readout particle population comprising one or more readout particles, incubating the cell population and the one or more readout particles within the microreactor, assaying the cell population for the presence of the extracellular effect, wherein the readout particle population or subpopulation thereof provides a direct or indirect readout of the extracellular effect, and determining, based on the results of the assaying step, whether one or more effector cells within the cell population exhibits the extracellular effect. In a further embodiment, the microreactor is a microfluidic chamber. In even a further embodiment, the microfluidic chamber is part of a microfluidic structure that includes membrane valves.

In this aspect, the effector cell is a cell that secretes a biological factor, e.g., an antibody. It is not necessary that the specific effector cell or effector cells, having the particular extracellular effect be initially identified so long as the presence of the extracellular effect is detected within a particular microreactor. That is, some or all of the cells in the microreactor where the effect is measured can be recovered if desired for further characterization to identify the specific cells providing the extracellular effect.

In one embodiment, if it is determined that a cell population comprising one or more effector cells exhibit the extracellular effect, the cell population or portion thereof is recovered to obtain a recovered cell population. Recovery, in one embodiment, comprises piercing the microfluidic chamber comprising the cell population comprising the one or more cells that exhibit the extracellular effect, with a microcapillary and aspirating the chamber's contents or a portion thereof to obtain a recovered aspirated cell population.

In one embodiment, if it is determined that a cell population comprising one or more effector cells exhibit the extracellular effect, the cell population or portion thereof is recovered to obtain a recovered cell population, and the recovered cell population is further analyzed as cell subpopulations. The method, in one embodiment comprises retaining a plurality of cell subpopulations originating from the recovered cell population in separate chambers of a microfluidic device, wherein each of the separate chambers comprises a readout particle population comprising one or more readout particles, incubating the individual cell subpopulations and the readout particle population within the chambers, and assaying the individual cell subpopulations for the presence of a second extracellular effect. The readout particle population or a subpopulation thereof provide a readout of the second extracellular effect and the second extracellular effect is the same extracellular effect or a different extracellular effect as the extracellular effect measured on the recovered cell population. Once the cell subpopulations are incubated and assayed, the method further comprises identifying, based on the results of the assaying step, a cell subpopulation from amongst the plurality that comprises one or more cells that exhibit the second extracellular effect on the readout particle population, or a subpopulation thereof.

In another aspect, the present invention relates to a method of identifying a cell population displaying a variation in an extracellular effect. In one embodiment, the method comprises, retaining a plurality of individual cell populations in separate microfluidic chambers, wherein at least one of the individual cell populations comprises one or more effector cells and the contents of the separate microfluidic chambers further comprise a readout particle population comprising one or more readout particles, incubating the individual cell populations and the readout particle population within the microfluidic chambers, assaying the individual cell populations for the presence of the extracellular effect, wherein the readout particle population or subpopulation thereof provides a readout of the extracellular effect. Once the cell populations are incubated and assayed, the method comprises identifying, based on the results of the assay, a cell population from amongst the plurality that exhibits a variation in the extracellular effect, as compared to one or more of the remaining cell populations of the plurality. In a further embodiment, the one or more effector cells comprise an antibody secreting cell. In another embodiment, the one or more effector cells comprise a plasma cell, B cell, plasmablast, a cell generated through the expansion of memory B cell, a hybridoma cell, a T cell, CD8+ T cell, and CD4+ T cell, a recombinant cell engineered to produce antibodies, a recombinant cell engineered to express a T cell receptor, or a combination thereof.

One or more cell populations exhibiting the extracellular effect or variation in the extracellular effect, in one embodiment, are recovered to obtain one or more recovered cell populations. Recovery, for example, is carried out with a microcapillary. Once one or more individual cell populations are identified and recovered, the one or more individual cell populations are further analyzed to determine the cell or cells responsible for the observed extracellular effect. In one embodiment, the method comprises retaining a plurality of cell subpopulations originating from the one or more recovered cell populations in separate chambers of a microfluidic device. Each of the separate chambers comprises a readout particle population comprising one or more readout particles. The individual cell subpopulations are incubated with the readout particle population within the chambers. The individual cell subpopulations are assayed for a variation of a second extracellular effect, wherein the readout particle population or subpopulation thereof provides a readout of the second extracellular effect. The second extracellular effect is the same extracellular effect or a different extracellular effect as the extracellular effect measured on the recovered cell population. Based on the second extracellular effect assay, one or more individual cell subpopulations are identified that exhibit a variation in the second extracellular effect. The one or more individual cell subpopulations in one embodiment are then recovered for further analysis. Extracellular effect assays are described throughout.

In one embodiment, cells from a recovered cell population or recovered cell subpopulation are retained in a plurality of vessels as cell subpopulations or sub-subpopulations, and each cell subpopulation or cell sub-subpopulation is present in an individual vessel. The individual subpopulations or sub-subpopulations are lysed to provide and one or more nucleic acids within each lysed cell subpopulation or lysed cell sub-subpopulation are amplified. In a further embodiment, the one or more nucleic acids comprise an antibody gene.

In one embodiment of the methods described herein, the incubating step includes exchanging the medium in the respective microreactors (e.g., microfluidic chambers) comprising the individual cell populations or subpopulations. Medium exchange is carried out, for example, to maintain the viability of the cells in the chamber or to provide reagents for carrying out an extracellular effect assay, or to perform multiple extracellular effect assays in a serial manner.

Incubating, in one embodiment, comprises incubating the cell populations or cell subpopulations with a plurality of accessory particles. The plurality of accessory particles is provided, for example, as additional reagents for the extracellular effect assay or to maintain cell viability. In one embodiment, the plurality of accessory particles comprises sphingosine-1-phosphate, lysophosphatidic acid, growth factor, cytokine, chemokine, neurotransmitter, virus particle, secondary antibody, fluorescent particle, a fluorescent substrate, a complement pathway inducing factor, a virus particle or an accessory cell. The accessory cell, in one embodiment, is a fibroblast cell, natural killer (NK) cell, killer T cell, antigen presenting cell, dendritic cell, recombinant cell, or a combination thereof.

The extracellular effect measured by the methods and devices described herein in one embodiment, is binding of an effector cell or molecule secreted by an effector cell to a cell surface protein, antagonism of a cell surface receptor, or agonism of a cell surface receptor present on a readout cell (a type of readout particle). In a further embodiment, the cell surface receptor is a receptor tyrosine kinase (RTK), a G-protein coupled receptor (GPCR), receptor serine-threonine kinase, receptor tyrosine phosphatase or a receptor guanylyl cyclase. The GPCR is not limited by class or species. For example, the GPCR, in one embodiment, is a GPCR provided in Table 3A or 3B, herein.

In another embodiment, the extracellular effect measured by the methods and devices described herein, is binding of an effector cell or molecule secreted by an effector cell to an ion channel, antagonism of an ion channel, or agonism of an ion channel. The ion channel, in one embodiment, is a $GABA_A$, Glycine (GlyR), serotonin (5-HT), nicotinic acetylcholine (nAChR), zinc-activated ion channel, ionotropic glutamate, AMPA, kainite, NMDA receptor or an ATP gated channel Where the extracellular effect is binding, agonism or antagonism of a cell surface receptor or ion channel, the effect in one embodiment is measured by detection of an increase in intracellular cAMP or calcium, expression of a protein reporter, or localization of a protein within a readout cell expressing the cell surface receptor or ion channel.

The extracellular effect in another embodiment, is a binding interaction between a molecule secreted by the one or more effector cells or a subset thereof, to one or more readout particles or one or more accessory particles, modulation of apoptosis, modulation of cell proliferation, a change in a morphological appearance of the readout particle, a change in localization of a protein within the readout particle, expression of a protein by the readout particle, neutralization of an accessory particle operable to affect the readout particle or a combination thereof.

In some embodiments, the extracellular effect is an effect of a cell product, secreted by an effector cell. The extracellular effect is binding interaction between a protein produced by an effector cell and either a readout particle or accessory particle. For example, the effector cell in one embodiment is an antibody secreting cell (ASC), and the readout or accessory particle comprises an epitope or an antigen. The binding interaction, in one embodiment, is a measure of one or more of antigen-antibody binding specificity, antigen-antibody binding affinity, and antigen-antibody binding kinetics. In another embodiment, the effector cell is an activated T cell that secretes a cytokine, and the readout particle includes one or more antibodies to capture the secreted cytokines.

The above methods and devices may be used to screen or select for cells are that may be rare, e.g. less than 1% of the cells in the population, or from about 1% to about 10% or from about 5% to about 10% of the cells being screened or selected.

In another aspect, functional antibodies and receptors discoverable by the methods herein are provided. In one embodiment of this aspect, the nucleic acid of an effector cell responsible for an extracellular effect is amplified and sequenced. The nucleic acid is a gene encoding for an secreted biomolecule (e.g., antibody, or fragment thereof), or a gene encoding a cell receptor or fragment thereof, for example a T-cell receptor. The antibody or fragment thereof or cell receptor or fragment thereof can be cloned and/or sequenced by methods known in the art.

BRIEF DESCRIPTION OF THE DRAWINGS

FIG. 20 shows top and cross-sectional view schematic diagrams of a method to detect the presence of at least one effector cell secreting an antibody with high affinity from a heterogeneous population of cells containing cells that secrete an antibody for the same antigen but with lower affinity.

FIG. 21 shows top and cross-sectional view schematic diagrams of a method of screening for antibodies with increased specificity for an antigen according to an embodiment of the invention in which readout particles displaying different epitopes are distinguishable by different optical characteristics.

FIG. 24 is an alignment of the extracellular domain for PDGFRα across human, rabbit, mouse and rat. (Top) Ribbon diagram showing structure of extracellular domain (ECD) of two PDGFRβ in complex with a dimer of PDGFBB (from Shim et al. (2010). *Proc. Natl. Acad. Sci. U.S.A.* 107, pp. 11307-11312, incorporated by reference herein in its entirety). Note, a PDGFRβ is shown since a similar structure for PDGFRα is expected but was not available. (Bottom) Alignment of ECD for PDGFRα across human, (SEQ ID NO. 79), mouse (SEQ ID NO. 80), rabbit (SEQ ID NO. 81), rat (SEQ ID NO. 82). Regions of variation from the human isoform are denoted by lighter shading and "*". The substantial variation indicates there are numerous epitopes available for antibody recognition, with rabbit having the most variation from human.

FIG. 51 is a top view schematic diagram of a chamber functionalized with two types of antibodies in order to segregate particles displaying different types of antibodies on their surface.

FIG. 52 is a top view schematic diagram of a serial, "flow-through" arrangement of microfluidic chambers in which each chamber is isolated from its neighbour by a valve positioned between the chambers.

FIG. 53 is a top view schematic diagram of a serial, "flow-through" arrangement of microfluidic chambers in which each chamber may be isolated from a flow channel shared by neighboring chambers by a "lid" structure.

FIGS. 54 and 55 are top view schematic diagrams of parallel, "flow-through" arrangements of microfluidic chambers in which neighboring chambers may share a common inlet channel and outlet bus channel.

FIG. 70A is a top view light microscopy image of a chamber embodiment with five effector cells shown in the right end of the effector zone (top) and four readout particles in the readout zone (bottom).

FIG. 70B is a top view fluorescence microscopy image of the chamber embodiment shown in FIG. 70A with some fluorescence associated with the effector cells at the right end of the effector zone and fluorescence associated with the four readout particles in the readout zone.

FIG. 70C is a top view light microscopy image of a chamber embodiment with one effector cell shown in the effector zone (left) and one readout particle in the readout zone (right).

FIG. 70D is a top view fluorescence microscopy image of the chamber embodiment shown in FIG. 70C with fluorescence associated with the readout particle in the readout zone.

FIG. 70E is a top view light microscopy image of a chamber embodiment with two effector cells in the effector zone (left) and six readout particles in the readout zone (right).

FIG. 70F is a top view fluorescence microscopy image of the chamber embodiment shown in FIG. 70E with some fluorescence associated with the readout particles in the readout zone.

FIG. 82 is a light microscopy image showing 2 chambers, one containing multiple effector cells with at least one of them secreting an antibody (top) and another chamber without any effector cell (bottom). The readout particles form aggregates when secreted antibodies present (top) and remain dispersed in the absence of antibody-secreting effector cell (bottom).

FIG. 83 is a fluorescence microscopy image showing the two chambers in 16G, one containing multiple effector cells with at least one of them secreting an antibody (top) and another chamber without any effector cell (bottom). Both chambers contain readout particles (protein A beads) that have been stained with a fluorescently labelled anti-human antibody to determine the presence of an extracellular effect.

FIG. 87 shows representative examples of affinity measurements obtained by microfluidic screening for two single primary mouse plasma cells producing antibodies against hen-egg lysozyme.

FIG. 88 is is a bar graph indicating that the remaining fluorescence level of beads in HyHEL5-positive chambers is higher than in the rest of the chambers at the end of the wash.

FIG. 89A is a top view light microscopy example of a chamber containing a heterogeneous population of cells (erythrocytes and human B cells).

FIG. 89B is a top view light microscopy example of a chamber containing a heterogeneous population of cells and a population of readout particles (protein A beads).

FIG. 89C is a top view fluorescence microscopy example of a chamber showing that at least one cell in the heterogeneous population secretes human IgG antibodies. The antibody was captured by the readout particles, which were stained with Dylight594-conjugated anti-human antibodies.

FIG. 89D is a top view light microscopy example of a chamber with a heterogeneous population of cells and a population of readout particles after flowing the H1N1 antigen into the chamber.

FIG. 89E is a top view fluorescence microscopy example of a heterogeneous population of cells in conjunction with a population of readout particles (protein A beads) after flowing the H1N1 antigen into the chamber. The H1N1 antigen was conjugated to Dylight 488 so as to differentiate antigen-specific staining from whole IgG staining.

FIG. 89F is a top view light microscopy example of a chamber after recovery of the cells.

Figure 94:
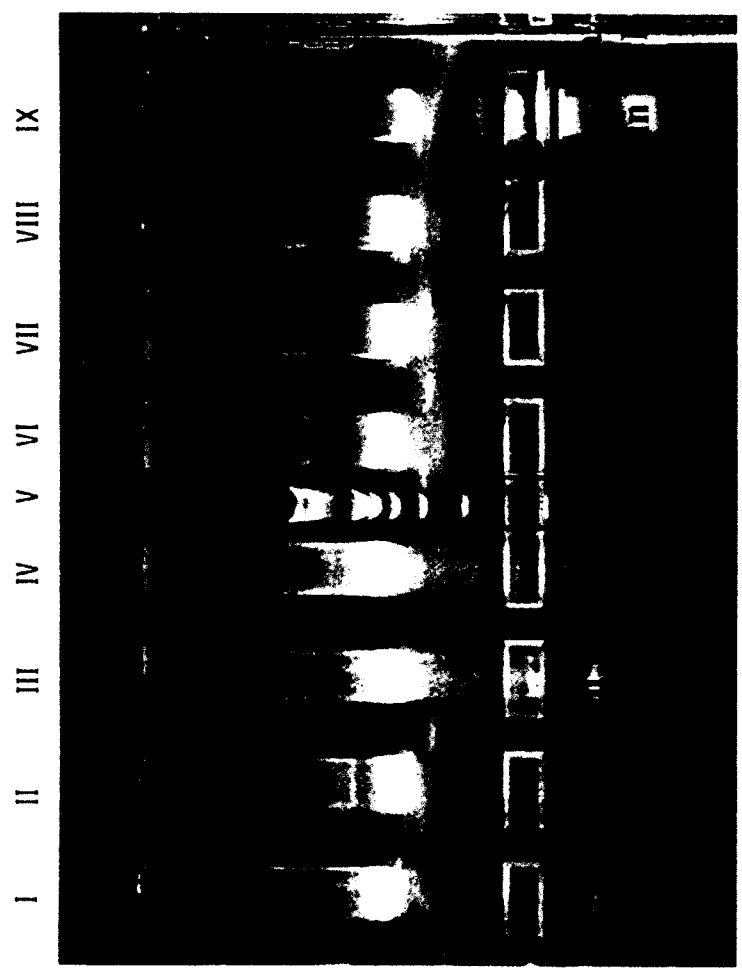

FIG. 94 is a picture of a Size Select® 2% agarose gel of antibody heavy and light chain gene specific PCR products after single cell screening in a microfluidic device. Lanes i to iv show the products of heavy chain PCR amplification of samples 3 to 6, respectively. Lane v shows the nucleic acid ladder. Lanes vi to viii show kappa chain PCR amplification of samples 3, 5, and 6, respectively. Lane ix shows lambda chain PCR amplification of sample 4.

Figures 95A, 95B:
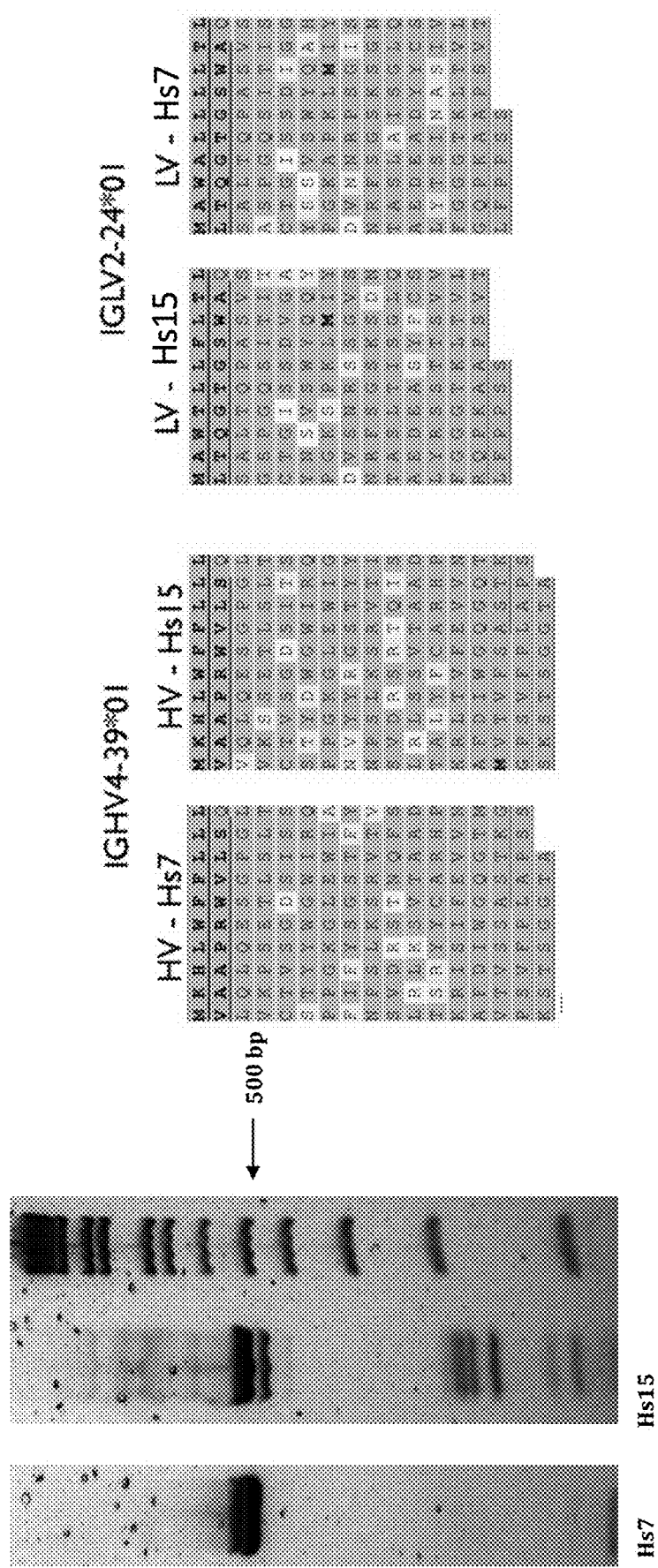

FIG. 95A is a gel showing the amplification of both heavy and light chains from two single cells secreting antibodies against influenza.

FIG. 95B shows the variable heavy and light amino acid sequences from 2 cells secreting antibodies (Hs7 antibody and Hs15 antibody) against H1N1 and H3N2. Hs7 heavy chain amino acid sequence: SEQ ID NO: 10, Hs7 light chain amino acid sequence: SEQ ID NO: 12; Hs15 heavy chain amino acid sequence: SEQ ID NO: 14, Hs15 light chain amino acid sequence: SEQ ID NO: 16.

FIG. 95C is the functional validation of recombinant human mAbs that cross-react with both H1N1 and H3N2.

Figure 96B:
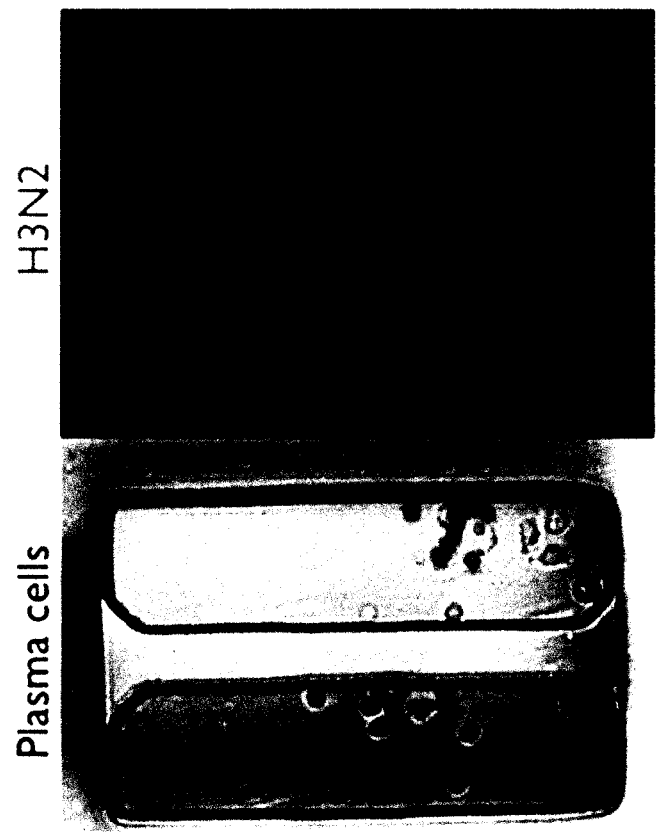
Figure 96A:
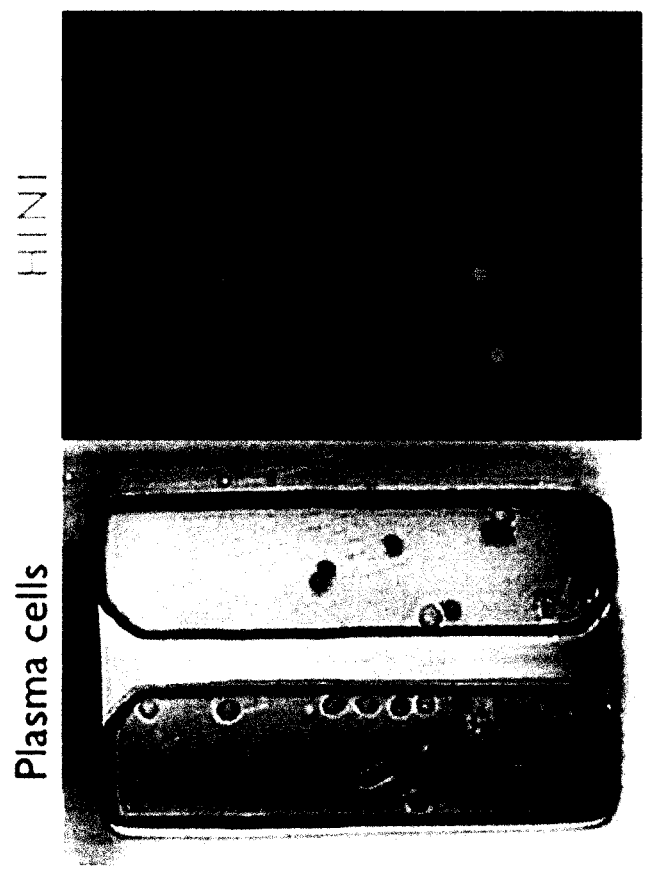

FIG. 96A shows an example of a chamber with a heterogeneous population of rabbit plasma cells containing at least one effector cell secreting an antibody against H1N1 detected by a fluorescent signal on readout capture beads.

FIG. 96B shows an example of a chamber with a heterogeneous population of rabbit plasma cells containing at least one effector cell secreting an antibody against H3N2 detected by a fluorescent signal on readout capture beads.

Figures 97A, 97B, 97C:
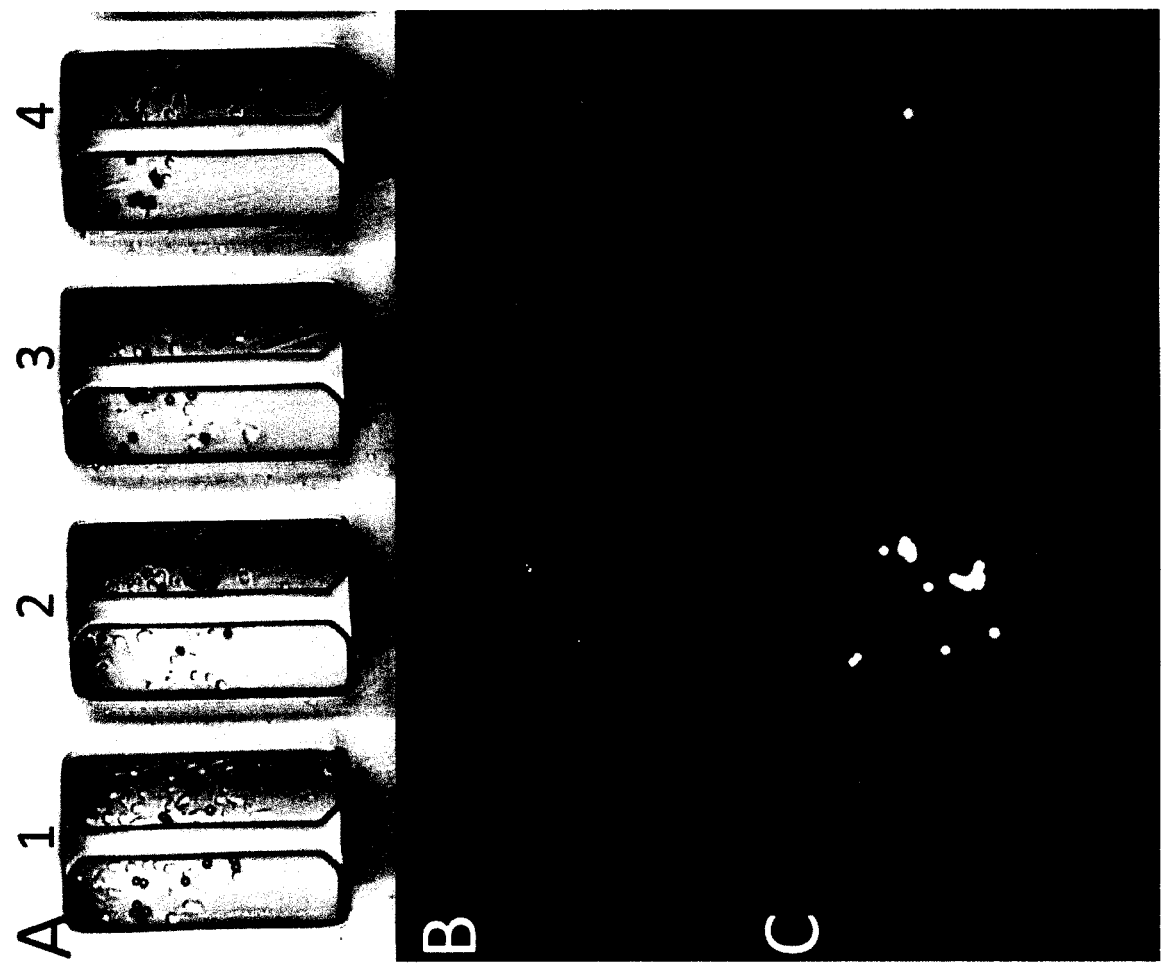

FIG. 97A shows bright field images of 4 chambers loaded with a plurality of enriched rabbit plasma cells FIG. 97B shows fluorescent images of the chambers in FIG. 123A after H1N1 detection. All chambers are negative and do not contain cells secreting antibodies against H1N1.

FIG. 97C shows fluorescent images of the chambers in FIG. 123C after H3N2 detection. Chambers exhibit variable bead intensities but all of them are positive and contain at least one cell secreting antibodies against H3N2.

Figure 97D:
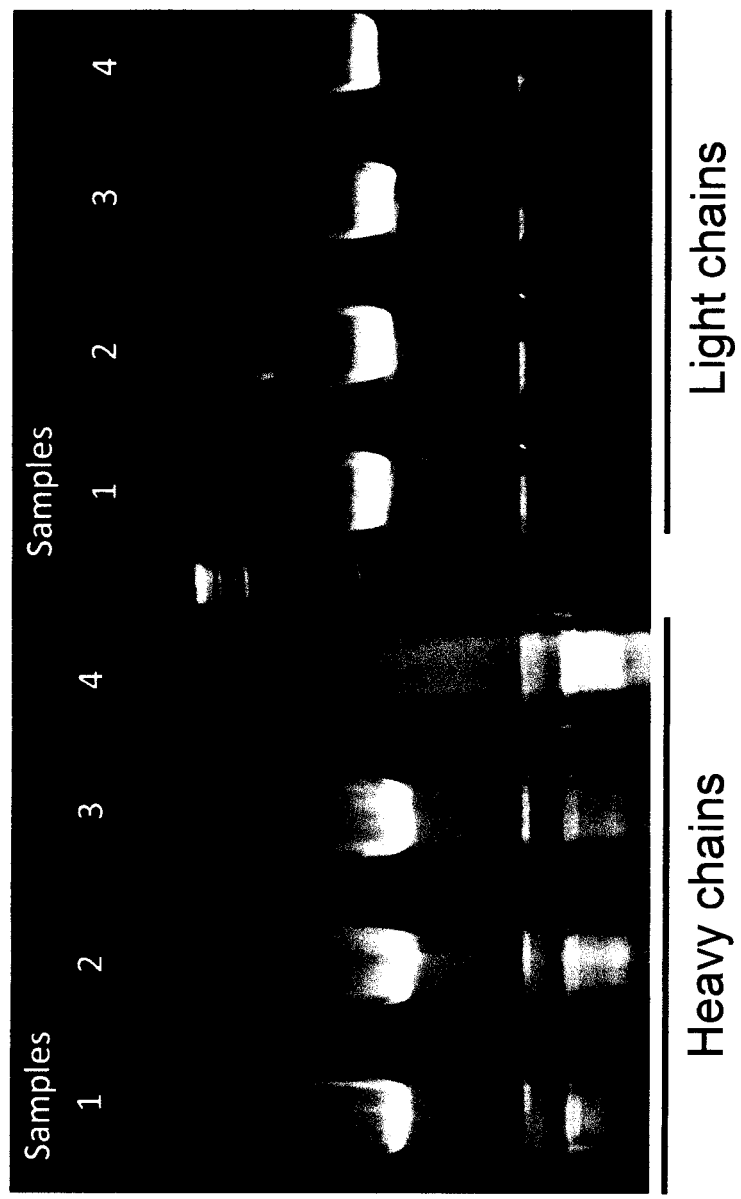

FIG. 97D is a gel showing the heavy and light chains amplified from rabbit cells after recovery from the H3N2-positive microfluidic chambers in FIG. 123C.

Figure 99:
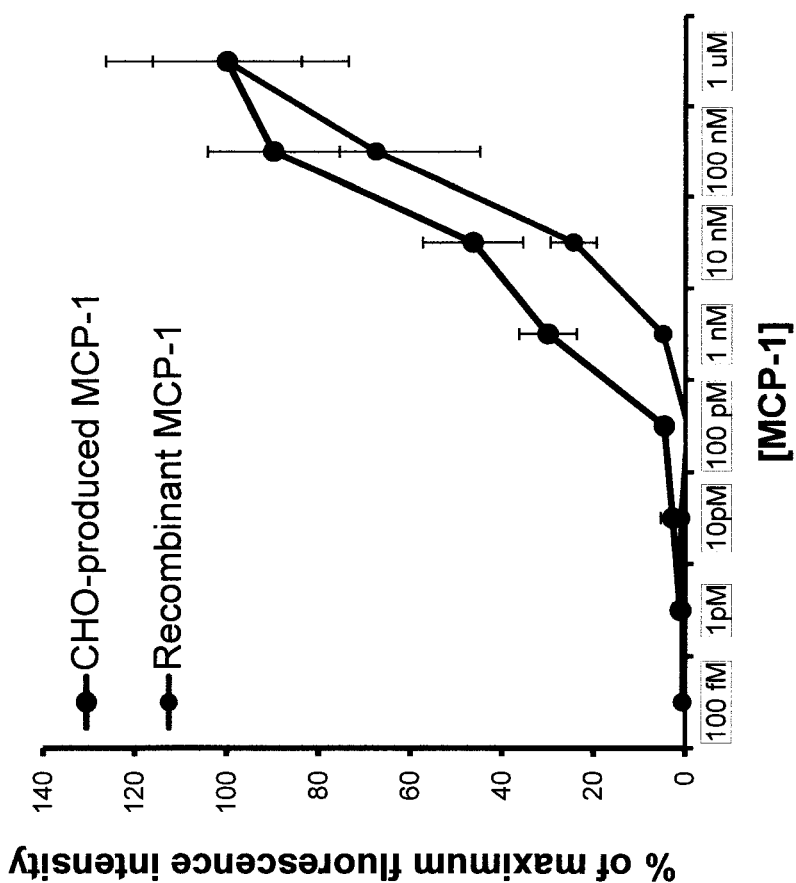
Figure 98:
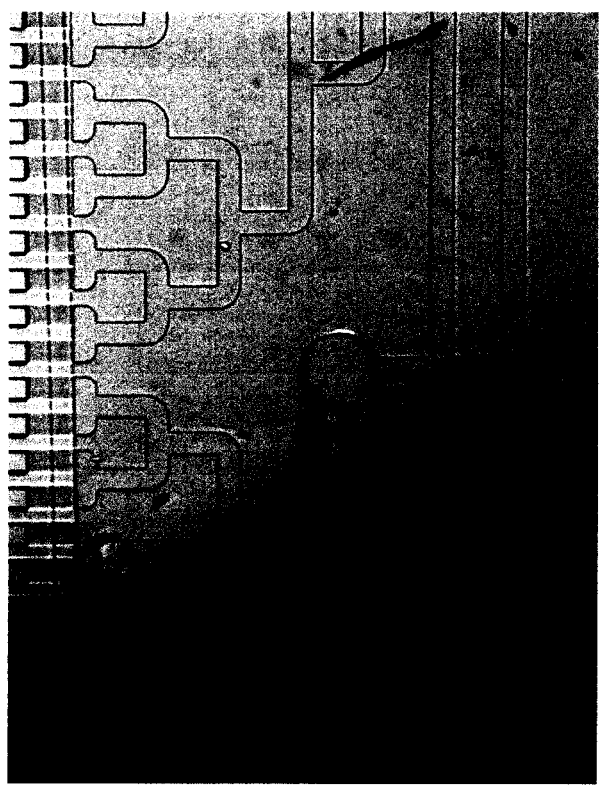
Figure 100:
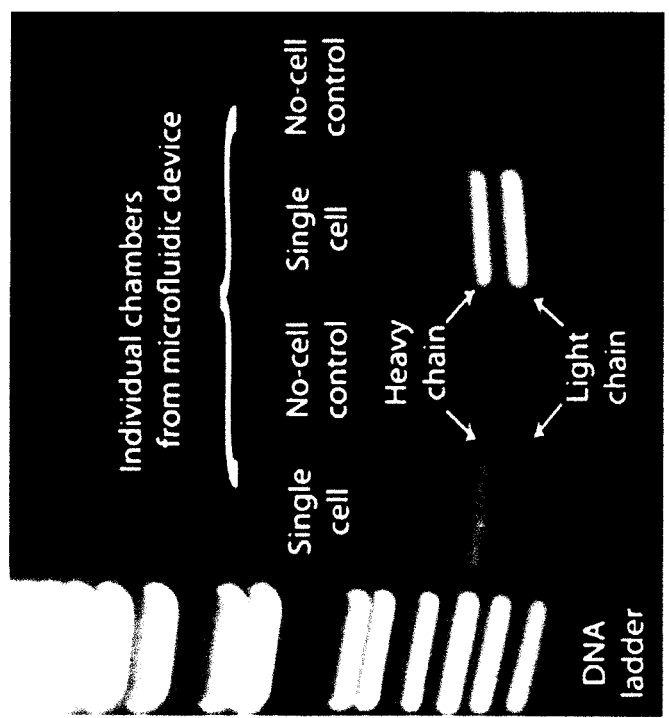

FIG. 98 shows an image of the capillary loaded with recovered cells approaching the injection port immediately before re-injection for enrichment FIG. 99 shows an example of the validation of human antibody sequences by cloning, expression and characterization of the antibodies FIG. 100 is a gel showing bands from RT-PCR amplification of hybridoma single cells recovered from a microfluidic device.

Figure 101:
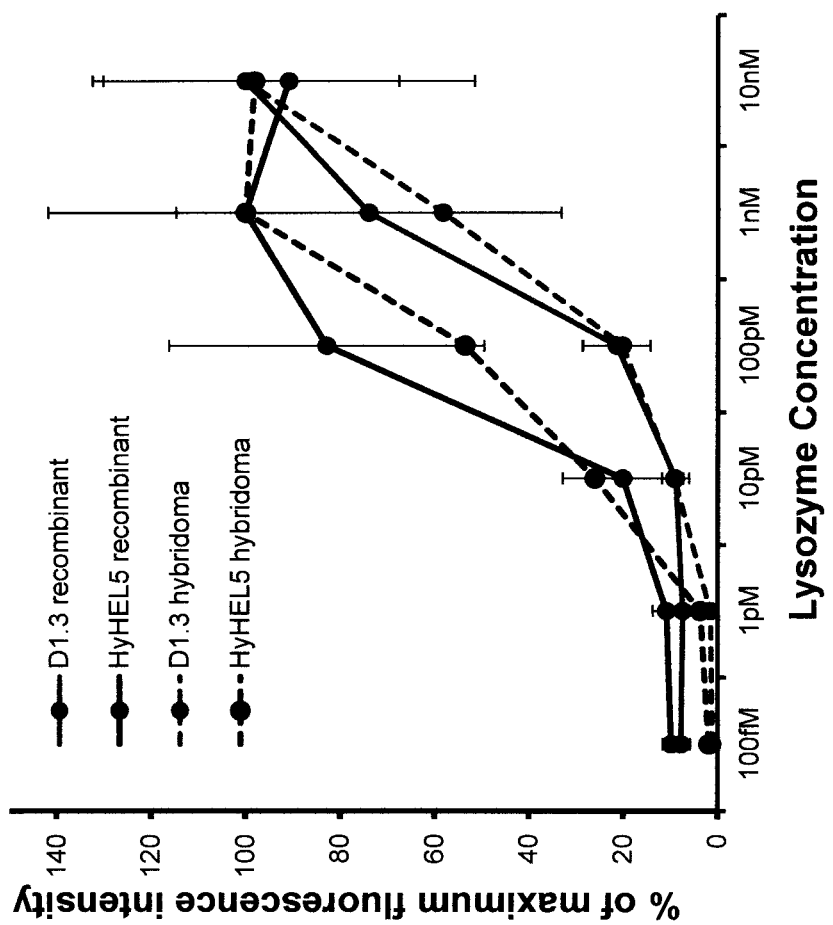

FIG. 101 is a graph that compares the affinities of anti-hen egg lysozyme antibodies produced by hybridomas (D1.3 and HyHEL5) and recombinant expression of the sequences retrieved from single D1.3 and HyHEL5 hybridoma cells screened in a microfluidic device. Anti-mouse antibody capture beads were incubated with cell supernatants from hybridomas or recombinant HEK293 cells expressing D1.3 and HyHEL5 antibodies, washed and incubated with different concentrations of the labeled antigen. Fluorescent measurements were normalized to the maximum bead intensity at the highest antigen concentration to validate the binding properties of the recombinantly produced antibodies.

Figure 102:
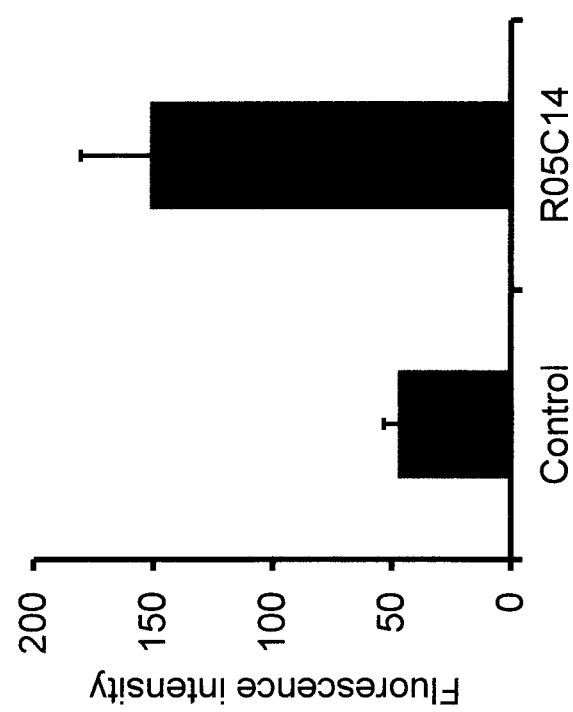

FIG. 102 is a graph that shows the fluorescent intensity of beads incubated with the supernatant from HEK293 cells (control) or HEK293 cells transiently expressing the antibody R05C14, followed by labeled hen-egg lysozyme (10 nM). The binding of a novel mouse antibody to hen-egg lysozyme was confirmed after the sequence R05C14 was obtained from a primary mouse plasma cell identified as antigen-specific in a microfluidic screen.

Figure 103:
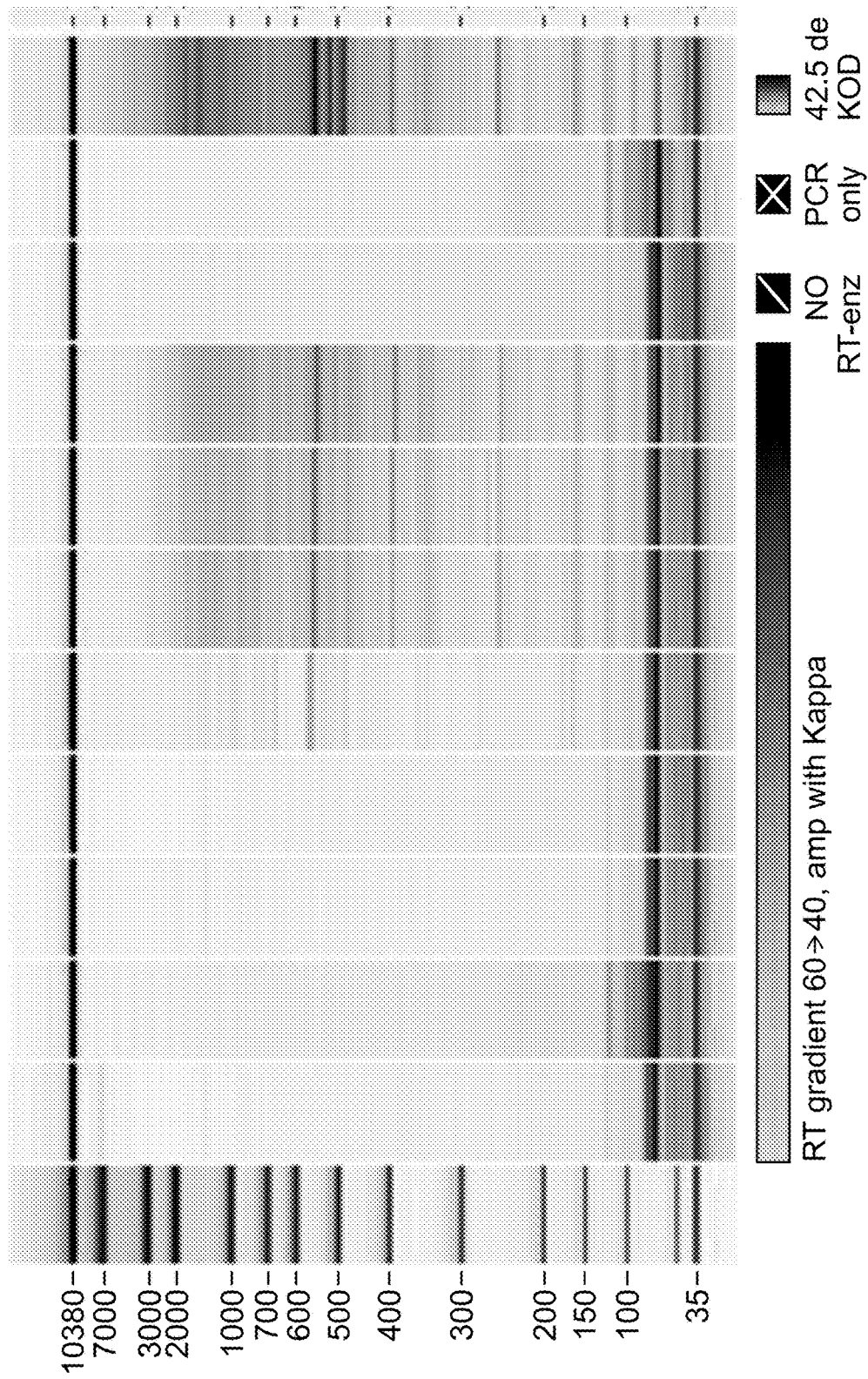
Figure 103:
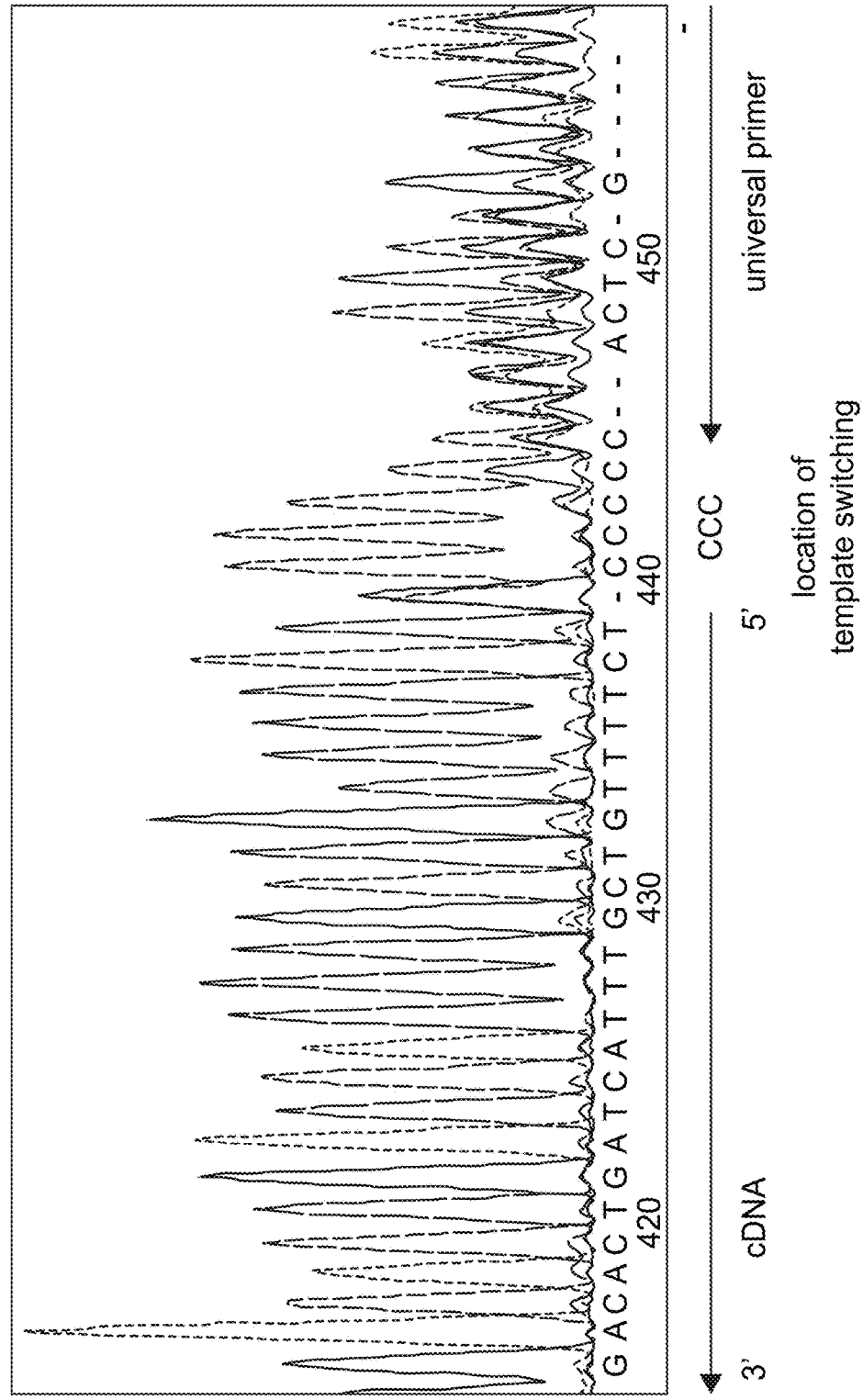

FIG. 103A is an image of a PCR gel showing the amplicons produced by the methods described in Example 25 using a gradient of RT temperatures ranging from 60° C. to 40° C.

FIG. 103B shows the results of Sanger sequencing of the band from 400 to 600 bp shown in FIG. 103A. The sequence was aligned and confirmed to match the variable region sequence of the heavy chain of D1.3.

Figure 104:
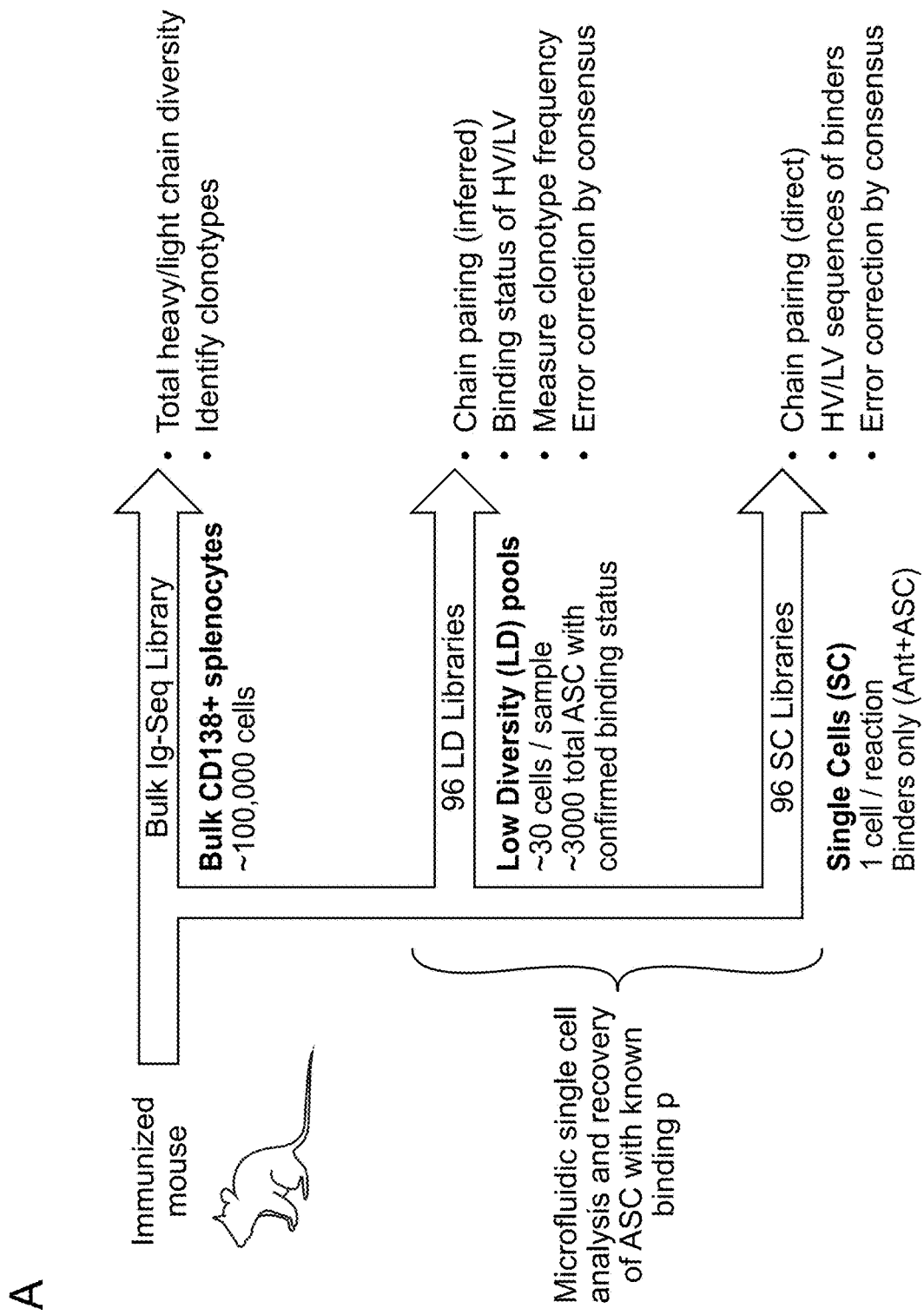
Figure 104:
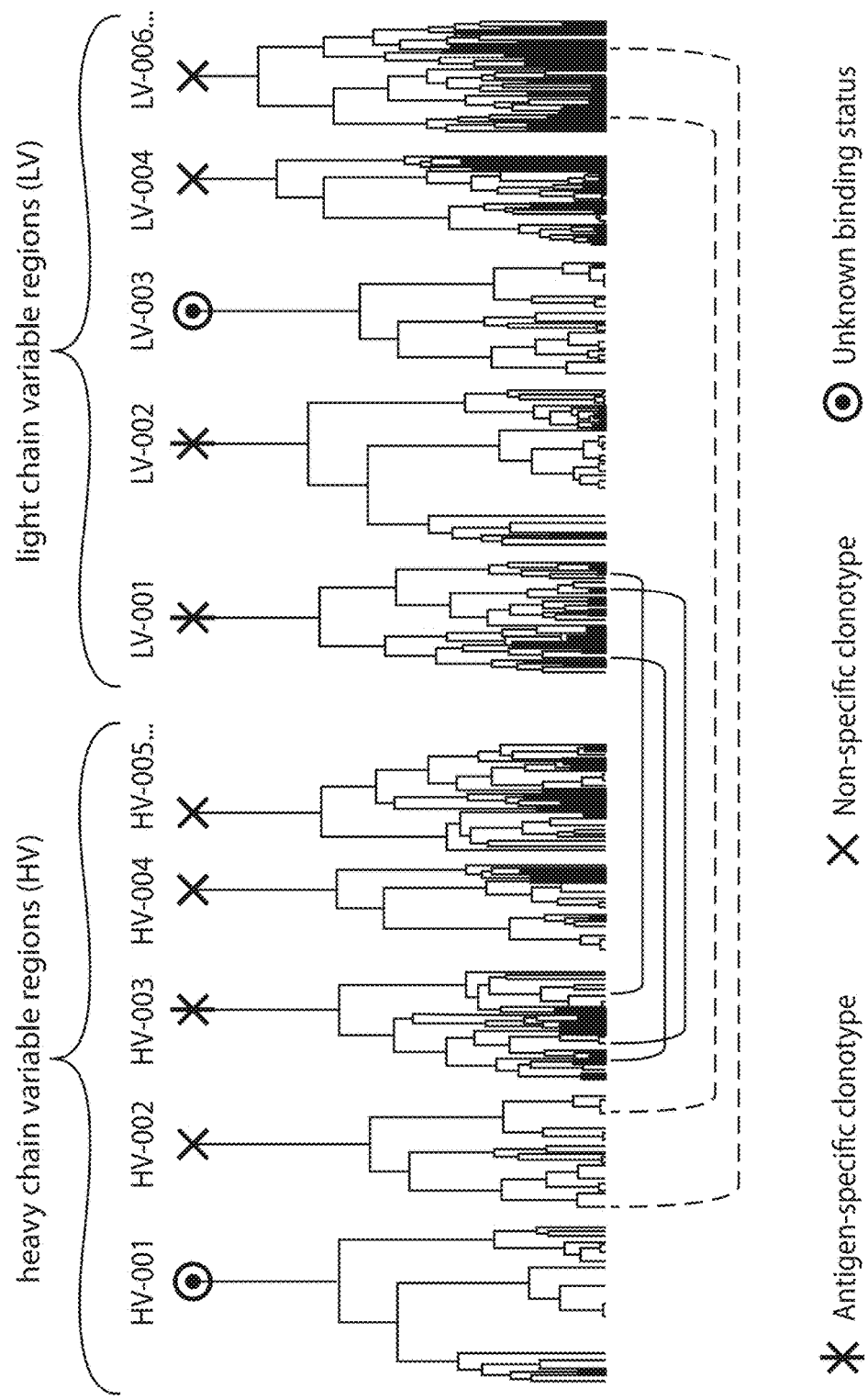
Figure 104:
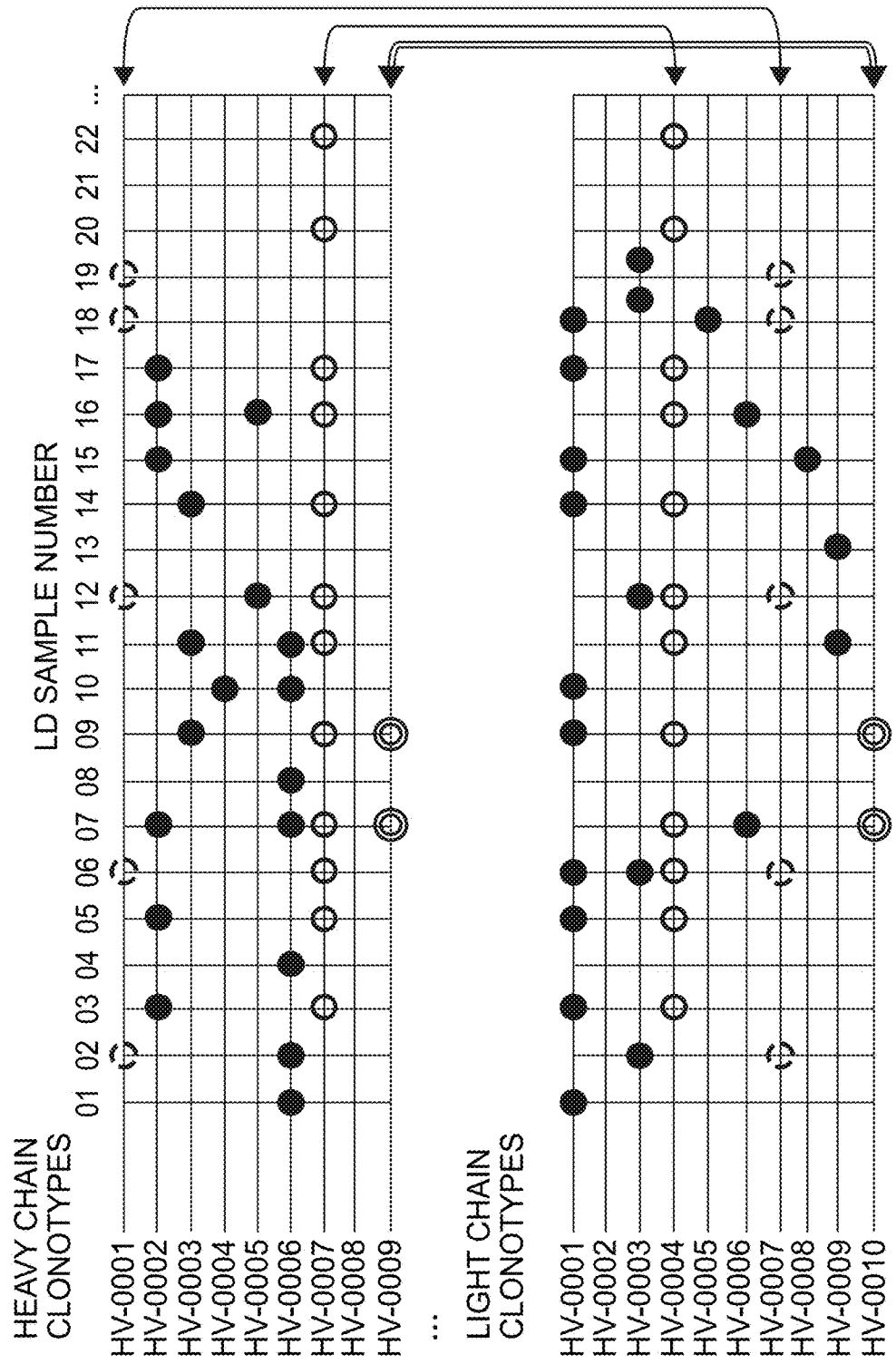

FIG. 104A-C are schematic representations of a method for the functional interpretation of the IgG repertoire based on next-generation sequencing.

FIG. 105A is a schematic of antigen detection multiplexing using beads of different fluorescent intensities FIG. 105B is a bright field image of three types of readout beads loaded in microfluidic chambers.

FIG. 105C is a fluorescent image of three types of readout beads with different intensities and antigens in microfluidic chambers.

FIG. 105D is a fluorescent image of three types of readout beads after detection with a rabbit anti-H1N1 antibody and a secondary anti-rabbit antibody, with only H1N1-coated beads (arrows) displaying a signal.

FIG. 105E shows the signal after H1N1 detection on three types of beads coated with different influenza strains and distinguished based on their fluorescent intensities.

FIG. 106A shows the toxicity response of L929 cells in the presence of actinomycin-D as a function of TNF-α concentration.

FIG. 106B shows an apoptosis and necrosis assay using L929 cells cultured in a microfluidic device in the presence of TNF-α and actinomycin-D.

Figure 107A:
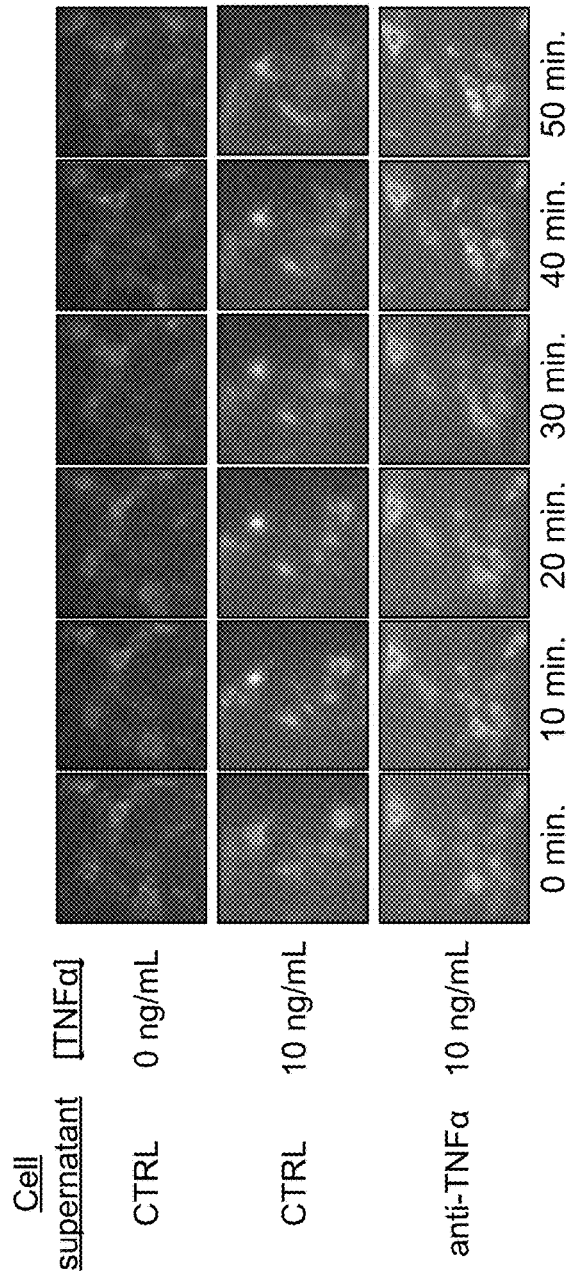

FIG. 107A shows time-lapse fluorescence microscopy images from TNFα functional assay. (A) Upper panel: In the absence of TNFα ligand fluorescence localization is cytoplasmic. Middle panel: Upon activation by TNFα ligand 10 ng/mL, a change in fluorescence from cytoplasmic to nuclear is observed. Lower panel: In the presence of cell supernatant containing an antibody that neutralizes TNFα ligand in addition to TNFα ligand 10 ng/mL, the fluorescence localization remains cytoplasmic.

Figure 107B:
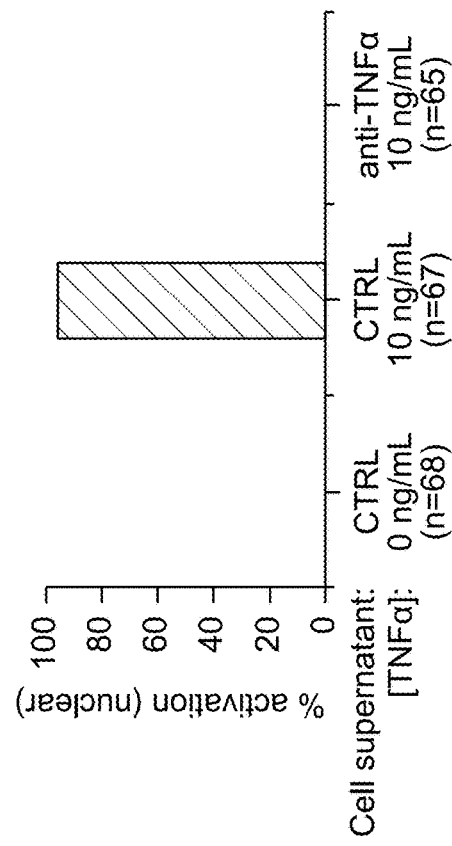

FIG. 107B is a plot showing frequency of activated cells exhibiting nuclear fluorescence localization. The number of cells quantified is indicated, n.

Figure 108:
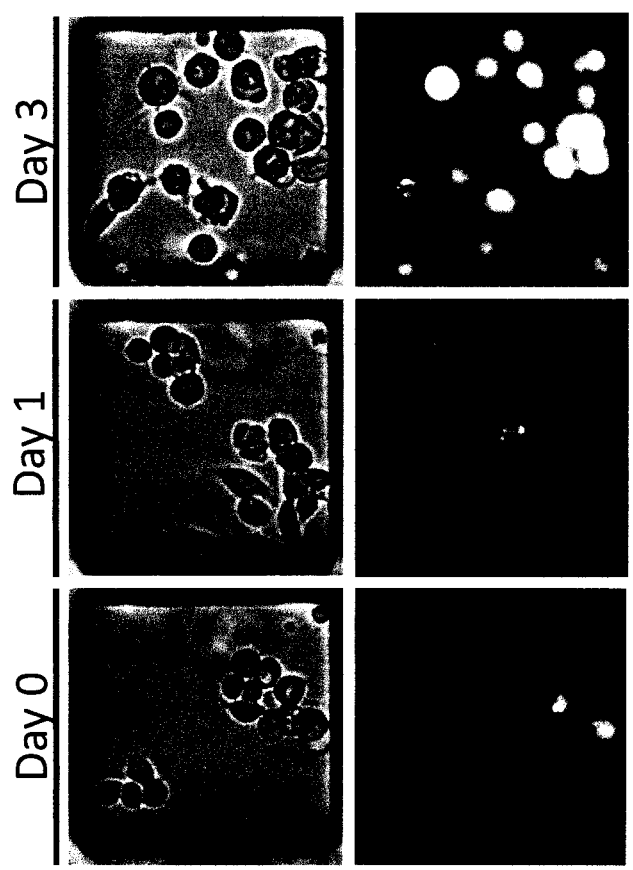

FIG. 108 shows optical micrographs at 0 days, 1 day and 3 days of SKBR3 cell populations in an individual microfluidic chambers. SKBR3 cells included an LC3-GFP reporter.

FIG. 109A shows a bright field image of a chamber containing a population of peripheral blood mononuclear cells incubated in the presence of IFNγ capture beads after activation with CEF peptides.

FIG. 109B shows a fluorescent image of a chamber containing at least one activated T cell secreting IFNγ after activation with CEF peptides.

FIG. 109C shows a bright field image of a chamber containing a T cell clone cultured for 5 days after activation with CEF peptides.

FIG. 109D shows a higher sensitivity using the microfluidic assay compared to ELISPOT to measure number of antigen-specific T cells in a population of peripheral blood mononuclear cells stimulated with CEF peptides.

Figure 110:
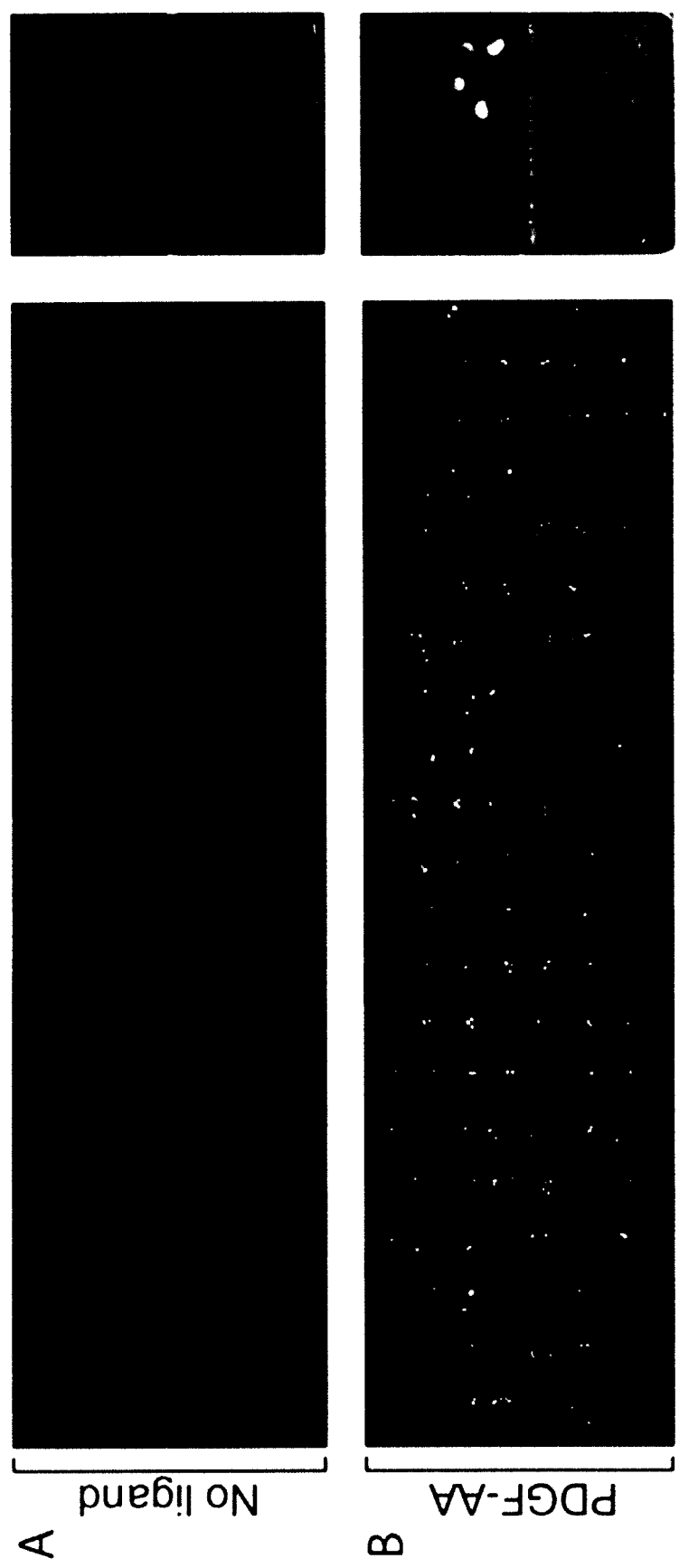
Figure 110C:
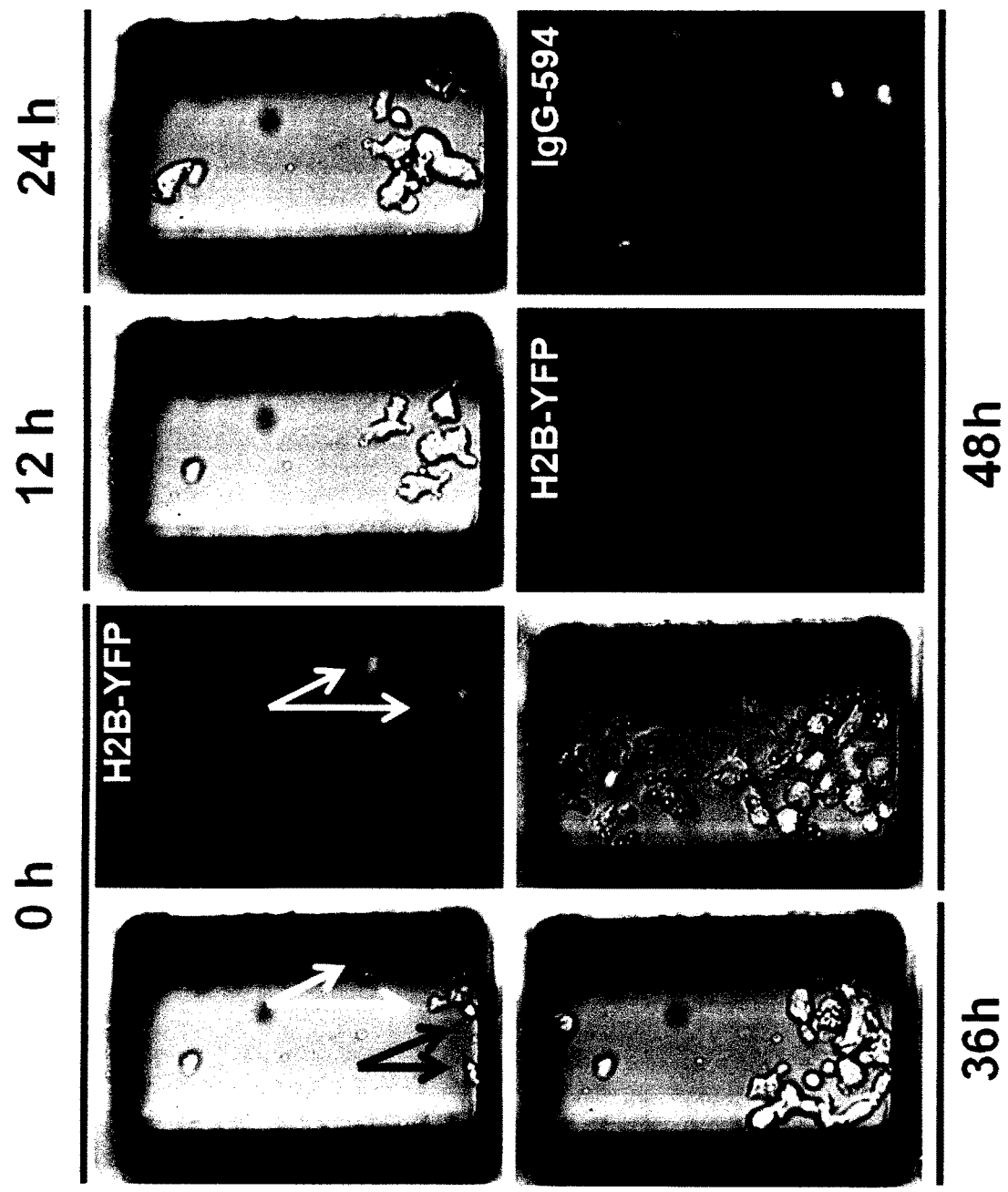

FIG. 110 are fluorescence microscopy images of chambers from 3 subarrays from a cell survival PDGFRα functional extracellular effect assay, showing YFP fluorescence readout in BaF3 clone expressing PDGFRα and histone 2B-YFP in the presence of (A) no ligand or (B) PDGF-AA 25 ng/mL for T=48 hours. Insets show close-up of individual microfluidic chambers. FIG. 110C shows micrographs of a population of enriched mouse splenocytes (2 cells, black arrow) co-cultured with a population of live readout cells (BaF3 overexpressing PDGFRA, white arrows) and containing at least one effector antibody-secreting cell after 12, 24, 36 and 48 hours of culture in a microfluidic device.

Figure 111:
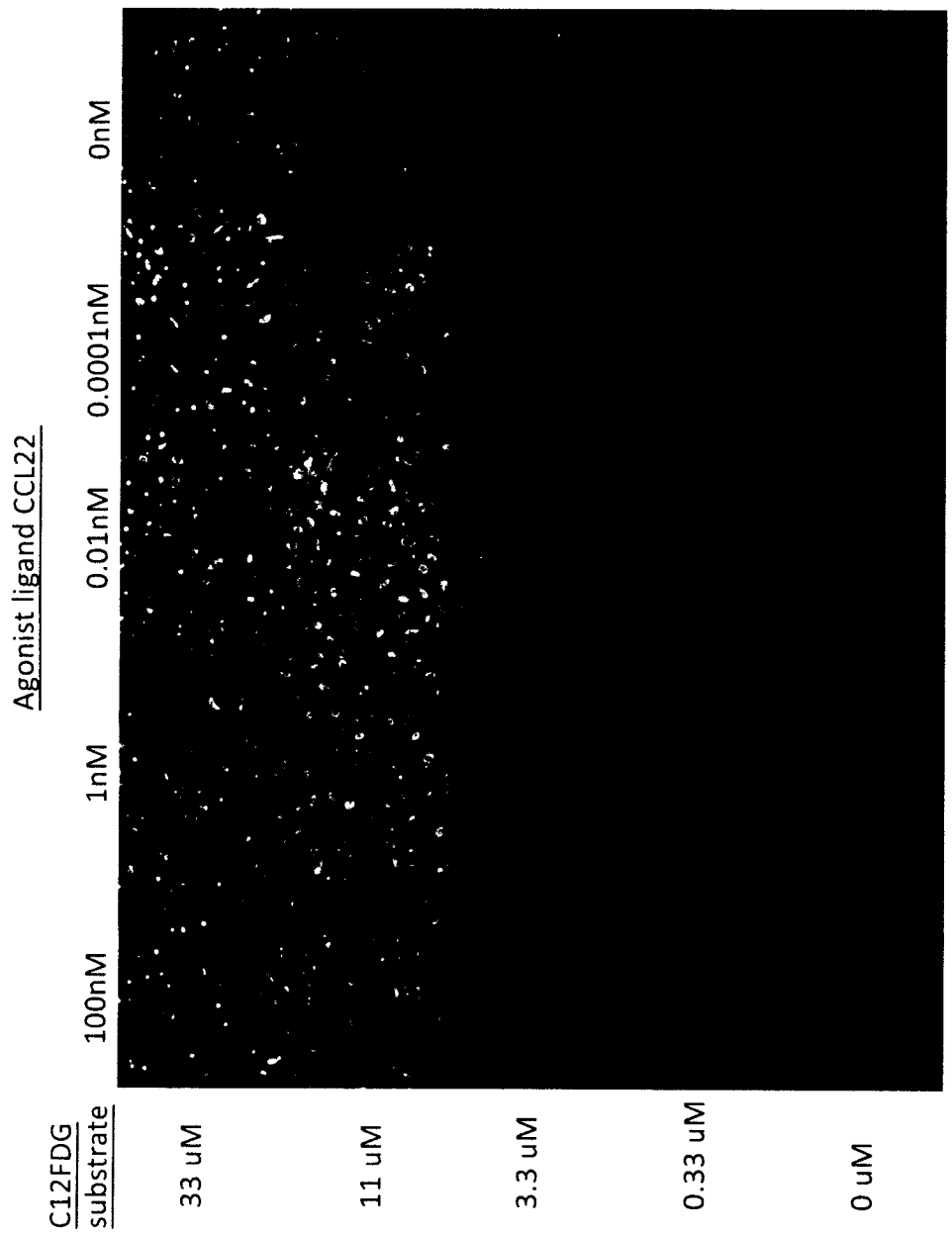

FIG. 111 shows fluorescent images obtained from a plate-based assay in which PathHunter® eXpress CCR4 CHO-K1 β-Arrestin GPCR reporter cells were incubated with different concentrations of the agonist CCL22, followed by different concentrations of the substrate $C_{12}FDG$. Activation of the GPCR CCR4 caused complementation of the β-galactosidase enzyme, which in turn cleaved the substrate into a fluorescent product.

Figure 112A:

FIG. 112A shows bright field and fluorescent images of a microfluidic-based GPCR signaling assay in which in which PathHunter® eXpress CCR4 CHO-K1 β-Arrestin GPCR reporter cells were loaded in a microfluidic device, incubated with the $C_{12}FDG$ substrate for 90 minute, followed by incubation with different concentrations of the agonist CCL12 for 90 min. Activation of the GPCR CCR4 by the agonist caused complementation of the β-galactosidase enzyme, which in turn cleaved the substrate into a fluorescent product.

Figure 112B:
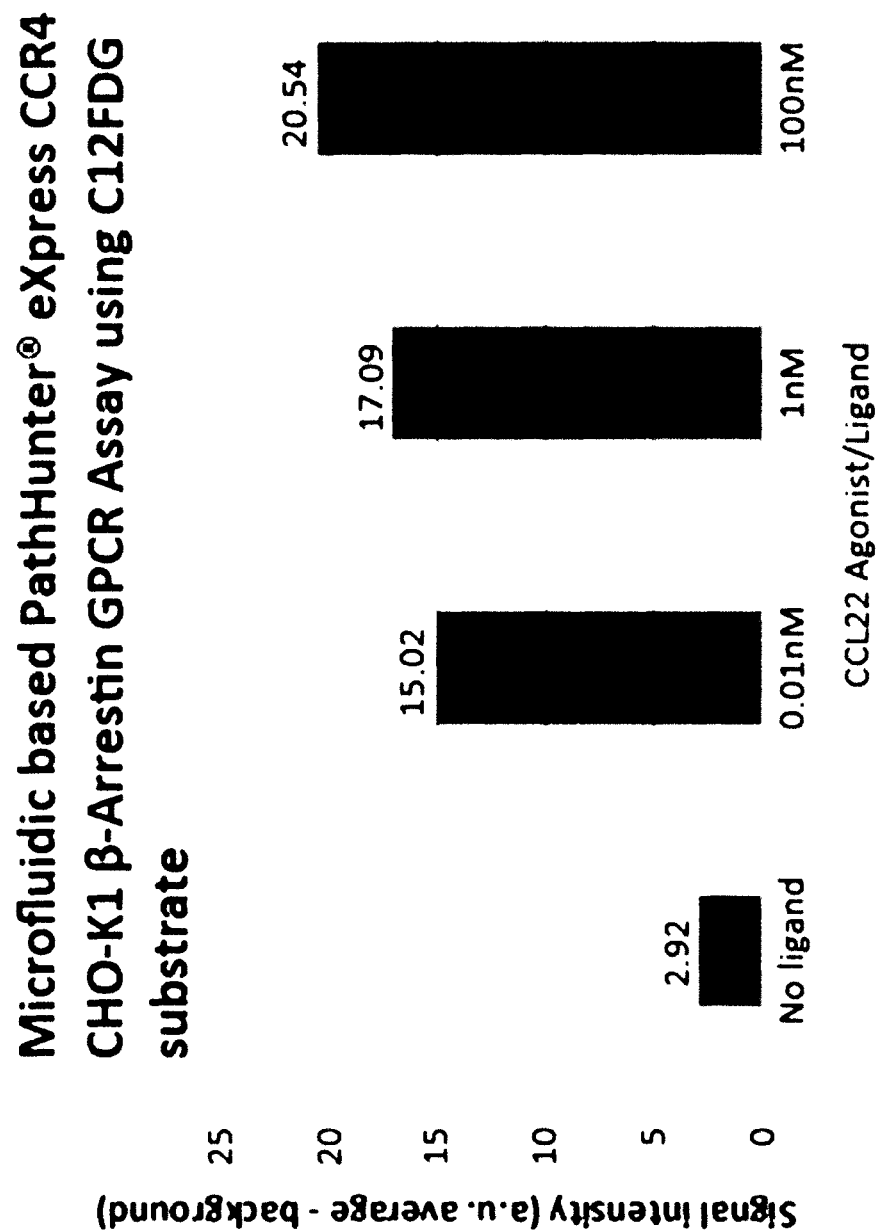

FIG. 112B is a graph representing the fluorescent intensity measurements of PathHunter® eXpress CCR4 CHO-K1 β-Arrestin GPCR reporter cells incubated with the substrate $C_{12}GDF$ and different concentrations of the agonist CCL12, as shown in FIG. 112A.

DETAILED DESCRIPTION OF THE INVENTION

As used herein, the singular forms "a", "an" and "the" include plural referents unless the context clearly dictates otherwise. Thus, for example, reference to "a thing" includes more than one such thing. Citation of references herein is not an admission that such references are prior art to the present invention.

"Readout," as used herein, refers to the method by which an extracellular effect is reported. A "readout particle population" can comprise one or more readout particles, as described herein.

"Extracellular effect," as used herein, is a direct or indirect effect on a readout particle that is extracellular of an effector cell, including but not limited to increased cellular proliferation, decreased growth, apoptosis, lysis, differentiation, infection, binding (e.g., binding to a cell surface receptor or an epitope), morphology change, induction or inhibition of a signaling cascade, enzyme inhibition, viral inhibition, cytokine inhibition, activation of complement. As provided herein, the extracellular effect in one embodiment is the binding of a biomolecule of interest, secreted by an effector cell, to a readout particle. In another embodiment, the extracellular effect is a response such as apoptosis of a readout cell or accessory cell.

The methods provided herein are used to identify an effector cell or cell population comprising an effector cell(s) that displays a variation in an extracellular effect. The variation in the extracellular effect is a variation compared to a control (negative or positive control), or a variation compared to one or more of other cell populations.

A "heterogeneous population" as referred to herein, particularly with respect to a heterogeneous population of particles or cells, means a population of particles or cells that includes at least two particles or cells that have a differing feature. For example, the feature in one embodiment is morphology, size, type of fluorescent reporter, a different cell species, phenotype, genotype, cell differentiation type, the sequence of one or more expressed RNA species or a functional property.

A "subpopulation," as referred to herein, means a fraction of a greater population of particles (cells). A population of cells in one embodiment is divided into subpopulations, for example, by isolating individual subpopulations in individual microfluidic chambers. Additionally, an individual subpopulation can be partitioned into further subpopulations, for example, in a plurality of microfluidic chambers or other reaction vessels. A subpopulation may also be a fraction of particles within a greater population, located in the same microfluidic chamber. A subpopulation contains one or more particles, and where a plurality of particles are present in a subpopulation, the individual particles within the plurality can be homogeneous or heterogeneous with respect to one another.

A "cell retainer" in one embodiment, defines at least one effector zone and at least one readout zone either continuously or intermittently. The retainer may be a structural element such as a valve, a cell fence, the orientation in an external field or field gradient (e.g., gravitational, magnetic, electromagnetic, acceleration, etc.), the orientation and/or localization of a locally generated field by an electrode or optical component or magnetic probe, surface modifications (for example texturing, coatings, etc.) that facilitate or inhibit cell adhesion, or by the specific gravity of a solution within the chamber, or may be achieved by a combination of one or more of the preceding.

"Coating" as used herein may be any addition to the chamber surface, which either facilitates or inhibits the ability of an effector cell or a readout particle to adhere to a surface of the chamber. The coating may be selected from one or more of the following: a cell; a polymer brush; a polymer hydrogel; self assembled monolayers (SAM), photo-grafted molecules, a protein or protein fragment having cell binding properties (for example, a cell binding domain from actin, fibronectin, integrin, protein A, protein G, etc.). More generally Arginine-glycine-aspartate-(serine) (RGD(S)) peptide sequence motif are used. Poly-L-Lysine is also widely used as a polymer coating with PDMS to enhance cell adhesion via electrostatic interactions; a phospholipid having cell binding properties, a cholesterol having cell binding properties, a glycoprotein having cell binding properties and a glycolipid having cell binding properties. In addition PDMS surface functionalization using biotinylated biomolecules is a simple, highly attractive and yet flexible approach. It is widely known that bovine serum albumin (BSA) due to hydrophobic domains readily adsorbs via hydrophobic effect on hydrophobic PDMS surfaces enabling further direct coupling of streptavidin based conjugates in the chambers (protein, DNA, polymers, fluorophores). Polyethylene glycol based polymers are also known for their bio-fouling properties and can be coated on PDMS surface (adsorption, covalent grafting), preventing cell adhesion. Poly(paraxyxlylene), e.g., parylene C can also be deposited using chemical vapor deposition (CDV) on PDMS surfaces and prevent cellular adhesion.

"Isolated," as used herein, refers the circumstances under which a given chamber does not permit substantial contamination of an effector cell and/or readout particle being analyzed with a particle(s) or biomolecule(s) of another chamber of the microfluidic device. Such isolation may be achieved, for example, by sealing a chamber or a set of chambers in the case of compound chambers, by limiting fluid communication between chambers or by restricting fluid flow between chambers.

An "inlet" or an "outlet," as used herein, includes any aperture whereby fluid flows into and out of a chamber. Fluid flow may be restricted through the inlet or outlet or both to isolate a chamber from its surrounding environment. There may be one or more valves to control flow, or flow may be controlled by restricting the fluid channels, which lead to the inlets and outlets with a layer which prevents flow (for example, a control layer or isolation layer). Alternatively, flow may be regulated by the rate at which fluids are passed through the device. The inlet or outlet may also provide fluid flow to the device for the delivery of an effector cell or readout particle, or other components carried in the flow as needed during analysis. In some embodiments, the inlet and outlet may be provided by a single aperture at the top of the chamber over which fluid flows from an inlet side to an outlet side.

A "magnet," as used herein, includes any ferromagnetic or paramagnetic material. "Ferromagnetic" as used herein is meant to include materials which may be comprised of iron, nickel, chromium, or cobalt or combinations thereof and various alloys, such that the magnetic material is attracted to a magnet or is a magnet itself. For example, a magnetic material may be made from ferromagnetic stainless steel or may be made from a rare earth magnet or a stainless steel having magnetic properties. A magnet may also be made by use of a ferrofluid in a defined shape or orientation. A magnet may also be implemented using a coil or other electrically actuated device designed to generate a magnetic field when energized with electrical current.

Figure 33:
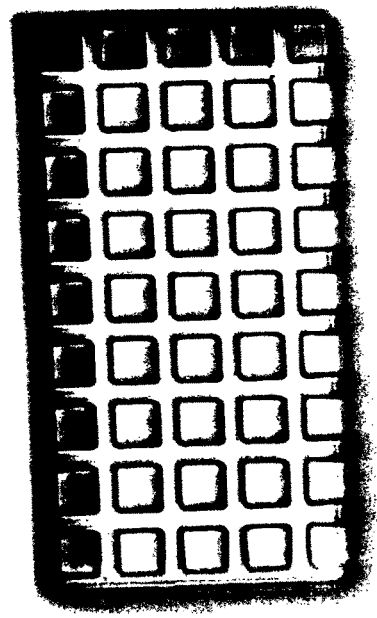
FIG. 33 is a top view of a chamber embodiment with a series of intersecting cell fences forming an array of wells, defining multiple effector and readout zones, on the lower surface of the chamber (overall chamber dimensions are 300 µm×160 µm).

An "array of wells," as used herein, refers to any array of structures within a chamber that may limit the movement of an effector cell and/or a readout particle by localizing one or the other to a particular readout zone or effector zone, whereby a zone (i.e., either effector or readout) may be defined by what type of particle resides within it. For example, one embodiment of an array of wells is shown in FIG. 33, where a series of intersecting cell fences form an array of wells on a surface of the chamber.

A "particle trap," as used herein, refers to a structure that is capable of spatially confining an effector cell or a readout particle(s) (bead(s)) to a specific spatial position to limit movement during an assay. A "cell fence" is one type of "particle trap." In one embodiment, a particle trap is used to confine effector cells, in which case it may be referred to as an "effector cell trap." In some embodiments, a particle trap will be used to confine readout particles, in which case it may be referred to as a "readout particle trap", or a "readout cell trap", as the case may be. A "particle trap," in one embodiment, allows for the particle being trapped to have a fixed position. Having a fixed position may simplify imaging and image analysis. Having a fixed position for a readout particle or particles may also have the advantage of limiting or controlling the diffusion distance between an effector cell and a readout particle. Having a fixed position may also prevent interaction of effector cells and readout particles.

A "textured surface," as used herein, may be any type of surface modification that would promote or reduce cell adhesion to the chamber surface. For example, the surface may be textured with one or more of: bumps, indentations, roughness, protrusions, hooks, pegs, wells, grooves, ridges, grain, weave, web, hydrophobicity, hydrophillicity, etc.

Figure 60:
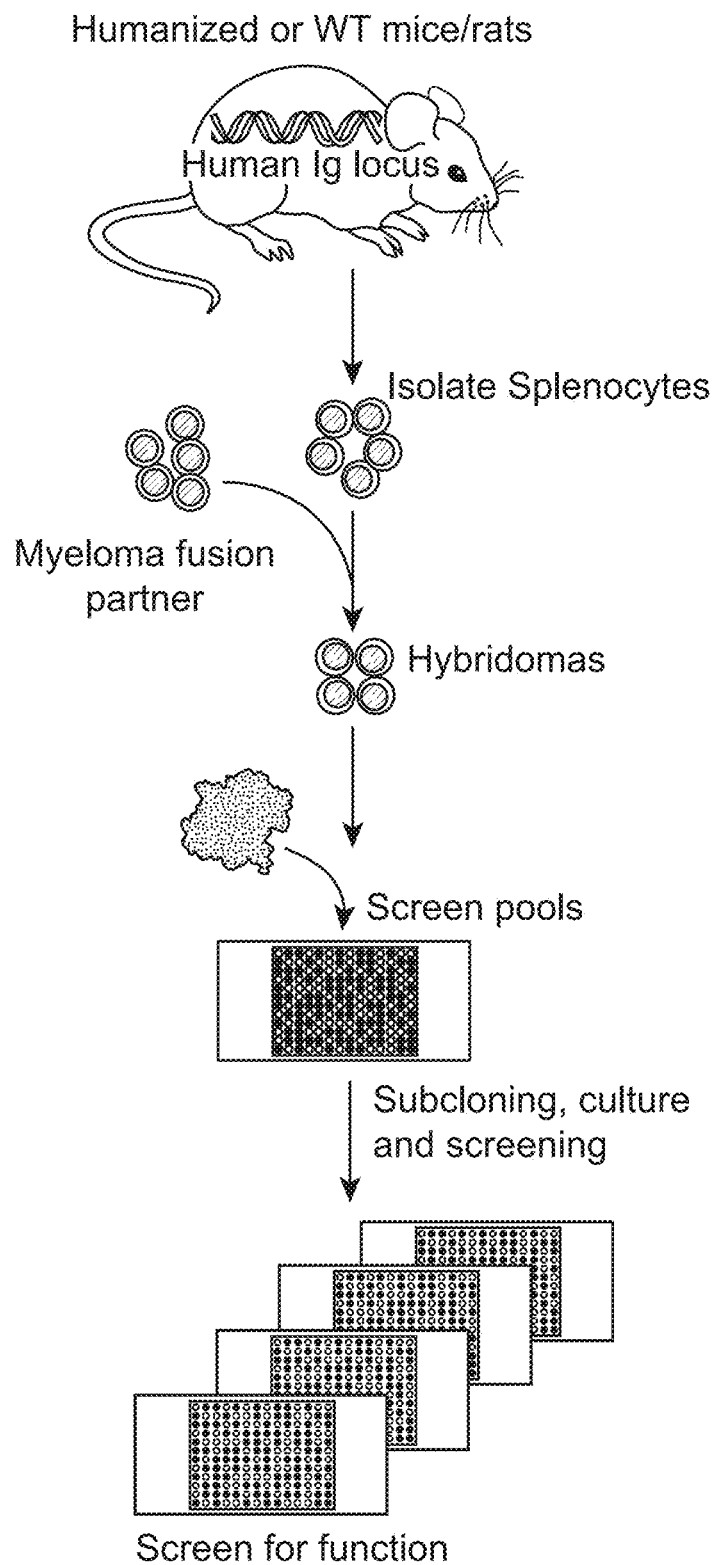
FIG. 60 is a schematic of the traditional hybridoma approach. Splenocytes from immunized mice are fused with myeloma cells. At a low efficiency, these fusions create viable "hybridomas" that can secrete mAbs and can be grown in culture. Pools of hybridomas are grown and assayed to detect presence of antigen-specific cells, which are then subcloned and expanded to generate sufficient mAbs for functional screening. This approach requires a suitable fusion partner and is largely restricted to use with mice or rats, although a proprietary hybridoma technology has also been developed for rabbits. Typical fusions result in less than 100 stable hybridomas and require ~9 weeks for culture and subcloning.

The human body makes millions to billions of different types of antibodies at any given time, each produced by a different single plasma cell called an "antibody secreting cell" or "ASC." Each ASC has a diameter of from about 7 µm about 15 µm, depending on source, a diameter approximately $1/10^{th}$ the width of a human hair, and generates only a minute amount of antibody. Of the billions of different ASCs in the human body, only a very rare few make an antibody that is suitable to be used as a therapeutic. When analyzed in the volume of conventional formats this small amount of antibody is too dilute, making it completely undetectable. For this reason antibody discovery currently requires that each ASC be isolated, fused to an immortal cancer cell to create a hybridoma and "grown," ultimately generating many thousands of identical cells that can produce enough antibody to be measured (See FIG. 60). For example, see McCullough and Spier (1990). Monoclonal Antibodies in Biotechnology: Theoretical and Practical Aspects, Chapter 2, Cambridge University Press, incorporated by reference herein in its entirety). This process is not only incredibly inefficient (99.9% of the starting immune cells are lost) but also very slow and expensive, requiring at minimum 3 months of labor before therapeutic function can be tested. As a result, the discovery of antibodies with optimal therapeutic properties is a major and unresolved bottleneck in drug development.

ASCs are terminally differentiated cells that cannot be directly expanded in culture. Existing methods for overcoming this issue as set forth above (e.g., the hybridoma method, see FIG. 60) are very inefficient, capturing only a tiny fraction of the antibody diversity (typically <0.1%). These approaches are also restricted to use with rodents and are very slow and expensive, requiring months of labor before therapeutic function can be tested. As explained below, the present invention overcomes these limitations by allowing for direct functional assays on antibodies and ASCs, regardless of source.

A variety of technologies have been advanced to increase the speed and throughput of antibody screening, but these technologies do so at the expense of information. Specifically, existing technologies are restricted to the selection of antibodies based on binding, affinity and specificity. While sufficient for research applications, many therapeutic applications require high affinity antibodies that do more than just bind to the target. Rather, therapeutic applications require antibodies that induce the desired biological response (e.g., agonists/antagonists of cell signaling; activation of immune responses; induction of apoptosis; inhibition of cellular growth or differentiation). Presently, all high-throughput antibody discovery technologies require that this functional characterization be performed downstream, after binding of a target is assessed, using methods that are cumbersome, costly, and low-throughput, even as compared to the hybridoma approach. For this reason the hybridoma method, developed over 40 years ago, is still a mainstay in therapeutic antibody discovery.

The present invention in one aspect, harnesses the small reaction volumes and massively parallel assay capabilities of a microfluidic platform in order to screen cell populations for a property of interest, referred to herein as an "extracellular effect." Each cell population optionally comprises one or more effector cells. The extracellular effect is not limited to a particular effect; rather, it may be a binding property (specificity, affinity) or a functional property, for example agonism or antagonism of a cell surface receptor. In one embodiment, the extracellular effect is an effect exerted by a secretion product of a particular effector cell.

Figure 1:
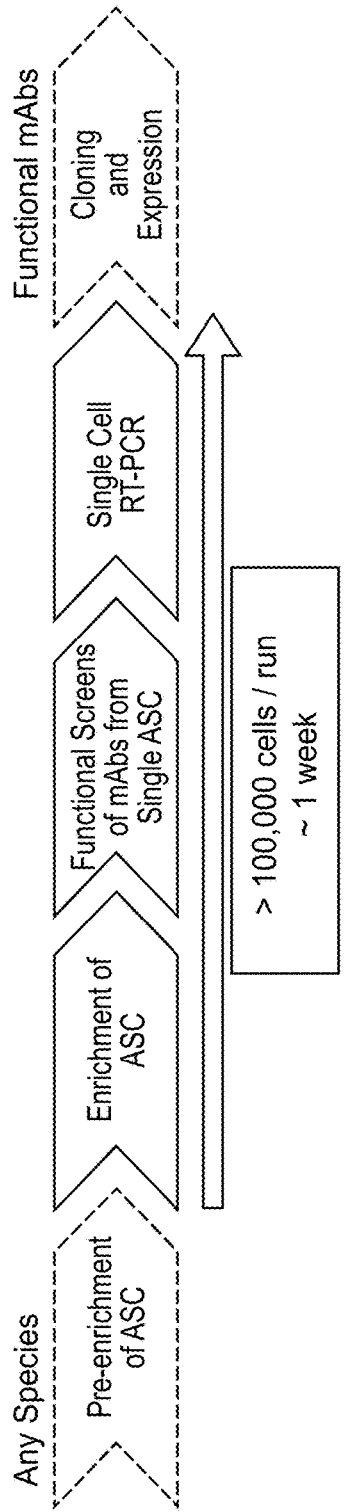
FIG. 1 a process flow diagram for one embodiment of a microfluidic approach for single effector cell identification and selection based on a microfluidic multicellular assay. Single cells are obtained from any animal and are optionally enriched for an effector cell population. High-throughput microfluidic analysis is used to perform functional screens on antibodies secreted from single effector cells, in some cases, present in heterogeneous cell populations. After one or multiple rounds of microfluidic analysis, cells are recovered and antibody variable region genes are amplified for sequencing (Vh/Vl) and cloning into cell lines. This process allows for the screening of over 100,000 cells in a single day, with sequences recovered on week later.

The integrated microfluidic devices and methods provided herein are based in part on the concept that small is sensitive—each device comprises many thousands of nanoliter volume cell analysis chambers, each approximately 100,000 times smaller than conventional plate-based assays. In these small nanoliter chambers, each single effector cell produces high concentrations of secreted biomolecule within minutes. For example, each sing ASC produces high concentrations of antibodies within minutes. This concentration effect, in one embodiment, is harnessed to implement cell-based screening assays that identify antibodies, made by single primary ASCs, with a specific functional property (ies), such as the modulation (e.g., agonism or antagonism) of cell surface receptor activity. Functional assays amenable for use with the methods and devices provided herein are described in detail below. Importantly, the in the screening methods provided herein, it is not necessary that a specific effector cell or subpopulation of effector cells, having the particular property be identified so long as the presence of the extracellular effect is detected within a particular microfluidic chamber comprising a cell population. Some or all of the cells within the chamber where the effect is measured can be recovered for further characterization to identify the specific cell or cells responsible for the extracellular effect. By completely eliminating the need for cell culture prior to screening, the single-cell approach provided herein enables, for the first time, the direct selection of functional antibodies from any species, in only days, and at a throughput of greater than 100,000 cells per run (FIG. 1).

The microfluidic devices and methods provided herein provide advantages over currently available strategies for assessing an extracellular effect of a single cell, for example, an extracellular effect of an antibody secreted by a single ASC. For example, the devices described herein are scalable, enable reduced reagent consumption and increased throughput to provide a large single cell assay platform for studies that would otherwise be impractical or prohibitively expensive. Moreover, currently available single cell assay platforms analyses require multiple cell handling and processing steps in conventional tubes in order to generate products needed for downstream analysis, for example qPCR. The inclusion of microfluidic cell handling and processing as described herein thus offers important avenues to improved throughput and cost, while also improving precision and sensitivity through small-volume confinement.

Without wishing to be bound by theory, the concentration enhancement and rapid diffusive mixing afforded by the nanoliter microfluidic chambers provided herein, along with precise cellular handling and manipulation (e.g., spatiotemporal control of medium conditions) enables the single cell analysis of effector cells such as immune cells (e.g., B cells, T cells, and macrophages) whose primary functions include the secretion of different effector proteins such as antibodies and cytokines.

Embodiments described herein provide microfluidic systems and methods capable of performing multicellular assays of secreted products from cell populations comprising one or more effector cells, followed by recovery of the cell populations for subsequent analysis. In some embodiments, the cell populations are heterogeneous cell populations. That is, two or more cells in a population differ in genotype, phenotype or some other property. Moreover, where cell populations are assayed in parallel on one device, at least two of the populations are heterogeneous with respect to one another (e.g., different number of cells, cell type, etc.). In the assays described herein, a readout particle population comprising one or more readout particles, which serve as detection reagents (e.g., readout cells expressing a cell receptor, readout bead, sensor, soluble enzyme, etc.) are exposed to a cell population comprising one or more effector cells, and secreted products from the one or more effector cells, at a sufficient concentration for a readout signal (e.g., a fluorescent signal) to be detected. In some embodiments, the readout signal reports a biological response/functional effect (e.g., apoptosis) induced by one or more the effector cells in the population on one or more readout particles (e.g., readout cells). For example, for an antibody produced from a given ASC, the ASC or a cell population comprising one or more ASCs, along with readout particle(s) and optionally accessory detection reagents are sequestered in a small volume so on a device, and the assay is carried out (chambers having a volume of about 100 pL to about 50 nL, e.g. about 1 nL to about 5 nL). Importantly, because effector cells in one embodiment are rare cells, not all cell populations assayed by the methods described herein will initially contain an effector cell. For example, where thousands of cell populations are assayed on a single device, in one embodiment, only a fraction of the chambers will comprise an effector cell. The methods provided herein allow for the identification of the chambers with the effector cell.

The present invention takes a different approach than previously described microfluidic methods. The latter take the approach of loading single cells at a density to maximize the number of single cells in individual chambers (for example, where droplets or microwells are used). This is accomplished by isolating single cells by limiting dilution followed by analysis of the fraction of chambers or volumes that contain a single cell. Such a strategy sacrifices throughput because the optimal single cell loading is achieved at approximately 1 cell per well average density. Similarly, the geometries described for these methods usually do not allow for more than a few cells in a chamber and in many cases are designed to physically accommodate only a single cell. Besides a decreased throughput, a number of technical challenges result from the approach of isolating and assaying a single cell in a single microfluidic chamber. For example, achieving sufficient cell concentrations to achieve a meaningful readout from heterogeneous populations, keeping individual cells alive due to nutrient depletion, the need for aeration, unwanted vapor permeation effects, poorly controlled medium conditions, and the need for waste removal, can pose serious problems for achieving a reliable reproducible single cell microfluidic assay. In many functional assays, like cell growth inhibition, it is necessary to keep both the effector cells and the readout cells alive for several days. Such an assay is not feasible in microwell based systems and droplets. However, as discussed herein, the present invention provides a robust platform for assays spanning days.

The devices and assays described herein provide single cell assays whereby one or more effector cells are present in individual cell populations, in single microfluidic chambers. The cell populations are assayed for their respective ability to exert an extracellular effect in each chamber, thereby providing a higher total throughput than previously described methods. Importantly, effects of a single effector cell can be detected within a larger cell population, for example a heterogeneous cell population. By taking the multicellular assay approach within a single microfluidic chamber, the embodiments described herein can operate at greater than or equal to 100 times the throughput reported previously. Once a cell population is identified that an extracellular effect on a readout particle, or a variation in an extracellular effect as compared to another population, the cell population, in one embodiment, is recovered and further assayed as individual cell subpopulations (e.g., the recovered cell population is assayed at limiting dilution) to determine which effector cell(s) within the population is responsible for the extracellular effect.

Methods and apparatuses known in the art which are designed to accommodate more than a single cell have limitations that make them unsuitable for the types of assays described herein, for example, maintaining cells in a viable state, the inability to selectively recover effector cells of interest, evaporation within a device, pressure variability, cross-contamination, device architecture that limits imaging capabilities (e.g., by providing particles in different focal planes, reduced resolution) and lack of throughput (WO 2012/072822 and Bocchi et al. (2012), each incorporated by reference in their entireties).

Embodiments described herein relate in part to functional effector cell assays (also referred to herein as extracellular effect assays) that allow for the detection of a single effector cell of interest present in an individual microfluidic chamber in a heterogeneous cell population. Specifically, in the case where a chamber contains a heterogeneous cell population, where each cell of the population secretes antibodies (i.e., a heterogeneous ASC population within a single microfluidic chamber), or only a fraction of the cells in the population secrete antibodies, whereby only one effector cell or a subpopulation of effector cells secretes an antibody that produces a desired extracellular effect on a readout particle(s), the embodiments described herein provide a method for measuring and detecting the desired extracellular effect. Once a chamber is identified that comprises a cell population exhibiting the effect, the population is recovered for downstream analysis, for example, by splitting the cell population into subpopulations at limiting dilution. As described below, in one embodiment, one or more heterogeneous populations of cells displaying an extracellular effect, are recovered and subjected to further screening at limiting dilution (e.g., from 1 to about 25 cells per assay), to determine which cell the extracellular effect is attributable to.

In one embodiment, a microfluidic assay is carried out on a plurality of cell populations, present in individual microfluidic chambers, to determine whether an effector cell within one of the populations secretes an antibody or other biomolecule that inhibits the growth of a readout cell. In this embodiment, even in the presence a heterogeneous cell population comprising a plurality of ASCs that secrete antibodies which do not affect the growth of the readout cell, the readout cell growth is still equally inhibited and the microfluidic chamber is identifiable as containing the desired effector cell and secretion product. The chamber's contents can then be recovered for further microfluidic analysis, or benchtop analysis, for example, at limiting dilution of the effector cells to determine which effector cell displays the effect. Antibody sequences can also be recovered by methods known to those of skill in the art.

Figure 2:
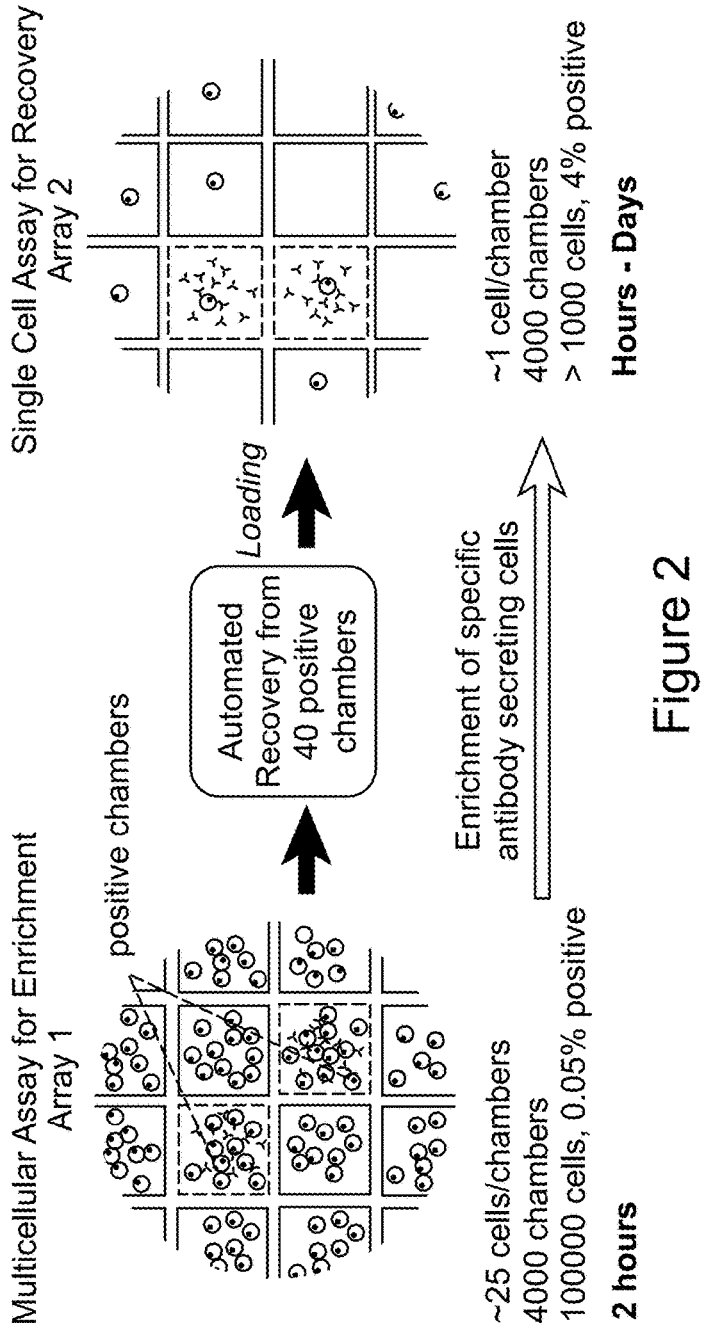
FIG. 2 is a process flow diagram for one embodiment of a microfluidic effector cell enrichment method. Effector cells are first loaded at an average concentration of 25 cells per chamber and incubated to create polyclonal mixtures of antibodies. Screening of polyclonal mixtures is used to identify chambers having a variation in an extracellular effect (e.g., binding, affinity, or functional activity). Forty positive chambers are then recovered to achieve an enriched population with ~4% of effector cells making antibodies of interest. The effector cells of the enriched population are then analyzed in a second array at limiting dilution to select a single ASC(s) having the variation in the extracellular effect. The time required for enrichment is about 4 hours and total screening throughput is 100,000 cells per run. Enrichment process may be performed twice if needed, and may use the same or different properties for each screen.

In one embodiment, novel antibodies are provided by the methods described herein. For example, one or more ASCs can be identified by the methods described herein, recovered, and their antibody genes sequenced and cloned.

Where single cells are loaded into individual chambers at a density of approximately 1 cell per chamber, the devices provided herein allow for the screening of approximately 1000 single cells (e.g., ASCs) per experiment. One or more of the single cells can be ASCs or a different type of effector cell. Although approximately 10-fold higher than hybridoma methods, it is desirable in many instances to screen tens of thousands, or even hundreds of thousands of cells. Examples of this include when ASCs cannot be obtained at high purity (e.g., for species for which ASC markers/antibodies are not available or cases of poor immune response), or when antibodies that bind are frequent but those with desired properties are exceedingly rare (such as blocking of a receptor). However, after identifying a cell population(s) that contain one or more effector cells displaying the extracellular effect of interest, the cell population(s), in one embodiment, are analyzed again, but at limiting dilution, e.g., as single cells in individual microfluidic chambers, or smaller populations in individual chambers (as compared to the first screen), in order to determine the identity of the individual effector cell(s) responsible for the extracellular effect. One embodiment of this two step screening method is shown in FIG. 2. Once the effector cell(s) is identified, its genetic information can be amplified and sequenced. In one embodiment, the genetic information comprises a novel antibody gene.

In the embodiment shown in FIG. 2, a microfluidic array is loaded at a density of approximately 25 cells per chamber, resulting in a total of approximately 100,000 cells in a single device. The chambers are then isolated and incubated, generating unique polyclonal mixtures of antibodies in each chamber. These antibodies are then screened to identify chambers that exhibit the desired extracellular effect, e.g., antigen binding, high binding affinity, antigen specificity or one or more functional properties. The contents of each positive chamber are then recovered. In one embodiment, recovery of each population is with a single microcapillary and the chamber contents are pooled in the microcapillary, and reloaded at limiting dilution onto the same device, or a different microfluidic device. In the embodiment shown in FIG. 2, the cells from array one are reloaded in different chambers at a density of approximately 1 cell per chamber. The cells from the recovered population(s) are then rescreened for the same extracellular effect, or for a different extracellular effect. The contents of the positive chambers from the second array are then recovered to identify antibody sequences of interest, e.g., by next generation sequencing and/or PCR. The antibody sequences, in one embodiment, are sequenced and cloned and therefore, in one embodiment, the methods provided herein allow for the discovery of novel antibody genes.

In another embodiment, cell populations displaying the extracellular effect are recovered using an integrated system microfluidic valves that allow chambers to be individually addressed (e.g., Singhal et al. (2010). *Anal. Chem.* 82, pp. 8671-8679, incorporated by reference herein in its entirety). Notably, the present invention is not limited to the type of extracellular effect assay carried out on the contents of the positive chambers of "array 1" (FIG. 2). For example, in some embodiments, it is desirable to further assay the contents of the positive chambers from "Array 1" via a benchtop method, rather than a second microfluidic array. Benchtop methods include, for example, RT-PCR and next generation sequencing.

With respect to the single cell and multicellular microfluidic assays described herein, reference is made herein to a "chamber" in which a cell population optionally comprising one or more effector cells is assayed for an extracellular effect, for example, a functional effect or a binding effect. However, one of ordinary skill in the art will recognize that the devices provided herein provide a massively parallel system that incorporates tens of thousands of chambers, and that assays are carried out in parallel in all or substantially all of the chambers, or all of the chambers in a subarray on one device, on a plurality of individual cell populations each optionally comprising an effector cell or a plurality of effector cells. Because of the rarity of some effector cells, not all cell populations will comprise an effector cell when present in a microfluidic chamber. Fluidic architectures to address multiple chambers individually or together, such as multiplexers, are described below.

Some of the embodiments described herein provide one or more of the following features:

The ability to load and concentrate a cell population comprising one or more effector cells into a microfluidic chamber having a small volume to assay the effector cell products, and to co-localize into within the chamber a readout particle (readout bead, readout cell, etc.) used to detect the presence of an individual effector cell product (e.g., secreted protein) having a desired property.

The ability to maintain the viability and/or growth of a cell population, assisted by the osmotic bath described herein as well as the ability to exchange medium around individual cells, at concentrations that have been reported previously to result in poor cell survival or growth using conventional culture methods or previously described microfluidic devices.

The ability to concentrate effector cell products within a chamber in a time sufficient to measure a desired effector cell product property prior to the effector cell becoming unhealthy or outgrowing its respective microfluidic chamber.

The ability to selectively exchange medium contents or add detection reagents to clusters of cells while maintaining populations of cells in the microfluidic chambers.

The ability to addressably recover a selected cell population using one or more microfluidic structures, a manual method or a robotic method.

The ability to transfer recovered populations of cells into a secondary lower-throughput screen that enables the analysis of an effector cell product from each single cell in the heterogeneous population, or a clone or plurality of clones generated from each single cell in the heterogeneous population.

The ability to directly analyze the aggregate genetic material from recovered heterogeneous populations of single cells and then use this information or genetic material to identify the genes associated with the cells of interest.

In some embodiments, a method of enriching for effector cells exhibiting an extracellular effect from a starting population of cells that includes one or more effector cells that exhibit the extracellular effect is provided. In one embodiment, the method includes retaining the starting population of cells in a plurality of microfluidic chambers to obtain a plurality of cell subpopulations. An average number of effector cells per chamber is greater than Y, the total number of cells in the population is greater than X and an expected fraction of effector cells in the population is 1/X. The cell subpopulations in the microfluidic chambers are subjected to an extracellular effect assay to identify one or more chambers containing one or more effector cells exhibiting the extracellular effect. Based on the results of the extracellular effect assay, one or more chambers are then identified as comprising one or more effector cells exhibiting the extracellular effect. The contents of the identified chamber(s) are then recovered to provide an enriched population of cells. The enriched population of cells enriched for the effector cells has a fraction of effector cells of 1/Y. In a further embodiment, 1/X is less than 0.05, or less than 0.01, or less than 0.001. The extracellular effect can be one or more of the extracellular effects described herein. In one embodiment, the starting population of cells are peripheral blood mononuclear cells (PBMCs) isolated from an animal that has been immunized or exposed to an antigen. In another embodiment, the starting population of cells is a population of B-cells isolated from an animal that has been immunized or exposed to an antigen. In yet another embodiment, the source of the starting population of cells is whole blood from the animal that has been immunized or exposed to an antigen.

As provided herein, in one aspect, the devices and methods of the invention are used to assay a cell population optionally comprising one or more effector cells for the presence of an extracellular effect. In another aspect, the devices and methods provided herein allow for identification of a cell population displaying a variation in an extracellular effect compared to other cell populations. In this aspect, a plurality of individual cell populations are retained in separate microfluidic chambers, wherein at least one of the individual cell populations comprises one or more effector cells and the separate microfluidic chambers further comprise a readout particle population comprising one or more readout particles. The cell populations are assayed for the presence of the extracellular effect, whereby the readout particle population or subpopulation thereof provides a readout of the extracellular effect. A cell population from amongst the plurality can then be identified that exhibits a variation in the extracellular effect, as compared to one or more of the remaining cell populations of the plurality. Once a cell population is identified that displays the variation in the extracellular effect, the population is recovered and may be further assayed at limiting dilution to identify the cell or cells within the population responsible for the extracellular effect.

Cell populations that can be analyzed herein are not limited to a specific type. For example, in one embodiment a starting population of cells partitioned into individual cell populations in microreactors may be peripheral blood mononuclear cells (PBMCs) isolated from an animal that has been immunized or exposed to an antigen. The starting population of cells in another embodiment are B-cells isolated from an animal that has been immunized or exposed to an antigen. The source of the starting population of cells may be whole blood from the animal that has been immunized or exposed to an antigen.

An "effector cell," as used herein, refers to a cell that has the ability to exert an extracellular effect. The extracellular effect is a direct or indirect effect on a readout particle, as described in detail below. The extracellular effect is attributable to the effector cell, or a molecule secreted by the effector cell, for example a signaling molecule, metabolite, an antibody, neurotransmitter, hormone, enzyme, cytokine, In one embodiment, the effector cell is a cell that secretes or displays a protein (e.g., T cell receptor). In embodiments described herein, the extracellular effect is characterized via the use of a readout particle, e.g., a readout cell or a readout bead, or a readout particle population or subpopulation. For example, in one embodiment described herein, the extracellular effect is the agonizing or antagonizing of a cell surface receptor, ion channel or ATP binding cassette (ABC) transporter, present on a readout cell or readout bead. In one embodiment, the effector cell is an antibody secreting cell (ASC). An ASC, as used herein, refers to any cell type that produces and secretes an antibody. Plasma cells (also referred to as "plasma B cells," "plasmocytes" and "effector B cells") are terminally differentiated, and are one type of ASC. Other ASCs that qualify as "effector cells" for the purposes of the present invention include plasmablasts, cells generated through the expansion of memory B cells, cell lines that express recombinant monoclonal antibodies, hybridoma cell lines. In another embodiment, the effector cell is a cell that secretes a protein. Other cell types that qualify as effector cells include T cells (e.g., CD8+ T cell, and CD4+ T cell), hematopoietic cells, cell lines derived from humans and animals, recombinant cell lines, e.g., a recombinant cell line engineered to produce antibodies, a recombinant cell line engineered to express a T cell receptor.

Individual cell populations optionally comprising one or more effector cells are assayed to determine whether the respective cell populations comprise an effector cell that exhibits an extracellular effect, or a variation in an extracellular effect as compared to another individual cell population or a plurality thereof. As stated above, when cell populations are assayed in parallel on one device, not all cell populations will comprise an effector cell, and the methods described herein allow for the identification of a cell population that contains one or more effector cells. Additionally, a cell population comprising an effector cell need not include multiple effector cells, or be a population of only effector cells. Rather, non-effector cells, in embodiments described herein, are included in the population. The non-effector cells can be a majority or minority of the population. A heterogeneous population comprising an effector cell need not include multiple effector cells. Rather, a heterogeneous cell population is heterogeneous as long as two cells are heterogeneous with respect to one another. A cell population can comprise zero effector cells, one effector cell or a plurality of effector cells. Similarly, a cell subpopulation can comprise zero effector cells, one effector cell or a plurality of effector cells.

The extracellular effect in one embodiment is the binding interaction with an antigen, or a functional effect. For example, in one embodiment, the extracellular effect is agonism or antagonism of a cell surface receptor, agonism or antagonism of an ion channel or agonism or antagonism of an ABC transporter, modulation of apoptosis, modulation of cell proliferation, a change in a morphological appearance of a readout particle, a change in localization of a protein within a readout particle, expression of a protein by a readout particle, neutralization of the biological activity of an accessory particle, cell lysis of a readout cell induced by an effector cell, cell apoptosis of a readout cell induced by the effector cell, cell necrosis of the readout cell, internalization of an antibody by a readout cell, internalization of an accessory particle by a readout cell, enzyme neutralization by the effector cell, neutralization of a soluble signaling molecule, or a combination thereof.

The presence and identification of an effector cell that secretes a biomolecule (e.g., antibody) that binds a target of interest (e.g., antigen) is readily ascertained in embodiments where the effector cell is present in a heterogeneous cell population comprising a plurality of effector cells that secrete antibodies that are not specific to the target of interest. In one embodiment, this is achieved in an individual microfluidic chamber by first capturing in the chamber, all or substantially all of the secreted antibodies of the population on a readout particle(s) (e.g., bead) functionalized to capture antibodies (for example, functionalized with protein G or protein A), addition of fluorescently labeled antigen into the chamber and imaging of the particle(s) to detect the presence or absence of an increase in fluorescence due to binding of the antigen to immobilized antibody(ies). An estimate of minimum number of antibodies captured on a bead that is required for reliable detection may be obtained by performing experiments to measure antibody secretion from single cells. In one embodiment, it is possible to detect antigen-specific antibodies secreted from a single ASC in a heterogeneous population of approximately 500 cells. In the case of the present invention, a cell population present in an individual microfluidic chamber can comprise from about two to about 500 cells, for example, about two to about 250 ASCs. As stated above, a cell population can contain cells other than effector cells and not all cell populations will contain an effector cell. This is particularly true when conventional enrichment protocols (e.g., FACS) are not able to be used to obtain a substantially pure cell population of the same cell type.

With respect to a heterogeneous cell population, all of the cells not be heterogeneous with respect to each other, provided that there are at least two cells in the population that are heterogeneous with respect to each other, for example, an effector cell and a non-effector cell. A heterogeneous cell population may consist of as few as two cells. A cell population or cell subpopulation may consist of a single cell. In principle, a heterogeneous cell population may include any number of cells that can be maintained in a viable state for the required duration of the extracellular effect assay, e.g., one of the extracellular effect assays provided herein. In one embodiment, the number of cells in a cell population is from 1 cell to about 500 cells per chamber. In one embodiment, where the imaging of individual cells or readout particles is required, the number of cells in a population is chosen to be insufficient to cover the floor of the chamber, so that the cells being imaged are arranged in a monolayer. Alternatively, the cell population includes a number of cells that is insufficient to form a bilayer covering a surface of the chamber.

In some embodiments, larger populations of cells can be present in a population within a single microfluidic chamber or microreactor, without inhibiting the detection of an effect that stems from a single effector cell or a small number of effector cells within the particular population. For example, in one embodiment, the number of cells in a cell population is from two to about 900, or from about 10 to about 900, or from about 100 to about 900. In another embodiment, the number of cells in a cell population is from two to about 800, or from about 10 to about 800, or from about 100 to about 800. In another embodiment, the number of cells in a cell population is from two to about 700, or from about 10 to about 700, or from about 100 to about 700. In another embodiment, the number of cells in a cell population is from two to about 600, or from about 10 to about 600, or from about 100 to about 600. In another embodiment, the number of cells in a cell population is from two to about 500, or from about 10 to about 500, or from about 100 to about 500. In another embodiment, the number of cells in a cell population is from two to about 400, or from about 10 to about 400, or from about 100 to about 400. In another embodiment, the number of cells in a cell population is from two to about 300, or from about 10 to about 300, or from about 100 to about 300. In another embodiment, the number of cells in a cell population is from two to about 200, or from about 10 to about 200, or from about 100 to about 200. In another embodiment, the number of cells in a cell population is from two to about 100, or from about 10 to about 100, for from about 50 to about 100. In another embodiment, the number of cells in a cell population is from two to about 90, or from about 10 to about 90, or from about 50 to about 900. In yet another embodiment, the number of cells in a cell population is from two to about 80, or from 10 to about 80, or from two to about 70, or from about 10 to about 70, or from about two to about 60, or from about 10 to about 60, or from about two to about 50, or from about 10 to about 50, or from about two to about 40, or from about 10 to about 40, or from two to about 30, or from about 10 to about 20, or from two to about 10. In some embodiments, the majority of cells in a cell population are effector cells.

In one aspect of the invention, a cell or cell population analyzed by the methods provided herein comprises one or more effector cells, e.g., an antibody secreting cell (ASC) or a plurality of ASCs. Cells, in one embodiment, are separated into a plurality of cell populations in thousands of microfluidic chambers, and individual cell populations comprising one or more effector cells (i.e., within single microfluidic chambers) are assayed for an extracellular effect. One or more individual cell populations are identified and recovered if an effector cell within the one or more populations exhibits the extracellular effect or a variation in an extracellular effect. The extracellular effect is determined by the user and in one embodiment, is a binding interaction with an antigen, cell surface receptor, ABC transporter or an ion channel.

Although the methods provided herein can be used to identify a single effector cell (alone or within a heterogeneous population) based on a binding interaction, e.g., antigen affinity and specificity, the invention is not limited thereto. Rather, identification of a cell population, in one embodiment, is carried out via the implementation of a direct functional assay. Accordingly, one aspect of the invention includes methods and devices that enable the direct discovery of an ASC within a cell population that secretes a "functional antibody," without the need to initially screen the "functional antibody" for binding properties such as affinity and selectivity to an antigen target.

Along these lines, in one aspect, functional antibodies and receptors discoverable by the methods herein are provided. In one embodiment of this aspect, the nucleic acid of an effector cell responsible for an extracellular effect is amplified and sequenced. The nucleic acid is a gene encoding for a secreted biomolecule (e.g., antibody, or fragment thereof), or a gene encoding a cell receptor or fragment thereof, for example a T-cell receptor. The antibody or fragment thereof or cell receptor or fragment thereof can be cloned and/or sequenced by methods known in the art. For example, in one embodiment, an ASC that secretes a functional antibody discoverable by the methods and devices provided herein is one that modulates cell signaling by binding to a targeted cell surface protein, such as an ion-channel receptor, ABC transporter, a G-protein coupled receptor (GPCR), a receptor tyrosine kinase (RTK) or a receptor with intrinsic enzymatic activity such as intrinsic guanylate cyclase activity.

In one aspect of the invention, a cell population comprising one or a plurality of effector cells is identified in a microreactor, e.g., microfluidic chamber, based on the result of an extracellular effect assay carried out in the chamber. If an extracellular effect or variation in extracellular effect is measured in the microreactor, the cell population is recovered and analyzed to determine the effector cell or effector cells within the population responsible for the effect (see, e.g., FIG. 2). In embodiments where the effector cell secretes antibodies, the DNA sequence that encodes the antibody produced by the ASC or ASCs can then be determined and subsequently cloned. In one embodiment, the antibody DNA sequences are cloned and expressed in cell lines to provide an immortal source of monoclonal antibody for further validation and pre-clinical testing.

As described herein, a heterogeneous cell population typically includes populations of cells having numbers ranging from 2 to about 1000, or from 2 to about 500, or from about 2 to about 250, or from about 2 to about 100. A heterogeneous cell population describes a population of cells that contains at least two cells with a fundamental difference in genotype, protein expression, mRNA expression or differentiation state where at least one of the cells is an effector cell. In particular, a heterogeneous cell population, in one embodiment, include two or more effector cells (e.g., from about to about 250 cells) that contain or express different immunoglobulin genes, that contain or express different genes derived from immunoglobin genes, that contain or express different genes derived from T cell receptor genes, secrete different immunoglobulin proteins, secrete different proteins derived from immunoglobulin proteins, secrete different proteins or express different proteins derived from T cell receptor proteins.

In one embodiment, a cell population comprises a population of cells genetically engineered to express libraries of molecules that may bind a target epitope, cells genetically engineered to express genes or fragments of genes derived from cDNA libraries of interest, cells genetically engineered with reporters for various biological functions, and cells derived from immortalized lines or primary sources. Notably, clones originating from a single cell, in one embodiment, are heterogeneous with respect to one another due to for example, gene silencing, differentiation, altered gene expression, changes in morphology, etc. Additionally, cells derived from immortalized lines or primary sources are not identical clones of a single cell and are considered heterogeneous with respect to one another. Rather, a clonal population of cells has originated from a single cell and has not been modified genetically, transduced with RNA, transduced with DNA, infected with viruses, differentiated, or otherwise manipulated to make the cells different in a significant functional or molecular way. Cells derived from a single cell, but which naturally undergo somatic hypermutation or are engineered to undergo somatic hypermutation (e.g., by inducing expression of activation-induced cytidine deaminase, etc.), are not considered clones and therefore these cells, when present together, are considered a heterogeneous cell population.

As provided throughout, in one aspect, methods and apparatuses are provided for assaying a plurality of individual cell populations each optionally comprising one or more effector cells, in order identify one or more of the cell populations that includes at least one effector cell having an extracellular effect on a readout particle population or subpopulation thereof, e.g., secretion of a biomolecule having a desired property. Once the cell population(s) is identified, in one embodiment, it is selectively recovered to obtain a recovered cell population. If multiple cell populations are identified, in one embodiment, they are recovered and pooled, to obtain a recovered cell population. The recovered cell population is enriched for effector cells, compared to the starting population of cells originally loaded onto the device in that the former has a larger percentage of effector cells as compared to the latter.

Subpopulations of the recovered cell population are assayed for the presence of a second extracellular effect on a readout particle population, wherein the readout particle population or subpopulation thereof provides a readout of the second extracellular effect. The extracellular effect can be the same effect that was assayed, on the identified cell population, or a different extracellular effect. In a further embodiment, the subpopulations of the identified population each comprise from about 1 to about 10 cells. In even a further embodiment, the subpopulations of the identified population comprise an average of 1 cell each. One or more of the subpopulations displaying the extracellular effect are then identified and recovered to obtain a recovered subpopulation, which in one embodiment, is enriched for effector cells. If multiple cell subpopulations are identified, in one embodiment, they are recovered and pooled, to obtain a recovered cell subpopulation. The genetic information from the recovered cell subpopulation can then be isolated, amplified and/or sequenced.

The present invention is not limited by the type of effector cell or cell population that can be assayed according to the methods of the present invention. Examples of types of effector cells for use with the present invention are provided above, and include primary antibody secreting cells from any species (e.g., human, mouse, rabbit, etc.), primary memory cells (e.g., can assay IgG, IgM, IgD or other immunoglobins displayed on surface of cells or expand/differentiate into plasma cells), T-cells, hybridoma fusions either after a selection or directly after fusion, a cell line that has been transfected (stable or transient) with one or more libraries of monoclonal antibodies (mAbs) (e.g., for affinity maturation of an identified mAb using libraries of mutants in fab regions or effector function optimization using identified mAbs with mutations in Fc regions or cell lines transfected with heavy chain (HC) and light chain (LC) combinations from amplified HC/LC variable regions obtained from a person/animal/library or combinations of cells expressing mAbs (either characterized or uncharacterized to look for synergistic effects, etc.).

Plasma cells (also referred to as "plasma B cells," "plasmocytes" and "effector B cells") are terminally differentiated, and are one type of effector cell (ASC) that can be assayed with the devices and methods of the invention. Other ASCs that qualify as "effector cells" for the purposes of the present invention include plasmablasts, cells generated through the expansion of memory B cells, cell lines that express recombinant monoclonal antibodies, primary hematopoietic cells that secrete cytokines, T cells (e.g., CD4+ and CD8+ T-cells), dendritic cells that display protein or peptides on their surface, recombinant cell lines that secrete proteins, hybridoma cell lines, a recombinant cell engineered to produce antibodies, a recombinant cell engineered to express a T cell receptor.

It will be appreciated that the cell populations for use with the invention are not limited by source, rather, they may be derived from any animal, including human or other mammal, or alternatively, from in vitro tissue culture. Cells may be analyzed directly, for example, analyzed directly after harvesting from a source, or after enrichment of a population having a desired property (such as the secretion of antibodies that bind a specific antigen) by use of various protocols that are known in the art, e.g., flow cytometry. Prior to harvesting from an animal source, in one embodiment, the animal is subject to one or more immunizations. In one embodiment, flow cytometry is used to enrich for effector cells prior to loading onto one of the devices provided herein, and the flow cytometry is fluorescence activated cell sorting (FACS). Where a starting cell population is used that has been enriched for effector cells, e.g., ASCs, and retained as individual cell populations in individual microfluidic chambers, the individual cell populations need not be comprised entirely of effector cells. Rather, other cell types may be present as a majority or minority. Additionally, one or more of the individual cell populations may contain zero effector cells.

There are several methods for the enrichment of ASCs derived from animals known to those of skill in the art, which can be used to enrich a starting population of cells for analysis by the methods and devices provided herein. For example, in one embodiment, FACS is used to enrich for human ASCs using surface markers $CD19^+$ $CD20^{low}CD27^{hi}CD38^{hi}$ (Smith et al. (2009). *Nature Protocols* 4, pp. 372-384, incorporated by reference herein in its entirety). In another embodiment, a cell population is enriched by magnetic immunocapture based positive or negative selection of cells displaying surface markers. In another embodiment, a plaque assay (Jerne et al. (1963). *Science* 140, p. 405, incorporated by reference herein in its entirety), ELISPOT assay (Czerkinsky et al. (1983). *J. Immunol. Methods* 65, pp. 109-121, incorporated by reference herein in its entirety), droplet assay (Powel et al. (1990). *Bio/Technology* 8, pp. 333-337, incorporated by reference herein in its entirety), cell surface fluorescent-linked immunosorbent assay (Yoshimoto et al. (2013), *Scientific Reports*, 3, 1191, incorporated by reference herein in its entirety) or a cell surface affinity matrix assay (Manz et al. (1995). *Proc. Natl. Acad. Sci. U.S.A.* 92, pp. 1921-1925, incorporated by reference herein in its entirety) is used to enrich for ASCs prior to performing one of the methods provided herein or prior to loading a starting cell population onto one of the devices provided herein.

In various embodiments, two or more effector cells within a cell population produce and secrete cell products, e.g., antibodies that have a direct or indirect effect on a readout particle population or subpopulation thereof. With respect to the devices provided herein, it is noted that not all chambers on the device necessarily include a cell population and/or a readout particle population, e.g., empty chambers or partially filled chambers may be present. Additionally, as provided throughout, within an individual chamber it may be only a subset of the cells within the cell population, or an individual cell within a population that produces and secretes antibodies. In some embodiments, cell populations in the microfluidic chambers do not comprise an effector cell. These chambers are identifiable by running one or more extracellular effect assays on each of the cell populations.

In some embodiments, it is desirable to have one or more accessory particles, which can include one or more accessory cells present in the microreactors, e.g., microfluidic chambers, to support the viability and/or function of one or more cells in the cell populations or to implement an extracellular effect assay. For example, in one embodiment an accessory cell, or plurality of accessory cells comprise a fibroblast cell, natural killer (NK) cell, killer T cell, antigen presenting cell, dendritic cell, recombinant cell, or a combination thereof.

An accessory particle or cells, or a population comprising the same, in one embodiment, is delivered to microreactors, e.g., microfluidic chambers together with the cell population. In other words, accessory cells in one embodiment are part of cell populations delivered to microfluidic chambers. Alternatively or additionally, the accessory particle(s) or accessory cell(s) are delivered to a chamber prior to, or after, the loading of the heterogeneous population of cells comprising an effector cell or plurality of effector cells to the microreactor or plurality of microreactors (e.g., microfluidic chamber or plurality of microfluidic chambers).

"Accessory particle" as referred to herein means any particle, including but not limited to a protein, protein fragment, cell, that (i) supports the viability and/or function of an effector cell, (ii) facilitates an extracellular effect, (iii) facilitates the measurement of an extracellular effect, or (iv) detection of an extracellular effect of an effector cell.

Accessory particles include but are not limited to proteins, peptides, growth factors, cytokines, neurotransmitters, lipids, phospholipids, carbohydrates, metabolites, signaling molecules, amino acids, monoamines, glycoproteins, hormones, virus particles or a combination thereof. In one embodiment, one or more accessory particles comprises sphingosine-1-phosphate, lysophosphatidic acid or a combination thereof As an example of an accessory cell, in one embodiment, a population of fibroblast cells (that do not secrete antibodies) is included within a cell population enriched for effector cells (e.g., ASCs) in order to enhance the viability of the effector cell(s) (e.g., ASC(s)) within the population. In another embodiment, a population of NK cells may be added as accessory particles to implement an antibody-dependent cell-mediated cytotoxicity assay, where the NK cells will attack and lyse the target cells upon binding of an antibody on their surface. In embodiments where functional cellular assays are carried out on one or more cell populations, it will be appreciated that the effector cell(s) within the one or more cell populations will need to stay viable for an extended period of time while within a chamber of the microfluidic device. To this end, accessory particles and/or accessory cells, in one embodiment, are used to sustain the viability of the cell population that optionally comprises one or more effector cells. As explained below, accessory particles, e.g., accessory cells can also be used to sustain or enhance the viability of a readout cell population or subpopulation thereof, either of which can be a single readout cell.

One advantage of embodiments described herein is that the analysis of more than one effector cell within a single microreactor (e.g., microfluidic chamber), and/or the analysis of single or a few effector cells in the presence of other cells, allows for much greater assay throughput and hence the identification and selection of desired effector cells that would otherwise be too rare to detect efficiently. This is advantageous in many instances where there are limited methods to enrich for a desired cell type or where such enrichment has deleterious effects such as the reduction of viability of the cells being assayed. One embodiment of the invention that has been built features an array of 3500 cell analysis chambers. When this device is operated with an average of 30 cells per chamber, the total assay throughput is 105,000 cells per experiment. This throughput may be used for the selection of tens or hundreds of effector cells that are present at less than, for example, 1% of the total cell population.

For example, antibody secreting cells may be identified and isolated without the need for enrichment based on surface markers. In B-cells isolated from peripheral mononuclear blood cells (PBMCs) following immunization, the frequency of ASCs may be between 0.01 and 1%. At a throughput of 105,000 cells per device run, it is possible to directly select for hundreds of ASCs without further purification. This is particularly important, since FACS purification of ASCs can reduce cell viability. This is also important because appropriate reagents for the enrichment of ASCs may not be available for a host species of interest. Indeed, following immunization, the frequency of antibody secreting cells in peripheral blood mononuclear cells (PBMCs) may be between 0.01 and 1% and is thus detectable by using the microfluidic arrays provided herein, for example, a microfluidic array of 3500 chambers loaded at an average density of 30 cells per chamber. Thus, since the isolation of peripheral blood mononuclear cells (PBMCs) may be performed on any species without specific capture reagents, some of the present methods provide for the rapid and economical selection of cells secreting antibodies of interest from any species.

ASCs from basal levels in humans, in one embodiment, are identified by the methods and devices provided herein. While animals can be immunized to generate new antibodies against most antigens, the same procedure cannot be performed widely in humans except for approved vaccines. However, humans that have been naturally exposed to an antigen, or vaccinated at some point in their lifespan, typically possess low basal levels of antibody-secreting cells for the antigen. The present invention can be used to identify and isolate extremely rare effector cells secreting specific antibodies from a large number of cells (e.g., greater than 100,000 per device run). Such methods are used herein for the discovery of functional antibodies, e.g., as therapeutics for autoimmune diseases and cancers where autoantibodies may be present.

As provided throughout, the present invention relates in part to extracellular effect carried out in a massively parallel fashion in single microfluidic chambers. The assays are carried out to measure and detect an extracellular effect exerted by an effector cell, or plurality thereof, present in a cell population. A population of readout particles or subpopulation thereof provides a readout of the extracellular effect. For example, the methods described herein allow for the identification of a heterogeneous cell population which contains an effector cell that exerts the extracellular effect, e.g., secretion of an antibody specific to a desired antigen, in a background of up to about 250 cells that do not exert the extracellular effect.

"Readout particle," as used herein, means any particle, including a bead or cell, e.g., a functionalized bead or a cell that reports a functionality or property, or is used in an assay to determine an extracellular effect (e.g., functionality or property) of an effector cell, or a product of an effector cell such as an antibody. As described herein, a "readout particle" can be present as a single readout particle or within a homogeneous or heterogeneous population of readout particles within a single microfluidic chamber. In one embodiment, a readout particle is a bead functionalized to bind one or more biomolecules secreted by an effector cell (e.g., one or more antibodies), or released by an effector or accessory cell upon lysis. A single readout particle may be functionalized to capture one or more different types of biomolecules, for instance a protein and/or nucleic acid, or one or more different monoclonal antibodies. In one embodiment, the readout particle is a bead or a cell that is capable of binding antibodies produced by an effector cell that produces and/or secretes antibodies. In some embodiments, an effector cell may also be a readout particle, e.g., where a secretion product of one effector cell in a population has an effect on a larger, or different, sub-population of the effector cells or, alternatively, where the secretion product of one effector cell is captured on the same cell for readout of the capture.

A "readout cell," as used herein, is a type of readout particle that exhibits a response in the presence of a single effector cell or a cell population comprising one or more effector cells, for example one or more effector cells that secrete antibodies. In various embodiments, the readout cell is a cell that displays a surface antigen or a receptor (e.g., GPCR or RTK) specific to a secreted molecule. In one embodiment, the binding of the secreted molecule to a readout cell is the extracellular effect. The readout cell may be fluorescently labeled and/or possess fluorescent reporters that are activated upon binding.

As described above, in some embodiments, a cell population subjected to the methods described herein comprises an ASC or a plurality of ASCs, and the readout particle population or subpopulation thereof displays a target epitope or a plurality of target epitopes. The readout particle population in one embodiment is a population of beads functionalized to capture antibodies by a particular epitope or epitopes. Alternatively or additionally, the readout particle population is specific for an antibody's Fc region, and therefore, does not discriminate between antibodies having different epitopes. The readout particle population or subpopulation thereof, in one embodiment is labeled with a fluorescently-conjugated molecule containing the target epitope, for example to perform an ELISA assay. Fluorescent based antibody and cytokine bead assays are known in the art, see, e.g., Singhal et al. (2010). Anal. Chem. 82, pp. 8671-8679, Luminex® Assays (Life Technologies), BD™ Cytometric Bead Array, the disclosures of which are incorporated by reference in their entireties. These methods can be used herein to determine whether an effector cell has an extracellular effect on a readout particle.

Moreover, as described herein, individual microreactors (e.g., microfluidic chambers) are structured so that reagent exchange within the individual chambers is possible, whereby cross-contamination is eliminated or substantially eliminated between chambers. This allows for the detection of multiple extracellular effects in a single chamber, for example, multiple antigen binding effects and/or functional effects in a single chamber, for example, by exchanging antigens and secondary antibodies to label the respective binding complexes, followed by imaging. In these serial detection embodiments, the assays can be carried out with the same fluorophores, as each reaction is performed serially after a wash step. Alternatively, different fluorophores can be used to detect different extracellular effects in a serial manner, or in parallel, in one microreactor (e.g., microfluidic chamber).

In another embodiment, the readout particle population is a readout cell population wherein at least some of the readout cells display a target epitope on their surfaces. In one embodiment, the readout cell population, or a subpopulation thereof, is alive and viable. In another embodiment, the readout cell population or a subpopulation thereof is fixed. As will be recognized from the discussion above, where antibody binding is assayed for, "antibody binding" is considered the extracellular effect of an effector cell or plurality of effector cells. Antibody binding can be detected by, for example, staining of the cell with one or more fluorescently labeled secondary antibodies. In another embodiment, binding of an antibody to the target epitope on a readout particle or readout cell causes the death of a readout cell, or some other readout cell response as discussed herein (e.g., secretion of biomolecule, activation or inhibition of a cell signaling pathway).

Readout cells in a population may be distinguished, e.g., by features such as morphology, size, surface adhereance, motility, fluorescent response. For example, in one embodiment, a population of readout cells is labeled on their surfaces, or intracellulary, in order to determine whether the readout cells exhibit a response as chosen by the user of assay. For example, a calcein, carboxyfluorescein succinymyl ester reporter (CFSE), GFP/YFP/RFP reporters can be used to label one or more reporter cells, including extracellular receptors and intracellular proteins and other biomolecules.

In some embodiments, the readout particle population is a heterogeneous readout particle population, which can be a heterogeneous readout cell population. Where, for example, an ASC or plurality of ASCs are present in a cell population, the individual readout particles in the population may display different target epitopes, or display two different cell receptors (e.g., a GPCR or RTK or a combination thereof). Accordingly, the specificity of the extracellular effect, e.g., the specificity of an antibody for a target epitope, or the inhibition of a specific cell surface receptor, can be assessed. In another embodiment, an effector cell within a cell population is an ASC, and the readout particle population comprises a heterogeneous bead population that non-selectively capture all antibodies (e.g., Fc region specific) and a bead population that is specific for a unique target epitope.

In one embodiment, accessory particles are provided to facilitate the measurement of an extracellular effect, or to facilitate the readout of an extracellular effect. As described throughout, an extracellular effect includes an effect that is exhibited by an effector cell secretion product (e.g., antibody). For example, in one embodiment, a natural killer (NK) cell is provided as an accessory particle, to facilitate the measurement of lysis of a readout cell. In this embodiment, the extracellular effect includes lysis of a readout cell that binds to a specific epitope or cell receptor, by the natural killer (NK) cell, when an antibody secreted by an effector cell binds to the aforementioned readout cell.

In some embodiments, accessory particles include proteins, protein fragments, peptides, growth factors, cytokines, neurotransmitters (e.g., neuromodulators or neuropeptides), lipids, phospholipids, amino acids, monoamines, glycoproteins, hormones, virus particles, or a factor required to activate the complement pathway, upon binding of an effector cell secretion product to a readout cell or a combination thereof. In one embodiment, one or more accessory particles sphingosine-1-phosphate, lysophosphatidic acid or a combination thereof. Various extracellular effects that are measurable with the devices and methods provided herein, including lysis of the readout cell that binds the antibody, are discussed in detail below.

For example, cytokines that can be used as accessory particles include chemokines, interferons, interleukins, lymphokines, tumor necrosis factors. In some embodiments the accessory particles are produced by readout cells. In some embodiments, a cytokine is used as an accessory particle and is one or more of the cytokines provided in Table 1, below. In another embodiment, one or more of the following cytokines is used as an accessory particle: interleukin (IL)-1α, IL-1β, IL-IRA, IL18, IL-2, IL-3, IL-4, IL-5, IL-6, IL-7, IL-8, IL-9, IL-10, IL-11, IL-12, IL-13, IL-14, IL-15, IL-16, IL17, IL-18, IL-19, IL-20, granulocyte colony-stimulating factor (G-CSF), granulocyte macrophage-colony stimulating factor (GM-CSF), leukemia inhibitor factor, oncostatin M, interferon (IFN)-α, IFN-γ, CD154, lymphotoxin beta (LTB), tumor necrosis factor (TNF)-α, TNF-β, transforming growth factor (TGF)-β, erythropoietin, megakaryocyte growth and development factor (MGDF), Fms-related tyrosine kinase 3 ligand (Flt-3L), stem cell factor, colony stimulating factor-1 (CSF-1), macrophage stimulating factor, 4-1BB ligand, a proliferation-inducing ligand (APRIL), cluster of differentiation 70 (CD70), cluster of differentiation 153 (CD153), cluster of differentiation 178 (CD17)8, glucocorticoid induced TNF receptor ligand (GITRL), LIGHT (also referred to as TNF ligand superfamily member 14, HVEM ligand, CD258), OX40L (also referred to as CD252 and is the ligand for CD134), TALL-1, TNF related apoptosis inducing ligand (TRAIL), tumor necrosis factor weak inducer of apoptosis (TWEAK), TNF-related activation-induced cytokine (TRANCE) or a combination thereof.

TABLE 1

Representative cytokines and their receptors.

| Name | Synonym(s) | Amino Acids | Chromosome | Molecular Weight | Cytokine Receptor(s)(Da) and Form | Receptor Location(s) |
|---|---|---|---|---|---|---|
| Interleukins | | | | | | |
| IL-1α | hematopoietin-1 | 271 | 2q14 | 30606 | CD121a, CDw121b | 2812, 2q12-q22 |
| IL-1β | catabolin | 269 | 2q14 | 20747 | CD121a, CDw121b | 2q12,2q12-q22 |
| IL-1RA | IL-1 receptor antagonist | 177 | 2q14.2 | 20055 | CD121a | 2q12 |
| IL-18 | interferon-γ inducing factor | 193 | 11q22.2-q22.3 | 22326 | IL-18Rα, β | 2q12 |
| Common g chain (CD132) | | | | | | |
| IL-2 | T cell growth factor | 153 | 4q26-q27 | 17628 | CD25, 122, 132 | 10p15-p14, 22q13.1, Xq13.1 |
| IL-4 | BSF-1 | 153 | 5q31.1 | 17492 | CD124, 213a13, 132 | 16p11.2-12.1, X, Xq13.1 |
| IL-7 | | 177 | 8q12-q13 | 20186 | CD127, 132 | 5p13, Xq13.1 |
| IL-9 | T cell growth factor P40 | 144 | 5q31.1 | 15909 | IL-9R, CD132 | Xq28 or Yq12, Xq13.1 |
| IL-13 | P600 | 132 | 5q31.1 | 14319 | CD213a1, 213a2, CD1243, 132 | X, X813.1-q28, 16p11.2-12.1, Xq13.1 |
| IL-15 | | 162 | 4q31 | 18086 | IL-15Ra, CD122, 132 | 10p14-p14, 22813.1, Xq13.1 |
| Common b chain (CD131) | | | | | | |
| IL-3 | multipotential CSF, MCGF | 152 | 5q31.1 | 17233 | CD123, CDw131 | Xp22.3 or Yp11.3, 22q13.1 |
| IL-5 | BCDF-1 | 134 | 5q31.1 | 15238, homodimer | CDw125, 131 | 3p26-p24, 22q13.1 |
| Also related | | | | | | |
| GM-CSF | CSF-2 | 144 | 5831.1 | 16295 | CD116, CDw131 | Xp22.32 or Yp11.2, 22q13.1 |
| IL-6-like | | | | | | |
| IL-6 | IFN-β2, BSF-2 | 212 | 7p21 | 23718 | CD126, 130 | 1q21, 5q11 |
| IL-11 | AGIF | 199 | 19q13.3-13.4 | 21429 | IL-11Ra, CD130 | 9p13, 5811 |
| Also related | | | | | | |
| G-CSF | CSF-3 | 207 | 17q11.2-q12 | 21781 | CD114 | 1p35-p34.3 |
| IL-12 | NK cell stimulatory factor | 219/328 | 3p12-p13.2/ 5q31.1-q33.1 | 24844/37169 heterodimer | CD212 | 19p13.1, 1p31.2 |
| LIF | leukemia inhibitory factor | 202 | 22q12.1-q12.2 | 22008 | LIFR, CD130 | 5p13-p12 |
| OSM | oncostatin M | 252 | 22q12.1-q12.2 | 28484 | OSMR, CD130 | 5p15.2-5p12 |
| IL-10-like | | | | | | |
| IL-10 | CSIF | 178 | 1q31-q32 | 20517, homodimer | CDw210 | 11q23 |
| IL-20 | | 176 | 2q32.2 | 20437 | IL-20Rα, β | ? |
| Others | | | | | | |
| IL-14 | HMW-BCGF | 498 | 1 | 54759 | IL-14R | ? |
| IL-16 | LCF | 631 | 15q24 | 66694, homotetramer | CD4 | 12pter-p12 |
| IL-17 | CTLA-8 | 155 | 2q31 | 17504, homodimer | CDw217 | 22q11.1 |
| Interferons | | | | | | |
| IFN-α | | 189 | 9p22 | 21781 | CD118 | 21822.11 |
| IFN-β | | 187 | 9p21 | 22294 | CD118 | 21822.11 |
| IFN-γ | | 166 | 12q14 | 19348, homodimer | CDw119 | 6q23-q24 |
| TNF | | | | | | |
| CD154 | CD40L, TRAP | 261 | Xq26 | 29273, homotrimer | CD40 | 20q12-q13.2 |
| LT-β | | 244 | 6p21.3 | 25390, heterotrimer | LTβR | 12p13 |
| TNF-α | cachectin | 233 | 6p21.3 | 25644, homotrimer | CD120a, b | 12p13.2, 1p36.3-p36.2 |
| TNF-β | LT-α | 205 | 6p21.3 | 22297, heterotrimer | CD120a, b | 12p13.2, 1p36.3-p36.2 |
| 4-1BBL | | 254 | 19p13.3 | 26624, trimer? | CDw137 (4-1BB) | 1p36 |
| APRIL | TALL-2 | 250 | 17p13.1 | 27433, trimer? | BCMA, TACI | 16p13.1, 17p11.2 |

TABLE 1-continued

Representative cytokines and their receptors.

| Name | Synonym(s) | Amino Acids | Chromosome | Molecular Weight | Cytokine Receptor(s)(Da) and Form | Receptor Location(s) |
|---|---|---|---|---|---|---|
| CD70 | CD27L | 193 | 19p13 | 21146, trimer? | CD27 | 12p13 |
| CD153 | CD30L | 234 | 9q33 | 26017, trimer? | CD30 | 1p36 |
| CD178 | FasL | 281 | 1q23 | 31485, trimer? | CD95 (Fas) | 10q24.1 |
| GITRL | | 177 | 1q23 | 20307, trimer? | GITR | 1p36.3 |
| LIGHT | | 240 | 16p11.2 | 26351, trimer? | LTbR, HVEM | 12p13, 1p36.3-p36.2 |
| OX40L | | 183 | 1q25 | 21050, trimer? | OX40 | 1p36 |
| TALL-1 | | 285 | 13q32-q34 | 31222, trimer? | BCMA, TACI | 16p13.1, 17p11.2 |
| TRAIL | Apo2L | 281 | 3q26 | 32509, trimer? | TRAILR1-4 | 8p21 |
| TWEAK | Apo3L | 249 | 17p13.3 | 27216, trimer? | Apo3 | 1p36.2 |
| TRANCE | OPGL | 317 | 13q14 | 35478, trimer? | RANK, OPG | 18q22.1, 8q24 |
| TGF-β | | | | | | |
| TGF-β1 | TGF-β | 390 | 19q13.1 | 44341, homodimer | TGF-βR1 | 9q22 |
| TGF-β2 | | 414 | 1q41 | 47747, homodimer | TGF-βR2 | 3p22 |
| TGF-β3 | | 412 | 14q24 | 47328, homodimer | TGF-βR3 | 1p33-p32 |
| Miscellaneous hematopoietins | | | | | | |
| Epo | erythropoietin | 193 | 7q21 | 21306 | EpoR | 19p13.3-p13.2 |
| Tpo | MGDF | 353 | 3q26.3-q27 | 37822 | TpoR | 1p34 |
| Flt-3L | | 235 | 19q13.1 | 26416 | Flt-3 | 13q12 |
| SCF | stem cell factor, c-kit ligand | 273 | 12q22 | 30898, homodimer | CD117 | 4q11-q12 |
| M-CSF | CSF-1 | 554 | 1p21-p13 | 60119, homodimer | CD115 | 5q33-q35 |
| MSP | Macrophage stimulating factor, MST-1 | 711 | 3p21 | 80379 | CDw136 | 3p21.3 |

Adapted from *Cytokines, Chemokines and Their Receptors*. Madame Curie Bioscience Database. (Landes Biosceince)

In one embodiment, an accessory particle is a cytokine or other factor operable to stimulate a response of the readout cell. For example, readout cells may be incubated with an effector cell or plurality thereof and pulsed with a cytokine that is operable to affect the readout cell. Alternatively or additionally, cytokine-secreting cells operable to affect the readout particles are provided to the chamber as accessory cells. Neutralization of the secreted cytokines by an effector cell secretion product in one embodiment, are detected by the absence of the expected effect of the cytokine on the readout cell. In another embodiment, an accessory particle is provided and is a virus operable to infect one or more readout cells, and neutralization of the virus is detected as the reduced infection of readout cells by the virus.

Notably, and as should be evident by the discussion provided above regarding accessory particles, the extracellular effect measurable and detectable by the devices and methods provided herein is not limited to the binding of an antibody to a target epitope. Rather an extracellular effect as described herein, in one embodiment, is a functional effect. The functional effect, in one embodiment is apoptosis, modulation of cell proliferation, a change in a morphological appearance of the readout particle, a change in aggregation of multiple readout particles, a change in localization of a protein within the readout particle, expression of a protein by the readout particle, secretion of a protein by the readout particle, triggering of a cell signaling cascade, readout cell internalization of a molecule secreted by an effector cell, neutralization of an accessory particle operable to affect the readout particle.

Once an extracellular effect is identified in a microreactor (e.g., microfluidic chamber) comprising a cell population, the population is recovered and a downstream assay can be performed on subpopulations of the recovered cell population, to determine which effector cell(s) is responsible for the measured extracellular effect. The downstream assay in one embodiment is a microfluidic assay. In a further embodiment, the downstream assay is carried out on the same device as the first extracellular effect assay. However, in another embodiment, the downstream assay is carried out in a different microfluidic device, or via a non-microfluidic method, for example, a benchtop single cell reverse transcriptase (RT)-PCR reaction. Antibody gene sequences of identified and recovered effector cells in one embodiment are isolated, cloned and expressed to provide novel functional antibodies.

Although functional effects of single ASCs are measurable by the methods and devices provided herein, affinity, binding and specificity can also be measured as the "effect" of an effector cell, e.g., an effect of an effector cell secretion product. For example, the binding assay provided by Dierks et al. (2009). *Anal. Biochem.* 386, pp. 30-35, incorporated by reference herein in its entirety, can be used in the devices provided herein to determine whether an ASC secretes an antibody that binds to a specific target.

In another embodiment, the extracellular effect is affinity for an antigen or cell receptor, and the method described by Singhal et al. (2010). *Anal. Chem.* 82, pp. 8671-8679, incorporated by reference herein for all purposes, is used to assay the extracellular effect.

In one embodiment, parallel analyses of multiple extracellular effects are carried out in one microreactor (e.g., microfluidic chamber) by employing multiple types of readout particles. Alternatively or additionally, parallel analyses of multiple functional effects are carried out on a single microfluidic device by employing different readout particles in at least two different chambers.

In one embodiment, the readout particle is an enzyme that is present as a soluble molecule, or that is tethered to the microfluidic chamber surface or to another physical support in the readout zone of the chamber. In this case, the binding of an antibody that inhibits the enzymatic activity of the readout particle, in one embodiment, is detected by reduced signal that reports on the enzymatic activity, including a fluorescent signal or colorometric signal or precipitation reaction.

In various embodiments, determining whether an effector cell or multiple effector cells within a cell population have an extracellular effect on a population of readout particles or subpopulation thereof involves light and/or fluorescence microscopy of the microfluidic chamber containing the cell population. Accordingly, one embodiment of the invention involves maintaining the readout particle population in a single plane so as to facilitate imaging of the particles by microscopy. In one embodiment, a readout particle population in a chamber is maintained in a single plane that is imaged through the device material, or portion thereof (e.g., glass or PDMS) to generate one, or many, high-resolution images of the chamber. In one embodiment, a high-resolution image is an image comparable to what is achieved using standard microscopy formats with a comparable optical instrument (lenses and objectives, lighting and contrast mechanisms, etc.).

According to one aspect of the invention, a method is provided for identifying a cell population comprising one or more effector cells that displays a variation in an extracellular effect. In one embodiment, the method comprises retaining a plurality of individual cell populations in separate microreactors (e.g., microfluidic chambers), wherein at least one of the individual cell populations comprises one or more effector cells and the contents of the separate microfluidic chambers further comprise a readout particle population comprising one or more readout particles. The cell populations and the readout particle populations are incubated within the microreactor, and the cell populations are assayed for the presence of the extracellular effect. The readout particle population or a subpopulation thereof provides a direct or indirect readout of the extracellular effect. Based on the results of the assay, it is determined whether a cell population from amongst the plurality comprising one or more effector cells that exhibit the extracellular effect.

In some embodiments, one or more of the individual cell populations and the readout particle populations are positioned in an "effector zone" and "readout zone" of a microreactor, respectively. However, the invention is not limited thereto. When effector zones and readout zones are employed, in one embodiment, each are essentially defined by the nature of the cells or particles positioned within it. That is, the one or more effector cells are segregated into the effector zone and the one or more readout particles are segregated into the readout zone. The effector zone is in fluid communication with the readout zone. Accordingly, in some embodiments, where a cell population and readout particles are provided to a chamber at low densities, e.g., less than two effector cells and readout particles per chamber, physical separation of the readout particles from an effector cell is accomplished. It will be recognized however, that the invention need not be practiced with discrete zones within a chamber. As should be evident by the present description, such a separation is not necessary to carry out the extracellular effect assays set forth herein.

The cell population and readout particle population can be loaded simultaneously into a microreactor (e.g., through different inlet ports or in one mixture through a single inlet port. Alternatively, the effector cells and readout particles are loaded serially into a microreactor (e.g., microfluidic chamber). A person skilled in the art will understand that the cell population can be provided to a microreactor prior to (or after) the loading of the readout particle(s) to the chamber. However, it is possible that the readout particle population and cell population be provided together as a mixture.

The devices and methods disclosed herein provide robust platforms for carrying out one or more extracellular effect assays on a plurality of cell populations, for example, to identify a cell population from the plurality displaying a variation in an extracellular effect. The variation is attributable to one or more effector cells present in the cell population. Each cell population is confined to a single microfluidic chamber, and the effector cell assay performed in each chamber of a device can be the same (e.g., all cell toxicity assays, all binding assays, etc.) or different (e.g., one binding assay, one apoptosis assay). The addressability of specific chambers on the device, for example with different readout particles and reagents for performing effector cell assays, makes diverse analyses methods possible.

The microfluidic devices described herein comprise a plurality of chambers, and each of the plurality has the capability for housing a cell population and a readout particle population, to determine whether any effector cell(s) in the cell population demonstrate an extracellular effect on a readout particle population or a subpopulation thereof. A readout particle population may consist of a single readout particle. As provided below, devices provided herein are designed and fabricated to assay a plurality of cell populations on one device, for example, where hundreds to thousands of cell populations are assayed on one device in order to identify one or more of the cell populations displaying a variation in the extracellular effect. At least a portion of the cell populations are heterogeneous with respect to one another. The variation, for example, is a variation compared to the extracellular effect displayed by other populations of the plurality. For example, in one embodiment, a method is provided for identifying a cell population(s) from among a plurality of cell populations, wherein the selected population(s) has a variation in an extracellular effect, as compared to the remaining cell populations. The variation in the extracellular effect is detectable for example, by a difference in fluorescence intensity of one of the chambers compared to the remaining plurality or a subplurality thereof.

According to one aspect of the invention, a method is provided for identifying a cell population from amongst a plurality of cell populations that displays a variation in an extracellular effect, wherein the extracellular effect is induced by the binding of one or more soluble factors secreted from an effector cell(s) to a readout particle population or subpopulation thereof. The readout particle population can be a homogeneous or a heterogeneous population. In one embodiment, a method provided herein involves retaining individual readout particle populations within different chambers of a microfluidic device. The number of readout particles analyzed can vary and will be determined according to considerations analogous to those for cell populations as outlined above.

An individual readout particle population and cell population are retained in a single chamber of one of the microfluidic devices provided herein. Optionally, the chamber is substantially isolated from other chambers of the microfluidic device that also comprise individual cell populations and a readout particle population, for example, to minimize contamination between chambers. However, isolation is not necessary to practice the methods provided herein. In one embodiment, where isolation is desired, isolation comprises fluidic isolation, and fluidic isolation of chambers is achieved by physically sealing them, e.g., by using valves surrounding the chambers. However, isolation in another embodiment is achieved without physically sealing the chamber, by limiting fluid communication between chambers so as to preclude contamination between one chamber and another chamber of the microfluidic device.

Once a chamber or plurality of chambers each comprising a cell population which optionally comprise one or more effector cells, and a readout particle population is isolated, the chamber or chambers, and specifically the cell population with the chamber (or chambers) is incubated. It will be appreciated that an initial incubation step can occur prior to the addition of readout particles, and/or after readout particles are added to a chamber comprising a cell population.

For example, an incubation step can include a medium exchange to keep the cell population healthy, or a cell wash step. Incubation can also comprise addition of accessory particles used to carry out an extracellular effect assay.

An incubating step, in one embodiment, includes controlling one or more of properties of the chamber, e.g., humidity, temperature and/or pH to maintain cell viability (effector cell, accessory cell or readout cell) and/or maintain one or more functional properties of the a cell in the chamber, such as secretion, surface marker expression, gene expression, signaling mechanisms, etc. In one embodiment, an incubation step includes flowing a perfusing fluid through the chamber. The perfusing fluid is selected depending on type of effector cell and/or readout cell is in the particular chamber. For example, a perfusing liquid in one embodiment, is selected to maintain cell viability, e.g., to replenish depleted oxygen or remove waste productions, or to maintain cellular state, e.g., to replenish essential cytokines, or to assist in assaying the desired effect, e.g., to add fluorescent detection reagents. Perfusion can also be used to exchange reagents, for example, to assay for multiple extracellular effects in a serial manner.

In another embodiment, incubating a cell population includes flowing a perfusing fluid through the chamber to induce a cellular response of a readout particle (e.g., readout cell). For example, the incubating step in one embodiment comprises adding a fluid comprising signaling cytokines to a chamber comprising the cell population. The incubating step can be periodic, continuous, or a combination thereof. For example, flowing a perfusing fluid to a microfluidic chamber or chambers is periodic or continuous, or a combination thereof. In one embodiment, the flow rate of an incubating fluid (e.g., perfusing fluid) is controlled by integrated microfluidic micro-valves and micro-pumps. In another embodiment, the flow of an incubating liquid is pressure driven, for example by using compressed air, syringe pumps or gravity to modulate the flow.

Once individual chambers within a device are provided with a cell population and a readout particle population, a method is carried out to determine whether a cell within the population exhibits an extracellular effect on the readout particle population or subpopulation thereof. The cell population and, readout particle population and/or subpopulation thereof, as appropriate, is then examined to determine whether or not a cell(s) within a population exhibits the extracellular effect, or if compared to other cell populations, a variation in the extracellular effect. It is not necessary that the specific cell or cells exhibiting the extracellular effect or variation thereof be identified within the chamber, so long as the presence and/or variation is detected within the chamber. In one embodiment, once a cell population is identified as exhibiting an extracellular effect or variation of the extracellular effect, the cell population is recovered for further characterization to identify the specific effector cell(s) responsible for the extracellular effect or variation thereof. In another embodiment, once the cell population is identified as exhibiting the extracellular effect or variation in extracellular effect, it is recovered and the nucleic acid from the cell population is amplified and sequenced.

The extracellular effect in one embodiment is a binding interaction between the protein produced by an effector cell(s) and a readout particle, e.g., a bead or a cell. In one embodiment, one or more of the effector cells in the population is an antibody producing cell, and the readout particle includes an antigen having a target epitope. The extracellular effect in one embodiment is the binding of an antibody to an antigen and the variation, for example, is greater binding as compared to a control chamber or other populations of the plurality. Alternatively, the variation in the extracellular effect is the presence of an effector cell that secretes an antibody with a modulated affinity for a particular antigen. That is, the binding interaction is a measure of one or more of antigen-antibody binding specificity, antigen-antibody binding affinity, and antigen-antibody binding kinetics. Alternatively or additionally, the extracellular effect is a modulation of apoptosis, modulation of cell proliferation, a change in a morphological appearance of a readout particle, a change in localization of a protein within a readout particle, expression of a protein by a readout particle, neutralization of the biological activity of an accessory particle, cell lysis of a readout cell induced by the effector cell, cell apoptosis of the readout cell induced by the effector cell, readout cell necrosis, internalization of an antibody, internalization of an accessory particle, enzyme neutralization by the effector cell, neutralization of a soluble signaling molecule or a combination thereof. In some embodiments, at least two different types of readout particles are provided to a chamber in which one of the types of readout particles does not include the target epitope.

Different types of readout particles may be distinguished by one or more characteristics such as by fluorescence labeling, varying levels of fluorescence intensity, morphology, size, surface staining and location in the chamber.

Once incubated with a cell population comprising an effector cell(s), the readout particle population or subpopulation thereof is examined to determine whether one or more cells within the cell population exhibits an extracellular effect on one or more readout particles, whether direct or indirect, or a variation in the extracellular effect. Cell populations are identified that have a variation in the extracellular effect assayed for, and then recovered for downstream analysis. Importantly, as provided throughout, it is not necessary that the specific effector cell(s), having the particular extracellular effect on the one or more readout particles be identified so long as the presence of the extracellular effect is detected within a particular microreactor (e.g., microfluidic chamber).

In some embodiments, the one or more effector cells within the cell population secretes defined biomolecules, e.g., antibodies, and the extracellular effect of these factors is evaluated on a readout particle or a plurality of readout particles (e.g., readout cells) in order to detect a cell population that demonstrates the extracellular effect. The extracellular effect, however, is not limited to an effect of a secreted biomolecule. For example, in one embodiment, the extracellular effect is an effect of a T-cell receptor, for example, binding to an antigen.

In one embodiment, a readout particle population is a heterogeneous population of readout cells and comprises readout cells engineered to express a cDNA library, whereby the cDNA library encodes for cell surface proteins. The binding of antibody to these cells is used to recover, and possibly to analyze, cells that secrete antibodies that bind to a target epitope.

In some embodiments, methods for measuring an extracellular effect on a readout particle population or subpopulation thereof includes the addition of one or more accessory particles to the chamber where the effect is being measured. For example, at least one factor required to activate complement on binding of an antibody to the readout cells may be provided as an accessory particle. As provided above, a natural killer cell or plurality thereof, in one embodiment, is added to a chamber as an accessory cell in cases where cell lysis is being measured. One of skill in the art will be able to determine what accessory particles are necessary, based on the assay being employed.

In some embodiments, where one or more readout particles include a readout cell displaying or expressing a target antigen, a natural killer cell, or a plurality thereof is provided to the chamber as an "accessory cell(s)" that facilitates the functional effect (lysis) being measured. The accessory cell can be provided to the chamber with the cell population, the readout particle(s), prior to the readout particle(s) being loaded, or after the readout particle(s) is loaded into the chamber. In embodiments where a natural killer cell is employed, the natural killer cell targets one or more readout cells to which an antibody produced by an effector cell has bound. The extracellular effect may thus include lysis of the one or more readout cells by the natural killer cell. Lysis can be measured by viability dyes, membrane integrity dyes, release of fluorescent dyes, enzymatic assays, etc.

In some embodiments, the extracellular effect is neutralization of an accessory particle (or accessory reagent) operable to affect the readout particle, e.g. a cytokine (accessory particle) operable to stimulate a response of the at least one readout cell. For example, cytokine-secreting cells operable to affect the readout particle cells may further be provided to the chamber. Neutralization of the secreted cytokines by an effector cell may be detected as the absence of the expected effect of the cytokine on the readout cell, e.g. proliferation. In another embodiment, the accessory particle is a virus operable to infect the readout cell(s), and neutralization of the virus is detected as the reduced infection of readout cells by the virus.

In some embodiments, the extracellular effect of one effector cell type may induce activation of a different type of effector cells (e.g., secretion of antibodies or cytokine) which can then elicit a response in the at least one readout cell.

As provided throughout, the methods and devices provided herein are used to identify an effector cell that exhibits a variation in an extracellular effect on a readout particle. The effector cell can be present as a single effector cell in a microfluidic chamber, or in a cell population within a single chamber. The extracellular effect, for example, can be an extracellular effect of a secretion product of the effector cell. In the case where the effector cell is present in a larger cell population, the extracellular effect is first attributed to the cell population, and the population is isolated and subpopulations of the isolated population are analyzed to determine the cellular basis for the extracellular effect. Subpopulation(s) displaying the extracellular effect can then be isolated and further analyzed at limiting dilution, for example as single cells, or subjected to nucleic acid analysis. In one embodiment, a subpopulation of an isolated cell population contains a single cell.

In one embodiment, the cell population comprises an ASC that secretes a monoclonal antibody. In one embodiment, a readout bead based assay is used in a method of detecting the presence of an effector cell secreting the antibody amid a background of one or more additional cells not secreting the antibody. For example, a bead based assay is employed in one embodiment, in a method of detecting an ASC within a cell population, whose antibody binds a target epitope of interest, in the presence of one or more additional ASCs that secrete antibodies that do not bind the target epitope of interest.

Figure 3:
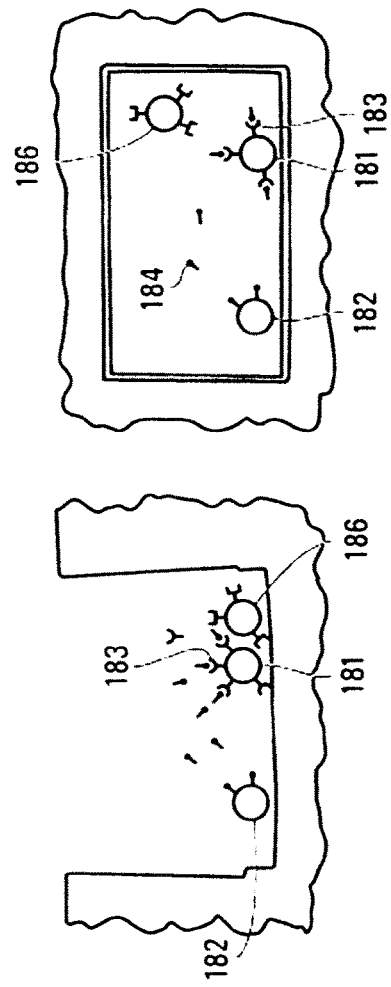
FIG. 3 shows top and cross-sectional view schematic diagrams of a method of identifying the presence of an effector cell that produces a biomolecule capable of specifically binding a target readout particle according to an embodiment of the invention.

In another embodiment, the ability of an antibody to bind specifically to a target cell is assessed. Referring to FIG. 3, the assay includes at least two readout particles, e.g., readout cells 181 and 186, in addition to at least one effector cell 182 (ASC). Readout cell 181 expresses a known target epitope of interest, i.e., target epitope 183, on its surface (either naturally or through genetic engineering) while readout cell 186 does not. The two types of readout cells 181 and 186 may be distinguishable from themselves and the effector cell 182 by a distinguishable fluorescent marker, other stain or morphology. Effector cell 182 secretes antibody 184 in the same chamber as readout cells 181 and 186. Antibody 184 secreted by effector cell 182 binds to readout cell 181 via target epitope 183, but does not bind to readout cell 186. A secondary antibody is used to detect the selective binding of antibody 184 to readout cell 181. The microfluidic chamber is then imaged to determine if antibody 184 binding to the readout cell 181 and/or readout cell 186 has occurred.

Such an assay may also be used to assess the location of antibody binding on or inside the readout cell(s) using high resolution microscopy. In this embodiment, the readout particles include different particle types (e.g., cell types) or particles/cells prepared in different ways (for example, by permeabilization and fixation) to assess binding specificity and/or localization. For instance, such an assay could be used to identify antibodies that bind the natural conformation of a target on live cells and the denatured form on fixed cells. Such an assay may alternatively be used to determine the location of an epitope on a target molecule by first blocking other parts of the molecule with antibodies against known epitopes, with different populations of readout particles having different blocked epitopes.

Figure 4:
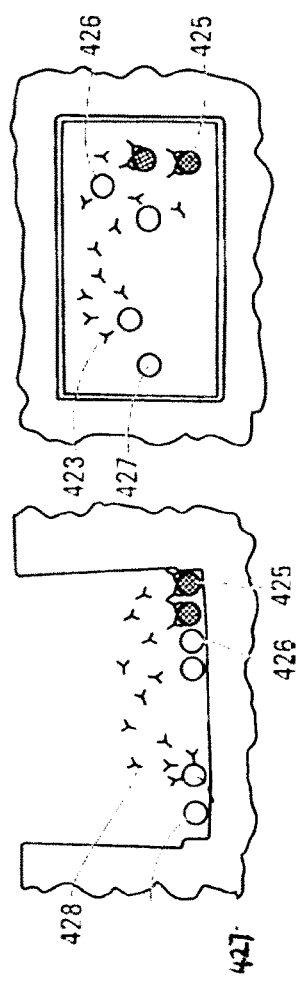
FIG. 4 shows top and cross-sectional view schematic diagrams of a method of identifying the presence of at least one effector cell that produces a biomolecule (e.g. antibody) that binds specifically to malignant cells but not normal cells.

In another embodiment, individual heterogeneous readout particle populations, (e.g., a readout cell population comprising malignant and normal cells) and individual cell populations, wherein at least one of the individual cell populations comprises an effector cell, are provided to a plurality of microfluidic chambers (e.g., greater than 1000 chambers) of one of the devices provided herein. For example, referring to FIG. 4, binding to one or more malignant readout cells 425 and absence of binding to healthy readout cells 426 in the population of readout cells is used to identify a cell population of interest containing one or more effector cells producing an antibody of interest, i.e., effector cell 427 producing antibody 428 specific to one or more of the malignant cells in the population. The two types of readout cells 425 and 426 within a chamber are distinguishable by at least one property, for example, fluorescence labeling, varying levels of fluorescence intensity, morphology, size, surface staining and location in the microfluidic chamber. The cells are then incubated within the individual chambers and imaged to determine if one or more of the chambers includes a cell population that exerts the extracellular effect, i.e., an ASC that secretes an antibody that binds to a malignant readout cell but not a healthy readout cell.

If present within a chamber, the cell population containing the one or more ASCs that secretes an antibody that binds a malignant readout cell 425, but not the healthy readout cells 426, can then be recovered to retrieve the sequences of the antibodies within the chamber, or to perform other downstream assays on the individual cells within the population, for example, an assay to determine which effector cell in the population has the desired binding property. Accordingly, novel functional antibodies are provided that are discovered by one or more of the methods described herein. The epitope on the malignant readout cell 425 may be known or unknown. In the later case, the epitope for the antibody can be identified by the method described below.

Figure 5:
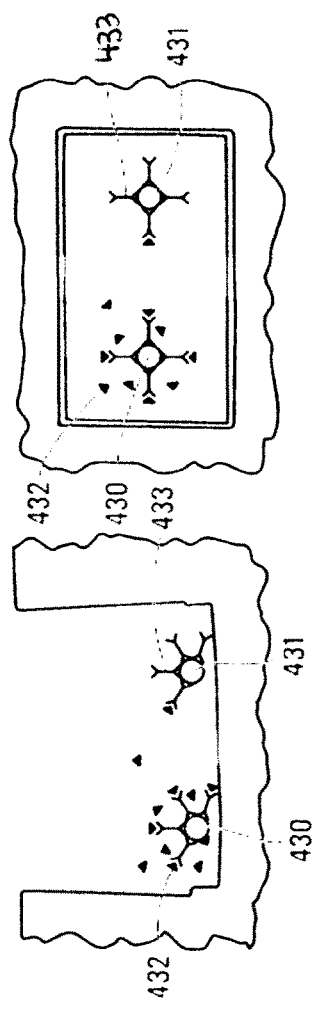
FIG. 5 shows top and cross-sectional view schematic diagrams according to one embodiment of the invention of a method of identifying the presence of an effector cell that produces a biomolecule that binds to a readout cell where a subpopulation of effector cells are functionalized to also act as readout cells.
Figure 6:
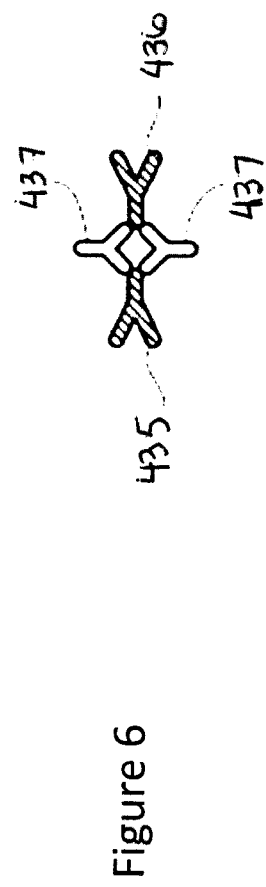
FIG. 6 is a schematic diagram of an antibody tetramer.

In one embodiment, a single cell type can serve as both an effector cell and a readout cell. Referring to FIG. 5, this assay is performed with a heterogeneous subpopulation of cells of a single cell type, i.e., effector cell 430 and readout cell 431, both functionalized to capture a molecule of interest 432 on their surfaces, for instance using tetrameric antibodies 433 directed against a surface marker and the molecule of interest 432, or an affinity-matrix on the cell to bind biotinylated antibodies. Referring to FIG. 6, a tetrameric antibody complex consists of an antibody (A) 435 that binds the cells and an antibody (B) 436 that binds antibodies secreted from the cells, wherein antibodies A and B are connected by two antibodies 437 that bind the Fc portion of antibodies A and B. Such tetrameric antibody complexes have been described in the art (Lansdorp et al. (1986). European Journal of Immunology 16, pp. 679-683, incorporated by reference herein in its entirety for all purposes) and are commercially available (Stemcell Technologies, Vancouver Canada). Using these tetramers, the secreted antibodies are captured and linked onto the surface of the cells, thus making the effector cells also function as readout particles. Once bound on the surface of cells these antibodies can be assayed for binding, for instance by the addition of fluorescently labeled antigen. For example, in the case where one is attempting to identify chambers that contain cells that secrete a monoclonal antibody that binds to a specific target, the antibodies that are secreted from effector cells can be captured on the surface of these effector cells, and others in the chamber, using appropriate capture agents. Referring again to FIG. 5, it is thus understood that effector cell 430 can also function as a readout cell, i.e., that the effector cell secreting a molecule of interest 432 may more efficiently capture the molecule of interest than readout cell 431.

Figure 7:
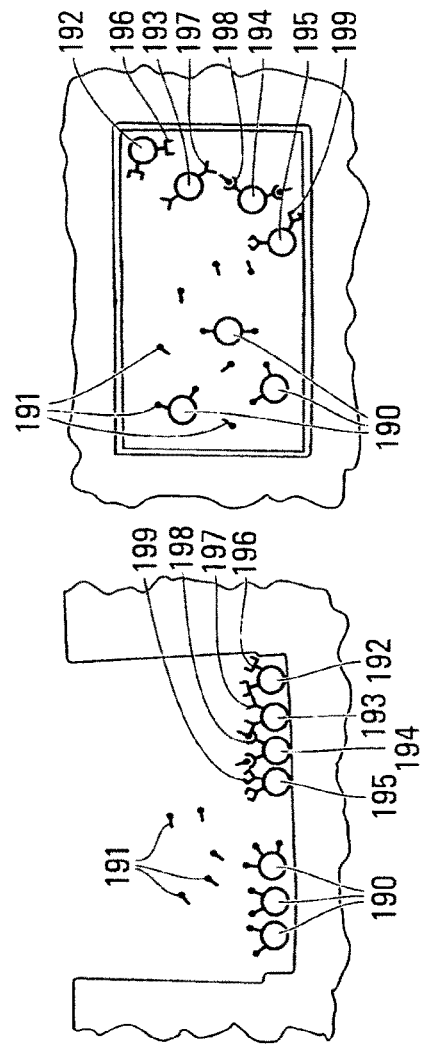
FIG. 7 shows top and cross-sectional view schematic diagrams of a method of screening for a target epitope/molecule to which an known biomolecule binds according to an embodiment of the invention.

In one embodiment, an extracellular effect assay is performed in parallel in a plurality of microfluidic chambers with a heterogeneous population of readout particles (e.g., a heterogeneous readout cell population) and a substantially homogeneous population of cells in each chamber, where the individual effector cells within the substantially homogeneous population each produces the same antibody. In a further embodiment, the readout particles are readout cells genetically engineered to express a library of proteins or protein fragments in order to determine the target epitope of the antibody secreted by the effector cells. Referring to FIG. 7, one embodiment of the assay includes a plurality of effector cells 190 secreting antibody 191. The assay further includes a heterogeneous readout cell population comprising readout cells 192, 193, 194, and 195 displaying epitopes 196, 197, 198, and 199, respectively. Effector cells 190 secrete antibodies 191 which diffuse toward readout cells 192, 193, 194, and 195. Antibodies 191 bind to readout cell 194 via target epitope 198, but do not bind to readout cells 192, 193, or 195. A secondary antibody may be used to detect the selective binding of antibodies 191 to readout cell 194.

Cell populations that include antibodies 191 that bind readout cell 194 (or another epitope) can then be recovered from the device and subjected to a further assay.

In one embodiment, a functional assay is provided to determine whether an individual ASC within a cell population activates cell lysis of a target cell, i.e., activates antibody-dependent cell-mediated cytotoxicity (ADCC). ADCC is a mechanism of cell-mediated immune defense whereby an effector cell of the immune system lyses a target cell, whose membrane-surface antigens have been bound by specific antibodies, i.e., antibodies secreted by an ASC within a particular microfluidic chamber provided herein. Classical ADCC is mediated by natural killer (NK) cells. However, macrophages, neutrophils and eosinophils can also mediate ADCC, and can be provided herein as accessory cells to be used in an ADCC extracellular effect assay.

Figure 8:
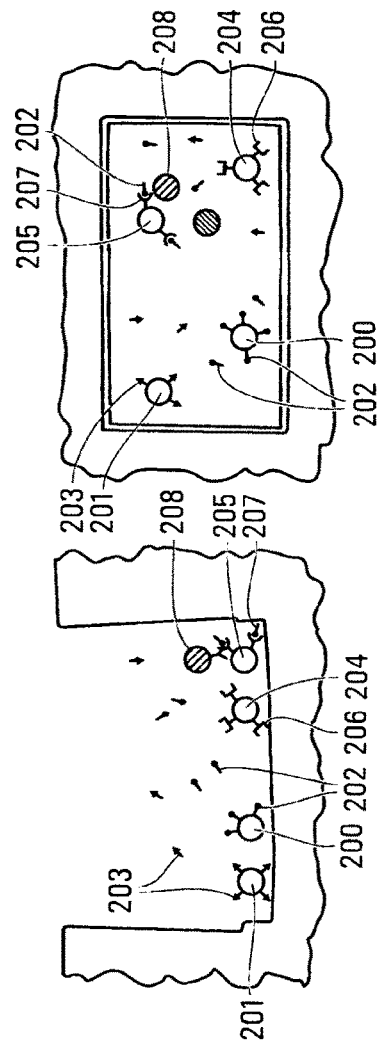
FIG. 8 shows top and cross-sectional view schematic diagrams of a method of identifying the presence of an effector cell which produces an antibody that specifically binds a target epitope/antigen according to an embodiment of the invention.

One embodiment of an ADCC assay provided herein includes a cell population comprising an effector cell or plurality thereof, a readout cell population (having an epitope of interest on their surfaces) and NK cells as accessory cells. The assay is run to determine if an ASC from the cell population induces the NK cells to attack the target cells and lyse them. Referring to FIG. 8, the illustrated embodiment includes cell population comprising ASCs 200 and 201 that secrete antibodies 202 and 203, respectively. The illustrated embodiment further includes a heterogeneous readout cell population comprising readout cells 204 and 205 displaying epitopes 206 and 207, respectively. ASCs 200 and 201 secrete antibodies 202 and 203 which diffuse toward readout cells 204 and 205. Antibodies 202 bind to readout cell 205 via target epitope 207, but do not bind to readout cell 204. Antibodies 203 do not bind to either of readout cells 204 and 205. NK cell 208 detects that readout cell 205 has been bound by antibodies 202 and proceeds to kill readout cell 205, while leaving unbound readout cell 204 alone.

A person skilled in the art will understand that the NK cells may be added to the chamber during or after the incubation of the effector cells with the readout cells, provided that they are added to the chamber in a manner that facilitates access to the readout cells. The NK cells may be from a heterogeneous population of accessory cells, for instance peripheral blood mononuclear cells. The NK cells may be from an animal- or human-derived cell line, and engineered to increase ADCC activity. A person skilled in the art will further understand that this assay could be performed with other hematopoietic cell types capable of mediating ADCC such as macrophages, eosinophils or neutrophils. In this case, macrophages, eosinophils or neutrophils are the accessory cells in the assay. Cell types capable of mediating ADCC can also be animal- or human-derived cell lines engineered to increase ADCC activity or to report signal upon binding antibodies on target cells. In the latter, the target cells are accessory particles while the cells mediating ADCC are the readout particles.

An ADCC extracellular effect assay can be performed on a single effector cell, a homogeneous cell population, or a heterogeneous cell population as depicted in FIG. 8. Similarly, an ADCC assay can be performed with a single readout cell, a homogeneous readout cell population, or a heterogeneous readout cell population, as depicted in FIG. 8. However, in many instances it is desirable to perform an ADCC assay with a plurality of readout cells to avoid the detection of false positives resulting from the random death of a readout cell.

Figure 9:
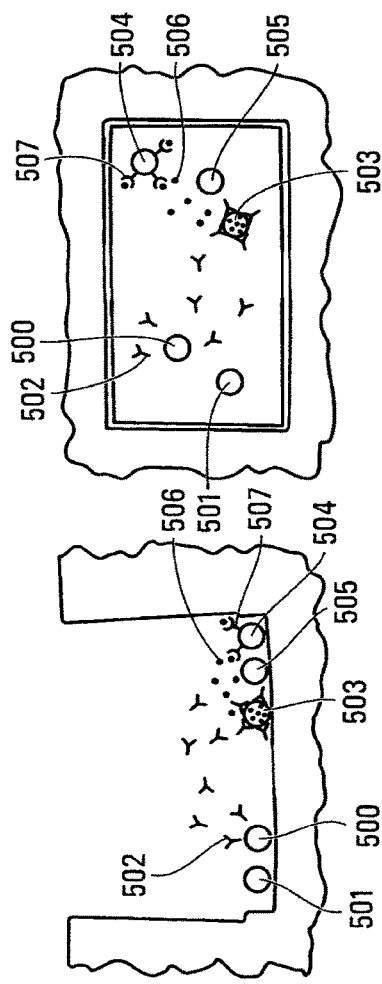
FIG. 9 shows top and cross-sectional view schematic diagrams of a method of quantifying cell lysis.

Cell lysis, in one embodiment, is quantified by a clonogenic assay, by the addition of a membrane integrity dye, by the loss of intracellular fluorescent molecules or by the release of intracellular molecules in solution. The released biomolecules are measurable directly in solution or captured onto readout particles for measurement. In some cases, additional accessory molecules are added, such as a substrate for a redox assay or a substrate for an enzymatic assay. Referring to FIG. 9, for example, a cell population comprising effector cell 500 secreting first biomolecule 502 and a second effector cell 501 that does not secrete first biomolecule 502, is incubated in the presence of a heterogeneous readout particle population, including readout cell 503 and readout particle 504, and an accessory particle (e.g., natural killer cell 505). Binding of first biomolecule 502 to readout cell 503 elicits the recruitment of natural killer cell 505 that causes readout cell 503 to lyse. Upon cell lysis, second biomolecule 506 is released from readout cell 503 and captured on readout particle 504, a different type of readout particle that is functionalized to capture second biomolecules 506, e.g., via molecule 507. Molecule 507, in one embodiment, is a protein, an antibody, an enzyme, a reactive group and/or a nucleic acid. Captured second biomolecule 506 can be any molecule present in readout cell 503 such as a protein, enzyme, carbohydrate or a nucleic acid. Binding of the second biomolecule 506 to readout particle 504, in one embodiment, is quantified using a fluorescence assay, a colorimetric assay, a bioluminescence assay or a chemoluminescence assay. The assay is performed directly on readout particle 504 or indirectly in the surrounding solution, for example, if captured biomolecule 506 is an enzyme that converts a substrate into a product with different optical properties. The assay is carried out in multiple chambers of one of the devices provided herein to determine if any of the chambers comprises an effector cell that secretes a biomolecule that induces cell lysis.

ADCC assays are known in the art and components are commercially available. For example, the Guava Cell Toxicity Kit for Flow Cytometry (Millipore), the ADCC Reporter Bioassay Core Kit (Promega), the ADCC Assay (GenScript), the LIVE/DEAD Cell Mediated Cytotoxicity Kit (Life Technologies) and the DELFIA cell toxicity assays can be utilized in the devices provided herein.

In another embodiment, the extracellular effect assay is a complement-dependent cytotoxicity (CDC) assay. In one CDC embodiment, a method is provided for identifying the presence of an ASC (or secreted antibody of an ASC) within a cell population that binds to a readout cell in the presence of soluble factors necessary and/or sufficient to induce lysis of the readout cell via the classic complement pathway. Accordingly, the assay is to determine whether an antibody secreted by an ASC stimulates lysis of one or more target cells by the classic complement pathway.

Figure 10:
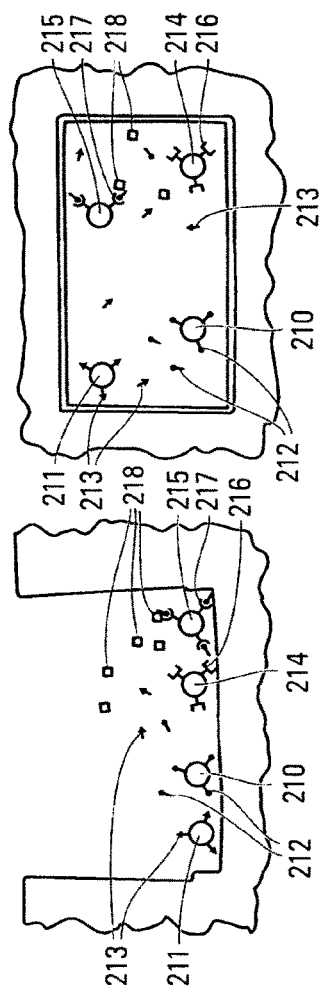
FIG. 10 shows top and cross-sectional view schematic diagrams of a method of identifying the presence of an effector cell which produces an antibody that specifically binds a target epitope/antigen according to an embodiment of the invention.

A CDC assay includes at least one effector cell and at least one readout cell, and one CDC embodiment is depicted in FIG. 10. The embodiment includes a cell population that includes effector cell 210 and effector cell 211 secreting antibodies 212 and 213, respectively. The illustrated embodiment further includes a heterogeneous readout cell population comprising readout cell 214 and readout cell 215 displaying epitopes 216 and 217, respectively. Effector cells 210 and 211 secrete antibodies 212 and 213 which diffuse toward readout cells 214 and 215. Antibodies 212 bind to readout cell 215 via target epitope 217, but do not bind to readout cell 214. Antibodies 213 do not bind to either of readout cells 214 and 215. Enzyme C1 218, an accessory particle, and one of the soluble factors necessary to induce lysis of cells via the classic complement pathway, binds to the complex of readout cell 215 with antibody 212 while leaving unbound readout cell 214 alone. Binding of enzyme C1 208 to the complex of readout cell 215 with antibody 212 triggers the classic complement pathway involving additional soluble factors necessary to induce lysis of cells via the class complement pathway (not shown), leading to the rupture and death of readout cell 215.

The soluble factors necessary to induce lysis of the readout cells (i.e., the accessory particles necessary for the assay) are added during or after the incubation of the effector cells with the readout cells, provided that they are added to the chamber in a manner that facilitates access to the readout cells. CDC assays provided herein can be performed on a single effector cell, a homogeneous effector cell population, or a heterogeneous cell population as depicted in FIG. 8. Similarly, the CDC assay can be performed with a single readout cell, a homogeneous readout cell population or a heterogeneous readout cell population, as depicted in FIG. 8. However, it is desirable in many instances to perform the CDC assay with a readout cell population to avoid the detection of false positives resulting from the random death of a readout cell.

Figure 11:
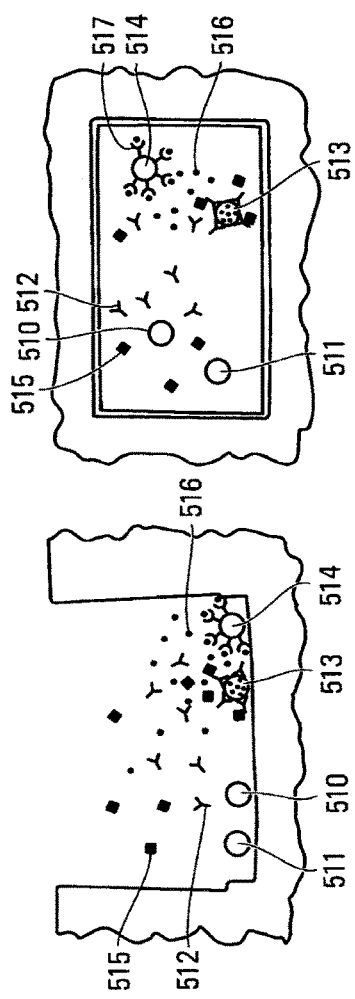
FIG. 11 shows top and cross-sectional view schematic diagrams of a method of quantifying cell lysis.

Cell lysis by the complement pathway is quantified according to methods known to those of skill in the art. For example, cell lysis is quantified by a clonogenic assay, by the addition of a membrane integrity dye, by the loss of intracellular fluorescent molecules or by the release of intracellular molecules in solution. The released biomolecules are measured directly in solution or captured onto readout particles. In some cases, additional accessory molecules may be added such as a substrate for a redox assay or a substrate for an enzymatic assay. Referring to FIG. 11, for example, a cell population, including an effector cell 510 secreting a first biomolecule 512 and a second effector cell 511 that does not secrete first biomolecule 512, is incubated in the presence of one or more heterogeneous readout particles, e.g., readout cell 513 and readout particle 514, in the presence of accessory particle 515 (e.g., complement proteins). Binding of biomolecule 512 to readout cell 513 in the presence of accessory particles 515 causes readout cell 513 to lyse. Upon cell lysis, second biomolecule 516 is released and captured on a readout particle 514, a second type of readout particle that is functionalized to capture biomolecule 516, e.g., via molecules 517. Molecules 517 may be one or more types of molecule such a protein, an antibody, an enzyme, a reactive group and/or a nucleic acid. Captured biomolecule 516 is not limited to type. Rather, captured biomolecule 516 can be any molecule present in readout cell 513 such as protein, enzyme, dye, carbohydrate or nucleic acid. Binding of the second biomolecule 516 to readout particle 514 is quantified using a fluorescence assay, a colorimetric assay, a bioluminescence assay or a chemoluminescence assay. It is understood that the assay may be performed directly on readout particle 514 or indirectly in the surrounding solution, for instance if captured biomolecule 516 is an enzyme that converts a substrate into a product with different optical properties.

Figure 12:
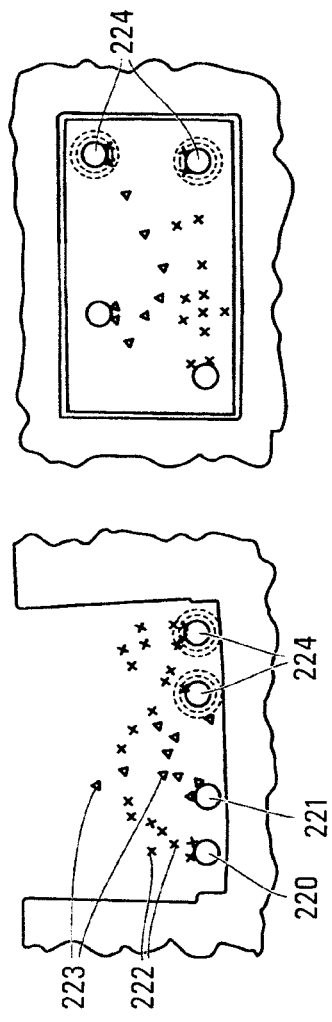
FIG. 12 shows top and cross-sectional view schematic diagrams of a method of identifying the presence of an effector cell which produces a biomolecule that induces growth of readout cells.

In another embodiment, an assay is provided to determine whether an effector cell, alone or within a cell population modulates cell growth. Specifically, the assay is used to determine whether the effector cell secretes a biomolecule, e.g., a cytokine or antibody that modulates the growth rate of readout cells. Referring to FIG. 12, the illustrated embodiment includes a cell population comprising effector cell 220 and effector cell 221 secreting biomolecules 222 and 223, respectively. The illustrated embodiment further includes a homogeneous readout cell population comprising readout cell 224. Effector cells 220 and 221 secrete biomolecules 222 and 223 which diffuse toward readout cells 224. Biomolecule 222 binds to readout cell 224 to induce growth of readout cell 224 (represented by perforated lines), whereas biomolecule 223 do not bind to readout cell 224. Microscopic imaging of the chamber is used to assess the growth of the readout cells 224 relative to cells in other chambers which are not exposed to the biomolecules.

A cell growth modulation assay can be performed using a cell population that optionally comprises one or more effector cells. As noted above, in some embodiments; not all cell populations will contain effector cells because of their rarity and/or difficulty to be enriched for in a starting population that is initially loaded onto one of the devices provided herein. The present invention allows for the identification of these rare cells by identifying cell populations that comprise one or more effector cells.

The cell growth modulation assay can also be performed with a single readout cell, or a heterogeneous readout cell population in a single chamber. However, in many instances, it is desirable to perform the cell growth modulation assay with a homogeneous readout cell population to permit a more accurate measurement of growth rate.

The cell growth modulation assay, in one embodiment, is adapted to screen for cells producing biomolecules that inhibit cell growth. In another embodiment, the method is adapted to screen for cells producing molecules that modulate, i.e., increase or decrease, proliferation rates of readout cells. Growth rate, in one embodiment, is measured by manual or automated cell count from light microscopy images, total fluorescence intensity of cell expressing a fluorescence, average fluorescence intensity of cells labeled with a dilutive dye (e.g. CFSE), nuclei staining or some other method known to those of skill in the art.

Commercially available assay to measure proliferation include the alamarBlue® Cell Viability Assay, the CellTrace™ CFSE Cell Proliferation Kit and the CellTrace™ Violet Cell Proliferation Kit (all from Life Technologies), each of which can be used with the methods and devices described herein.

Figure 13:
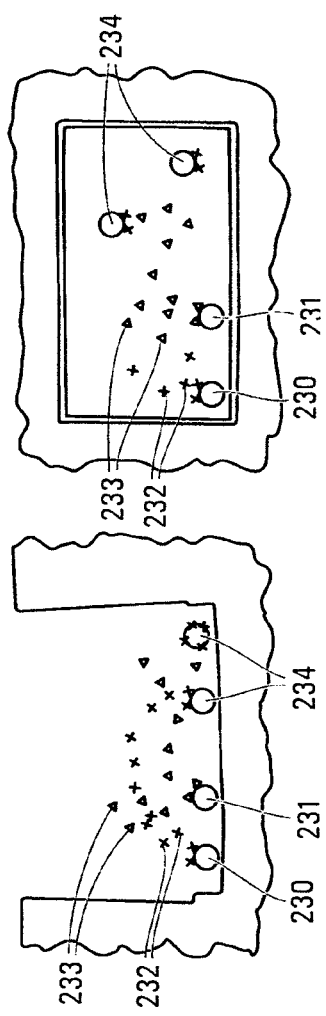
FIG. 13 shows top and cross-sectional view schematic diagrams of a method of identifying the presence of an effector cell which produces a biomolecule that stimulates readout cells to undergo apoptosis.

In another embodiment, an apoptosis functional assay is provided to select a cell population comprising one or more effector cells that induces apoptosis of another cell, i.e., a readout cell or an accessory cell. In one embodiment, the method is used to identify the presence of an effector cell that secretes a biomolecule, e.g., a cytokine or an antibody that induces apoptosis of a readout cell or accessory cell. Referring to FIG. 13, the illustrated embodiment includes a cell population comprising effector cell 230 and effector cell 231 secreting biomolecule 232 and biomolecule 233, respectively. The illustrated embodiment further includes a homogeneous readout cell population comprising readout cell 234. Effector cell 230 and effector cell 231 secrete biomolecules 232 and 233, which diffuse toward readout cells 234. Biomolecule 232 binds to readout cell 234 and induces apoptosis of readout cell 234, whereas biomolecule 233 does not bind to the readout cell. Microscopic imaging of the chamber, in one embodiment, is used to assess apoptosis using, potentially with the inclusion of stains and other markers of apoptosis that are known in the art (e.g., Annexin 5, terminal deoxynucleotidyl transferase (TdT)-mediated dUTP nick end labeling, mitochondrial membrane potential disruption, etc.). In one embodiment, cell death rather than apoptosis using commercially available dyes or kits is measured, for example with propidium iodide (PI), LIVE/DEAD® Viability/Cytotoxicity Kit (Life Technologies) or LIVE/DEAD® Cell-Mediated Cytotoxicity Kit (Life Technologies).

An apoptosis assay, in one embodiment, is performed on a cell population comprising a single effector cell, a cell population optionally comprising one or more effector cells or a cell population comprising one or more effector cells. In one embodiment, the apoptosis assay is performed with a single readout cell, or a heterogeneous readout cell population. However, in many instances, it is desirable to perform the apoptosis assay with a homogeneous readout cell population to permit a more accurate assessment of apoptosis.

Figure 14:
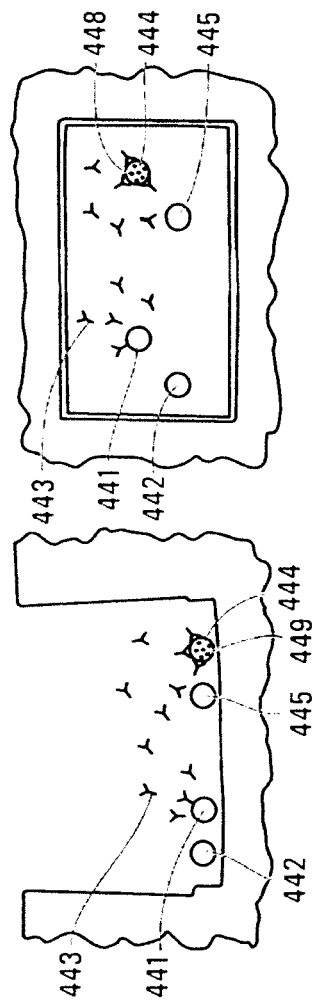
FIG. 14 shows top and cross-sectional view schematic diagrams of a method of identifying the presence of an effector cell which produces a biomolecule that stimulates autophagy in readout.

In another embodiment, the microfluidic devices provided herein are used to select an effector cell that secretes a biomolecule, e.g., a cytokine or antibody that induces autophagy of a readout cell. One embodiment of this method is shown in FIG. 14. Referring to FIG. 14, the illustrated embodiment includes a cell population comprising effector cell 441 and effector cell 442, wherein effector cell 441 secretes biomolecule 443. The illustrated embodiment further includes a heterogeneous readout cell population including first readout cell 444 displaying a target epitope 449 and second type of readout cell 445 lacking the target epitope. Effector cell 441 secretes biomolecules 443, which diffuses toward first type of readout cell 444 and second type of readout cell 445. Biomolecule 443 binds to first type of readout cell 444 and induces autophagy of first type of readout cell 444, whereas biomolecules 443 does not bind to the second type of readout cell 445. Microscopic imaging of the chamber, in one embodiment, is used to assess autophagy using cell lines engineered with autophagy reporters that are known in the art (e.g., FlowCellect™ GFP-LC3 Reporter Autophagy Assay Kit (U20S) (EMD Millipore), Premo™ Autophagy Tandem Sensor RFP-GFP-LC3B Kit (Life Technologies)).

In one embodiment, an autophagy assay is performed on a cell population comprising a single effector cell, a cell population optionally comprising one or more effector cells or a cell population comprising one or more effector cells. In one embodiment, an autophagy assay is performed with a single readout cell, or a heterogeneous readout cell population, or a homogeneous readout cell population. The assay, in one embodiment, is performed with a homogeneous readout cell population.

Figure 15:
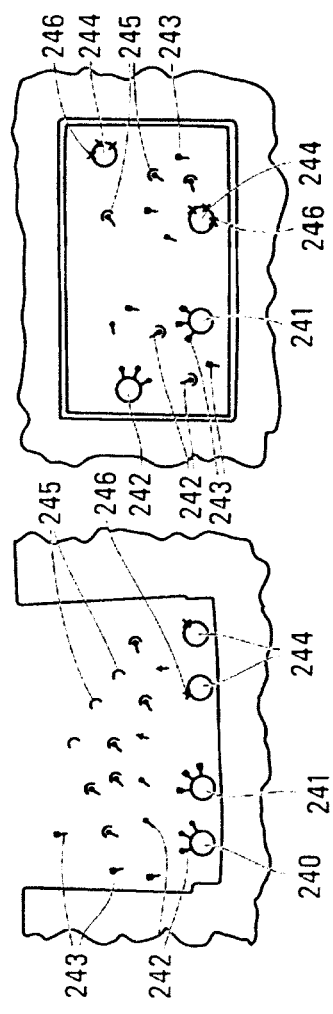
FIG. 15 shows top and cross-sectional view schematic diagrams of a method of identifying the presence of an effector cell which produces a biomolecule that neutralizes a cytokine of interest.

In another embodiment, a method is provided for identifying the presence of an effector cell or to select an effector cell that secretes a biomolecule, e.g., an antibody, that interferes with the ability of a known biomolecule, e.g., a cytokine, to induce a readout cell to undergo a response. The response is not limited by type. For example, the response in one embodiment is selected from cell death, cell proliferation, expression of a reporter, change in morphology, or some other response selected by the user of the method. One embodiment of the method is provided in FIG. 15. Referring to FIG. 15, the illustrated embodiment includes a cell population comprising effector cell 240 and effector cell 241 secreting biomolecules 242 and 243, respectively. The illustrated embodiment further includes a homogeneous readout cell population comprising readout cell 244. Effector cells 240 and 241 secrete antibodies 242 and 243, which diffuse into the medium within the chamber. The chamber is pulsed with cytokines 245, which normally have a known effect on readout cells 244. Antibodies 242 bind to cytokines 245, and thereby prevent them from binding to readout cells 244. Accordingly, the expected response is not observed, indicating that one of effector cell 240 and 241 is secreting an antibody capable of neutralizing the ability of cytokine 245 to stimulate the readout cells 244 to undergo a response.

In one embodiment, a cytokine neutralization assay is used to identify the presence of an effector cell that produces a biomolecule targeting a receptor for the cytokine, present on the readout cell. In this case, binding of an antibody, e.g., antibody 242 to receptors 246 for cytokine 245 on readout cells 244 blocks the interaction of the cytokine and the receptor, so that no response would be stimulated. The cytokine receptor, in another embodiment, is "solublized" or "stabilized," for example, is a cytokine receptor that has been engineered via the Heptares StaR® platform.

The response to the cytokine, in one embodiment, is ascertained by microscopic measurements of the associated signaling as known in the art including, but not limited to cell death, cell growth, the expression of a fluorescent reporter protein, the localization of a cellular component, a change in cellular morphology, motility, chemotaxis, cell aggregation, etc. In one embodiment, the response of chambers with effector cells are compared to chambers lacking effector cells to determine whether the response is inhibited. If a response is inhibited, the effector cells within the chamber are harvested for further analysis.

In one embodiment, a cytokine assay is performed within an individual microreactor on a cell population comprising a single effector cell, a cell population optionally comprising one or more effector cells or a cell population comprising one or more effector cells. Of course, the method can be carried out in parallel in a plurality of microchambers on a plurality of cell populations. In one embodiment, the cytokine assay is performed with a single readout cell, or a heterogeneous readout cell population. In one embodiment, the method is carried out with a homogeneous readout cell population to permit a more accurate assessment of stimulation, or rather lack thereof, of the readout cells.

Examples of commercially available cytokine-dependent or cytokine-sensitive cell lines for such assays include, but are not limited to TF-1, NR6R-3T3, CTLL-2, L929 cells, A549, HUVEC (Human Umbilical Vein Endothelial Cells), BaF3, BW5147.G.1.4.OUAR.1, (all available from ATCC), PathHunter® CHO cells (DiscoveRx) and TANGO cells (Life Technologies). A person skilled in the art will understand that primary cells (e.g., lymphocytes, monocytes) may also be used as readout cells for a cytokine assay.

In one embodiment, a signaling assay is used to identify a cell population comprising one or more effector cells that secretes a molecule (e.g., an antibody or a cytokine) that has agonist activity on a receptor of a readout cell. Upon binding to the receptor, the effect on the readout cell population may include activation of a signaling pathway visualized by expression of a fluorescent reporter, translocation of a fluorescent reporter within a cell, a change in growth rate, cell death, a change in morphology, differentiation, a change in the proteins expressed on the surface of the readout cell, etc.

Several engineered reporter cell lines are commercially available and can be used to implement such an assay. Examples include PathHunter Cells® (DiscoveRx), TANGO™ cells (Life Technologies) and EGFP reporter cells (ThermoScientific).

Figure 16:
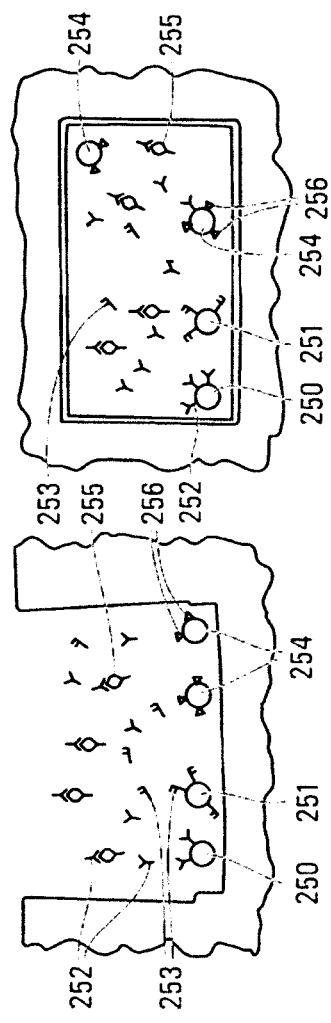
FIG. 16 shows top and cross-sectional view schematic diagrams of a method of identifying the presence of an effector cell which produces a biomolecule that inhibits the ability of a virus to infect a cell.

In one embodiment, a virus neutralization assay is carried out to identify and/or select a cell population comprising one or more effector cells that secretes a biomolecule, e.g., an antibody that interferes with the ability of a virus to infect a target readout cell or target accessory cell. One embodiment of this method is shown in FIG. 16. Referring to FIG. 16, the illustrated embodiment includes a cell population comprising effector cell 250 and effector cell 251 secreting biomolecules, e.g., antibodies 252 and 253, respectively. The illustrated embodiment further includes a homogeneous readout cell population comprising readout cell 254. Effector cells 250 and 251 secrete biomolecules, e.g., antibodies 252 and 253, which diffuse into the medium within the chamber. The chamber is then pulsed with virus 255 (accessory particle), which normally infects readout cells 254. Antibody 252 or 253 binds to virus 255, and thereby prevents the virus from binding to readout cell 254. Accordingly, the expected infection is not observed, indicating that one of effector cells 250 or 251 secretes an antibody capable of neutralizing virus 255.

A virus neutralization assay is also amenable for identifying the presence of an effector cell that produces a biomolecule which binds a receptor for the virus on the readout cell. In this case, binding of an antibody, e.g., antibody 252 to receptor 256 of virus 255 on readout cell 254 blocks the interaction of the virus and the receptor, so that no infection would be observed.

Assessment of viral infection may be done using methods known in the art. For example, the virus can be engineered to include fluorescent proteins that are expressed by the readout cell following infection, the expression of fluorescent proteins within the readout cell that are upregulated during viral infection, the secretion of proteins from a readout cell or accessory cell, which are captured and measured on readout particles that are increased during viral infection, the death of the of a readout cell or accessory cell, the change in morphology of a readout cell or accessory cell, and/or the agglutination of readout cells.

In one embodiment, within an individual microreactor, a virus neutralization assay is performed on a cell population comprising a single effector cell, a cell population optionally comprising one or more effector cells or a cell population comprising one or more effector cells. In one embodiment, the virus neutralization assay is performed with a single readout cell, or a heterogeneous readout cell population. In one embodiment, the method is carried out with a homogeneous readout cell population to permit a more accurate assessment of the stimulation, or rather lack thereof, of the readout cells to undergo the response. Of course, the method can be carried out in parallel in a plurality of microchambers on a plurality of cell populations.

For example, commercially available cell lines for virus neutralization assays are MDCK cells (ATCC) and CEM-NKR-CCR5 cells (NIH Aids Reagent Program) can be used with the methods and devices described herein.

Figure 17:
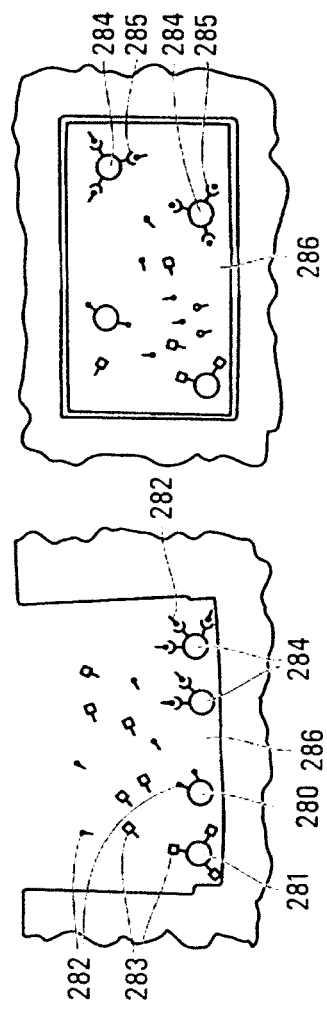
FIG. 17 shows top and cross-sectional view schematic diagrams of a method of identifying the presence of an effector cell which produces a biomolecule that inhibits the function of a target enzyme according to an embodiment of the invention.

In another embodiment, an enzyme neutralization assay is performed to determine whether an effector cell displays or secretes a biomolecule that inhibits a target enzyme. One embodiment of the method is provided in FIG. 17. Referring to FIG. 17, the illustrated embodiment includes a cell population comprising effector cell 280 and effector cell 281 secreting biomolecules, e.g., proteins 282 and 283, respectively. The illustrated embodiment further includes a homogeneous readout particle population, e.g., beads 284, to which a target enzyme 285 is conjugated. However, in another embodiment, the target enzyme 285 is linked to the surface of the device, or is soluble. Proteins 282 and 283 diffuse through the medium and protein 282 binds to target enzyme 285, thereby inhibiting its activity, whereas protein 283 does not bind to the target enzyme. Detection of the enzymatic activity, or rather lack thereof, on a substrate present in the chamber, in one embodiment, is assessed by methods known in the art including but not limited to fluorescent readouts, colorometric readouts, precipitation, etc.

In another embodiment, an enzyme neutralization assay is performed on a cell population comprising a single effector cell, a cell population optionally comprising one or more effector cells or a cell population comprising one or more effector cells, per individual chamber. In one embodiment, the enzyme neutralization assay is performed with a single readout particle in an individual chamber. In one embodiment, an enzyme neutralization assay is carried out on a plurality of cell populations to identify a cell population having a variation in a response of the assay.

Figure 18:
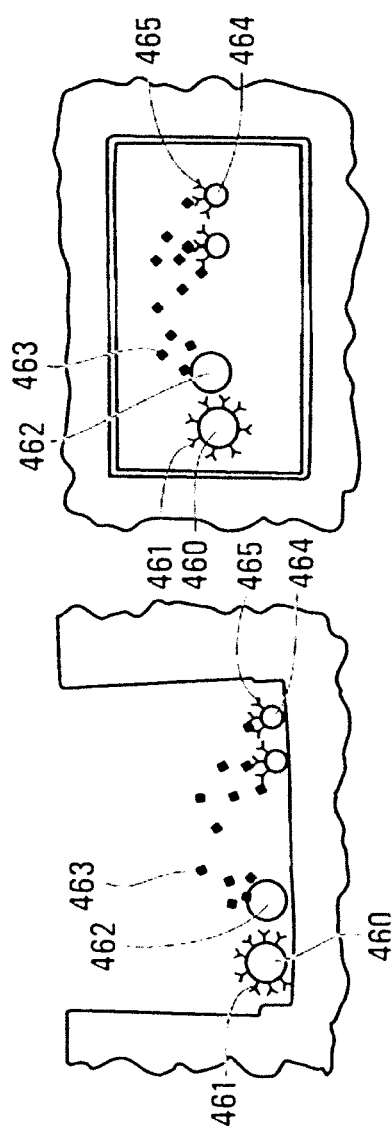
FIG. 18 shows top and cross-sectional view schematic of a method of identifying presence of an effector cell that displays a molecule that elicits the activation of a second type of effector cell, which in turn secretes molecules that have an effect on a readout particle.

In another embodiment, an assay method is provided for identifying the presence of an effector cell that displays or secretes a molecule that elicits the activation of a second type of effector particle, which in turn secretes a molecule that has an effect on a readout particle. Accordingly, in this embodiment, a cell population is provided to individual microfluidic chambers. One embodiment of this method is provided in FIG. 18. Referring to FIG. 18, the illustrated embodiment includes a cell population that includes one effector cell 460 that displays a molecule 461 on its surface (e.g., an antibody, a surface receptor, a major histocompatibility complex molecule, etc.), which activates an adjacent effector cell of different type, in this case effector cell 462, which induces the secretion of another type of molecule 463 (e.g., cytokine, antibody) that is captured by the readout particle 464. In this example, the readout particles 464 are functionalized with an antibody 465 or receptor specific to the secreted molecule 463.

In another embodiment, the effector cell, upon activation by an accessory particle, may exhibit changes in phenotype such as proliferation, viability, morphology, motility or differentiation. In this case the effector cell is also a readout particle. This effect can be caused by the accessory particles and/or by autocrine secretion of proteins by the activated effector cells.

Figure 19:
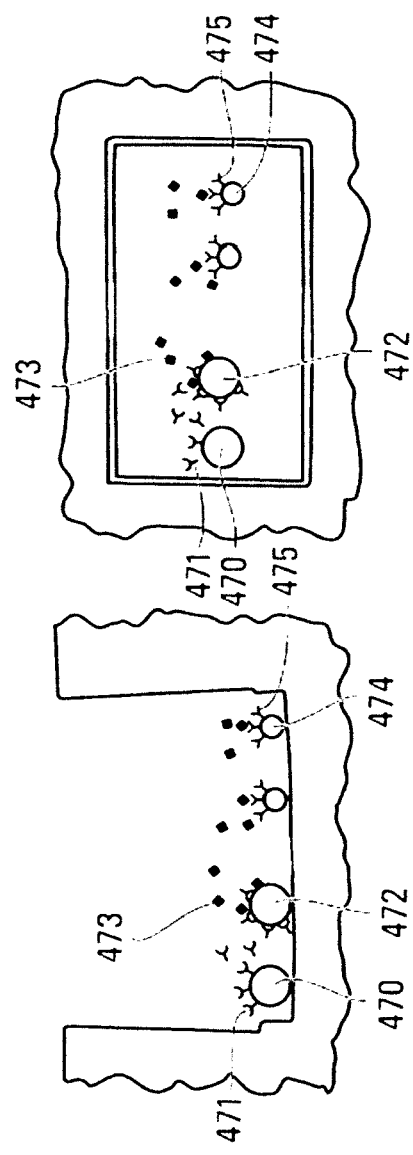
FIG. 19 shows top and cross-sectional view schematic diagrams of a method of identifying presence of an effector cell that secretes a molecule that elicits the activation of a second type of effector cell, which in turn secretes molecules that have an effect on a readout particle.

Referring to FIG. 19, the illustrated embodiment includes a cell population comprising effector cell 470 that secretes a molecule 471 (e.g., antibody, cytokine, etc.), which activates a second effector cell of different type, in this case effector cell 472. Effector cell 472, once activated, secretes another type of molecule 473 (e.g., cytokine, antibody) that is captured by readout particles 474. In this example, the readout particles 474 are functionalized with an antibody 475 or receptor specific to the secreted molecule 473.

As provided herein, monoclonal antibodies with low off-rates are detectable in the presence of a large background (in the same chamber) of monoclonal antibodies that are also specific to the same antigen but which have faster off-rates. However, affinity is also measurable with the devices and methods provided herein, and therefore, on-rate can also be measured. These measurements depend on the sensitivity of the optical system as well as the binding capacity of the capture reagents (e.g., beads). To assay for specificity, the capture reagents (readout particles) may be designed to present the epitope of interest so that it only binds antibodies with a desired specificity.

Referring to FIG. 20, the illustrated embodiment includes a homogeneous cell population secreting antibodies specific for the same antigen but with different affinities. This assay is used to identify an effector cell within a population containing at least one effector cell producing an antibody with high affinity. Effector cells 450 and 451 secrete antibodies 453 and 454 with low affinities for a target epitope (not shown) while effector cell 452 secretes antibodies 455 with higher affinity for the target epitope. Antibodies 453, 454, and 455 are captured by a homogeneous readout particle population comprising readout bead 456. The readout beads are then incubated with a fluorescently labeled antigen (not shown), which binds to all antibodies. Upon washing with a non-labeled antigen (not shown), the fluorescently labeled antigen remains only if readout beads display high-affinity antibody 455 on their surfaces.

Referring to FIG. 21, another illustrated embodiment includes effector cells 260 secreting biomolecules, e.g., antibody 261. The illustrated embodiment further includes a heterogeneous readout particle population that optically distinguishable readout particles, e.g., beads 262 and 263 displaying different target epitopes 264 and 265, respectively. Antibody 261 diffuses in the chamber, where it binds to epitope 264, but not 265. Preferential binding of antibody 261 to epitope 264 in one embodiment, is observed in terms of fluorescence of bead 262 but not bead 263.

In the illustrated embodiment, beads 262 and 263 are optically distinguishable by shape in order to assess cross-reactivity. However, readout particles are also be distinguishable by other means, e.g., one or more characteristics such as fluorescence labeling (including different fluorescence wavelengths), varying levels of fluorescence intensity (e.g., using Starfire™ beads with different fluorescence intensities, morphology, size, surface staining and location in the microfluidic chamber).

In one embodiment, beads 262 and 263 are optically distinguishable when segregated into separate readout zones, e.g., by a cell fence. Alternatively, different color fluorophores can be used to optically distinguish readout beads.

Alternatively, specificity may be measured by inclusion of another antibody that competes with the secreted antibody to bind the target epitope. For instance, in one embodiment the presence a secreted antibody bound to a readout particle displaying the antigen is identified with a fluorescently labeled secondary antibody. The subsequent addition of a non-labeled competing antibody generated from a different host and known to bind a known target epitope on the antigen results in decreased fluorescence due to displacement of the secreted antibody only if the secreted antibody is bound to the same target epitope as the competing antibody. Alternatively, specificity is measured by adding a mixture of various antigens that compete with binding of the secreted antibody to the target epitope if the secreted antibody has low specificity. Alternatively, specificity is measured by capturing secreted antibody on a bead and then using differentially labeled antigens to assess the binding properties of the secreted antibody.

The specificity measurements described herein, when conducted on a cell population that includes two or more effector cells that secrete antibody that bind one of the targets, are inherently polyclonal measurements.

Figure 22:
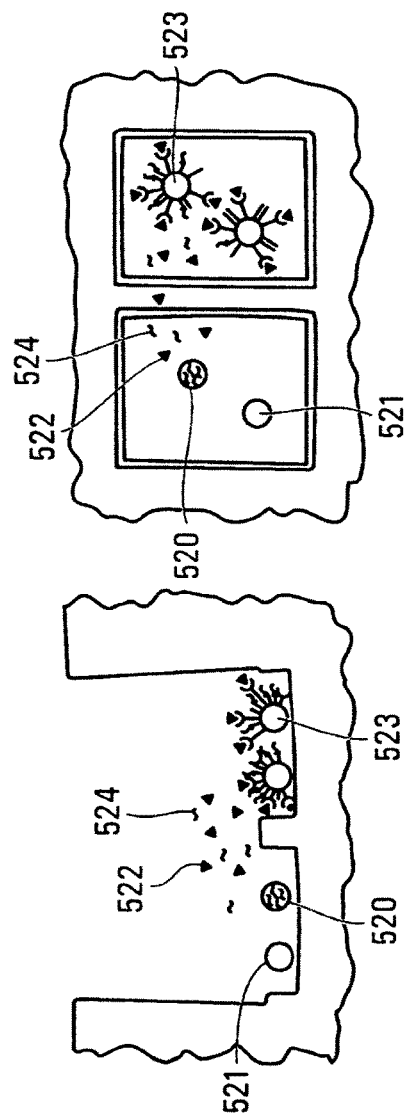
FIG. 22 shows top and cross-sectional view schematic diagrams of a method of simultaneously identifying the presence of a cell secreting a biomolecule in a homogeneous or heterogeneous population of effector cells and analyzing one or more intracellular compounds affected by the molecule.

In various embodiments of the invention, a method for identifying the presence of an effector cell secreting a biomolecule is coupled with the analysis of the presence or absence of one or more intracellular compounds of the effector cell. Referring to FIG. 22, a cell population comprising at least one effector cell type 520 that secretes a biomolecule of interest 522 (e.g., an antibody, or a cytokine) and another effector cell type 521 that does not secrete the biomolecule of interest, is incubated in the presence of a readout particle population comprising readout particle 523 functionalized to capture the biomolecule of interest. After an incubation period, the cell population including effector cell types 520 and 521 is lysed to release the intracellular contents of the cells in the population. Readout particles 523 are also functionalized to capture an intracellular biomolecule of interest 524 (e.g., a nucleic acid, a protein, an antibody, etc.). Cell lysis can be achieved by different methods known to those of skill in the art.

In one embodiment, methods are provided for identifying polyclonal mixtures of secreted biomolecules with desirable binding properties. Assays may be performed as with heterogeneous mixtures of effector cells producing antibodies with known affinities for a target epitope, target molecule, or target cell type. Binding of the target in the context of the mixture can then be compared to binding of the target in the context of the individual effector cells alone to determine, for example, if mixtures provide enhanced effects.

Multifunctional analysis that combines the binding and/or functional assays described herein may be performed by having multiple readout regions, multiple effector regions, multiple readout particle types, or some combination thereof. For example, perfusion steps can be carried out between extracellular effect assays to exchange reagents for different functional experiments.

Figure 23:
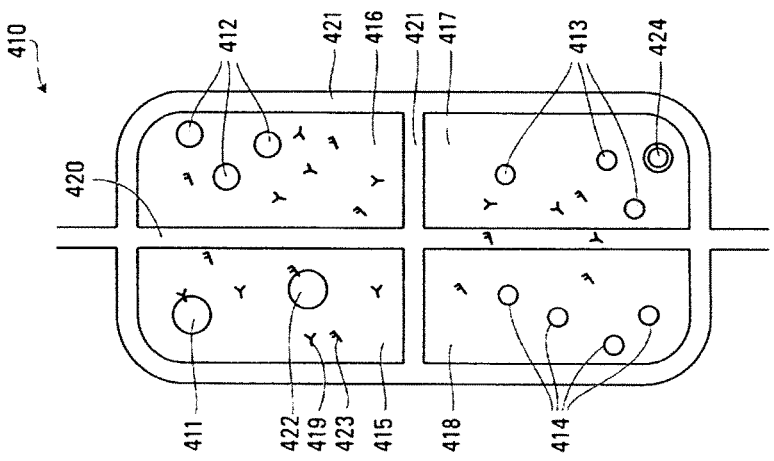
FIG. 23 is a top view schematic diagram of a method of evaluating the extracellular effect of an effector cell on multiple sets of readout particles simultaneously.

One embodiment of a multifunctional assay is provided in FIG. 23. Referring to FIG. 23, a microfluidic chamber for simultaneously evaluating the extracellular effect of an effector cell on three subsets of readout particles is shown generally at 410. Microfluidic includes cell fences 420 and 421 which divide the chamber into four zones. While cell fences 420 and 421 are depicted in this example as being at right angles to each other, a person skilled in the art will understand that the precise positioning of the fence could vary so long as four zones are created. Moreover, a person skilled in the art will understand that cell fences are not necessary to carry out a multifunctional assay (either serially or in parallel). In one embodiment, a structure other than a cell fence is included to result in the creation zones, so long as the different zones are addressable in terms of the delivery of cell populations and readout particles. In another embodiment, the multifunctional assay is carried out without a cell fence or structure. Rather, each assay is performed in the chamber simultaneously or serially, for example, with fluorescent molecules that emit light at different wavelengths.

In the embodiment depicted in FIG. 23, effector cells 411 and 422 secreting antibodies 419 and 423, respectively, are delivered to the upper left region of chamber 410, thereby defining effector zone 415. Readout particles 412, 413, and 414 are delivered to the remaining regions, thereby defining readout zones 416, 417, and 418, respectively. Readout particles 412, 413, and 414, in one embodiment, make up a heterogeneous population of readout particles. For example, in one embodiment, readout particles 412 and 414 are beads of different sizes displaying different epitopes of the same antigen, and readout particles 413 are cells displaying the antigen in the presence of a natural killer cell 424. Accordingly, the presence or absence of an effector cell that can selectively bind a given epitope and induce the killing of readout cells by natural killer cells can be evaluated simultaneously in a single chamber.

Alternatively, readout particles 412, 413, and 414 are identical and allow for multiple independent measurements of an extracellular effect conferred by a single set of effector cells in a single chamber. Alternatively, particles 412 and 414 are distinguishable and the assay is performed serially.

In one embodiment, the presence of one or more extracellular effects is analyzed. Depending on the effect, one of skill in the art will recognize that the presence or the absence of the combined extracellular effects may be desired. Similarly, it is also possible that the desired properties include the presence of one or more types of extracellular effect and the absence of a different type of extracellular effect. For instance, in one embodiment, a multifunctional assay is used to identify an effector cell secreting an antibody that binds to a receptor epitope on a readout cell but that does not induce the activation of the corresponding signaling pathway.

In one embodiment, a multifunctional assay is carried out in a chamber comprising multiple effector zones, for example, by introducing different effector cells, or combinations of effector cells, into the different regions. For example, in one embodiment, different cell populations producing antibodies of known affinity for a target antigen are introduced into different effector zones of a chamber. Binding of the target in the context of the mixtures can then be compared to binding of the target in the context of the individual effector cells alone. Accordingly, such use of multiple effector zones allows for the screening of multiple combinations in a single chamber.

In one embodiment of the assays provided herein, after readout particles are incubated with a cell population in a microfluidic chamber, a fluorescent measurement is taken to determine if a cell within the population demonstrates an extracellular effect. In this embodiment, the readout particle population is fluorescently labeled and a change in fluorescence is correlated with the presence and/or size of the extracellular effect. The readout particle population can be fluorescently labeled directly or indirectly. In some embodiments, as provided throughout, accessory particles (e.g., accessory cells) are provided to a chamber to aid in facilitating the fluorescent readout. As will be appreciated by one of skill in the art, care is taken to design assays that provide readout particles and effector cells in one focal plane, to allow for accurate imaging and fluorescent measurement.

In one embodiment, readout particle responses are monitored using automated high resolution microscopy. For example, imaging can be monitored by using a 20× (0.4 N.A.) objective on an Axiovert 200 (Zeiss) or DMIRE2 (Leica) motorized inverted microscope. Using the automated microscopy system provided herein allows for complete imaging of a 4000 chamber array, including 1 brightfield and 3 fluorescent channels, in approximately 30 minutes. This platform can be adapted to various chip designs, as described in Lecault et al. (2011). *Nature Methods* 8, pp. 581-586, incorporated by reference herein in its entirety for all purposes. Importantly, the imaging methods used herein achieve a sufficient signal in effect positive chambers while minimizing photodamage to cells.

Figure 73:
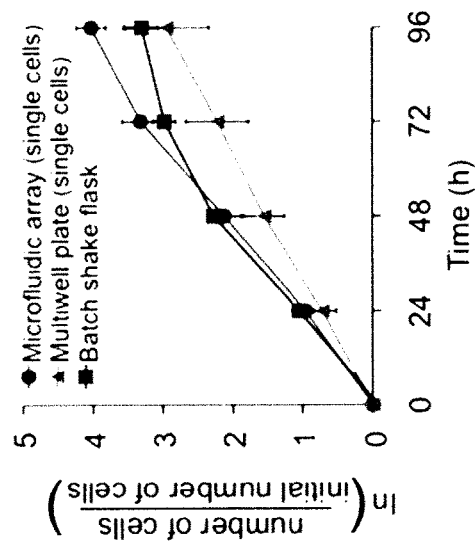
FIG. 73 demonstrate robust cell culture of CHO antibody-secreting cells in the microfluidic array compared to batch shake flasks and single cells seeded in 96-multiwell plates.

In one embodiment, the effector cell assays provided herein benefit from long-term cell culture, and therefore require that the effector cells maintained in the device are viable and healthy cells. It will be appreciated that in embodiments where readout cells or accessory cells are used in an effector cell assay, that they too be maintained in a healthy state and are viable and healthy. The fluidic architectures provided herein enable careful and precise control of medium conditions to maintain effector and readout cell viability so that functional assays can be carried out. For example, some cell types require autocrine or paracrine factors that depend on the accumulation of secreted products. For instance, CHO cell growth rates are highly dependent on seeding density. Confining a single CHO cell in 4-nL chamber corresponds to a seeding density of 250,000 cells/ml, which is comparable to conventional macroscale cultures. As shown in FIG. 73, single CHO cells have a higher growth rate in a microfluidic device than when plated in a multiwell plate. Because they thrive at high seeding densities, CHO cells may not require perfusion for multiple days. However, other cell types, in particular those that are cytokine-dependent (e.g. ND13 cells, BaF3 cells, hematopoietic stem cells), typically do not reach high concentrations in macroscale culture and may require frequent feeding in the microfluidic device to prevent cytokine depletion. The cytokines may be added to the medium or produced by feeder cells. For instance, bone marrow derived stromal cells and eosinophils have been shown to support the survival of plasma cells because of their production of IL-6 and other factors (Wols et al., (2002), *Journal of Immunology* 169, pp. 4213-21; Chu et al. (2011), *Nature Immunology*, 2, pp. 151-159, incorporated by reference herein in their entireties). In this case the perfusion frequency can be modulated to allow sufficient accumulation of paracrine factors while preventing nutrient depletion.

In one aspect, the present invention provides a method for determining whether a cell population optionally comprising one or more effector cells exerts an extracellular effect a readout particle (e.g., a cell comprising a cell surface receptor). The effector cell can be present in a heterogeneous cell population, a homogeneous population, or as a single cell. In one embodiment, the effector cell is an antibody secreting cell. The one or more extracellular properties, in one embodiment, comprise an extracellular effect on a readout particle, for example, the inhibition (antagonism) or activation (agonism) of a cell surface receptor (e.g., the agonist and/or antagonist properties of an antibody secreted by an antibody secreting cell) on a readout cell. In a further embodiment, the extracellular effect is an agonist or antagonist effect on a transmembrane protein, which in a further embodiment is a G protein coupled receptor (GPCR), a receptor tyrosine kinase (RTK), an ion channel or an ABC transporter. In a further embodiment, the receptor is a cytokine receptor. An extracellular effect on other metabotropic receptors besides GPCRs and RTKs can be assessed, for example, an extracellular effect on a guanylyl cyclase receptor can be assessed incubating a cell population with a readout cell population expressing the guanylyl cyclase receptor.

In embodiments where a readout cell is used, the readout cell can be alive or fixed. With respect to a fixed readout cell, the extracellular effect in one embodiment, is an effect on an intracellular protein of the fixed readout cell. Extracellular effects can also be measured on extracellular proteins of an alive or fixed readout cell, or a secreted protein of an alive readout cell.

In another embodiment, a readout cell expresses one of the following types of cell receptors, and the extracellular effect assay measures binding, agonism or antagonism of the cell receptor: receptor serine/threonine kinase, histidine-kinase associated receptor.

In embodiments where a particular receptor (e.g., receptor serine/threonine kinase, histidine-kinase associated receptor or GPCR) is an orphan receptor, that is, the ligand for activating the particular receptor is unknown, the methods provided herein allow for the discovery of a ligand for the particular orphan receptor by performing an extracellular assay on readout cells expressing the orphan receptor, and identifying a cell population or subpopulations comprising an effector cell having a variation of an extracellular effect on the readout cell expressing the orphan receptor.

In one embodiment, the cell surface protein is a transmembrane ion channel. In a further embodiment, the ion channel is a ligand gated ion channel and the extracellular effect measured in the microfluidic assay is modulation of the ion channel gating, for example, opening of the ion channel by agonist binding or closing/blocking of the ion channel by antagonist binding. The antagonist or agonist can be for example, a biomolecule (e.g., antibody) secreted by one or more effector cells in the heterogeneous population of cells comprising one or more effector cells. Extracellular assays described herein can be used to measure the extracellular effect of an effector cell on a cell expressing a ligand gated ion channel in the Cys-loop superfamily, an ionotropic glutamate receptor and/or an ATP gated ion channel. Specific examples of anionic cys-loop ion gated channels include the $GABA_A$ receptor and the glycine receptor (GlyR). Specific examples of cationic cys-loop ion gated channels include the serotonin (5-HT) receptor, nicotinic acetylcholine (nAChR) and the zinc-activated ion channel. One or more of the aforementioned channels can be expressed by a readout cell to determine whether an effector cell has an extracellular effect on the respective cell by agonizing or antagonizing the ion channel. Ion flux measurements typically occur in short periods of time (i.e., seconds) and require precise fluidic control for their implementation. Examples of commercially available ion channel assays include Fluo-4-Direct Calcium Assay Kit (Life Technologies), FLIPR Membrane Potential Assay Kit (Molecular Devices). Ion-channel expressing cell lines are also commercially available (e.g. PrecisION™ cell lines, EMD Millipore).

In one embodiment, the cell surface protein is an ATP-binding cassette (ABC) transporter, and the extracellular effect measured is the transport of a substrate across a membrane. The readout particles can be membrane vesicles derived from cells expressing the protein (e.g., GenoMembrane ABC Transporter Vesicles (Life Technologies)), which can be immobilized on beads. For instance, the ABC transporter could be a permeability glycoprotein (multidrug resistant protein) and the effect can be measured by the fluorescence intensity of calcein in readout cells. The Vybrant™ Multidrug Resistance Assay Kit (Molecular Probes) is commercially available to implement such an assay.

An extracellular effect can also be assessed on a readout cell expressing an ionotropic glutamate receptor such as the AMPA receptor (class GluA), kainite receptor (class GluK) or NMDA receptor (class GluN). Similarly, an extracellular effect can also be assessed on a readout cell expressing an ATP gated channel or a phosphatidylinositol 4-5-bisphosphate (PIP2)-gated channel.

As provided throughout, the present invention provides a method of identifying a cell population displaying a variation in an extracellular effect. In one embodiment, the method comprises, retaining a plurality of individual cell populations in separate microfluidic chambers, wherein at least one of the individual cell populations comprises one or more effector cells and the contents of the separate microfluidic chambers further comprise a readout particle population comprising one or more readout particles, incubating the individual cell populations and the readout particle population within the microfluidic chambers, assaying the individual cell populations for the presence of the extracellular effect, wherein the readout particle population or subpopulation thereof provides a readout of the extracellular effect. In one embodiment, the extracellular effect is an effect on a receptor tyrosine kinase (RTK), for example, binding to the RTK, antagonism of the RTK, or agonism of the RTK. RTKs are high affinity cell surface receptors for many polypeptide growth factors, cytokines and hormones. To date, there have been approximately sixty receptor kinase proteins identified in the human genome (Robinson et al. (2000). *Oncogene* 19, pp. 5548-5557, incorporated by reference in its entirety for all purposes). RTKs have been shown to regulate cellular processes and to have a role in development and progression of many types of cancer (Zwick et al. (2001). *Endocr. Relat. Cancer* 8, pp. 161-173, incorporated by reference in its entirety for all purposes).

Where the extracellular effect is an effect on an RTK, the present invention is not limited to a specific RTK class or member. Approximately twenty different RTK classes have been identified, and extracellular effects on members of any one of these classes can be screened for with the methods and devices provided herein. Table 2 provides different RTK classes and representative members of each class, each amenable for use herein when expressed on a readout particle, e.g., readout cell or vesicle. In one embodiment, a method is provided herein for screening a plurality of cell populations in a parallel manner in order to identify one or more populations comprising an effector cell having an extracellular effect on an RTK of one of the subclasses provided in Table 2. In one embodiment, the method further comprises isolating the one or more cell populations comprising the ASC having the extracellular effect to provide an isolated cell population and further subjecting the isolated subpopulation to one or more additional extracellular effect assay, at limiting dilution, to identify the ASC having the extracellular effect. The additional extracellular effect assay can be carried out via a microfluidic method provided herein, or a benchtop assay. Alternatively, once a cell population is identified that has a cell exhibiting an extracellular effect on the RTK, the cell population is recovered, lysed and the nucleic acid amplified. In a further embodiment, the nucleic acid is one or more antibody genes.

In one embodiment, the present invention relates to the identification of a cell population comprising an effector cell that antagonizes or agonizes an RTK (i.e., the extracellular effect), for example, via a secretion product, e.g., a monoclonal antibody. The effector cell is present a lone effector cell, or is present in a cell population comprising one or more effector cells.

TABLE 2

RTK classes and representative members of each class.

| RTK class | Representative members | Representative Ligands | Cellular Process(es) |
|---|---|---|---|
| RTK class I (epidermal growth factor receptor (EGFR) family, also known as the ErbB family) | ErbB-1 (epidermal growth factor receptor) | epidermal growth factor (EGF) transforming growth factor α (TGF-α) heparin-binding EGF-like growth factor (HB-EGF) amphiregulin (AREG) betacellulin epigen epiregulin | overexpression implicated in turmorigenesis |
| | ErbB-2 (human epidermal growth factor receptor 2 (HER2)/ cluster of differentiation 340 (CD340)/ proto-oncogene Neu) | Monoclonal antibody trastuzumab (Herceptin) | turmorigenesis (e.g., breast, ovarian, stomach, uterine) |
| | ErbB-3 (human epidermal growth factor receptor 2 (HER3)) | Neuregulin 1 Proliferation associated protein 2G4 (PA2G4) (EBP1 or ErbB3 binding protein 1) Phosphatidylinositol 3 kinase regulatory subunit alpha (PIK3R1) Regulator of G protein signaling 4 (RGP4) | Proliferation and differentiation Oncogenesis (overexpression) |
| | ErbB-4 (human epidermal growth factor receptor 2 (HER4)) | heparin-binding EGF-like growth factor (HB-EGF) betacellulin epiregulin Neuregulin 1 Neuregulin 2 Neuregulin 3 Neuregulin 4 | Mutations in the RTK have been associated with cancer |
| RTK class II (Insulin receptor family) | Insulin receptor | Insulin insulin-like growth factor 1 (IGF-1)/ somatomedin C insulin-like growth factor 2 (IGF-2) | inducing glucose uptake |
| RTK class III (Platelet derived growth factor (PDGF) receptor family) | PDGFRα | PDGF A/B/C and D | Fibrosis |
| | PDGFRβ | PDGF A/B/C and D | cancer |
| | Mast/stem cell growth factor receptor (SCFR)/c-Kit/CD117 | Stem cell factor (SCF)/c-kit ligand/steel factor | Oncogenesis Cell survival, proliferation, differentiation |
| | Colony stimulating factor 1 receptor/(CD 115)/macrophage colony-stimulating factor receptor (M-CSFR) | Colony stimulating factor 1 | Production, differentiation and function of macrophages |
| | Cluster of differentiation antigen 135 (CD 135)/ Fms-like tyrosine kinase 3 (FLT-3) | Flt3 ligand (FLT3L) | Expressed on surface of many hematopoietic progenitor cells Mutated in acute myeloid leukemia Cell survival Proliferation differentiation |
| RTK class IV (FGF receptor family) | Fibroblast growth factor receptor-1 (CD331) Fibroblast growth factor receptor-2 (CD332) | Fibroblast growth factor 1-10 | Wound healing Embryonic development angiogenesis |

TABLE 2-continued

RTK classes and representative members of each class.

| RTK class | Representative members | Representative Ligands | Cellular Process(es) |
|---|---|---|---|
| | Fibroblast growth factor receptor-3 (CD333)<br>Fibroblast growth factor receptor-4 (CD334)<br>Fibroblast growth factor receptor-6 | | |
| RTK class V<br>(VEGF receptor family)<br>(membrane bound or soluble depending on alternative splicing) | VEGFR1<br><br>VEGFR2<br><br><br><br>VEGFR3 | VEGF-A<br>VEGF-B<br>VEGF-A<br>VEGF-C<br>VEGF-D<br>VEGF-E<br>VEGF-C<br>VEGF-D | Mitogenesis<br><br>Cell migration<br>Vasculogenesis<br>angiogenesis |
| RTK class VI<br>(Hepatocyte growth factor receptor family) | Hepatocyte growth factor receptor (GHFR) (encoded by MET or MNNG HOS transforming gene). | Hepatocyte growth factor | Deregulated in certain malignancies, leads to angiogenesis<br>Stem cells and progenitor cells express<br>Mitogenesis, morphogenesis |
| RTK class VII<br>(Trk receptor family) | Tropomyosin-receptor kinases (Trk)<br>TrkA<br>TrkB<br>TrkC | Neurotrophins<br>Nerve growth factor (TrkA)<br>Brain-derived neurotrophic factor (BDNF) (TrkB)<br>Neurotrophin-3 (NT3) (TrkC) | Regulate synaptic strength and plasticity in the mammalian nervous system |
| RTK class VIII<br>(Ephrin (Eph) receptor family) | EphA<br>(1, 2, 3, 4, 5, 6, 7, 8, 9, 10)<br><br>EphB (1, 2, 3, 4, 5, 6) | Ephrin-A (Ephrin-A1-5)<br><br><br>Ephrin-B (1-4 and ephrin-B6) | Embryonic development<br>Axon guidance<br><br>Formation of tissue boundaries<br>Retinopic mapping<br>Cell migration<br>Cell segmentation<br>Angiogenesis<br>Cancer |
| RTK class IX<br>(AXL receptor family) | Tyrosine-protein kinase receptor UFO (AXL) | Tensin-like C1 domain containing phosphatase (TENC1) | epithelial-to-mesenchymal transition-induced regulator of breast cancer metastasis<br>Regulation of cell migration |
| RTK class X<br>(Leukocyte receptor tyrosine kinase (LTK) family) | Leukocyte receptor tyrosine kinase (LTK) | Insulin receptor substrate 1 (IRS-1)<br>Src homology 2 domain containing protein (Shc)<br>Phosphatidylinositol 3-kinase regulatory subunit alpha (PIK3R1) | Apoptosis<br>Cell growth and differentiation |
| RTK class XI<br>(TIE receptor family) | Tyrosine kinase with immunoglobulin-like and EGF-like domains (TIE) 1<br>TIE 2 | Angiopoietin 1 (Tie2 agonist)<br>Angiopoietin 2 (Tie2 antagonist)<br>Angiopoietin 3 (Tie2 antagonist)<br>Angiopoietin 4 (Tie2 agonist) | Promotion of angiogenesis<br>TIE1 has a proinflammatory effect and may play a role in atherosclerosis (Chan et al. (2008). Biochem. Biophys. Res. Commun. 371, pp. 475-479. |
| RTK class XII<br>(Receptor typrosine kinase-like orphan receptors (ROR) family) | ROR-1 (neurotrophic tyrosine kinase, receptor-related 1 (NTRKR1)<br>ROR-2 | Wnt ligands (ROR-2) | ROR-1 modulates neurite growth in the central nervous system. |
| RTK class XIII<br>(discoidin domain receptor (DDR) family) | DDR-1 (CD167a)<br>DDR-2 | Various types of collagen | DDR-1 is overexpressed in breast, ovarian, esophageal and pediatric brain tumors |
| RTK class XIV<br>(RET receptor family) | Rearranged during transfection (RET) proto-oncogene<br>3 different isoforms (51, 43, 9) | Glial cell line-derived nuerotrophic factor (GDNF) family ligands | Loss of function associated with Hirschsprung's disease<br>Gain of function mutations associated with various types of cancer (e.g., medullary thyroid carcinoma, multiple endocrine neoplasias type 2A and 2D) |
| RTK class XV<br>(KLG receptor family) | Tyrosine-protein kinase-like 7 (PTK7)/CCK-4 | No ligand has been identified | Development<br>Oncogenesis (colon cancer, melanoma, breast cancer, acute myeloid leukemia)<br>Wnt pathway regulation<br>Angiogenesis |
| RTK class XVI<br>(Related to receptor tyrosine kinase(RYK) receptor family) | RYK receptor (different isoforms due to alternative splicing) | Wnt ligands | Stimulating Wnt signaling pathways such as regulation of axon pathfinding |

TABLE 2-continued

RTK classes and representative members of each class.

| RTK class | Representative members | Representative Ligands | Cellular Process(es) |
| --- | --- | --- | --- |
| RTK class XVII (Muscle-Specific kinase (MuSK) receptor family) | Muscle-Specific kinase (MuSK) receptor | Agrin (nerve-derived proteoglycan) | Formation of the neuromuscular junction |

In one embodiment, the RTK is a platelet derived growth factor receptor (PDGFR), e.g., PDGFRα. PDGFs are a family of soluble growth factors (A, B, C, and D) that combine to form a variety of homo- and hetero-dimers. These dimers are recognized by two closely related receptors, PDGFRα and PDGFRβ, with different specificities. In particular, PDGF-α binds selectively to PDGFRα and has been shown to drive pathological mesenchymal responses in fibrotic diseases, including pulmonary fibrosis, liver cirrhosis, scleroderma, glomerulosclerosis, and cardiac fibrosis (see Andrae et al. (2008). *Genes Dev.* 22, pp. 1276-1312, incorporated by reference herein in its entirety). It has also been demonstrated that constitutive activation of PDGFRα in mice leads to progressive fibrosis in multiple organs (Olson et al. (2009). *Dev. Cell* 16, pp. 303-313, incorporated by reference herein in its entirety). Thus therapies that inhibit PDGFRα have high potential for the treatment of fibrosis, a condition that complicates up to 40% of diseases, and represents a huge unmet medical problem in the aging population. Although antibodies (Imatinib and Nilotinib) have been explored as inhibitors of PDGFRα, each has significant off-target effects on other central RTKs, including c-kit and Flt-3, resulting in numerous side effects. Thus, while Imatinib and Nilotinib can effectively inhibit PDGFRα and PDGFRβ, their side effects make them unacceptable in the treatment of fibrotic diseases, highlighting the potential for highly specific antibody inhibitors. The present invention overcomes this problem by providing in one embodiment, antibodies with greater PDGFRα specificity, as compared to Imatinib and Nilotinib.

PDGFRα has been previously established as a target for the treatment of fibrosis. Two anti-human PDGFRα mAb antagonists entering early clinical trials for the treatment of cancer are in development (see, e.g., Shah et al (2010). *Cancer* 116, pp. 1018-1026, incorporated by reference herein in its entirety). The methods provided herein facilitate the identification of an effector cell secretion product that binds to the PDGFRα. In a further embodiment, the secretion product blocks the activity of both human and murine PDGFRα in both cancer and fibrosis models.

One embodiment of the effector cell assay to determine whether an effector cell secretion product binds to PDGFRα is based on the use of suspension cell lines (e.g., 32D and Ba/F3) that are strictly dependent on the cytokine IL-3 for survival and growth, but can be cured of this "IL-3 addiction" through the expression and activation of nearly any tyrosine kinase. This approach was first used by Dailey and Baltimore to evaluate the BCR-ABL fusion oncogene and has been used extensively for high-throughput screening of small molecule tyrosine kinase inhibitors (See, e.g., Warmuth et al. (2007). *Curr. Opin. Oncology* 19, pp. 55-60; Daley and Baltimore (1988). *Proc. Natl. Acad. Sci. U.S.A.* 85, pp. 9312-9316, each incorporated by reference in their entireties for all purposes). To monitor signaling, PDGFRα and PDGFRβ (both human and mouse forms) are expressed in 32D cells (readout cells), a murine hematopoietic cell line that does not naturally express either receptor. This allows for separation of each pathway, something that is otherwise difficult since both receptors are often co-expressed. Expression of human PDGFRα/β in 32D cells has been previously confirmed to give a functional PDGF-induced mitogenic response (Matsui et al. (1989). *Proc. Natl. Acad. Sci. U.S.A.* 86, pp. 8314-8318, incorporated by reference in its entirety). In the absence of IL-3, 32D cells do not divide at all, but PDGF stimulation of the cells expressing the RTK relieves the requirement for IL-3 and gives a rapid mitogenic response that is detectable by microscopy. The detectable response, in one embodiment, is cell proliferation, a morphological change, increased motility/chemotaxis, or cell death/apoptosis in the presence of an antagonist. An optical multiplexing method, in one embodiment, is used to simultaneously measure the inhibition/activation of both PDGFRα and PDGFRβ responses in one of the devices provided herein. In another embodiment, inhibition/activation of both PDGFRα and PDGFRβ responses in one of the devices provided herein is measured by two extracellular assays, carried out serially in the same microfluidic chamber.

Full length cDNA for human/mouse PDGFRα and PDGFRβ (Sino Biological), in one embodiment, is expressed in 32D cells (ATCC; CRL-11346) using modified pCMV expression vectors that also include an IRES sequence with either GFP or RFP, thereby making two types of "readout cells," each distinguishable by fluorescent imaging. The readout cells are characterized to optimize medium and feeding conditions, determine the dose response to PDGF ligand, and to characterize the morphology and kinetics of response. The use of suspension cells (such as 32D or Ba/F3) provides the advantage that single cells are easily identified by image analysis, and are also physically smaller (in projected area) than adherent cells so that a single chamber can accommodate ≥100 readout cells before reaching confluence. In another embodiment, instead of 32D cells, Ba/F3 cells, another IL-3 dependent mouse cell line with similar properties to 32D are used as readout cells. Both 32D and Ba/F3 cells are derived from bone marrow, grow well in medium optimized for ASCs, and also secrete IL-6 which is a critical growth factor for the maintenance of ASCs (see, e.g., Cassese et al. (2003). *J. Immunol.* 171, pp. 1684-1690, incorporated by reference in its entirety herein).

Preclinical models for evaluating the role of PDGFR developed. Specifically, two models of cardiac fibrosis are provided herein. The first is based on ischemic damage (isoproterenol-induced cardiac damage; ICD) and the second is based on coronary artery ligation-induced myocardial infarction (MI). Upon damage, the fibrotic response is initiated by the rapid expansion of PDGFRα+/Sca1+ positive progenitors, accounting for over 50% of the cells proliferating in response to damage followed by differentiation of these progeny into matrix producing PDGFRα low/Sca1 low myofibroblasts. Gene expression by RT-qPCR demonstrates expression of multiple markers related to fibrotic matrix deposition, including α-smooth muscle actin (αSMA) and collagen type I (Col1), which are detectable in (Sca1+) progenitors, but are substantially up-regulated in the differentiated population. In one embodiment, a cell population is identified that comprises an effector cell that secretes a monoclonal antibody that attenuates progenitor expansion leading to reduced fibrosis. This extracellular effect assay is carried out by monitoring two independent markers: early proliferation of Sca1+/PDGFRα+ progenitors cells and Col1-driven GFP. Specifically, following MI, fibrotic responses are characterized by GFP expression first in PDGFRα+/Sca1+ progenitors, and later, with increased intensity, in the emerging myofibroblast population.

The present invention provides methods and devices for screening a plurality of cell populations in a parallel manner to identify one or more of the cell populations having an extracellular effect, or a variation in an extracellular effect as compared to another population in the plurality. The identified cell population comprises one or more effector cells that are responsible for the extracellular effect. The extracellular effect, for example, is an extracellular effect on a GPCR, e.g., GPCR binding, agonism or antagonism. As described herein, the extracellular effect need not be attributable to every cell in the population, or even multiple cells. Rather, the methods provided herein allow for the detection of an extracellular effect of a single effector cell, when the effector cell is present in a heterogeneous population comprising tens to hundreds of cells (e.g., from about 10 to about 500 cells, or from about 10 to about 100 cells), or comprising from about 2 to about 100 cells, e.g., from about 2 to about 10 cells.

GPCRs are a superfamily of seven transmembrane receptors that includes over 800 members in the human genome. Each GPCR has its amino terminus located on the extracellular face of the cell and the C-terminal tail facing the cytosol. On the inside of the cell GPCRs bind to heterotrimeric G-proteins. Upon agonist binding, the GPCR undergoes a conformational change that leads to activation of the associated G-protein. Approximately half of these are olfactory receptors with the rest responding to a gamut of different ligands that range from calcium and metabolites to cytokines and neurotransmitters. The present invention, in one embodiment, provides a method for selecting one or more ASCs that have an extracellular effect on a GPCR. The GPCR is not limited herein. Rather, screening methods for any GPCR are amenable for use with the present invention.

The type of G-protein that naturally associates with the specific GPCR dictates the cell signaling cascade that is transduced. For Gq coupled receptors the signal that results from receptor activation is an increase in intracellular calcium levels. For Gs coupled receptors, an increase in intracellular cAMP is observed. For Gi coupled receptors, which make up 50% of all GPCRs, activation results in an inhibition of cAMP production. For embodiments where the effector cell property is activation of a Gi coupled GPCR, it is sometimes necessary to stimulate the readout cell(s) with a nonspecific activator of adenylyl cyclase. In one embodiment, the adenyl cyclase activator is forskolin. Thus, activation of the Gi coupled receptor by one or more effector cells will prevent forskolin induced increase in cAMP. Forskolin, accordingly, can be used as an accessory particle in one or more GPCR extracellular effect assays provided herein.

The present invention, in one embodiment, provides means for determining whether an effector cell (e.g., an ASC) within a cell population has an extracellular effect on a GPCR. The GPCR is present on one or more readout particles in a microfluidic chamber and the extracellular effect in one embodiment, is binding to the GPCR, a demonstrated affinity or specificity, inhibition or activation.

The GPCR may be a stabilized GPCR, such as one of the GPCRs made by the methods of Heptares Therapeutics (stabilized receptor, StaR® technology). The effector cell (e.g., ASC), in one embodiment, is present as a single cell, or in a homogeneous or heterogeneous cell population within a microfluidic chamber. In one embodiment, the methods and devices provided herein are used to identify one or more cell populations each comprising one or more ASCs that secrete one or more antibodies that demonstrate an extracellular effect on one of the GPCRs set forth in Table 3A and/or Table 3B, or one of the GPCRs disclosed in International PCT Publication WO 2004/040000, incorporated by reference in its entirety. For example, in one embodiment, the GPCR belongs to one of the following classes: class A, class B, class C, adhesion, frizzled.

In another embodiment, the extracellular effect is an effect on an endothelial differentiation, G-protein-coupled (EDG) receptor. The EDG receptor family includes 11 GPCRs (S1P1-5 and LPA1-6) that are responsible for lipid signalling and bind lysophosphatidic acid (LPA) and sphingosine 1-phosphate (SIP). Signalling through LPA and SIP regulates numerous functions in health and disease, including cell proliferation, immune cell activation, migration, invasion, inflammation, and angiogenesis. There has been little success in generating potent and specific small molecule inhibitors to this family, making mAbs a very attractive, alternative. In one embodiment, the EDG receptor is S1P3 (EDG3), S1PR1 (EDG1), the latter of which has been shown to activate NF-κB and STATS in several types of cancers including breast, lymphoma, ovarian, and melanoma, and plays a key role in immune cell trafficking and cancer metastasis (Milstien and Spiegel (2006). *Cancer Cell* 9, pp. 148-15, incorporated by reference in its entirety herein). A monoclonal antibody that neutralizes the SIP ligand (Sonepcizumab) has recently entered phase 11 trials for treatment of advanced solid tumours (NCT00661414). In one embodiment, the methods and devices provided herein are used to identify and isolate an ASC that secretes an antibody with greater affinity than Sonepcizumab, or an antibody that inhibits S1P to a greater extent than Sonepcizumab. In another embodiment, the extracellular effect is an effect on the LPA2 (EDG4) receptor. LPA2 is overexpressed in thyroid, colon, stomach and breast carcinomas, as well as many ovarian tumours, for which LPA2 is the primary contributor to the sensitivity and deleterious effects of LPA.

In one embodiment, cell populations are assayed for whether they exhibit an extracellular effect on a chemokine receptor, present on a readout particle. In a further embodiment, the chemokine receptor is C-X-C chemokine receptor type 4 (CXCR-4), also known as fusin or CD184. CXCR4 binds SDF1α (CXCL12), a strong chemotactic for immune cell recruitment also known as C-X-C motif chemokine 12 (CXCL12). DNA immunizations were used to generate 92 hybridomas against this target, 75 of which exhibited different chain usage and epitope recognition (Genetic Eng and Biotech news, August 2013), indicating that hybridoma selections capture only a small portion of available antibody diversity. Signalling through the CXCR4/CXCL12 axis has been shown to play a central role in tumour cell growth, angiogenesis, cell survival and to be implicated in mediating the growth of secondary metastases in CXCL12-producing organs like liver and bone marrow (Teicher and Fricker (2010). *Clin. Cancer Res.* 16, pp. 2927-2931, incorporated by reference herein in its entirety).

In another embodiment, cell populations are screened for their ability to exert an effect on the chemokine receptor CXCR7, which was recently found to bind SDF1α. Unlike CXCR4 which signals through canonical G protein coupling, CXCR7 signals uniquely through the β-arrestin pathway.

In another embodiment, the GPCR is protease activated receptors (PAR1, PAR3, and PAR4), which is a class of GPCRs activated by thrombin-mediated cleavage of the exposed N-terminus and are involved in fibrosis. In yet another embodiment, the GPCR is one of the GPCRs in Table 3A or Table 3B, below.

In embodiments where an extracellular effect is an effect on a GPCR, the invention is not limited to the particular GPCR. For example, cell lines that express particular GPCRs, engineered to provide a readout of binding, activation or inhibition, are commercially available for example, from Life Technologies (GeneBLAzer® and Tango™ cell lines), DiscoveRx, Cisbio, Perkin Elmer, etc., and are amenable for use as readout cells herein.

In one embodiment, a GPCR from one of the following receptor families is expressed on one or more readout cells herein, and an extracellular effect is measured with respect to one or more of the following GPCRs: acetylcholine receptor, adenosine receptor, adreno receptor, angiotensin receptor, bradykinin receptor, calcitonin receptor, calcium sensing receptor, cannabinoid receptor, chemokine receptor, cholecystokinin receptor, complement component (C5AR1), corticotrophin releasing factor receptor, dopamine receptor, endothelial differentiation gene receptor, endothelin receptor, formyl peptide-like receptor, galanin receptor, gastrin releasing peptide receptor, receptor ghrelin receptor, gastric inhibitory polypeptide receptor, glucagon receptor, gonadotropin releasing hormone receptor, histamine receptor, kisspeptin (KiSS1) receptor, leukotriene receptor, melanin-concentrating hormone receptor, melanocortin receptor, melatonin receptor, motilin receptor, neuropeptide receptor, nicotinic acid, opioid receptor, orexin receptor, orphan receptor, platelet activating factor receptor, prokineticin receptor, prolactin releasing peptide, prostanoid receptor, protease activated receptor, P2Y (purinergic) receptor, relaxin receptor, secretin receptor, serotonin receptor, somatostatin receptor, tachykinin receptor, vasopressin receptor, oxytocin receptor, vasoactive intestinal peptide (VIP) receptor or the pituitary adenylate cyclase activating polypeptide (PACAP) receptor.

TABLE 3A

GPCRs amenable for expression in Readout Cells or as Part of a Stabilized Readout Particle.

| Family | Human gene symbol | Human Gene Name |
|---|---|---|
| Calcitonin receptors | CALCR | calcitonin receptor |
| Calcitonin receptors | CALCRL | calcitonin receptor-like |
| Corticotropin-releasing factor receptors | CRHR1 | corticotropin releasing hormone receptor 1 |
| Corticotropin-releasing factor receptors | CRHR2 | corticotropin releasing hormone receptor 2 |
| Glucagon receptor family | GHRHR | growth hormone releasing hormone receptor |
| Glucagon receptor family | GIPR | gastric inhibitory polypeptide receptor |
| Glucagon receptor family | GLP1R | glucagon-like peptide 1 receptor |
| Glucagon receptor family | GLP2R | glucagon-like peptide 2 receptor |
| Glucagon receptor family | GCGR | glucagon receptor |
| Glucagon receptor family | SCTR | secretin receptor |
| Parathyroid hormone receptors | PTH1R | parathyroid hormone 1 receptor |
| Parathyroid hormone receptors | PTH2R | parathyroid hormone 2 receptor |
| VIP and PACAP receptors | ADCYAP1R1 | adenylate cyclase activating polypeptide 1 (pituitary) receptor type I |
| VIP and PACAP receptors | VIPR1 | vasoactive intestinal peptide receptor 1 |
| VIP and PACAP receptors | VIPR2 | vasoactive intestinal peptide receptor 2 |
| Adenosine | ADORA1 | Adenosine A1 receptor |
| Adenosine | ADORA2A | Adenosine A2 receptor |
| Adenosine | ADRB3 | Adenosine 3 receptor |
| Chemokine | CXCR1 | C-X-C chemokine receptor 1 |
| Chemokine | CXCR2 | C-X-C chemokine receptor 2 |
| Chemokine | CXCR3 | C-X-C chemokine receptor 3 |
| Chemokine | CXCR4 | C-X-C chemokine receptor 4 |
| Chemokine | CXCR5 | C-X-C chemokine receptor 5 |
| Chemokine | CXCR6 | C-X-C chemokine receptor 6 |
| Chemokine | CXCR7 | C-X-C chemokine receptor 7 |
| Chemokine | CCR1 | C-C chemokine receptor type 1 |
| Chemokine | CCR2 | C-C chemokine receptor type 2 |
| Chemokine | CCR3 | C-C chemokine receptor type 3 |
| Chemokine | CCR4 | C-C chemokine receptor type 4 |
| Chemokine | CCR5 | C-C chemokine receptor type 5 |
| Chemokine | CCR6 | C-C chemokine receptor type 6 |
| Chemokine | CCR7 | C-C chemokine receptor type 7 |
| Chemokine | CMKLR1 | Chemokine receptor-like 1 |
| Complement component | C5AR1 | Complement component AR1 receptor |
| Lysophospholipid (LPL) receptor | LPAR1 | lysophosphatidic acid receptor 1 |
| Lysophospholipid (LPL) receptor | LPAR2 | lysophosphatidic acid receptor 2 |
| Lysophospholipid (LPL) receptor | LPAR3 | lysophosphatidic acid receptor 3 |

TABLE 3A-continued

GPCRs amenable for expression in Readout Cells
or as Part of a Stabilized Readout Particle.

| Family | Human gene symbol | Human Gene Name |
| --- | --- | --- |
| Lysophospholipid (LPL) receptor | LPAR4 | lysophosphatidic acid receptor 4 |
| Lysophospholipid (LPL) receptor | LPAR5 | lysophosphatidic acid receptor 5 |
| Lysophospholipid (LPL) receptor | LPAR6 | lysophosphatidic acid receptor 6 |
| Lysophospholipid (LPL) receptor | S1PR1 | sphingosine-1-phosphate receptor 1 |
| Lysophospholipid (LPL) receptor | S1PR2 | sphingosine-1-phosphate receptor 2 |
| Lysophospholipid (LPL) receptor | S1PR3 | sphingosine-1-phosphate receptor 3 |
| Lysophospholipid (LPL) receptor | S1PR4 | sphingosine-1-phosphate receptor 4 |
| Lysophospholipid (LPL) receptor | S1PR5 | sphingosine-1-phosphate receptor 5 |

TABLE 3B

GPCRs amenable for expression in Readout Cells or as Part of a Stabilized Readout Particle.

| GPCR (Gene symbol) | Ligand(s) |
| --- | --- |
| 5-hydroxytryptamine 1A receptor (HTR1A) | 5-hydroxytryptamine |
| 5-hydroxytryptamine 1B receptor (HTR1B) | 5-hydroxytryptamine |
| 5-hydroxytryptamine 1D receptor (HTR1D) | 5-hydroxytryptamine |
| 5-hydroxytryptamine 1e receptor (HTR1E) | 5-hydroxytryptamine |
| 5-hydroxytryptamine 1F receptor (HTR1F) | 5-hydroxytryptamine |
| 5-hydroxytryptamine 2A receptor (HTR2A) | 5-hydroxytryptamine |
| 5-hydroxytryptamine 2B receptor (HTR2B) | 5-hydroxytryptamine |
| 5-hydroxytryptamine 2C receptor (HTR2C) | 5-hydroxytryptamine |
| 5-hydroxytryptamine 4 receptor (HTR4) | 5-hydroxytryptamine |
| 5-hydroxytryptamine 5a receptor (HTR5A) | 5-hydroxytryptamine |
| 5-hydroxytryptamine 5b receptor (HTR5BP) | 5-hydroxytryptamine |
| 5-hydroxytryptamine 6 receptor (HTR6) | 5-hydroxytryptamine |
| 5-hydroxytryptamine 7 receptor (HTR7) | 5-hydroxytryptamine |
| Acetylcholine M1 receptor (CHRM1) | acetylcholine |
| Acetylcholine M2 receptor (CHRM2) | acetylcholine |
| Acetylcholine M3 receptor (CHRM3) | acetylcholine |
| Acetylcholine M4 receptor (CHRM4) | acetylcholine |
| Acetylcholine M5 receptor (CHRM5) | acetylcholine |
| Adenosine A1 receptor (ADORA1) | adenosine |
| Adenosine A2A receptor (ADORA2A) | adenosine |
| Adenosine A2B receptor (ADORA2B) | adenosine |
| Adenosine A3 receptor (ADORA3) | adenosine |
| $\alpha_{1A}$-adrenoceptor (ADRA1A) | Adrenaline, noradrenaline<br>agonists<br>cirazoline, desvenlafaxine, etilefrine, metaraminol, methoxamine, midodrine, naphazoline, oxymetrazoline, phenylephrine, synephrine, tetrahydrozoline, xylometazoline<br>antagonists<br>alfuzosin, arotinolol, carvedilol, doxazosin, indoramin, labetalol, moxislyte, phenoxybenzamine, phentolamine, prazosin, quetiapine, risperidone, silodosin, tamsulosin, terazosin, tolazoline, trimazosin |
| $\alpha_{1B}$-adrenoceptor (ADRA1B) | Adrenaline, noradrenaline |
| $\alpha_{1D}$-adrenoceptor (ADRA1D) | Adrenaline |
| $\alpha_{2A}$-adrenoceptor (ADRA2A) | Adrenaline |
| $\alpha_{2B}$-adrenoceptor (ADRA2B) | Adrenaline, noradrenaline<br>agonists<br>salbutamol, bitolterol mesylate, isoproterenol, levosalbutamol, metaproterenol, formoterol, salmeterol, terbutaline, clenbuterol, ritodrine<br>antagonists<br>butoxamine, Beta blockers |
| $\alpha_{2C}$-adrenoceptor (ADRA2C) | Adrenaline, noradrenaline |
| $\beta_1$-adrenoceptor (ADRB1) | Adrenaline, noradrenaline<br>nitrosamine 4-(methylnitrosamino)-1-(3-pyridyl)-1-butanone (NNK)<br>agonists<br>denopamine, dobutamine, xamoterol<br>antagonists<br>acebutol, atenolol, betaxolol, bisoprolol, esmolol, metoprolol, nebivolol, vortioxetine |
| $\beta_2$-adrenoceptor (ADRB2) | Adrenaline |
| $\beta_3$-adrenoceptor (ADRB3) | Adrenaline |

TABLE 3B-continued

GPCRs amenable for expression in Readout Cells or as Part of a Stabilized Readout Particle.

| GPCR (Gene symbol) | Ligand(s) |
|---|---|
| Angiotensin recptor 1 ($AT_1$) (AGTR1) | Angiotensisn I, angiotensin II, angiotensin III |
| Angiotensin recptor 2 ($AT_2$) (AGTR2) | Angiotensisn II, angiotensin III |
| Angiotensin recptor 4 | Angiotensisn IV (angiotensin II metabolite) |
| Apelin receptor (APLNR) | Apelin-13, apelin-17, apelin-36 |
| Bile acid receptor (GPBAR1) | Chenodeoxycholic acid, cholic acid, deoxycholic acid, lithocholic acid |
| Bombesin receptor $BB_1$ (NMBR) | Gastrin-releasing peptide, neuromedin B |
| Bombesin receptor $BB_2$ (GRPR) | Gastrin-releasing peptide, neuromedin B |
| Bombesin receptor $BB_3$ (BRS3) | |
| Bradykinin recpetor B1 | bradykinin |
| Bradykinin recpetor B2 | bradykinin |
| Calcium sensing receptor (CaSR) | Calcium |
| | Magnesium |
| G-protein coupled receptor family C group 6 member A (GPRC6A) | |
| Cannabinoid $CB_1$ receptor (CNR1) | 2-arachidonoylglycerol anandamide |
| Cannabinoid $CB_2$ receptor (CNR2) | 2-arachidonoylglycerol anandamide |
| C-X-C chemokine receptor type 4 (CXCR2) | Interleukin 8 |
| | Growth-related oncogene-alpha (GRO-α) |
| C-X-C chemokine receptor type 4 (CXCR4) | Stromal cell-derived factor-1 (SDF1) |
| Cholecystokinin A receptor (CCKAR or CCK1) | Cholecystokinin peptide hormones (CCK) |
| Cholecystokinin B receptor (CCKAR or CCK2) | Cholecystokinin peptide hormones (CCK) |
| | Gastrin |
| Cholecystokinin recptor CCK1 (CCKAR) | CCK-33, CCK-4, CCK-8, gastrin-17 |
| Cholecystokinin recptor CCK2 (CCKBR) | CCK-33, CCK-4, CCK-8, gastrin-17 |
| endothelin receptor A (ETA) | Endothelin-1 |
| endothelin receptor B1 (ETB1) | Endothelin-1 |
| | Endothelin-3 |
| endothelin receptor B2 (ETB2) | Endothelin-1 |
| | Endothelin-3 |
| endothelin receptor C (ETC) | Endothelin-1 |
| Frizzled 1 (FZD1) | Wnt-1, Wnt-2, Wnt-3a, Wnt-5a, Wnt-7b |
| Frizzled 2 (FZD2) | Wnt-5a |
| Frizzled 3 (FZD3) | Wnt protein ligand |
| Frizzled 4 (FZD4) | Wnt protein ligand |
| Frizzled 5 (FZD5) | Wnt protein ligand |
| Frizzled 6 (FZD6) | Wnt-3a, Wnt-4, Wnt-5a |
| Frizzled 7 (FZD7) | Wnt protein ligand |
| Frizzled 8 (FZD8) | Wnt protein ligands |
| Frizzled 9 (FZD9) | Wnt protein ligands |
| Frizzled 10 (FZD10) | Wnt protein ligands |
| $GABA_{B1}$ Receptor | Agonist |
| $GABA_{B2}$ Receptor (B1 and B2 assemble as heterodimer) | GABA, Baclofen, gamma-hydroxybutyrate, phenibut, 3-aminopropylphosphinic acid, lesogaberan, SKF-97541, CGP-44532 |
| | Allosteric modulator |
| | CGP-7930, BHFF, Fendiline, BHF-177, BSPP, GS-39783 |
| | Antagonists |
| | 2-OH-saclofen, saclofen, phaclofen, SCH-50911, CGP-35348, CGP-52432, SGS-742, CGP-55845 |
| Gastrin-releasing peptide receptor (GRPR), also referred to as $BB_2$ | Gastrin releasing peptide |
| G protein-coupled estrogen receptor 30 (GPR30) | Oestrogen |
| Luteinizing hormone/choriogonadotropin receptor (LHCGR), also referred to as Lutenizing hormone receptor (LHR) and lutropin/choriogonadotroptin receptor (LCGR) | Luteinizing hormone |
| | Chroinic gonadotropins |
| Lysophosphatidic acid receptor 1 (LPA1) | Lysophosphatidic acid |
| Lysophosphatidic acid receptor 2 (LPA2) | Lysophosphatidic acid |
| Lysophosphatidic acid receptor 3 (LPA3) | Lysophosphatidic acid |
| Melanocortin 1 receptor (MC1R), also referred o as melanocyte-stimulating hormone receptor (MSHR), melanin-activating peptide receptor and melanotropin receptor | Melanocortins (pituitary peptide hormones) including adrenocorticotropic hormone (ACTH) and melanocyte-stimulating hormone (MSH) |
| Neuromedin B receptor | Neuromedin B |
| Prostaglandin E2 receptor EP2 | Prostaglandin E2 |
| Prostaglandin E2 receptor EP4 | Prostaglandin E2 |
| Protease-activated receptor 1 | Thrombin |
| Protease-activated receptor 2 | Trypsin |
| Protease-activated receptor 3 | Thrombin |

TABLE 3B-continued

GPCRs amenable for expression in Readout Cells or as Part of a Stabilized Readout Particle.

| GPCR (Gene symbol) | Ligand(s) |
|---|---|
| Protease-activated receptor 4 | Thrombin |
| Smoothened | Sonic hedgehog |
| Thyrotropin receptor (TSH receptor) | Thyrotropin |
| Metabotropic glutamate receptor 1(GRM1) | L-glutamic acid |
| Metabotropic glutamate receptor 2 (GRM2) | L-glutamic acid |
| Metabotropic glutamate receptor 3 (GRM3) | L-glutamic acid |
| Metabotropic glutamate receptor 4 (GRM4) | L-glutamic acid |
| Metabotropic glutamate receptor 5 (GRM5) | L-glutamic acid |
| Metabotropic glutamate receptor 6 (GRM6) | L-glutamic acid |
| Metabotropic glutamate receptor 7 (GRM7) | L-glutamic acid |
| Metabotropic glutamate receptor 8 (GRM8) | L-glutamic acid |
| G protein-coupled receptor 56 (GPR56) | |
| G protein-coupled receptor 64 (GPR64) | |
| G protein-coupled receptor 97 (GPR97) | |
| G protein-coupled receptor 98 (GPR98) | |
| G protein-coupled receptor 110 (GPR110) | |
| G protein-coupled receptor 111 (GPR111) | |
| G protein-coupled receptor 112 (GPR112) | |
| G protein-coupled receptor 113 (GPR113) | |
| G protein-coupled receptor 114 (GPR114) | |
| G protein-coupled receptor 115 (GPR115) | |
| G protein-coupled receptor 116 (GPR116) | |
| G protein-coupled receptor 123 (GPR123) | |
| G protein-coupled receptor 124 (GPR124) | |
| G protein-coupled receptor 125 (GPR125) | |
| G protein-coupled receptor 126 (GPR126) | |
| G protein-coupled receptor 128 (GPR128) | |
| G protein-coupled receptor 133 (GPR133) | |
| G protein-coupled receptor 144 (GPR144) | |
| latrophilin 1 (LPHN1) | |
| latrophilin 2 (LPHN2) | |
| latrophilin 3 (LPHN3) | |

In one embodiment, an effector cell is assayed for an extracellular effect on a readout cell expressing a GPCR by one or more of the assays provided in Table 4, below. In another embodiment, a readout particle population comprises a vesicle or a bead functionalized with a membrane extracts (available from Integral Molecular), or a stabilized solubilized GPCR (e.g., Heptares).

GPCRs can be phosphorylated and interact with proteins called arrestins. The three major ways to measure arrestin activation are: (i) microscopy—using a fluorescently labeled arrestin (e.g., GFP or YFP); (ii) using enzyme complementation; (iii) using the TANGO™ Reporter system (β-lactamase) (Promega). In one embodiment, the TANGO™ Reporter system is employed in a readout cell or plurality of readout cells. This technology uses a GPCR linked to a transcription factor through a cleavable linker. The arrestin is fused to a crippled protease. Once the arrestin binds to the GPCR, the high local concentration of the protease and the linker result in cleavage of the linker, releasing the transcription factor into the nucleus to activate transcription. The β-lactamase assay can be run on live cells, does not require cell lysis, and can be imaged in as little as 6-hours of agonist incubation.

In one embodiment, a β-arrestin GPCR assay that can be universally used for the detection of antagonists and agonists of GPCR signaling is used in the methods and devices provided herein to identify and an effector cell that secretes a biomolecule that binds to a GPCR (Rossi et al. (1997). Proc. Natl. Acad. Sci. U.S.A. 94, pp. 8405-8410, incorporated by reference in its entirety for all purposes). This assay is based on a β-galactosidase (β-Gal) enzyme-complementation technology, now commercialized by DiscoveRx. The GPCR target is fused in frame with a small N-terminal fragment of the β-Gal enzyme. Upon GPCR activation, a second fusion protein, containing β-arrestin linked to the N-terminal sequences of β-Gal, binds to the GPCR, resulting in the formation of a functional β-Gal enzyme. The β-Gal enzyme then rapidly converts non-fluorescent substrate Di-β-D-Galactopyranoside (FDG) to fluorescein, providing large amplification and excellent sensitivity. In this embodiment, readout cells (with GPCRs) are preloaded, off chip, with cell-permeable pro-substrate (acetylated FDG) which is converted to cell-impermeable FDG by esterase cleavage of acetate groups. Although fluorescein is actively transported out of live cells, by implementing this assay within a microfluidic chamber the fluorescent product is concentrated, providing greatly enhanced sensitivity over plate-based assays. DiscoveRx has validated this assay strategy, used in microwell format, across a large panel of GPCRs.

In one embodiment, activation of a GPCR by an effector cell is determined in a microfluidic format by detecting the increase in cytosolic calcium in one or more readout cells. In a further embodiment, the increase in cytosolic calcium is detected with one or more calcium sensitive dyes. Calcium sensitive dyes have a low level of fluorescence in the absence of calcium and undergo an increase in fluorescent properties once bound by calcium. The fluorescent signal peaks at about one minute and is detectable over a 5 to 10 minute window. Thus, to detect activity using fluorescent calcium the detection and addition of the agonist are closely coupled. In order to achieve this coupling, the effector cell is exposed simultaneously to the population of readout cells and the one or more calcium sensitive dyes. In one embodiment, the one or more calcium sensitive dyes are one provided in a FLIPR™ calcium assay (Molecular Devices).

The recombinant expressed jellyfish photoprotein, aequorin, in one embodiment, is used in a functional GPCR screen, i.e., an extracellular effect assay where the extracellular effect is the modulation of a GPCR. Aequorin is a calcium-sensitive reporter protein that generates a luminescent signal when a coelenterazine derivative is added. Engineered cell lines with GPCRs expressed with a mitochondrially targeted version of apoaequorin are available commercially (Euroscreen). In one embodiment, the one or more of the cell lines available from Euroscreen is used as a population of readout cells in a method of assessing an extracellular effect of an effector cell, or a variation in an extracellular effect.

In one embodiment, an extracellular effect on a GPCR is measured by using one of the ACTOne cell lines (Codex Biosolutions), expressing a GPCR and a cyclic nucleotide-gated (CNG) channel, as a population of readout cells. In this embodiment, the extracellular effect assay works with cell lines that contain an exogenous Cyclic Nucleotide-Gated (CNG) channel. The channel is activated by elevated intracellular levels of cAMP, which results in ion flux (often detectable by calcium-responsive dyes) and cell membrane depolarization which can be detected with a fluorescent membrane potential (MP) dye. The ACTOne cAMP assay allows both end-point and kinetic measurement of intracellular cAMP changes with a fluorescence microplate reader.

A reporter gene assay, in one embodiment, is used to determine whether an effector cell modulates a particular GPCR. In this embodiment, the modulation of the GPCR is the extracellular effect being assessed. A reporter gene assay, in one embodiment, is based on a GPCR second messenger such as calcium (AP1 or NFAT response elements) or cAMP (CRE response element) to activate or inhibit a responsive element placed upstream of a minimal promoter, which in turn regulates the expression of the reporter protein chosen by the user. Expression of the reporter, in one embodiment, is coupled to a response element of a transcription factor activated by signaling through a GPCR. For example, reporter gene expression can be coupled to a responsive element for one of the following transcription factors: ATF2/ATF3/AFT4, CREB, ELK1/SRF, FOS/JUN, MEF2, GLI, FOXO, STAT3, NFAT, NFκB. In a further embodiment, the transcription factor is NFAT. Reporter gene assays are available commercially, for example from SA Biosciences Reporter proteins are known in the art and include, for example, β-galactosidase, luciferase (see, e.g., Paguio et al. (2006). "Using Luciferase Reporter Assays to Screen for GPCR Modulators," Cell Notes Issue 16, pp. 22-25; Dual-Glo™ Luciferase Assay System Technical Manual #TM058; pGL4 Luciferase Reporter Vectors Technical Manual #TM259, each incorporated by reference in their entireties for all purposes), GFP, YFP, CFP, β-lactamase. Reporter gene assays for measuring GPCR signaling are available commercially and can be used in the methods and devices described herein. For example, the GeneBLAzer® assay from Life Technologies is amenable for use with the present invention.

In one embodiment, overexpression of a G protein in a reporter cell is carried out to force a cAMP coupled GPCR to signal through calcium. This is referred to as force coupling.

In one embodiment, a Gq coupled cell line is used as a readout cell line in the methods described herein. In one embodiment, the Gq coupled cell line reports GPCR signaling through β-lactamase. For example, one of the cell-based GPCR reporter cell lines (GeneBLAzer®, Life Technologies). The reporter cell line can be division arrested or include normal dividing cells.

cAMP responsive element-binding protein (CREB) is a transcription factor as mentioned above, and is used in one embodiment for a Gs and/or Gi coupled GPCR. In a further embodiment, forskolin is utilized as an accessory particle. The CRE reporter is available in plasmid or lentiviral form to drive GFP expression from SA Biosciences, and is amenable for use with the methods and devices described herein. For example, the assay system available from SA Biosciences in one embodiment is employed herein to produce a readout cell (world-wide-website: sabiosciences.com/reporter_assay_product/HTML/CCS-002G.html). Life Technologies also has CRE-responsive cell lines that express specific GPCRs, and these can be used in the methods described herein as well as readout cells.

In one embodiment, one or more effector cells present in a cell population are assayed for the ability to activate or antagonize a GPCR present on one or more readout cells by detecting the increase or decrease in cAMP levels inside the one or more readout cells. ELISA based assays, homogeneous time-resolved fluorescence (HTRF) (see Degorce et al. (2009). Current Chemical Genomics 3, pp. 22-32, the disclosure of which is incorporated by reference in its entirety), and enzyme complementation can all be used with the microfluidic devices and assays provided herein to determine cAMP levels in readout cells. Each of these cAMP detection methods requires cell lysis to liberate the cAMP for detection, as it is the cyclic AMP that is actually measured.

Assays for measuring cAMP in whole cells and for measuring adenyl cyclase activity in membranes are commercially available (see, e.g., Gabriel et al. (2003). Assay Drug Dev. Technol. 1, pp. 291-303; Williams (2004). *Nat. Rev. Drug Discov.* 3, pp. 125-135, each incorporated by reference in their entireties), and are amenable for use in the devices and methods provided herein. That is, cell populations in one or more microfluidic chambers can be assayed according to these methods.

Cisbio International (Codolet, France) has developed a sensitive high-throughput homogenous cAMP assay (HTRF, see Degorce et al. (2009). Current Chemical Genomics 3, pp. 22-32, the disclosure of which is incorporated by reference in its entirety) based on time resolved fluorescence resonance energy transfer technology and can be used herein to screen for an effector cell exhibiting an effect on a GPCR. The method is a competitive immunoassay between native cAMP produced by cells and a cAMP-labeled dye (cAMP-d2). The cAMP-d2 binding is visualized by a MaB anti-cAMP labeled with Cryptate. The specific signal (i.e., energy transfer) is inversely proportional to the concentration of cAMP in the sample, in this case, the amount of cAMP activated in a readout cell by an effector cell or an effector cell secretion product. As cAMP is being measured, readout cells are first lysed to free the cAMP for detection. This assay has been validated for both $G_s$-($β_2$-adrenergic, histamine $H_2$, melanocortin $MC_4$, CGRP and dopamine $D_1$) and $G_{i/o}$-coupled (histamine $H_3$) receptors.

cAMP assay kits based on fluorescence polarization are also commercially, e.g., from Perkin Elmer, Molecular Devices and GE Healthcare, and each is amenable for use as an effector cell assay in the methods and devices provided herein. Accordingly, one embodiment of the present invention comprises selecting an effector cell and/or cell population comprising one or more effector cells based on the result of a cAMP fluorescence polarization assay. The method is used in one embodiment to determine whether the effector cell activates (agonism) or inhibits (antagonism) on a particular GPCR.

In one embodiment, the AlphaScreen™ cAMP assay from Perkin Elmer, a sensitive bead-based chemiluminescent assay requiring laser activation, is used in the devices provided herein to screen for an effector cell having an effect on a readout cell, specifically, the activation or inhibition of a GPCR.

DiscoveRx (world-wide-website: discoverx.com) offers a homogenous high-throughput cAMP assay kit called Hit-Hunter™ based on a patented enzyme (β-galactosidase) complementation technology using either fluorescent or luminescent substrates (Eglen and Singh (2003). *Comb Chem. High Throughput Screen* 6, pp. 381-387; Weber et al. (2004). *Assay Drug Dev. Technol.* 2, pp. 39-49; Englen (2005). *Comb. Chem. High Throughput Screen* 8, pp. 311-318, each incorporated by reference in their entireties). This assay can be implemented herein to detect an effector cell having an extracellular effect or a variation in an extracellular effect on a readout cell expressing a GPCR.

Cellular events that result from GPCR receptor activation or inhibition can also be detected to determine an effector cell's property(ies) (e.g., an antibody producing cell's ability to activate or antagonize) on a readout cell. For example, in the case of the Gq coupled receptors, when the GPCR is activated, the Gq protein is activated, which results in the phospholipase C cleavage of membrane phospholipids. This cleavage results in the generation of inositol triphosphates 3 (IP3). Free IP3 binds to its target at the surface of the endoplasmic reticulum causing a release of calcium. The calcium activates specific calcium responsive transcription vectors such as nuclear factor of activated T-cells (NFAT). Thus, by monitoring NFAT activity or expression, an indirect readout of the GPCR in a readout cell is established. See. e.g., Crabtree and Olson (2002). *Cell* 109, pp. S67-S79, incorporated by reference herein in its entirety.

Once activated more than 60% of all GPCRs are internalized. Utilizing a tagged GPCR (typically done with a C-terminal GFP tag) the distribution of the receptor in one embodiment, is imaged in the presence and absence of ligand. Upon ligand stimulation a normally evenly distributed receptor will often appear as endocytosed puncta.

TABLE 4

GPCR functional assays for use with the present invention.

| Assay | Biological measurements | Reagents (accessory particles) | Basis | Endpoint | Notes |
|---|---|---|---|---|---|
| Europium-GTP ™ binding (Perkin Elmer) | Membrane-based GPCR mediated Guanine nucleotide exchange | Europium-GTP | Binding of europium-labeled GTP to receptor activated G proteins | Time-resolved fluorescence | Proximal to receptor activation, nonradioactive. |
| AlphaScreen ™ (Perkin Elmer) | Cell-based cAMP accumulation | cAMP MAb conjugated acceptor bead, streptavidin-coated donor beads with chemoluminescence compound, biotinyl-cAMP | cAMP competes with biotinyl-cAMP binding to high-affinity streptavidin-coated donor beads, loss of signal due to reduced proximity of acceptor-donor bead | Luminescence | High sensitivity, homogeneous, amenable to automation, broad linear range of detection |
| Fluorescence polarization (Perkin Elmer, Molecular Devices, GE Healthcare) | Cell- or membrane-based cAMP accumulation | cAMP MAb, fluorescent cAMP | cAMP competes with Fluor-cAMP binding to cAMP MAb, loss of signal due to decrease in rotation and polarization | Fluorescence polarization | Homogeneous, amenable to automation |
| HTRF cAMP (Cisbio) | Cell-based, cAMP accumulation | cAMP MAb conjugated with eurocryptate, acceptor molecule labeled cAMP | cAMP competes with acceptor-labeled cAMP binding to europium-conjugated cAMP MAb, loss of signal due to reduced europium-acceptor molecule proximity | Time-resolved fluorescence | Broad linear range, high signal-to-noise, homogenous, amenable to automation |
| HitHunter ™ (DiscoveRx) | Cell-based, cAMP accumulation | cAMP MAb, ED-cAMP (enzyme fragment dono-cAMP conjugate) conjugated peptide, acceptor protein, lysis buffer | cAMP competes with ED-cAMP for complementation of β-Gal activity with binding of acceptor peptide, loss of signal as enzyme complementation is reduced | Fluorescence or luminescence | Low compound interference, high sensitivity, homogeneous, amenable to automation |
| IP$_1$ ™ (Cisbio) | Cell-based IP$_1$ accumulation | Europium-conjugated IP$_1$ MAb, acceptor labeled IP$_1$ | Loss of signal as IP$_1$ competes for binding of acceptor-labeled IP$_1$ binding to europium-MAb | Time-resolved fluorescence | Homogeneous, can be used for constitutively active Gq-coupled GPCRs |
| FLIPR ™ (Molecular Devices) | Cell-based, increases in intracellular calcium | Caldium sensitive dye; caldium-3 | Increased fluorescence as intracellular dye binds calcium | Fluorescence | Sensitive, homogeneous, amenable to automation |
| AequoScreen ™ (EuroScreen) | Cell-based, increases in intracellular calcium | Cell lines expressing select GPCRs along with promiscuous or chimeric G proteins and a mitochondrially targeted version of apoaequorin | Calcium-sensitive aequorin generates a luminescent signal when a coelenterazine derivative is added | Luminescence | Sensitive, homogeneous, amenable to automation |
| Reporter gene | Cell-based, increases in reporter gene expression due to increases in | Several promoter plasmids and reporters | GPCR changes in secondary messengers alter expression of a selected reporter gene | Fluorescence, luminescence, absorbance | Homogeneous, amplification of signal |

TABLE 4-continued

GPCR functional assays for use with the present invention.

| Assay | Biological measurements | Reagents (accessory particles) | Basis | Endpoint | Notes |
|---|---|---|---|---|---|
|  | second messengers activated by GPCR binding |  |  |  |  |
| Melanophore (Arena Pharmaceuticals) | Cell-based, changes in pigment dispersion |  | Melanosomes aggregate with inhibition of PKA disperse with activation of PKA or PKC | Absorbance | Sensitive, homogeneous, no cell lysis, amenable to automation |

Adapted from Thomsen et al. (2005). *Current Opin. Biotechnol.* 16, pp. 655-665, incorporated by reference herein in its entirety for all purposes.

One embodiment of a work flow for a single cell antibody secreting cell (ASC)/antibody selection pipeline is shown in FIG. 1. In this embodiment, a host animal is immunized with a target antigen and cells are obtained from spleen, blood, lymph nodes and/or bone marrow one week following a final immunization boost. These samples are then optionally enriched for ASCs by flow cytometry (e.g., FACS) or magnetic bead purification using established surface markers (if available) or using microfluidic enrichment. The resulting ASC enriched population is then loaded into a microfluidic array of nanoliter volume chambers, with a loading concentration chosen to achieve from about one to about 500 cells per chamber, or from about one to about 250 cells per chamber. Depending on the pre-enrichment step, individual chambers will comprise multiple ASCs, single ASCs or zero ASCs. Chambers are then isolated by closing microvalves and incubated to allow for antibodies to be secreted in the small chamber volume. Because ASCs typically secrete antibodies at a rate of 1000 antibody molecules per second, and the volume of individual chambers provided herein are on the order of 2 nL, a concentration of about 10 nM of each secreted monoclonal antibody is provided in about 3 hours (each ASC secretes a unique monoclonal antibody). In a further embodiment, integrated microfluidic control is then used for delivery and exchange of reagents in order to implement image-based effector cell assays, which are read out using automated microscopy and real-time image processing. Individual ASCs or cell population comprising one or more ASCs that secrete antibodies with desired properties (e.g., binding, specificity, affinity, function) are then recovered from individual chambers. Further analysis of the recovered cell populations at limiting dilution is then carried out. In the case that an individual ASC is provided to a chamber and recovered, further analysis of the individual ASC can also be carried out. For example, in one embodiment, the further analysis includes single cell RT-PCR to amplify paired HV and LV for sequence analysis and cloning into cell lines.

In another embodiment, after an animal is immunized and cells are obtained from spleen, blood, lymph nodes and/or bone marrow, the cells make up a starting population that are loaded directly into individual chambers of a microfluidic device provided herein, i.e., as a plurality of cell populations, wherein individual cell populations are present in each microfluidic chamber. An extracellular effect assay is then carried out in the individual chambers on the individual cell populations to determine if any of the individual cell populations comprise one or more effector cells responsible for an extracellular effect.

Although a host animal can be immunized with a target antigen prior to microfluidic analysis, the invention is not limited thereto. For example, in one embodiment, cells are obtained from spleen, blood, lymph nodes or bone marrow from a host (including human) followed by an enrichment for ASCs. Alternatively, no enrichment step takes place and cells are directly loaded into chambers of a device provided herein, i.e., as a plurality of cell populations, where individual cell populations are present in each chamber.

The methods provided herein allow for the selection of antibodies from any host species. This provides two key advantages for the discovery of therapeutic antibodies. First, the ability to work in species other than mice and rats allows for the selection of mAbs to targets with high homology to mouse proteins, as well as mAbs to human proteins that cross-react with mice and can thus be used in easily accessible pre-clinical mouse models. Second, mouse immunizations often result in responses that feature immunodominance to a few epitopes, resulting in a low diversity of antibodies generated; expanding to other species thus greatly increases the diversity of antibodies that recognize different epitopes. Accordingly, in embodiments described herein, mice rats and rabbits are used for immunizations, followed by the selection of ASCs from these immunized animals. In one embodiment, a rabbit is immunized with an antigen, and ASCs from the immunized rabbit are selected for with the methods and devices provided herein. As one of skill in the art will recognize, rabbits offer advantages of a distinct mechanism of affinity maturation that uses gene conversion to yield greater antibody diversity, larger physical size (more antibody diversity), and greater evolutionary distance from humans (more recognized epitopes).

The immunization strategy, in one embodiment is a protein, cellular, and/or DNA immunization. For example, for PDGFRα, the extracellular domain obtained from expression in a mammalian cell line, or purchased from a commercial source (Calixar) is used to immunize an animal. For CXCR4, in one embodiment, virus-like particle (VLP) preparations, a nanoparticle having a high expression of GPCR in native conformation, from a commercial source (Integral Molecular) is used. Cell-based immunization is performed by overexpression of full-length proteins in a cell line (e.g., 32D-PDGFRα cells for mice/rats, and a rabbit fibroblast cell line (SIRC cells) for rabbits; including protocols in which a new cell line is used in the final boost to enrich for specific mAbs. A variety of established DNA immunization protocols are also amenable for use with the present invention. DNA immunization has become the method of choice for complex membrane proteins since it 1) eliminates the need for protein expression and purification, 2) ensures native conformation of the antigen, 3) reduces the potential for non-specific immune responses to other cell membrane antigens, and 4) has been proven effective for challenging targets (Bates et al. (2006). *Biotechniques* 40, pp. 199-208; Chambers and Johnston (2003). *Nat. Biotechnol.* 21, pp. 1088-1092; Nagata et al. (2003). *J. Immunol. Methods* 280, pp. 59-72; Chowdhury et al. (2001). *J. Immunol Methods* 249, pp. 147-154; Surman et al. (1998). *J. Immunol. Methods* 214, pp. 51-62; Leinonen et al. (2004). J. Immunol. Methods 289, pp. 157-167; Takatasuka et al. (2011). *J. Pharmacol. and Toxicol. Methods* 63, pp. 250-257, each incorporated by reference in their entireties for all purposes). All immunizations are performed in accordance with animal care requirements and established protocols.

Anti-PDGFRα antibodies have been previously produced in rats, mice, and rabbits, and comparison of the extracellular domain of PDGFRα shows several sites of substantial variation (FIG. 24). Thus it is expected that a good immune response is obtainable from this antigen. Anti-CXCR4 mAbs have also been previously generated using both lipoparticles and DNA immunizations, so that this target is likely to yield a good immune response. If needed, we will investigate using the co-expression of GroE1 or GM-CSF (either co-expressed or as a fusion) as a molecular adjuvant, as well as testing of different adjuvants and immunization schedules (Takatsuka et al. (2011). *J. Pharmacol. and Toxicol. Methods* 63, pp. 250-257 Fujimoto et al. (2012). *J. Immunol. Methods* 375, pp. 243-251, incorporated by reference in their entireties for all purposes).

The devices provided herein are based on Multilayer Soft Lithography (MSL) microfluidics (Unger et al. (2000). *Science* 7, pp. 113-116, incorporated by reference in its entirety). MSL is a fabrication method that provides for increased sensitivity through small volume reactions; high scalability and parallelization; robust cell culture; flexibility and fluid handling control needed for complex assays; and greatly reduced cost and reagent consumption.

The number of effector cells isolated per device run (i.e., number of cells in each chamber of a device) is a function of the concentration of cells in a cell suspension loaded onto a device, the frequency in the cell suspension of the specific effector cells being selected for, and the total number of chambers on a device. Devices with arrays up to and greater than 40,000 effector cell assay chambers are contemplated.

Figure 25:
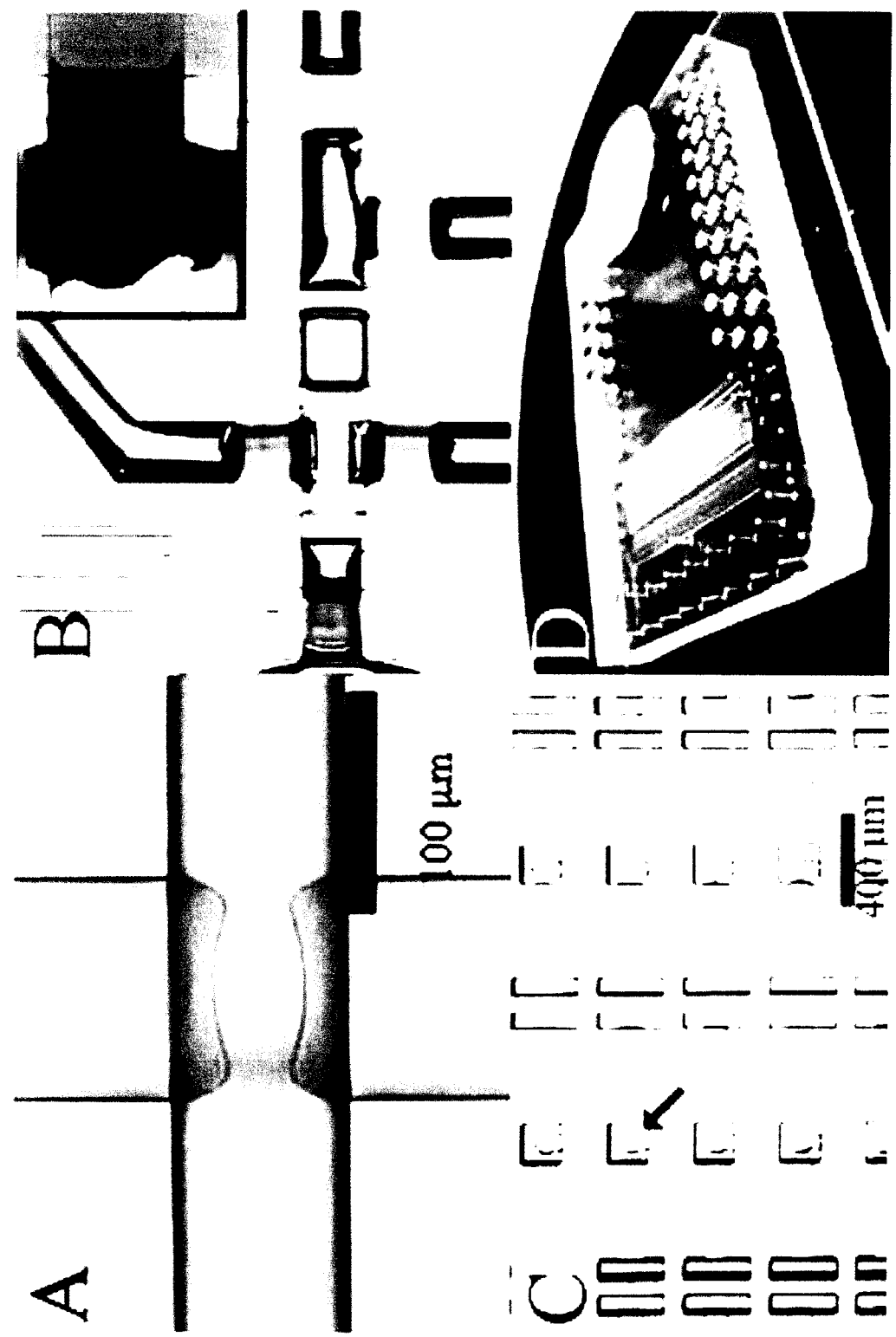
FIG. 25 provides images showing various aspects of multilayer soft lithography microfluidics. (A) Optical micrograph of a valve made using MSL. Two crossing microfabricated channels, one "flow channel" for the active fluids (vertical) and one control channel for valve actuation (horizontal), create a valve structure. The flow channel is separated from the control channels by a thin elastomeric membrane to create a "pinch valve". Pressurization of the control channel deflects the membrane to close off the flow channel. (B) Section of a device integrating multiple valves (filled with green and blue food dye). (C) Section of a device fabricated at UBC having a total of 16,000 valves, 4000 chambers, and over 3000 layer-layer interconnects (arrow). (D) Example of a microfluidic device with penny for scale.

Amongst all microfluidics technologies, MSL is unique in its rapid and inexpensive prototyping of devices having thousands of integrated microvalves (Thorsen et el. (2002). *Science* 298, pp. 58-584, incorporated by reference in its entirety). These valves can be used to build higher-level fluidic components including mixers, peristaltic pumps (Unger et al. (2000). *Science* 7, pp. 113-116) and fluidic multiplexing structures (Thorsen et el. (2002). *Science* 298, pp. 58-584; Hansen and Quake (2003). *Curr. Opin. Struc. Biol.* 13, pp. 538-544, incorporated by reference in their entireties herein) thus enabling high levels of integration and on-chip liquid handling (Hansen et al. (2004). *Proc. Natl. Acad. Sci. U.S.A.* 101, pp. 14431-1436; Maerkl and Quake (2007). *Science* 315, pp. 233-237, each incorporated by reference in their entireties). (FIG. 25).

FIG. 25A shows an optical micrograph of a valve made by MSL. Two crossing microfabricated channels, one "flow channel" for the active fluids (vertical) and one control channel for valve actuation (horizontal), create a valve structure. The flow channel is separated from the control channels by a thin elastomeric membrane to create a "pinch valve." Pressurization of the control channel deflects the membrane to close off the flow channel. FIG. 25B shows a section of an MSL device integrating multiple valves (filled with green and blue food dye). FIG. 25C is a section of a device having a total of 16,000 valves, 4000 chambers, and over 3000 layer-layer interconnects (arrow). FIG. 25D shows an example of a microfluidic device with penny for scale. Devices shown are for illustration of the MSL fabrication technology.

The assay chambers of a device, in one embodiment has an average volume of from about 100 pL to about 100 nL. For example, in one embodiment, one or more properties of an effector cell is assayed within a microfluidic chamber comprising a cell population wherein the volume of the microfluidic chamber is about 100 pL, about 200 pL, about 300 pL, about 400 pL, about 500 pL, about 600 pL, about 700 pL, about 800 pL, about 900 pL or about 1 nL. In another embodiment, the volume of the microfluidic chamber is about 2 nL. In another embodiment, the volume of the microfluidic chamber for assaying a property of an effector cell in a cell population is from about 100 pL to about 100 nL, from about 100 pL to about 50 nL, from about 100 pL to about 10 nL, from about 100 pL to about 1 nL, from about 50 pL to about 100 nL, from about 50 pL to about 50 nL, from about 50 pL to about 10 nL or from about 50 pL to about 1 nL. In even another embodiment, the volume of the microfluidic chamber for assaying a property of an effector cell in a cell population is about 10 nL, about 20 nL, about 30 nL, about 40 nL, about 50 nL, about 60 nL, about 70 nL, about 80 nL, about 90 nL or about 100 nL.

The MSL fabrication process takes advantage of well-established photolithography techniques and advances in microelectronic fabrication technology. The first step in MSL is to draw a design of flow and control channels using computer drafting software, which is then printed on high-resolution masks. Silicon (Si) wafers covered in photoresist are exposed to ultraviolet light, which is filtered out in certain regions by the mask. Depending on whether the photoresist is negative or positive, either areas exposed (negative) or not (positive) crosslinks and the resist will polymerize. The unpolymerized resist is soluble in a developer solution and is subsequently washed away. By combining different photoresists and spin coating at different speeds, silicon wafers are patterned with a variety of different shapes and heights, defining various channels and chambers. The wafers are then used as molds to transfer the patterns to polydimethylsiloxane (PDMS). In one embodiment, prior to molding with PDMS and after defining photoresist layers, molds are parylene coated (chemical vapor deposited poly(p-xylylene) polymers barrier) to reduce sticking of PDMS during molding, enhance mold durability and enable replication of small features In MSL, stacking different layers of PDMS cast from different molds on top of each other is used to create channels in overlapping "flow" and "control" layers. The two (or more) layers are bound together by mixing a potting prepolymer component and a hardener component at complementary stoichiometric ratios to achieve vulcanization. In order to create a simple microfluidic chip, a "thick" layer (e.g., between from about 200-2000 μms) is cast from the mold containing the flow layer, and the "thin" layer (e.g., between from about 25 to about 300 μms) is cast from the mold containing the control layer. After partial vulcanization of both layers, the flow layer is peeled off its mold, and aligned to the control layer (while still present on its mold, by visual inspection. The control and flow layers are allowed to bond, for example at 80° C. for about 15-60 minutes. The double slab is then peeled from the control mold, and inlet and outlet holes are punched and the double slab is bonded to a blank layer of PDMS (i.e., a flat layer of PDMS with no structural features). After allowing more time to bond, the completed device is mounted on a glass slide. Fluid flow in the device is controlled using off-chip computer programmable solenoids which actuate the pressure applied to fluid in the channels of the control layer. When pressure is applied to these control channels, the flexible membrane between the overlapping orthogonal control and flow lines deflects into the flow channel, effectively valving the flow. Different combinations of these valves can be used to create peristaltic pumps, multiplexer controls and isolate different regions of the chip With respect to the flow layer, assay chambers and channels for controlling fluidic flow to and from the assay chambers are defined by the photoresist layers. As will be appreciated by one of skill in the art, the thickness of a photoresist layer can be controlled in part by the speed of spin coating and the particular photoresist selected for use. The bulk of the assay chambers, in one embodiment, are defined by an SU-8 100 feature which sits directly on the Si wafer. As known to those of skill in the art, SU-8 is a commonly used epoxy-based negative photoresist. Alternatively, other photoresists known to those of skill in the art can be used to define assay chambers with the heights described above. In some embodiments, the assay chambers have a height and width of 50-500 µM and 50-500 µM, respectively, as defined by the SU-8 features.

Figure 26:
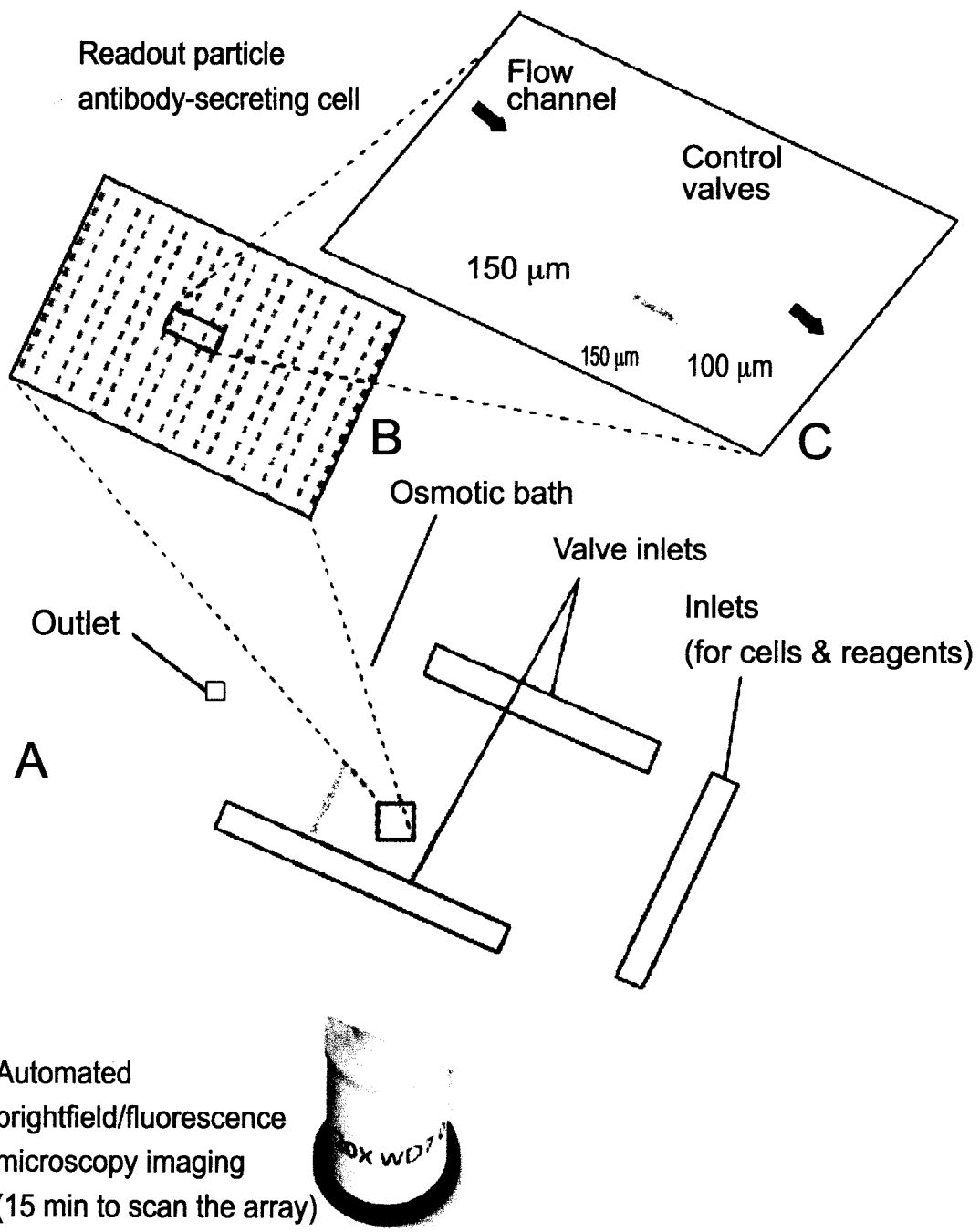
FIG. 26 is a schematic of one device of the invention. (A) Schematic showing the structure of a microfluidic device for antibody selection from single antibody-secreting cells. (B) Array of 4,032 analysis chambers. Each chamber is isolated during incubation and media can be exchanged within minutes. (C) Close up of an individual chamber. Cells, readout particles and reagents are injected sequentially, settling down by gravity. Imaging is performed using automated brightfield/fluorescence microscopy.

MSL fabrication techniques allow for a wide range of device densities, and chamber volumes to be fabricated. For the devices provided herein, in one embodiment, from about 2000 to about 10,000 effector cell analysis chambers are provided in a single integrated device. The effector cell analysis chambers, in one embodiment, have an average volume of from about 1 nL to about 4 nL, for example, from about 1 nL to about 3 nL, or from about 2 nL to about 4 nL. The effector cell analysis chambers, in one embodiment, are connected in a serial format, as depicted in FIG. 26. By way of illustration, a device with 4032 individual analysis chambers (average volume of 2.25 nL) connected in serial format achieve a screening throughput of approximately 100,000 cells per run (FIG. 8). The integrated microfluidic valves harnessed in the devices provided herein allow for chamber isolation, and programmable washing with reagents selected from a plurality of inlets, for example from 2 to about 32 inlets, 2 to about 20 inlets, 2 to about 15 inlets, 2 to about 10 inlets, or from 2 to about 9 inlets, or from 2 to about 8 inlets, or from 2 to about 7 inlets or from 2 to about 6 inlets. Additional inlets are provided to control valve pressure (FIG. 26).

The devices provided herein harness a gravity-based immobilization of cells and/or particles. Gravity based immobilization allows for perfusion of non-adherent cell types, and in general, buffer and reagent exchange within chambers. Each chamber has a cubic geometry with an access channel passing over the top (FIG. 26). For example, a chamber provided herein, in one embodiment, has the following dimensions: 50-250 µm×50-250 µm×50-250 µm; l×w×h, e.g., 150 µm×100 µm×150 µm; l×w×h. During loading, particles (e.g., cells or beads) follow streamlines and pass over tops of chambers, but fall to the bottom of the chambers when the flow is stopped. Due to the laminar flow profile, the flow velocity is negligible near the chamber bottom. This allows for perfusion of the chamber array, and the exchange of reagents via combined convection/diffusion, without disturbing the location of non-adherent cells (or beads) in the chambers.

Figure 27:
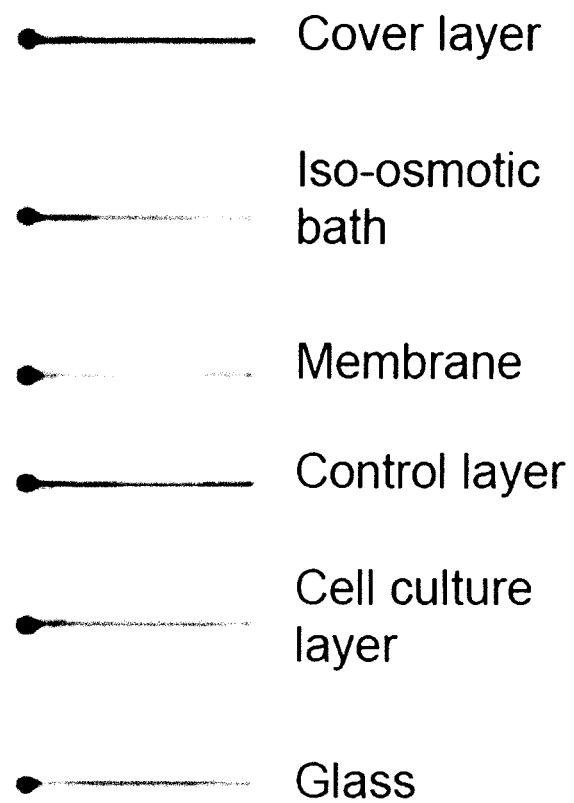
FIG. 27 is a schematic of the layers that are assembled during one embodiment of device fabrication.
Figure 28:
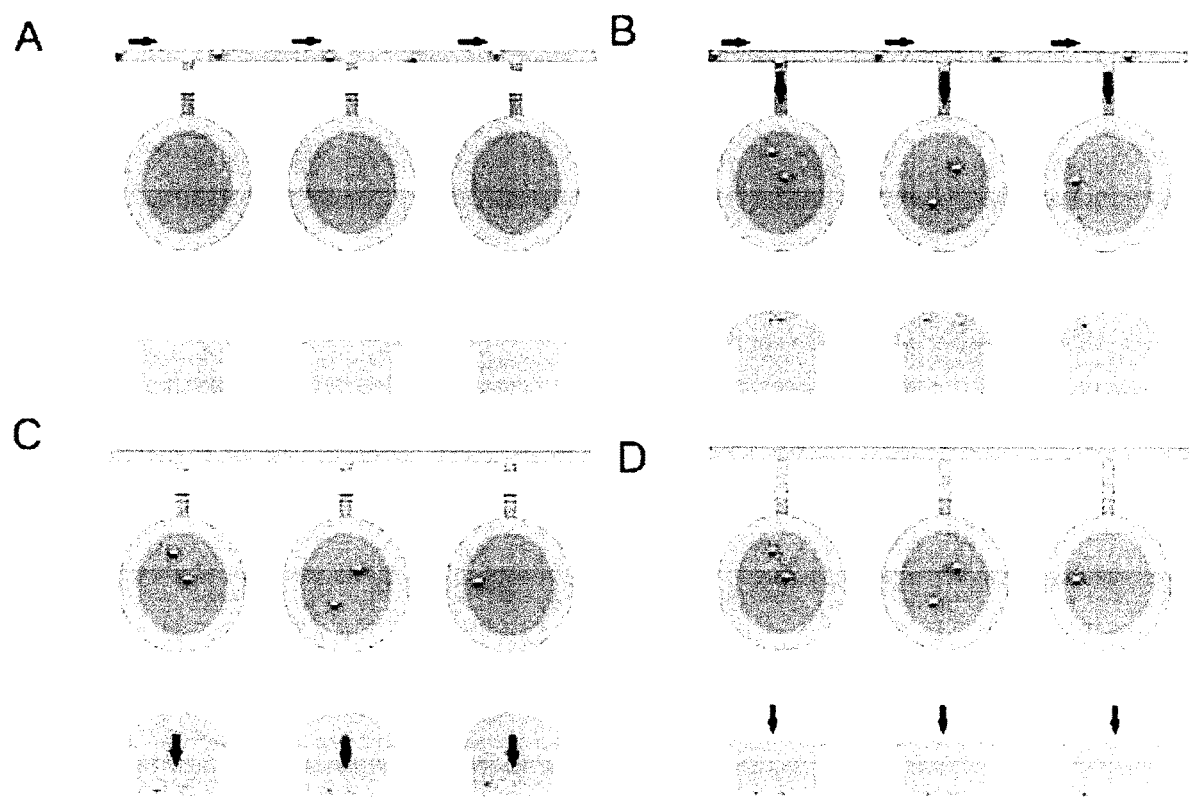
FIG. 28 (A) Top view and side view of inflatable chamber design. Chambers have a circular geometry, with a larger circular "lip" at the top, and are overlaid by a recess separated by a thin membrane. Valve connecting chambers to a flow channel is sealed and cells are loaded down the flow channel. (B) Valves to chambers are opened and pressure is applied to inflate the chambers, causing cells to enter the tops of chambers. (C) Valves are closed to seal chambers, and cells fall to the chamber floor. Channel is flushed with fresh medium. (D) Valves are opened and pressure is released, causing chambers to "deflate" back to their original volume. Repetition of this process may be used to exchange medium and/or add soluble factors.

Importantly, the devices provided herein allow for the long term culture and maintenance of cells, whether effector, accessory or of the readout variety. Microfluidic arrays of chambers are fabricated within a thick membrane (e.g., from about 150 µm to about 500 µm thick, about 200 µm thick, about 300 µm thick, about 400 µm thick or about 500 µm thick) of PDMS elastomer that is overlaid a reservoir of medium, for example 1 mL of medium as described previously (Lecault et al. (2011). Nature Methods 8, pp. 581-586, incorporated by reference herein in its entirety for all purposes). The proximity of the medium reservoir (osmotic bath) to the cell chambers effectively blocks evaporation (through the gas-permeable PDMS material) and ensures robust cell viability and where cells are not fully differentiated, growth over several days, and is critical for achieving long-term culture in nL volumes with growth rates and cellular responses that are identical to µL volume formats. FIG. 27 shows a schematic of the layers of the devices used herein.

The membrane design of the devices provided herein also enables the selective recovery of cells from any chamber by piercing the upper membrane with a microcapillary.

The device architectures provided herein are designed so that the soluble secretion products of effector cells are not washed away from a chamber when additional components, e.g., accessory particles or cell signaling ligands are added to the chamber. Additionally, the devices provided herein allow for the addition of components to a chamber without the introduction of cross-contamination of secretion products (e.g., antibodies) between individual chambers of a device. In embodiments where chambers are connected in serial, medium exchange requires flushing the entire array. Flushing the entire array, in one embodiment, results in the loss of antibody from each chamber and introduces cross-contamination to downstream chambers. However, where secretion products bind to a surface of a chamber or a readout particle bound to a surface, cross-contamination and/or loss of secretion products is not a significant problem, as secretion products are immobilized.

In one embodiment, cross-contamination and/or loss of secretion product is minimized by using an "inflatable chamber" design as shown in FIG. 28A-D. Each chamber has a single inlet, and are connected to a common channel through a short "access channel" controlled by a microvalve. The top of each chamber is overlaid by a recess, separated from the chamber by a thin (~10 µm) membrane, thus allowing for significant volume expansion when the chamber is pressurized. In one embodiment, chambers are inflatable to 2× volume, e.g., for 2 nL to 4 nL or 1 nL to 2 nL or 2.5 nL to 5 nL. In another embodiment, chambers are inflatable to 1.5× volume, e.g., for 2 nL to about 3.5 nL by application. Particles (cells or beads), in one embodiment, are loaded into inflatable chambers by inflating the chamber, allowing the particle to settle under gravity, and then deflating chamber. Similarly, a process of sequential inflation, diffusive mixing, and deflation, allows for washing of the chamber contents and/or exchange of medium. This approach enables the addition of soluble ligand without losing secretion products, as they are only diluted by less than 50%. Inflatable chambers also eliminate the potential for cross-contamination since the chambers are not connected in serial. The simplicity of this architecture allows for the integration of dense arrays, and in one embodiment, is applicable in devices having 10,000 chambers on an area of just over one square inch.

Figure 29:
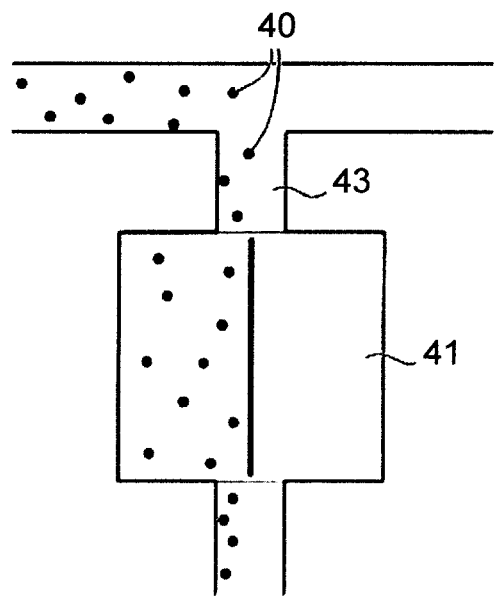
FIG. 29 is a schematic diagram of a microfluidic chamber having a cell fence according to an embodiment of the invention illustrating the use of laminar flow to direct particles to one side of the cell fence.
Figure 30:
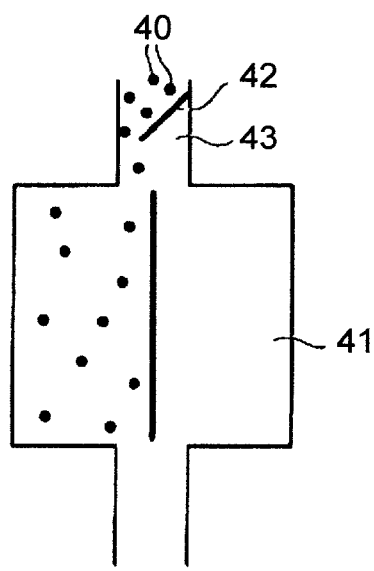
FIG. 30 is a schematic diagram of a microfluidic chamber having a cell fence according to an embodiment of the invention illustrating the use of a restriction upstream of the chamber inlet to preferentially direct particles to the one side of the inlet channel.

In one embodiment, the microfluidic devices provided herein are operated in flow conditions that suppress inertial effects and are dominated by viscosity. This fluid flow regime is characterized by a low Reynolds number $Re=\rho du/\eta$, where $\rho$ is the density of the fluid, d is the characteristic length scale of the channel, u is the characteristic velocity of the flow, and η is the viscosity of the fluid. At low Re the fluid flow streamlines become predictable and can be designed for the desired effect. Referring to FIGS. 29 and 30, for instance, if the goal is to load effector cells 40 only on the left side of the chamber 41, the device in one embodiment, is designed with a restriction upstream, e.g., formed by deflector 42 in FIG. 30, of the chamber that preferentially directs effector cells to the left side of the inlet channel 43. As effector cells 40 enter into the chamber 41 under flow, they continue into the left side of the chamber, following the streamlines of the flow, provided that the time of transport is chosen such that the effector particles do not diffuse substantially across streamlines. Similarly, readout particles, in one embodiment, are directed to the right of the chamber by use of an auxiliary channel connected to the inlet channel that results in the positioning of the readout particles in the right side of the inlet channel. In another embodiment, the readout particles are introduced through a different channel that accesses the chamber, including the outlet channel. It will be understood by those of skill in the art that the design of laminar flow profiles provides great flexibility in the direction of particles to a specific region of the chamber, if specific placement within a chamber is desired.

Segregation of effector cells from readout particles in a particular chamber can also be achieved via the use of a structural element, by manipulating the flow within a flow channel or channels of the device, stochastic loading, a magnetic field, an electric field or dielectric field, a gravitational field, a modification to a surface of the microfluidic chamber that affects adhesion, and relative buoyancy of the effector cells and the readout particles, or a combination thereof.

In one embodiment, effector cells and/or readout cells are confined to a chamber or a portion of a chamber (e.g., an effector zone or readout zone) using a structural element within the chamber.

"Effector zone" as used herein, is a region of a microfluidic chamber in which an effector cell, a population of effector cells (or subpopulation thereof), is retained.

"Readout zone" as used herein, is a region of a microfluidic chamber in which a readout particle is kept segregated from effector cells, and in which a functionality of the effector cell(s) may be detected. For example, when an "effector zone" and a "readout zone" are three dimensional regions of a microfluidic device, they may be individual chambers (for example, a compound chamber), where the chambers are in fluid communication with one another.

As described herein, in one embodiment, one or more structural elements are used for the distribution of effector cells and/or readout particles within one or more chambers. In a further embodiment, the one or more structural elements are used for the retaining of effector cells and/or readout particles within defined regions of a chamber, e.g., an effector zone and/or readout zone. In some embodiments, the use of such structural elements is coupled with the use of a field (e.g., gravity, dielectric, magnetic, etc.) to achieve a retaining function. For example, in one embodiment, a cell fence is utilized to trap cells (effector or readout) at a certain chamber location. Cell fences have been described previously in PCT Application Publication No. 2012/162779, and the disclosure of which is incorporated by reference in its entirety for all purposes. "Cell fence," as used herein, refers to any structure which functions to restrict the movement of cells and readout particles, but which may permit the movement of other cell products, within a microfluidic chamber.

Figure 31:
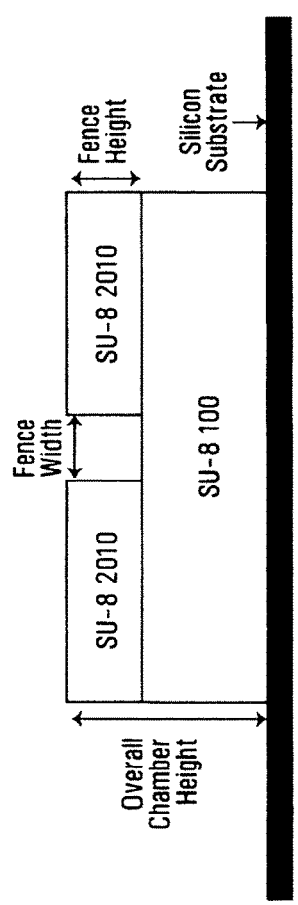
FIG. 31 is a schematic depiction of a reusable mold made from multiple layers of photoresist on a silicon wafer substrate, which is used for PDMS microfluidic device fabrication.

In embodiments where cell fences are utilized, each fence is defined by a thinner SU-8 2010 feature which sits on top of the SU-8 100 feature. Such a structure is depicted schematically in FIG. 31. Fabrication of cell fences have been described previously in PCT Application Publication No. 2012/162779, the disclosure of which is incorporated by reference in its entirety. In one embodiment where a cell fence is utilized to capture an effector cell or a population of cells optionally comprising one or more effector cells, microfluidic chambers are defined using SU-8 100 negative photoresist (typically 160 μm in height) following standard protocols, except that the final step, development is omitted. Specifically, a Si wafer spun with SU-8 100 photoresist is cooled after the post-exposure bake, and instead of developing the photoresist, SU-8 2010 is spun on top of the undeveloped SU-8 100, typically at a height 10-20 μm. The thickness of the SU-8 2010 determines the height of the fence. The depth of each chamber was the combined height of both photoresist layers.

In alternative cell fence embodiments, the SU-8 100 layer is fully developed, and the wafer is coated with an additional layer of SU-8 100 which is higher than the first layer, the difference becoming the height of the fence.

Structural elements described herein may provide for the retention of effector cells and readout particles on different sides of a chamber by use of gravity; in this case gravity is directed towards the floor of the chamber and provides a force that impedes the cell from rising over the fence. It should be noted that microscopic particles may be subject to Brownian motion that may cause them to "diffuse" over a fence in a stochastic manner. However, the probability that a particle will spontaneously rise over the fence by Brownian motion is determined by the Boltzmann distribution and is proportional to the Boltsmann factor $e^{-E/KT}$, where E is the potential energy of rising the particle to a height equal to the height of the fence (E=volume of particle×the difference between the density of the particle and the density of the liquid×gravity×the height of the fence), K is the Boltzmann constant, and T is the temperature of the liquid. Thus, one of skill in the art can design and fabricate the height of a fence such that the probability of a particle spontaneously "diffusing" over the fence is negligibly small. It will also be appreciated by one of skill in the art that a fence of a given height presents a barrier to some particles (e.g., beads or cells), depending on the potential energy required to pass over the fence, but will not present a barrier to particles having appropriately low apparent mass in the liquid. For example, a fence having a height of about 20 μm does not allow for a cell to spontaneously pass by diffusion, but presents essentially no barrier to the diffusion of proteins. In one embodiment, gravity used in conjunction with a structural element for retaining cells. However, other forces such as magnetic gradient forces, dielectric forces, centrifugal forces, flow forces, or optical forces, may be similarly used.

Figure 32:
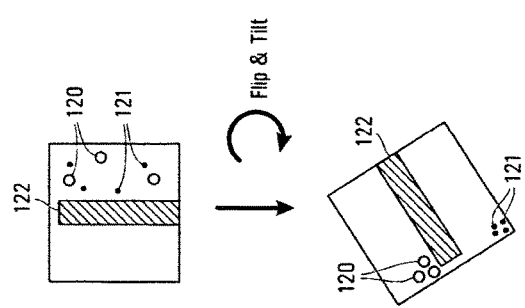
FIG. 32 is a schematic diagram of a microfluidic chamber having a cell fence according to an embodiment of the invention illustrating the use of a cell fence that selectively separates particles based on particle size.

Structural elements may also be effective in retaining effector cells or readout particles by providing a mechanical barrier to passage. For instance, the use of a fence that reaches to within a gap 'd' of the roof of a chamber, where 'd' is smaller than the diameter of all effector cells or readout particles, acts as a barrier without the need for application of another force. Such a structure may also be designed to selectively partition effector cells or particles on different sides of a chamber by designing the gap 'd' to allow for one type of particle to pass but not the other. Referring to FIG. 32, for example, in one embodiment, effector cells 120 have a diameter of 10 microns, and a mixture of the effector cells and readout particles 121 (having a diameter of 1 micron)

are loaded into one side of a chamber that is separated from the other side by a fence 122 having a 5 micron gap (as measured to the roof of the chamber). By tipping the device appropriately, the 1 micron readout particles 121 are transferred to the other side of the chamber, while leaving the effector cells 120 on the other side. In such a manner, the effector cells are positioned in the effector zone of a chamber while the readout particles are partitioned in the readout zone.

Figure 34:
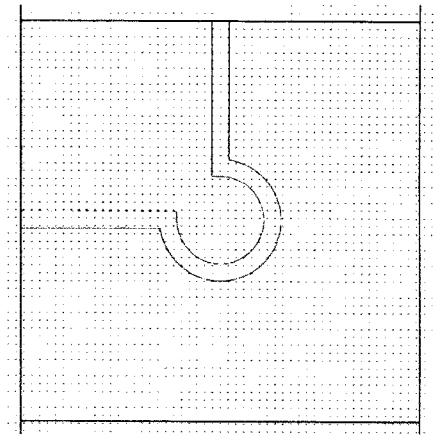
FIG. 34 is a drawing of particle trap embodiment (grid pitch is 2 µm) for a chamber having two perpendicular cell fences connected by a generally circular portion defining a particle trap.

Wells within a chamber can also be used to sequester assay reagents, effector cells and/or readout cells. For example, representative device geometries are shown in FIGS. 33 and 34. In one embodiment, a chamber is designed with an array of wells, whereby small wells are defined at the bottom of a chamber (FIG. 33). Wells may be any shape, and are designed based on the effector cell or readout particle they are designed to associate with. Both square and circular shaped wells are amenable for use with the devices described herein, and generally, any polygon shaped well is amenable for use in a chamber. Various prototypes were fabricated with square and circular wells, as well as square and circular 'posts.' Effector cells and readout particles are loaded into the device at concentration such that each well within a chamber contains a subpopulation of cells or readout particles. For example, in one embodiment, each well within a chamber is addressed to contain one or zero effector cells. Such a design can spatially constrain the particles/cells. In embodiments where discrete "effector zones" and "readout zones" are utilized, an effector cell defines the well in which it resides as an "effector zone" and a readout particle defines the well in which it resides as a "readout zone".

FIG. 34 shows a "bead trap" embodiment that can be used in the devices of the present invention. This design spatially confines a plurality of readout particles (e.g., a plurality of beads or readout cells) or cell population to a specific spatial position within a chamber. Such a design overcomes problems that can be associated with beads or particles that otherwise move during an assay, thereby simplifying downstream imaging and image analysis. Having a fixed position for the readout particle is also advantages due to the diffusion distance between effector cell and readout particle being better controlled.

The operation of a bead trap (shown in FIG. 34), in one embodiment, occurs as follows: readout particles are loaded into a chamber and then allowed to settle by gravity to the bottom of the chambers, while the chamber is tipped toward the upper right corner (i.e., the zone enclosed by the perpendicular cell fences and generally circular particle trap opening toward the upper right quadrant). After the readout particle or particles have settled to the bottom of the chamber, the device could be tipped in the opposite direction (along the same axis) so that the readout particle or particles slide or roll along the bottom of the chamber and into the circular 'trap' feature in the center of the chamber. As mentioned above the same method and device may be employed to sequester effector cells.

In one embodiment, effector cells and readout particles are positioned within a chamber into an effector zone and readout zone using micro-fabricated structures that are designed to retain one or more types of particles (e.g., cells). For example, in one embodiment, the flow of effector cells or readout particles may be designed to intersect with micro-fabricated cup structures that are designed to retain particles but which allow the flow to pass through. Such structures can be designed such that they can accommodate only a fixed number of particles or cells, or a defined size range of particles or cells, making the structures selective for different particle types. Such traps may be positioned substantially in the chamber or at the inlet and outlets of the chambers.

Figure 35:
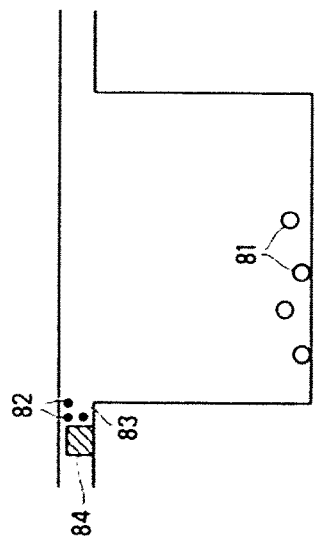
FIG. 35 is a schematic diagram of a microfluidic chamber according to an embodiment of the invention illustrating the use of micro-fabricated structures positioned at the outlet to retain particles of a certain size in the chamber.

In another embodiment, referring to FIG. 35, effector cells 81 are provided at the bottom of a chamber using gravitation, while readout particles 82 are positioned at the outlet 83 of the chamber using a trap structure 84 that is fabricated in the outlet channel.

Figure 36:
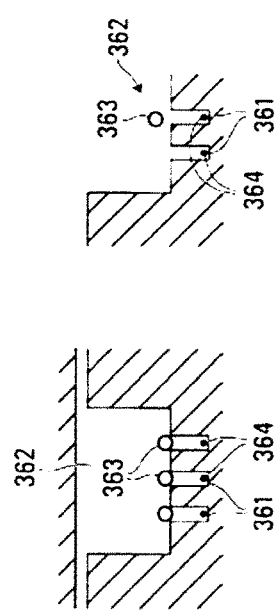
FIG. 36 is a side view schematic diagram of a microfluidic chamber comprising dead-end cups at the bottom of the chamber.

According to one embodiment of the invention, one or more recesses (also referred to herein as "cups") at the bottom of a chamber are provided to segregate effector cells from readout particles. Referring to FIG. 36, for example, dead-end cups 361 are provided at the bottom of a chamber 362 which have a width smaller than the average diameter of the effector cell 363 but greater than the diameter of the readout particle 364. In this configuration, readout particles 364 sink to the bottom of the cups 361 while effector cells 363 are retained above the cup entrance. In some embodiments, the bottom of the cup 361 is accessed through a porous membrane and channel structures beneath, to augment fluidic access to the readout particles in dead-end cups that are covered with effector cells.

Figure 37:
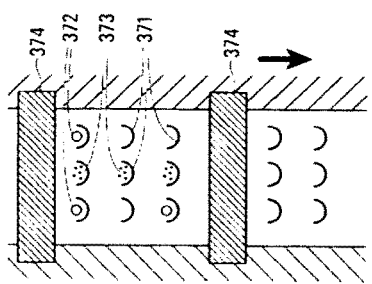
FIG. 37 is a side view schematic diagram of a chamber according to an embodiment of the invention in which structural elements are positioned in the flow channel to retain effector cells and readout particles.

In one embodiment, structural elements are positioned in a flow channel or chamber to retain one or more particles or cells. Referring to FIG. 37, structural elements 371 (or functionalized surface patches, etc) may be positioned in the flow channel (not necessarily a microwell) to retain one or more effector cells 372 and/or one or more readout particles 373. For example, trap structures may be designed to retain particles or cells with specific physical properties (e.g. size) or may be non-specific (random distribution of effector cell and readout particle). Valves 374 can be used to separate adjacent chambers.

Figure 38:
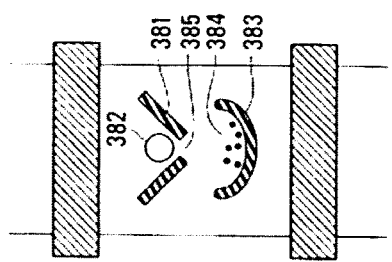
FIG. 38 is a side view schematic diagram of a chamber according to an embodiment of the invention in which structural elements are positioned sequentially in a chamber to segregate and retain particles on the basis of size.

In an extension of the design described above (e.g., FIG. 37), structural elements in the flow channel are designed to retain effector cells and readout particles in close proximity to one another. Referring to FIG. 38, in one embodiment, one unit includes an effector cell trap 381 to trap an effector cell 382, and microstructure 383 to retain one or more readout particles 384. Readout particles with a diameter smaller than the gap of the cell trap pass the cell trap and are retained in the microstructure 383 located downstream of effector cell trap 331. Effector cells with a diameter larger than gap 385 in the effector cell trap 381 are retained, as discussed above. In another embodiment, microstructures are designed so that the distance and location of different types of readout particles (or effector cells) are well defined.

Figure 39:
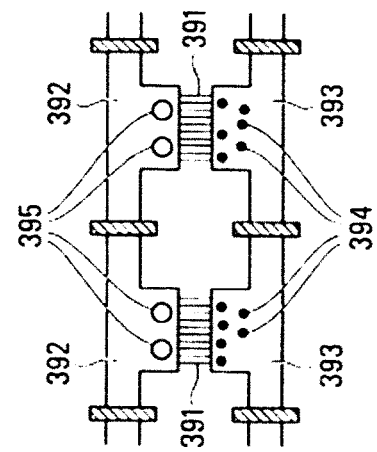
FIG. 39 is a top view schematic diagram of a serial, flow through arrangement of microfluidic chambers in which a porous membrane is used to separate effector cells from readout particles.

In addition to barriers such as fences between effector cells and readout particles, porous membranes may also function as a barrier and therefore, are amenable for use with the present invention. For example, referring to FIG. 39, in one embodiment, a porous membrane 391 (also referred to as a diffusion channel) is fabricated between effector cell chambers 392 holding effector cells 395 and readout particle chambers 393 holding readout particles 394, providing a horizontal arrangement. In such horizontal arrangements, the porous membrane 391, in one embodiment, is substituted by a sieve valve or a fluidic channel with a cross-section smaller than the diameter of the effector cells or readout particles. Sieve valves have previously been described in U.S. Patent Application Publication No. 2008/0264863, the disclosure of which is incorporated by reference in its entirety for all purposes.

In another embodiment, a porous membrane is fabricated between PDMS layers to provide a vertical arrangement. In this embodiment, an effector zone is provided in one PDMS layer and the readout zone is provided in the second PDMS layer. One advantage of a vertical arrangement is that the spacing between the effector zone and the readout zone is well-defined.

Porous membranes incorporated within PDMS devices have been reported previously, for example, by Aran et al. (2010). *Lab Chip* 10, pp. 548-552; Cheuh et al. (2007). *Anal. Chem.* 79, pp. 3504-3508, the disclosure of which is incorporated by reference in its entirety herein for all purposes. In one embodiment, a porous membrane is fabricated according to one of the following embodiments. In another embodiment, a PDMS layer is made porous by adding an immiscible fluid to the uncured components of the PDMS. During the baking step, the immiscible fluid evaporates. In yet another embodiment, a PDMS membrane is perforated following curing using laser ablation or another removal technique. In even another embodiment, a PDMS membrane is cast on one or more microstructures with a height exceeding the thickness of the membrane in order to make the PDMS membrane porous.

Figure 40:
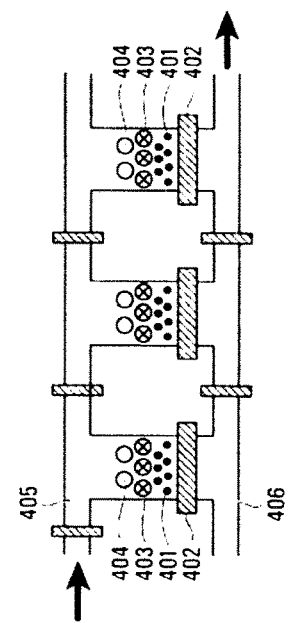
FIG. 40 is a top view schematic diagram of a serial, flow through arrangement of microfluidic chambers in which a layer of non-functionalized beads is used to separate effector cells from readout particles.

In one embodiment, a structure that retains one or more effector cells and/or readout particles is a temporary structure and/or removable. In one embodiment, as illustrated in FIG. 40, readout particles 401 (e.g., beads) are stacked against a sieve valve 402 (a valve that blocks only part of the channel cross-section). A layer of non-functional beads 403 are then stacked against the readout particles 401, providing a barrier. A layer of effector cells 404 are then provided, and stacked against the layer of non-functional beads 403. As will be understood from FIG. 40, effector cells 404, in one embodiment, are provided through the feed channel 405. Effector cell assays measuring the effect of one or more effector cells 404 on one or more readout particles 401, in one embodiment, are carried out using the lower bus channel 406. One advantage of temporary structures is that chamber contents are recoverable, and in some embodiments, selectively recoverable, through the lower bus channel by opening one or multiple of the sieve valves.

In addition to microfabricated retention methods or fields, hydrogels such as agarose are amenable for use in order to localize effector cells and/or readout particles. For example, in one embodiment, readout particles and/or effector cells can be loaded in liquid agarose, for example, photosensitive agaraose, which solidifies on-chip. As such, the movement of effector cells or readout particles is restricting, which simplifies the imaging process while still allowing diffusive transport. Upon re-melting of the agarose, in one embodiment, selective remelting, effector cells are recovered using microfluidic methods discussed herein. In another embodiment, immobilized cells are selectively recovered using a micromanipulator or a robotic method.

In one embodiment, segregation of effector cells and readout particles in a particular zone within a chamber, or a particular chamber, in one embodiment, is achieved by a specific flow profile, stochastic loading, a magnetic field, an electric field or dielectric field, a gravitational field, a modification to a surface of the microfluidic chamber, and selecting a particular relative buoyancy of the effector cells and the readout particles, or a combination thereof. For example, in one embodiment, either the cell population is labeled with magnetic particles or the readout particles are magnetic, such that provision of a magnetic field to the top surface of a particular chamber draws the cell population or readout particles upward, and away from either the readout particles, in the case that the cells are magnetically labeled, or the cell population, in the case where readout particles are magnetically labeled. In another embodiment, the specific gravity of the fluid in which the cell population and readout particles are incubated can be chosen to facilitate separation of the effector cells and readout particles based on their relative buoyancy. Certain particle and cell sequestration methods are discussed in greater detail below.

Effector cells and readout particles, in one embodiment, are distributed within a chamber by functionalizing one or more walls of the chamber. In one embodiment, the surface functionalization is performed by graft, covalently linking, adsorbing or otherwise attaching one or more molecules to the surface of the chamber, or modifying the surface of the chamber, such that the adherence of cells or particles to the chamber surface is altered. Nonexclusive examples of such functionalizations for use herein are the non-specific adsorption of proteins, the chemical coupling of proteins, the non-specific adsorption of polymers, the electrostatic adsorption of polymers, the chemical coupling of small molecules, the chemical coupling of nucleic acids, the oxidization of surfaces, etc. PDMS surface functionalization has been described previously, and these methods can be used herein to functionalize surfaces of the devices provided herein (see, e.g., Zhou et al. (2010). *Electrophoresis* 31, pp. 2-16, incorporated by reference herein for all purposes). Surface functionalizations described herein, in one embodiment, selectively bind one type of effector cell (e.g., an effector cell present in a cell population), or selectively bind one type of readout particle. In another embodiment, the surface functionalization is used to sequester all readout particles present in a chamber.

In yet another embodiment, a surface functionalization or a plurality of different surface functionalizations are spatially defined within a chamber of a device. Alternatively, a surface functionalization or plurality of surface functionalizations covers the entire chamber. Both of these embodiments are useful for the distribution of effector cells are readout particles into distinct locations within a microfluidic chamber. For instance, in embodiments where the entire chamber is functionalized with a molecule that binds all types of introduced readout particles, the particles are directed to different regions of the device, using the methods described above, where they become immobilized on the surface. In another embodiment, the entire chamber may be functionalized to bind only one specific type of readout particle. In this case, all particles, in one embodiment, are first directed to one region using one of the methods described herein, causing a subset of particles to adhere to the chamber surface in the functionalized region, followed by exerting a force towards a different region that displaces only the particles that do not bind the functionalized surface or surfaces. In yet another embodiment, regions of the device (e.g., different chambers or regions within a single chamber) are functionalized with different molecules that selectively bind different subsets of effector cells and/or readout particles, such that inducing the interaction of the effector cells and/or readout particles with substantially the entire chamber surface results in the partitioning of different particle or cell types in different regions. As described herein, it is intended that surface functionalization may be used in isolation or in combination with the other methods described herein for effector cell and readout particle manipulation. Multiple combinations of particle and cell sequestration methods, together with multiple fluidic geometries are possible.

Figure 41:
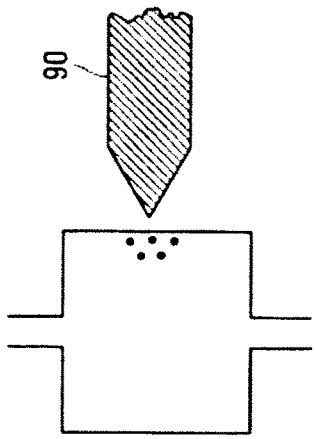
FIG. 41 is a schematic diagram of a microfluidic chamber according to an embodiment of the invention illustrating the use of a magnetic field to position particles within the chamber.

In another embodiment, effector cells and/or readout particles are positioned within a chamber by the use of a magnetic field. It will be understood that to manipulate and position an effector cell(s) and/or a readout cell(s) magnetically, the effector cell(s) and/or a readout cell(s) are first functionalized with or exposed to magnetic particles that bind to them. In one embodiment, the magnetic field is externally created, i.e., by the use of a magnet outside of the microfluidic device, using a permanent magnetic, an electromagnet, a solenoid coil, or of other means. In another embodiment, referring to FIG. 41, the magnetic field is generated locally by a magnetic structure 90 integrated into, or separate from, the device. The magnetic field, in one embodiment is applied at different times, and in one embodiment, the magnetic field is applied in conjunction with particle loading, to influence the position of effector cells and/or readout particles that respond to a magnetic field.

It will be appreciated by those skilled in the art that commercially available beads or nanoparticles that are used in the separation and or purification of biological samples can be used in the devices and methods provided herein. For example, "Dynabeads" (Life Technologies) are superparamagnetic, monosized and spherical polymer particles, and in one embodiment, are used in the devices and methods provided herein as readout particles. Magnetic particles conjugated with molecules that specifically bind different target epitopes or cell types are well-known in the art, and are also amenable for use with the devices and methods provided herein. When in the presence of a magnetic field having a non-uniform property, such magnetic particles are subjected to a force that is directed towards the gradient of the magnetic field. This gradient force, in one embodiment, is applied to position particles within a chamber.

Figure 42:
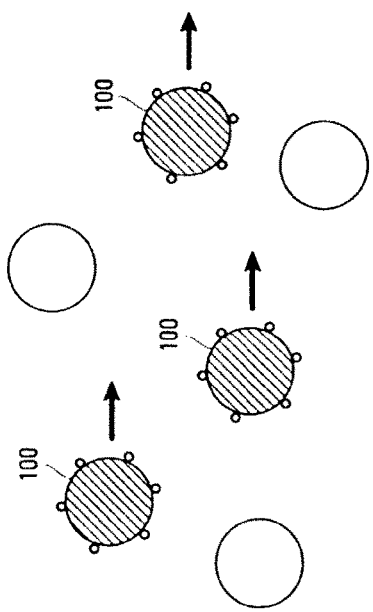
FIG. 42 is a schematic diagram of a method of separating particles according to an embodiment of the invention using a magnetic field to direct one type of particle to which magnetic particles are coupled to a position within a chamber while having little or no effect on particles to which the magnetic particles are not coupled.

Referring to the embodiment depicted in FIG. 42, it will be appreciated that a gradient force may be used to specifically apply a force to a subset of particles in order to preferentially direct one subtype, i.e., particles 100, within a chamber. In one embodiment, this gradient force is applied before particles enter the chamber in order to position them at a given position of the inlet channel, thereby resulting in particle loading to a specific region of the chamber. In another embodiment, the gradient force is applied prior to, during, or after the loading of particles into the chambers.

Figure 43:
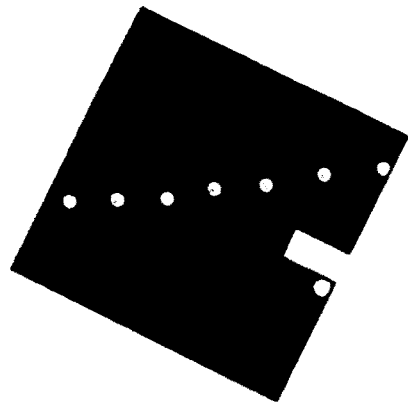
FIG. 43 is a cross-sectional view of a chamber embodiment with cell fence, where the chamber has been tipped to facilitate readout particle (bead) loading into the readout zone.

In addition to flow forces, a cell or particle (e.g., effector particle or readout particle) in the flow may be subject to "body forces" that are derived from the action of an external field. The orientation of the microfluidic devices provided herein, within a gravitational field may be used to direct effector cells and readout particles to a specific region of a device chamber. As illustrated in FIG. 43, one such method involves physically tilting the entire microfluidic device and sample holder along the axis of a fence, and waiting for a sufficient time period for the respective particles to settle by gravity to either side of the fence. In one embodiment, the tilt angle is from about 30 to about 50 degrees, for example from about 30 degrees to about 45 degrees. However, it should be understood that this angle can be adjusted depending on the cell or particle loaded, the flow rate, and the viscosity of the solution. It will be appreciated that the tipping of a device in different orientations may be used to direct multiple sets of particles to multiple distinct regions, depending on the timing of the tipping and the introduction of the particles.

Figure 44:
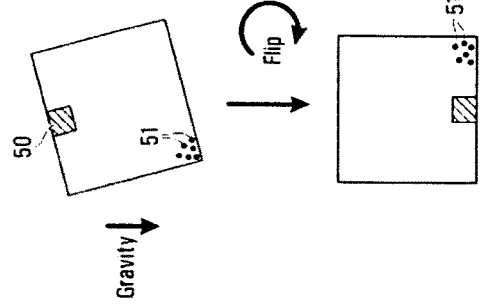
FIG. 44 is a schematic diagram of a microfluidic chamber having a cell fence according to an embodiment of the invention illustrating the use of rotation of the chamber to preferentially direct particles to the one side of the fence.

A person skilled in the art will understand that the use of gravity to direct particles within a chamber can be accomplished in multiple steps. Referring to FIG. 44, by way of example, a device is turned substantially upside down, and the particles 51 are directed to one side of a chamber roof by tipping the device. Next, the device is rotated back to the upright position quickly, such that the particles do not move far during the process of returning the device to the upright position. The particles then settle to the floor of the chamber, but remain on the right side of the chamber due to the presence of fence 50. In this way, features on the roof of the chamber can be used to segregate particle types, followed by transfer of the particles to the floor of the respective chamber without substantially changing the lateral positioning of the particles within the chamber. It will be understood by those in the art that the time for flipping the device in order to localize particles as described above is dependent in part on the velocity at which the particles fall through the liquid and the maximum displacement that can be accepted for accurate positioning. The velocity of a particle falling through a fluid is in the direction of the gravitational field and can be calculated according to the following equation, which is known to those of skill in the art:

$$U = V_{particle} * (\rho_{particle} - \rho_{liquid}) * g * \gamma^{-1}$$

Where $V_{particle}$ defines the volume of the particle, g is the acceleration of gravity, and is the drag coefficient of the particle. For a spherical particle, $\gamma$ is well approximated by the Stokes drag equation as:

$$\gamma_{sphere} = 6\pi\eta r$$

In some embodiments of the invention where gravity is used to position particles within a chamber, the effective size and/or density of the particles are manipulated by using smaller particles that bind on the particles surface. For example, the effector cell may be exposed to ferromagnetic microbeads that are functionalized to bind the effector cell, thereby causing the effector cell to have a much higher effective density and to have a slightly larger drag coefficient, the net effect of which is to make the cell fall faster through the gravitational field.

Figure 45:
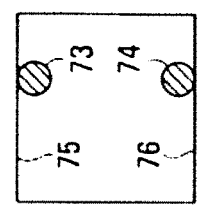
FIG. 45 is a schematic diagram of a method of separating effector cells and readout particles according to an embodiment of the invention using differential density of the effector cell and readout particle.

Also within the scope of the invention, and related to the use of gravity for the positioning of particles, is the use of buoyancy of the particles within the fluid in order to direct fluid flow and effector cell and readout particle positioning. Referring to FIG. 45, for example, in one embodiment, effector cell 74 and readout particle 73 have different densities, such that the density of effector cell 74 is greater than that of the liquid in the chamber 77, and the density of the readout particle is less than that of the liquid, and the device is placed within a gravitational field such that the gravitational field is directed downwards in the chamber from the roof 75 to the floor 76, the effector cell and the readout particle are partitioned to the floor and the roof of the device, respectively, thereby defining the effector and readout regions of the chamber 77. In one embodiment, this effect is controlled by the addition of components to the liquid that change the density and/or by modification of the particles, or selection of the readout particle 73 and effector cell 74, such that they have the appropriate density differences. It should be noted that by exchanging medium in the chamber the partitioning of particles may be reversibly modulated. Such an exchange is within the scope of the present invention.

Effector cells and/or readout particles, in one embodiment, are partitioned to different regions of a chamber by the use of an electrostatic field and/or dielectric field that impart a force to the particles. These fields, in one embodiment, are generated externally to the device. In another embodiment, the electrostatic and/or dielectric field is generated locally using one or more micro-fabricated electrodes within the microfluidic device. Such electrodes can be defined in a metal film on the substrate the device is mounted on, integrated into a separate layer of the device, or defined by filling microfluidic channels with a conducting liquid. There are many examples of the integration of electrodes within microfluidic devices and various geometries and methods for integration will be apparent to those skilled in the art. For example, the electrodes disclosed by Li et al. (2006). *Nano Letters* 6, pp. 815-819, incorporated by reference herein in its entirety), are amenable for use with the present invention.

Figure 46:
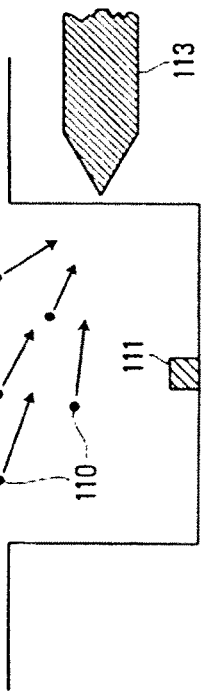
FIG. 46 is a schematic diagram of a microfluidic chamber comprising an integrated electrode according to an embodiment of the invention illustrating the use of a dielectric field to position particles within the chamber.

In one embodiment, a dielectric field is applied to one of the devices described herein, and the dielectric field is designed with a frequency that results in a differential force on particles having differential properties, which results in the separation of the particles by differential properties. An example of using dielectric fields to position effector cells and readout particles within a chamber using a dielectric field produced by an integrated electrode is shown in FIG. 46. In this embodiment, effector cells 110 are loaded into a chamber having a fence structure 111 at the bottom, through an inlet channel 112 situated on the top of the device. On loading the effector cells 110, an electrode 113 is used to generate a dielectric field with a gradient that results in a force on the effector cells 110. This force, directed towards one side of the chamber, causes the effector cells 110 to selectively fall (under the influence of gravity) into the effector region of the chamber. Repeating this process with readout particles, an electrode on the other side (readout zone) of the chamber may then be used to load the readout particles into the readout zone. Such dielectric manipulations provide a force that may be used in a variety of configurations or processes for the purpose of partitioning effector cells and readout particles.

In yet another embodiment, acoustic waves, such as acoustic standing waves, are used to trap, position and/or retain effector cells and/or readout particles.

In yet another embodiment, effector cells and/or readout particles are stochastically loaded into the effector and readout zones of a microfluidic chamber with high efficiency by appropriate design of the chamber geometry and the loading density. For example, FIG. 33 shows a microfluidic chamber having an array of 45 microwells that are fabricated at the bottom of the chamber having a volume of approximately 2 nanoliters. The loading of effector cells and readout particles into the microwells of the microfluidic chamber, in one embodiment, is achieved using gravity as described above. If the number of effector cells and readout particles is maintained sufficiently low there is a low probability that two effector cells and/or readout particles are positioned within the same microwell within the microfluidic chamber.

The number of effector cells and readout particles per chamber can be selected such that the probability of having a chamber without both a readout particle and an effector cell is very low. As an example, in one embodiment, the concentrations of effector cells and readout particles are chosen such that there is an average of three of each type per chamber. Assuming a random distribution of particles within the microwells the chance of having k particles of either type in a given microwell of a chamber is given by Poisson statistics as:

$$P(\text{more than one in a microwell}) = \lambda^k e^{-\lambda}/k!$$

where $\lambda$=the average number of particles per micro-well of the microfluidic chamber, which in this example is $(3+3)/45=0.133$. Thus, the probability of having 0 or 1 particles in a microwell in this embodiment is:

$$P(k=0)=e^{-0.133}=87.5\%, \text{ and } P(k=1)=11.7\%.$$

Thus, in this embodiment, the chance of having more than one particle is given by $P(k>1)=100\%-87.5\%-11.7\%=0.83\%$. The chance of having zero micro-wells within a given chamber containing more than one particle may then be calculated according to binomial statistics as:

$$P(\text{no wells with more than one particle}) = (1-0.0083)^{45} = 69\%.$$

Thus, in this example approximately 70% of the chambers will have no microwell with more than one particle. It will be appreciated that this analysis represents a lower bound to the fraction of useful chambers since in chambers where some micro-wells have more that one particle in at least one micro-well a useful measurement will still be possible using the other chambers.

It is further considered that the micro-wells may be designed with a size such that they will not accommodate more than one particle. In this case the tipping of the device after loading may be used to ensure all particles are contained within a micro-well of the device and that no micro-wells have more than one particle. It is also understood that different types of particles, including different effector or readout particles, may be loaded in a sequential fashion or together depending on the design of the assay. Finally, it is understood that this geometry, while using microwells, maintains the advantages of chamber isolation since the array of micro-wells is contained within a small chamber that may have the capability for being isolated from other chambers.

As noted above, the one or more of the methods a described above, in one embodiment, are combined are used to achieve segregation of a population of cells optionally comprising one or more effector cells from a population of readout particles, in an effector zone and readout zone of a microfluidic chamber, respectively. Additionally, one or more of the methods described above, in one embodiment, are used to achieve segregation of a cell subpopulation from an original cell population, or to segregate a subpopulation of readout particles from a population of readout zones, for example, in specific regions of an effector zone or readout zone of a microfluidic chamber.

Figure 47:
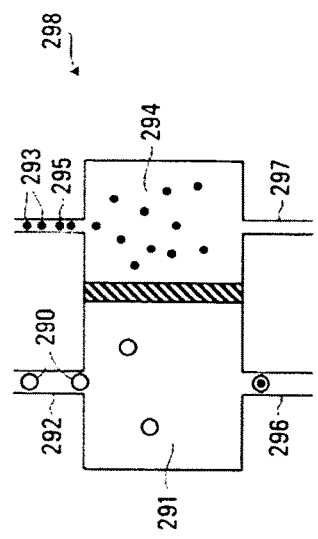
FIG. 47 shows a top view schematic diagram of a chamber according to an embodiment of the invention in which effector cells and readout particles are introduced to the chamber via separate inlets.

Effector cells and readout particles, in one embodiment, are delivered to a chamber using a common inlet and segregated upon entry into the chamber. Alternatively, effector cells and readout particles are introduced to the chamber via separate inlets specific for the effector zone and readout zone. Referring to FIG. 47, a chamber 298 according to an embodiment of the invention is shown. Effector cells 290 are introduced into effector zone 291 via effector cell inlet 292, while readout particles 293 are introduced into readout zone 294 of the chamber via readout particle inlet 295. In the illustrated embodiment, effector zone 291 and readout zone 294 have respective outlets 296 and 297, however the invention is not limited thereto. Specifically, the effector zone 291 and readout zone 294, in another embodiment, have a common outlet.

Figure 48:
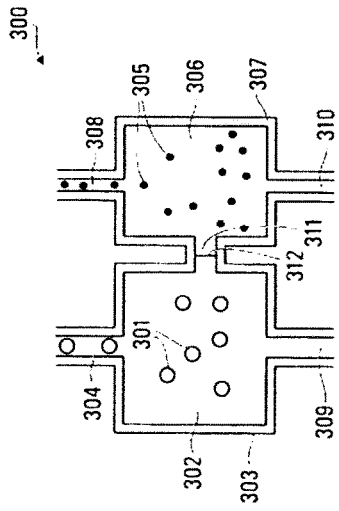
FIG. 48 is a top view schematic diagram of a compound chamber according to an embodiment of the invention in which an effector zone subchamber and a readout zone sub chamber may be placed in fluid communication with each other.

In another embodiment, a compound chamber (i.e., a chamber comprising a plurality of subchambers) is used to provide an effector zone and readout zone. One embodiment of a compound chamber 300 is shown at FIG. 48. In one embodiment, a cell population comprising one or more effector cells 301 is delivered to effector zone 302 defined by effector cell subchamber 303 of compound chamber 300 via the cell inlet 304. Similarly, readout particles 305 are delivered to readout zone 306 defined by readout particle subchamber 307 of compound chamber 300 via readout particle inlet 308. In the illustrated embodiment (FIG. 48), effector cell subchamber 303 and readout particle subchamber 307 have respective outlets 309 and 310. Effector cell subchamber 303 and readout particle subchamber 307 are in fluid communication via aperture 311. Valve 312, in one embodiment, is provided in aperture 311 to render the aperture reversibly sealable.

Figure 49:
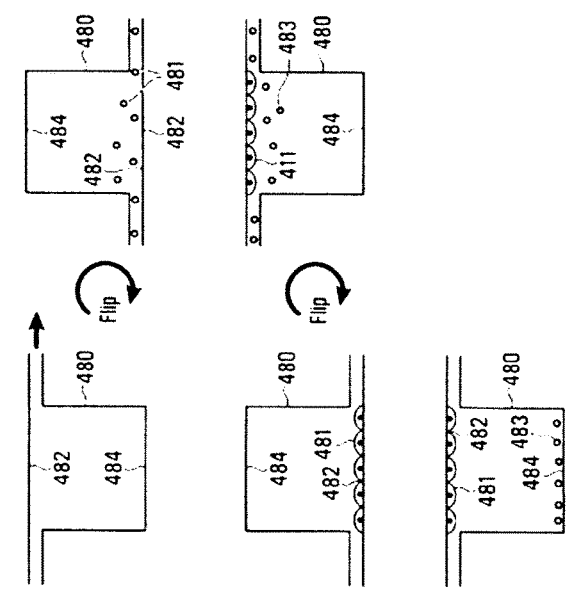
FIG. 49 is a schematic diagram of a method of separating effector cells and readout particles using surface functionalization to confine anchorage-dependent readout cells in a readout zone at the chamber ceiling and gravity to confine suspension effector cells on the bottom of the chamber.

In one embodiment, adherence is used to separate effector cells from readout particles in some embodiments. For example, the skilled artisan is directed to the embodiment shown at FIG. 49. In FIG. 49, chamber 480 is functionalized with a coating solution to enable adhesion of anchorage-dependent readout cells. The chamber is then inverted to load anchorage-dependent readout cells 481 until they adhere to top surface 482. The chamber 480 is then inverted again to load a suspension of cells 483, which are allowed to settle by gravity to bottom surface 484 of the chamber 480, effectively separating the cell population and the anchorage-dependent readout cells 481 into separate effector and readout zones. The cell population, in one embodiment, comprises one or more effector cells.

Figure 50:
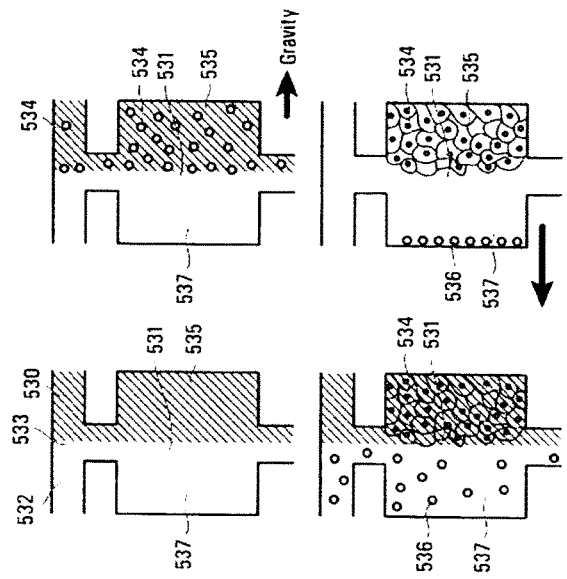
FIG. 50 is a top view schematic diagram of a chamber functionalized to maintain adherent cells on only one side while suspension cells are segregated to the opposite side by gravity.

In the embodiment depicted in FIG. 50, a coating solution 530 promoting cell adhesion is introduced into half of chamber 531 by flowing the coating solution and a second solution 532, e.g., phosphate buffered saline, in T junction 533 with laminar flow. Adherent readout ells 534 are then introduced into chamber 531, and directed to the side with adherent coating 535 by gravity (represented by arrow). After an attachment period, unbound readout cells 534 are washed from the chamber 531. A cell population 536 is then loaded in the chamber 531. The cell population 536 is maintained on the opposite side 537 of the chamber 531 by gravity while the adherent readout cells 534 stay on the side with adherent coating 535. The cell population, in one embodiment, comprises one or more effector cells.

Referring to the embodiment depicted in FIG. 51, two solutions, e.g., solution A 540 comprising an antibody against target A (anti-A antibody) and solution B 541 comprising an antibody against target B (anti-B antibody), are loaded into chamber 542 from different sides of T junction 543, and allowed to coat the functionalized chamber 542 surface (e.g., protein-A coated PDMS). Using laminar flow, the first half 544 of the chamber 542 becomes coated with the anti-A antibody while the second half 545 is coated with the anti-B antibody. Two different types of particles, first particle 546 displaying antigen A on its surface and second particle 547 displaying antigen B on its surface are then introduced into chamber 542. Segregation of the two types of particles can be achieved by tilting chamber 542 first on one side, and then the other, so that once a particle reaches the section coated with the antibody against its displayed antigen, it remains on the proper side of the chamber.

Once a chamber is loaded with a cell population and a readout particle or readout particle population, and optionally additional reagent(s) for carrying out an assay on the cell population, the chamber, in one embodiment, is fluidically isolated from one or more remaining chambers of the microfluidic device. In one embodiment, isolation of the chamber is achieved by physically sealing it, e.g., using one or more valves to fluidically isolate the chamber from its surrounding environment. As will be understood by one of skill in the art, a valve as described herein is controlled via a "control channel," and by applying sufficient pressure to the control channel, a particular valve can be actuated. In one embodiment, subsections (e.g., an effector zone and a readout zone) of a given chamber, or one subchamber of a compound chamber (i.e., a chamber comprising a plurality of subchambers or wells), are isolated from one another by physically sealing the subsections or subchambers, to fluidically isolate the subsections and/or subchambers, e.g., by using one or more valves.

In another embodiment, isolation of a chamber from its surrounding environment is achieved without physically sealing the chamber. Rather, isolation is achieved by limiting the fluid communication between chambers to preclude significant contamination between one chamber and another chamber of the microfluidic device. For example, instead of using a one or more valves, adjacent chambers are separated by the use of an immiscible fluid phase, such as an oil, to block chamber inlets and/or outlets. Alternatively, chambers are designed with inlets and outlets such that the diffusion of molecules in and out of chambers is sufficiently slow that it does not significantly impede the analysis of effect of secreted products within particular chambers.

Various chamber arrangements are described throughout.

FIG. 52 shows a chamber architecture for use with embodiments of the invention. The architecture includes chambers 311 (fabricated in the "flow layer") arranged in a column with each chamber isolated from its neighbor by a valve 312 ("control channel" layer). In another embodiment, valves are located above each chamber (a "lid chamber") as illustrated in FIG. 53, resulting in a higher on-chip feature density than the column architecture. In the embodiment depicted on the left of FIG. 53, the width of the chambers 321 are less than the width of the rounded feed channel 323 (e.g., to deliver effector cells and/or readout particles), in which case the valve 322 seals the perimeter of the chambers. Rounded channels, as discussed in detail herein, are fabricated with by molding PDMS on certain types of photoresist, such as Megaposit SPR220 Series (Microchem) and AZ 40 XT (MicroChemicals). In the embodiment depicted on the right of FIG. 53, the chamber 321 width exceeds the width of the feed channel. In this embodiment, chambers are isolated by a single valve 322 that simultaneously closes the inlet and outlet of each chamber.

Importantly, the microfluidic devices of the invention are not limited to serially arranged chambers addressed in a "flow-through" mode where chambers are arranged in columns in which the outlet of one chamber connects to the inlet of an adjacent downstream chamber. Rather, a number of different chamber arrangements and filling modes are provided herein and encompassed by the invention. For example, in one embodiment, chambers are arranged in parallel such that multiple chambers are addressed simultaneously through the same feed channel. In a further embodiment, parallel chamber arrays are used in "dead-end" filling mode (i.e., where the chambers do not comprise an outlet).

FIGS. 54 and 55 show various parallel chamber arrangement embodiments of the invention. In these embodiments, each column of chambers 331 (FIG. 54) and chambers 331 (FIG. 55) share a common inlet channel 332 and outlet bus channel 333. In these configurations, cross-contamination between chambers is prevented using valves 334. FIG. 55 shows an embodiment where an effector zone 335 of a chamber can be fluidically isolated from the readout zone 336 of the same chamber 331. Specifically, as illustrated in FIG. 55, the chamber 331, in one embodiment, comprises a compound chamber in which an effector zone 335 is separated from a readout zone 336 by sealable channel 337 (e.g., sealable with a valve 337). Contamination between individual chambers, in one embodiment, is reduced as secreted products from each chamber are not transported through chambers located further downstream on the device. Importantly, reagents in the feed channels can be replaced while chambers remain isolated, eliminating the risk of gradient effects that could occur in serially arranged chambers.

Figure 56:
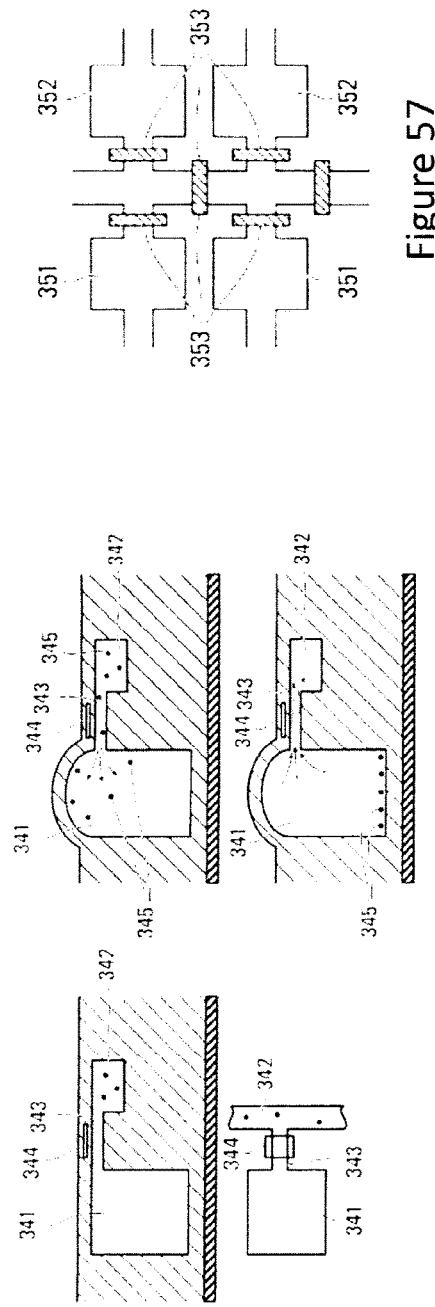
FIG. 56 is top and side view schematic diagrams of a "dead-end" filled chamber for used in a parallel arrangement of microfluidic chambers.

In some embodiments, for example, as illustrated in FIG. 56, a single connection between a chamber and a channel, which may be controlled by a valve, can function as both an inlet and an outlet depending on the direction of the flow, into or out of the chamber. Referring to FIG. 56, a chamber 341 is connected to a feed channel 342 via a single connecting channel 343 that is under the control of a valve 344. In this case the chamber walls are made from an elastic and gas permeable material. This allows for the chamber to be "dead-end" filled through the connecting channel 343 by pushing the air in the chamber 341 into the PDMS material. A top-down view of this architecture is provided in the bottom left of FIG. 56, where the chamber 341 is connected to the feed channel 342 through a single connecting channel 343. A valve 344 can be actuated to fluidically isolate the chamber 341 from the feed channel 342. The top left drawing in FIG. 56 shows a cross section of the same architecture.

Once the chamber 341 is filled, flow can still be directed into (FIG. 56, top right) or out of (FIG. 56, bottom right) the chamber 341 by modulating the pressure applied to the chamber, which causes the chamber 341 to expand or compress in volume. The ability to modulate and change the chamber volume is advantageous in the assaying of particles 345 (e.g., cells) within the chamber 341. For example, in one embodiment, particles 345 are introduced into the chamber 341 by bringing them into the feed channel 342, by applying a pressure to the feed channel 342 that is higher than that of the chamber 341, and then opening the valve 344 to the chamber 341 to allow the flow to enter the chamber 341. In another embodiment, the valve 344 is first opened and then the pressure of the feed channel 342 increased. Once inside the chamber 341, the particles 345, e.g., effector cells or readout particles, will fall to the bottom of the chamber under the effect of gravity.

In a further embodiment, pressure of the feed channel 342 is then reduced, causing the chamber 341 to relax back to its original volume with the flow to be directed out of the chamber. Since the particles 345 (e.g., effector cells and/or readout particles), are at the bottom of the chamber 341, they are substantially removed from the flow and remain in the chamber when the pressure is reduced. Feed channel 342 pressure modulations may also be used to periodically add fresh medium to the chamber 341 in order to maintain the viability and growth of cells, whether effector cells or readout cells. In this embodiment, the chamber 341 is inflated with fresh medium which mixes with the medium already in the chamber by diffusion. Once mixed, a portion of the fluid inside the chamber 341 is removed and the process repeated as desired by the user. Importantly, by flushing the feed channel 342 with the chamber 341 closed to the feed channel between subsequent steps of medium addition (e.g., by actuation of valve 344), the contents of a chamber within an array do not contaminate other chambers in the chamber array.

This same approach of feed channel pressure modulations, in one embodiment, is used to add reagents to a chamber that are required or sufficient to observe and measure the effect of one or more effector cells on one or more readout particles within the chamber. For instance, and described in detail below, a cell population comprising one or more effector cells is assayed in one embodiment, for the ability of the one or more of the effector cells to neutralize a cytokine. In this case, a chamber may be first loaded with the cell population, for example a cell population comprising one or more effector cells that secrete antibodies. The antibodies are tested within the chamber for their ability to neutralize a cytokine. For example, in one embodiment, the cytokine neutralization effect is measured by providing readout particles to the chamber, whereby the readout particles comprise cells that are responsive to the cytokine, for instance by expression of a fluorescent protein. In one embodiment, individual chambers are first isolated and incubated to allow for the accumulation of a sufficient amount of the antibody. A volume of medium containing the cytokine is then added to the chambers by inflating them, thereby maintaining the antibodies in the chambers and not allowing for cross-contamination between chambers. The chambers, in a further embodiment, are then incubated with additional volume exchanges as required to determine if the chamber contains an effector cell that secretes an antibody that is capable of neutralizing the cytokine.

The above strategy may also be achieved without the use of mechanisms to modulate the volume of chambers. For example, a chamber, in one embodiment, is constructed to have two separate compartments (e.g., separate chambers, or subchambers or wells within an individual chamber) that are independently flushed with reagents, and which may also be isolated from other chambers on the device. The exchange of medium with fresh medium, or medium containing other components/reagents needed for a particular assay, in one embodiment, is implemented by isolating one compartment of a chamber, e.g., a "reagent compartment," from the other compartment, where the "other compartment" contains the effector cells and readout particles, flushing the reagent compartment, and then reconnecting the compartments to allow for mixing by diffusion or by another means such as pumping between the two compartments.

Figure 57:
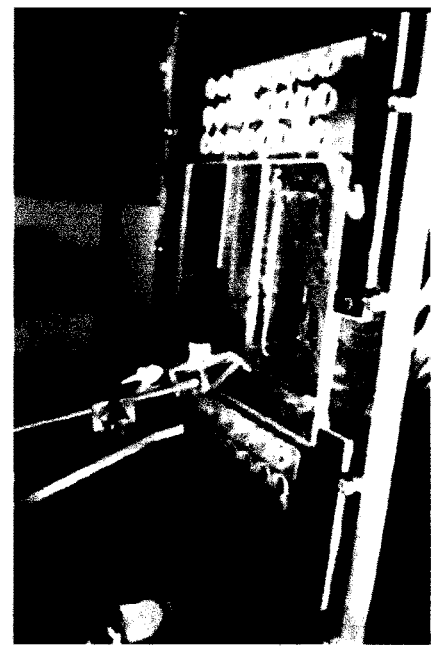
FIG. 57 is a schematic diagram of a parallel arrangement of dead-end filled chambers which can provide compound chamber functionality.

As discussed herein, an effector zone and readout zone of a chamber, in one embodiment, are fluidically isolated from one another via one or more valves. This architecture can be further extended to chambers that are dead-end filled and in communication with each other. As illustrated in FIG. 57, separating the effector zone 351 and the read-out zone 352, e.g., by valves 353, offers the advantage of individual addressability: reagents in each zone may be exchanged independently and/or assays may be subsequently performed on both the effector cells and read out particles. Note that the dead end portion of the channel is not depicted in FIG. 57.

As provided throughout, in one aspect, the present invention relates to a method of identifying a cell population comprising an effector cell having an extracellular effect and in another aspect, methods are provided for identifying a cell population having a variation in an extracellular effect. Once it is determined that the cell population demonstrates the extracellular effect, or a variation of an extracellular effect, the cell population or portion thereof is recovered to obtain a recovered cell population. Recovery, in one embodiment, comprises piercing the microfluidic chamber comprising the cell population comprising the one or more cells that exhibit the extracellular effect, with a microcapillary and aspirating the chamber's contents or a portion thereof to obtain a recovered aspirated cell population.

The recovered cell population(s), once recovered, in one embodiment, are subjected to further analysis, for example to identify a single effector cell or a subpopulation of effector cells from the recovered cell population that is responsible for the variation in the extracellular effect. The recovered cell population(s) can be analyzed in limiting dilution, as subpopulations for a second extracellular effect, which can be the same or different from the first extracellular effect. Cell subpopulations having the second extracellular effect can then be recovered for further analysis, for example for a third extracellular effect on a microfluidic device, or by a benchtop method, for example RT-PCR and/or next generation sequencing.

Various methods for the recovery of one or more cells from a specific chamber(s) are amenable for use herein.

Figure 58:
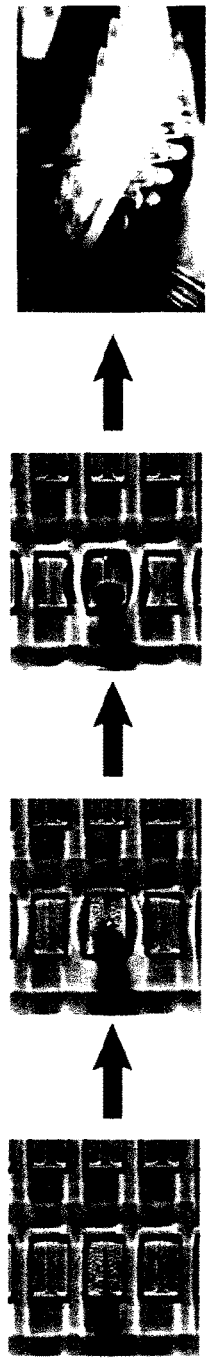
FIG. 58 are images of a microfluidic instrument for cell recovery and an image sequence during cell recovery. Top: From left to right. Optical micrograph of image sequence during cell recovery with cells in chamber, capillary piercing chamber roof (far left), empty chamber following aspiration, and capillary dispensing cells into tube (far right). Bottom left: Image of custom-built microfluidic screening instrument including (i) Microcapillary mounted on robotic micromanipulator, (ii) digital pneumatics for nanoliter flow aspiration/dispensing, (iii) X-Y translation mount, (iv) incubator insert with mounts for recovery tubes, (v) scanning X-Y stage for image acquisition across the array, (vi) inverted microscope, (vii) cooled Hamamatzu CCD camera for high-sensitivity fluorescent imaging, (Viii) control solenoids for capillary operation. Bottom right: Close up of microfluidic device mounted beneath incubator insert with capillary positioned for cell recovery. (C) Optical micrograph of image sequence during cell recovery with cells in chamber (top left), capillary piercing chamber roof (top right), empty chamber following aspiration (bottom left), and capillary dispensing cells into tube (bottom right). (D) Performance of cell recovery. When operating in Mode I, multiple chambers are aspirated before dispensing. This is used for two-step screening (enrichment) of cells or for recovery of pools of cells. Recovery from each chamber takes approximately 3 seconds. When operating in Mode II, the contents of a single chamber are aspirated and dispensed followed by 4 washing steps to ensure no carryover between single cells.

The PDMS membrane design of the devices provided herein enables the selective recovery of cells from any chamber by piercing the upper membrane with a microcapillary. In one embodiment, cell recovery from a chamber is carried out based in part on the methods set forth by Lecault et al. (2011). *Nature Methods* 8, pp. 581-586, incorporated by reference herein in its entirety for all purposes. The membrane above a particular chamber is pierced with the microcapillary and cells are aspirated (FIG. 58, top). The same microcapillary can be used to recover multiple cell populations on one device. Recovered cells can then be deposited in microfuge tubes for further analysis, for example, RT-PCR analysis or subjected to a further functional assay on the same microfluidic device or a different microfluidic device.

In one embodiment, once effector cells from identified chambers are recovered, they are reintroduced into the same device at a different region, at limiting dilution (e.g., either a single cell per chamber or smaller populations than the initial assay) to determine which effector cell(s) is responsible for the variation in the extracellular effect, i.e., by performing another extracellular assay on the recovered cells (See, e.g., FIG. 2).

In one embodiment, one or more cell population are recovered with a microcapillary by aspirating the contents of the chamber containing the cell population to provide a recovered aspirated cell population. In a further embodiment, recovered aspirated cell population is reinjected into a microfluidic device with the microcapillary, wherein the microcapillary pierces one wall of the microfluidic device. Pressure is then applied to the microcapillary to flow the recovered aspirated cell population into separate chambers of the microfluidic device, and the microcapillary is retracted to cause the wall of the microfluidic structure to substantially re-seal.

Recovery, in one embodiment is automated and using a robotic microcapillary instrument (FIG. 58, bottom). However, recovery can also be accomplished manually with a microcapillary. The recovery methods provided herein allow for the recovery from 100 chambers with >95% efficiency in 15 minutes. Alternatively, the recovered effector cells can be introduced into a second device or analyzed via benchtop methods to determine the identity of particular cell(s) responsible for the variation in the extracellular effect.

A microcapillary, as stated above in one embodiment, is used to recover one or more cell populations (or subpopulations, depending on whether a microfluidic enrichment has taken place) from a microfluidic chamber. and aspirating the chamber's contents or a portion thereof to obtain a recovered aspirated cell population. The cells in the one or more cell populations (or subpopulations) are substantially recovered by aspirating the chamber contents into the microcapillary, to provide a recovered aspirated cell population (or subpopulation). The microcapillary in one embodiment, has a diameter of from about 5 µm to about 200 µm. In a further embodiment, the microcapillary has a diameter of from about 5 µm to about 200 µm, or from about 5 µm to about 150 µm, or from about 5 µm to about 100 µm, or from about 5 µm to about 75 µm, or from about 5 µm to about 50 µm, or from about 50 µm to about 200 µm, or from about 100 µm to about 200 µm, or from about 150 µm to about 200 µm.

In some embodiments, the microcapillary has a beveled tip. In some embodiments, the microcapillary has an oval, square or circular cross section. Additionally, as shown in FIG. 58, the microcapillary in some embodiments is mounted on a robotic micromanipulation system on a microscope to provide an automated recovery apparatus.

In one embodiment, the microcapillary provided herein has a single barrel. However, the microcappilary in other embodiments has multiple barrels, for example a double barrel, a triple barrel, or more than three barrels.

A cell or cells can also be selectively recovered by using microfluidic valves to uniquely address the specified chamber and to direct flow to flush the single cell or multiple cells from the chamber to an outlet port for recovery. Cell adherence to the device substrate, in one embodiment, can be minimized by methods known to those of skill in the art, for example, purging or coating the microfluidic substrate with Trypsin. In another embodiment, a plurality of chambers comprising cells of interest are simultaneously recovered through a single port, e.g., via the use of addressable valve arrays to control fluid flow. In another embodiment, cells from chambers that are not of interest are first removed from the device, either by washing or lysis. The remaining contents of the device including the cells of interest are then recovered by flushing to a desired port.

In one embodiment, the contents of a chamber comprising an effector cell displaying a variation in an extracellular effect are recovered from the device by aspiration, for example, by using a microcapillary fabricated to have an appropriate size and shape. In some embodiments, the recovery method comprises piercing the top of the chamber comprising the cell(s) of interest with the microcapillary and aspirating the cell(s) of interest. In one embodiment, the membrane reseals or substantially reseals after piercing is complete. In another embodiment, recovery of the contents of a chamber comprising an effector cell displaying a variation in an extracellular effect (e.g., one or more ASCs) is performed by first cutting a wall of the chamber to create an access point and then extracting cells by aspiration using a microcapillary. In yet another embodiment, the microfluidic device used to assay the extracellular effect is fabricated such that the chambers are exposed by peeling away the material on one wall, thereby leaving an open micro-well array. Identified chambers (i.e., chamber(s) comprising an effector cell displaying a variation in an extracellular effect) are then aspirated from their respective chambers. In order to facilitate the precise extraction of microfluidic well contents, aspiration tools such as microcapillary tubes, in one embodiment, are mounted on a robotic micromanipulator, or a manual micromanipulator (FIG. 58). However, aspiration in other embodiments is performed manually.

In some cases, it is desirable to extract a subset of cells from a given chamber. For instance, methods provided herein allow for the removal of cells from a specific region of a microfluidic chamber, for example, a readout zone or an effector zone. In one embodiment, the recovery method provided herein comprises aspiration of individual single cells in a serial manner.

Recovery of one or more cells from one or more microfluidic chambers, in one embodiment, comprises magnetic isolation/recovery. For example, in one embodiment, a microfluidic chamber is exposed to a magnetic particle (or plurality of magnetic particles) that adheres to the one or more cells within the chamber. Adherence can be either selective for a single cell, a subpopulation of the population of cells in the well(s), or non-selective, i.e., the magnet can adhere to all cells. In this case, instead of aspirating cells into a micro-capillary, cells labeled with magnetic particles are drawn to a magnetic probe that creates a magnetic field gradient. The probe, in one embodiment, is designed to enable the magnetic field to be turned on and off, causing cells to adhere to it for removal and then be released during deposition. (EasySep Selection Kit, StemCell Technologies).

Single cells or a plurality of cells harvested from chambers, in one embodiment, are deposited into one or more receptacles for further analysis, for example, open microwells, micro-droplets, tubes, culture dishes, plates, petri dishes, enzyme-linked immunosorbent spot (ELISPOT) plates, a second microfluidic device, the same microfluidic device (in a different region), etc. The choice of receptacle is determined by one of skill in the art, and is based on the nature of the downstream analysis and/or storage.

In some embodiments, cell-derived products or intracellular materials are recovered from microfluidic chambers of interest, alternatively or in addition to the recovery of a single cell or plurality cells. For example, if a microfluidic chamber is identified as having a cell that demonstrates a variation in an extracellular effect, in one embodiment, the secretion products from the chamber are is recovered for downstream analysis (e.g., sequence analysis). In another embodiment, the cell or plurality of cells is lysed on the microfluidic device, e.g., within the chamber that the first assay is performed, and the lysate is recovered. In one embodiment, the lysate is subjected to further on chip processing, for example, to isolate protein, mRNA or DNA from the cell or plurality of cells. The RNA of the cell or plurality of cells within a single chamber, in one embodiment, is selectively recovered by using microfluidic valves to flush through a specified chamber using a reagent that causes the release of the RNA from the cells. This material is then collected at the outlet port. In another embodiment, the cells in all wells or a subset of wells are lysed using a lysis reagent, and then the contents of a given chamber or subset of chambers are recovered. In another embodiment, the cells within a chamber of interest or chambers of interest are lysed in the presence of beads that capture the RNA released from the cells followed by recovery of the beads, for example, by using the techniques described above for cell recovery. In this case the RNA may also be converted to cDNA using a reverse transcriptase enzyme prior to or subsequent recovery. One example of how to accomplish on chip mRNA isolation, cDNA synthesis and recovery can be found in *Anal. Chem* 78 (2006), pp. 3084-3089, the contents of which are incorporated by reference in their entirety for all purposes.

Following the recovery of cells or cell-derived materials from a chamber or chambers of interest, these materials or cells are analyzed to identify or characterize the isolate or the single cell or plurality of cells. As mentioned above, further analysis can be via a microfluidic assay (See, e.g., FIG. 2), or a benchtop assay. The present invention allows for multiple rounds of microfluidic analysis, for example to identify a cell subpopulation from a recovered cell population that displays a second extracellular effect, a third extracellular effect and or a fourth extracellular effect. By repeating the extracellular effect assays on recovered cell populations, the user of the method obtains highly enriched cell populations for a functional feature of interest, or multiple functional features of interest.

In one embodiment, one or more cell populations exhibiting the extracellular effect or variation in the extracellular effect are recovered to obtain one or more recovered cell populations. Once one or more individual cell populations are identified and recovered, the one or more individual cell populations are further analyzed to determine the cell or cells responsible for the observed extracellular effect. In one embodiment, the method comprises retaining a plurality of cell subpopulations originating from the one or more recovered cell populations in separate chambers of a microfluidic device. Each of the separate chambers comprises a readout particle population comprising one or more readout particles. The individual cell subpopulations are incubated with the readout particle population within the chambers. The individual cell subpopulations are assayed for a variation of a second extracellular effect, wherein the readout particle population or subpopulation thereof provides a readout of the second extracellular effect. The second extracellular effect is the same extracellular effect or a different extracellular effect as the extracellular effect measured on the recovered cell population. Based on the second extracellular effect assay, one or more individual cell subpopulations are identified that exhibit a variation in the second extracellular effect. The one or more individual cell subpopulations in one embodiment, are then recovered for further analysis. The second extracellular effect assay is one of the extracellular effect assays described herein.

One or more individual cell subpopulations are recovered, for example, with a microcapillary, as described in detail above. The microcapillary, in one embodiment, is used to reinject recovered cell subpopulations into the same microfluidic device, or a different microfluidic device, to further enrich for a population of cells displaying an extracellular effect. For example, a plurality of cell subpopulations originating from the recovered cell subpopulation, in one embodiment, are retained in separate chambers of a microfluidic device, wherein each of the separate chambers comprises a readout particle population comprising one or more readout particles. The cell subpopulations are incubated with the readout particle populations within the microfluidic chambers and the cell subpopulations are assayed for the presence of a third extracellular effect. The readout particle population or subpopulation thereof provides a readout of the third extracellular effect. Based on the results of the assaying step, it is determined whether one or more cells within one or more of the cell subpopulations exhibits the third extracellular effect. The one or more cell subpopulations can then be recovered as described herein.

In one embodiment, cells from a recovered cell population or recovered cell subpopulation or plurality of cell populations or subpopulations are retained in a plurality of vessels as cell subpopulations. The term cell sub-subpopulation is meant to refer to a subpopulation of an already recovered cell subpopulation. However, one of skill in the art will recognize that a cell subpopulation can be partitioned into further subpopulations, and the use of the term "sub-subpopulation" is not necessary to make this distinction. Each cell subpopulation is present in an individual vessel. The individual subpopulations or sub-subpopulations are lysed to provide and one or more nucleic acids within each lysed cell subpopulation or lysed cell sub-subpopulation are amplified. In a further embodiment, the one or more nucleic acids comprise an antibody gene.

Several approaches including microfluidic analysis may be used for this downstream analysis, depending on the nature of the cells, the number of cells in the original screen, and the intent of the analysis. In one embodiment, where a population effector cells is recovered from a chamber, or a plurality of populations are recovered from multiple chambers, each cell of the plurality is isolated into an individual vessel (e.g. individual microfluidic chamber) and analysis is performed on each effector cell individually. The individual cell analysis can be a microfluidic analysis (FIG. 2), or a benchtop analysis. In another embodiment, where a population effector cells is recovered from a chamber, or a plurality of populations are recovered from multiple chambers, the cell populations are reintroduced onto the same microfluidic device in a separate region (or a second device), and the cells are isolated at a limiting dilution, i.e., as "cell subpopulations," for example, the cells are isolated at a density of a single cell per chamber, or from about two to about ten cells per chamber and a second extracellular effect assay is performed. The downstream analysis (microfluidic or otherwise) may be on any size cell subpopulations, for example, the same size as the initial extracellular effect cell assay, or a smaller population size, e.g., a single cell, two cells, from about two cells to about 20 cells, from about two cells to about 25 cells. Readout particles are introduced into the chambers comprising the cell subpopulations, and the second extracellular effect assay is performed. The contents of chambers that comprise a cell subpopulation displaying a variation in the extracellular effect are harvested for further analysis. This further analysis can be microfluidic analysis (e.g., by performing a third extracellular effect assay, single cell PCR), or a benchtop analysis (e.g., PCR, next generation sequencing).

In one embodiment, individual recovered effector cells are expanded in culture by distributing the plurality of cells at limiting dilution into a plurality of cell culture chambers in order to obtain clones from the recovered cells. For example, in an embodiment where a plurality of effector cells of a cell line engineered to express a library of antibodies are present in a chamber or chambers of interest, the cells from the chamber or chambers are subjected to limiting dilution in order to isolate single effector cells that were present in the chamber. The single effector cells are then used to obtain clonal populations of each respective effector cell. One or more of the clonal populations can then be analyzed to asses which effector cell produces the antibody of interest by measuring the properties of the antibodies secreted (e.g., by ELISA or a functional assay).

Alternatively or additionally, cells are recovered from a microfluidic chamber, isolated, e.g., by limiting dilution, and expanded to obtain sufficient material for the sequencing or amplification and purification of one or more genes of interest, e.g., a gene that encodes an antibody of interest. In yet another embodiment, cells are recovered from a microfluidic chamber, isolated, e.g., by limiting dilution, and used for single-cell DNA or mRNA amplification, e.g., by the polymerase chain reaction (PCR) or reverse transcriptase (RT)-PCR, followed by sequencing, to determine the sequence of one or more genes of interest. In even another embodiment, cells of interest are recovered from one or more microfluidic chambers, isolated, e.g., by limiting dilution, and subsequently used for single-cell DNA or mRNA amplification of the genes of interest, followed by the cloning of these genes into another cell type for subsequent expression and analysis.

In one embodiment, the recovered cell population(s) or subpopulation(s) may be isolated and used for an in vivo analysis, for example by injecting them into an animal, or exapanded in culture followed by subjecting the cells to one or more functional assays previously carried out on the microfluidic device.

In one embodiment, a cell population or subpopulation is recovered that displays a variation in an extracellular effect (e.g., after a first or second microfluidic extracellular effect assay) and one or more nucleic acids of the cells are subjected to amplification. Amplification, in one embodiment, is carried out by the polymerase chain reaction (PCR), 5'-Rapid amplification of cDNA ends (RACE), in vitro transcription or whole transcriptome amplification (WTA). In a further embodiment, amplification is carried out by reverse transcription (RT)-PCR. RT-PCR can be on single cells, or a plurality of cells of the population. Although single cell RT-PCR is becoming common place as an analytical method, the amplification of antibody genes presents a nontrivial challenge due to multiple gene usage and variability. Two main approaches for recovery of antibody genes from single cells include RT-PCR using degenerate primers and 5' rapid amplification of cDNA ends (RACE) PCR. In one embodiment, the RT-PCR method is based on gene-specific template-switching RT, followed by semi-nested PCR and next-generation amplicon sequencing.

Figure 59:
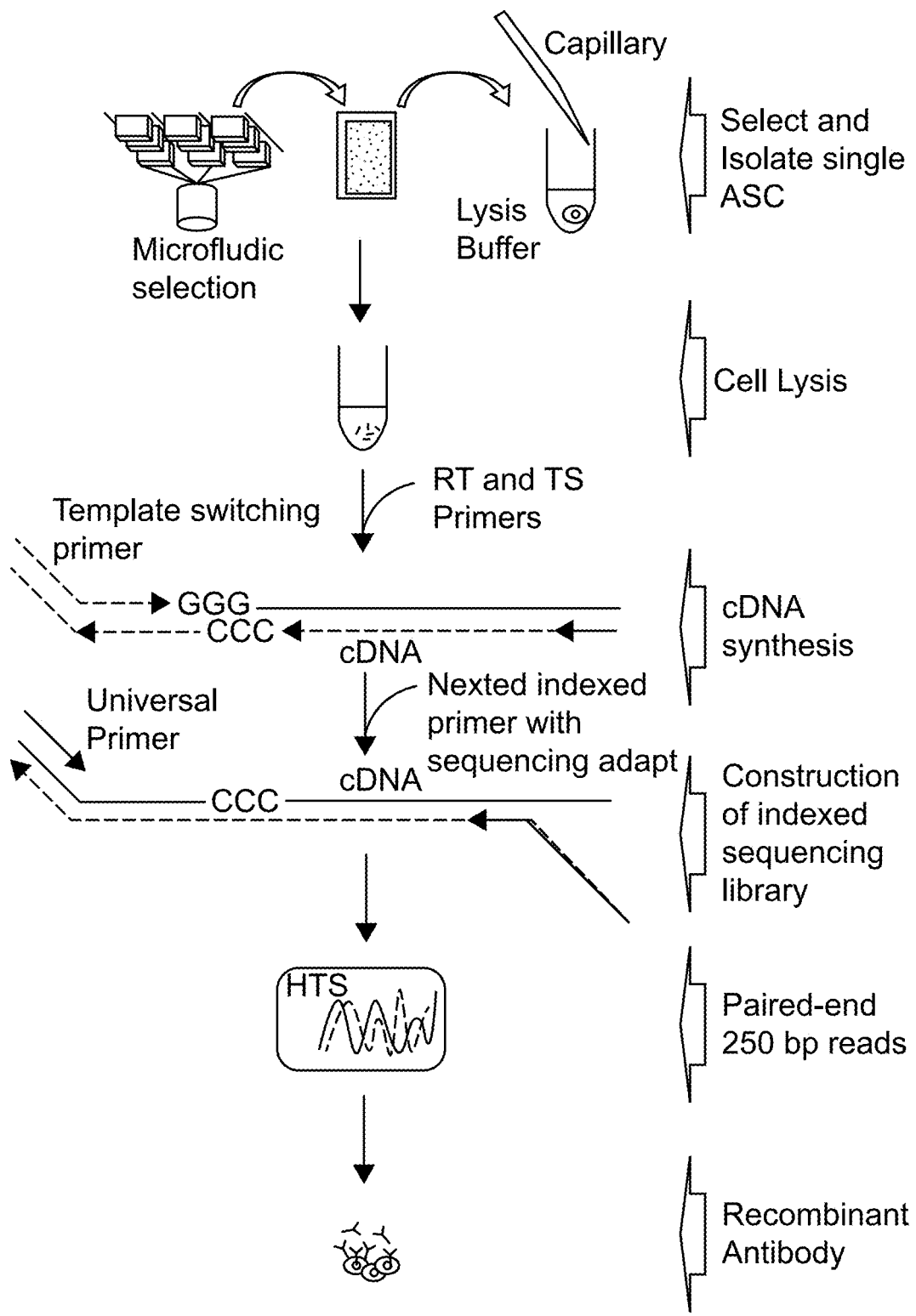
FIG. 59 is a schematic of single cell HV/LV approach using template-switching. Single cells are deposited into microfuge tubes and cDNA is generated from multiplexed gene-specific primers targeting the constant region of heavy and light chains. Template-switching activity of MMLV enzyme is used to append the reverse complement of a template-switching oligo onto the 3' end of the resulting cDNA. Semi-nested PCR, using multiplexed primers that anneal to the constant region of heavy and light chain and a universal primer complementary to the copied template switching oligo, is used to amplify cDNA and introduce indexing sequences that are specific to each single cell amplicon. Amplicons are then pooled and sequenced.

One embodiment of an RT-PCR method for use with identified effector cells having a variation in an extracellular effect is shown at FIG. 59. The schematic shows a single cell HV/LV approach using template switching reverse transcription and multiplexed primers. In this embodiment, single cells are deposited into microfuge tubes and cDNA is generated from multiplexed gene-specific primers targeting the constant region of heavy and light chains. Template-switching activity of MMLV enzyme is used to append the reverse complement of a template-switching oligo onto the 3' end of the resulting cDNA (Huber et al. 1989). *J. Biol. Chem.* 264, pp. 4669-4678; Luo and Taylor (1990). J. Virology 64, pp. 4321-4328; each incorporated by reference in their entireties for all purposes). Semi-nested PCR (common 3' primers and multiplexed nested primers positioned inside the RT primer region) using multiplexed primers at constant region of heavy and light chain, and a universal primer complementary to the copied template switching oligo, is used to amplify cDNA and introduce indexing sequences that are specific to each single cell amplicon. The resulting single cell amplicons are pooled and sequenced.

In some cases, a recovered cell population, following recovery from the microfluidic device, is not further isolated into single cells. For example, if the plurality of cells isolated from a chamber contain a cell that secretes an antibody of interest (e.g., present in a population of one or more additional cells that secrete other antibody(ies)), the plurality of cells, in one embodiment, is expanded in culture to generate clonal populations of the cells of the plurality, some of which make the desired product (i.e., the antibody of interest). In another embodiment, a plurality of cells isolated from a microfluidic well is lysed (either on the microfluidic device or subsequent to recovery), followed by amplification of the pooled nucleic acid population and analysis by sequencing. In this case, a bioinformatics analysis of the sequences obtained may be used to infer, possibly using information from other sources, which of the sequences is likely to encode for the protein of interest (for example, an antibody). Importantly, the analysis method afforded by the present invention is greatly simplified, as compared to bulk analysis of a large numbers of cells, due to the limited number of cells that are recovered. This limited number of cells provides a reduced complexity of the genomic information within the population of cells.

In one embodiment, the amplified DNA sequences of the plurality of cells are used to create libraries of sequences that are recombinantly expressed in an immortalized cell line, according to methods known to those of skill in the art. This cell line may then be analyzed, possibly by first isolating clones, to identify the genes of interest. In some instances these libraries are used to screen for combinations of genes that result in a protein complex of interest. For example, in one embodiment, genes expressed in cells of interest include both heavy and light chains of antibody genes in order to identify gene pairings that have the desired properties. The complexity of such analyses is greatly reduced by the fact that the number of cells analyzed in the original screen is small. For example, if there are 10 cells in the original screen there are only 100 possible antibody heavy and light chain pairings. By comparison, bulk samples typically have thousands of different antibody sequences, corresponding to millions of possible pairings.

In some instances, recovered cells may contain different cell types that can be isolated using methods known to those of skill in the art. For instance, if the microfluidic chamber comprises both antibody secreting cells and fibroblasts, used to maintain the antibody secreting cells, the antibody secreting cells in one embodiment, are separated from the fibroblasts after recovery using affinity capture methods.

EXAMPLES

The present invention is further illustrated by reference to the following Examples. However, it should be noted that these Examples, like the embodiments described above, are illustrative and are not to be construed as restricting the scope of the invention in any way.

Example 1

Fabrication of Microfluidic Devices

Figure 62:
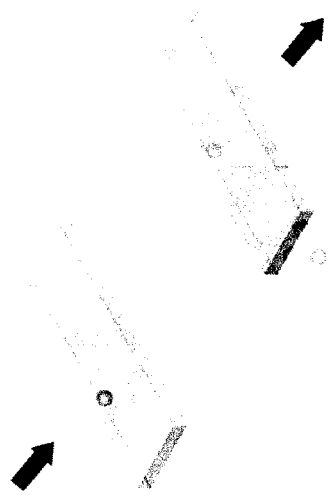
FIG. 62 is a schematic of the chamber of the microfluidic device shown in FIG. 61.
Figure 61:
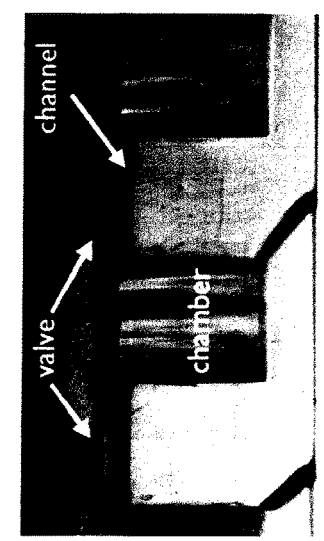
FIG. 61 is an image showing a cross-section view of the microfluidic chamber array contained within a thin membrane with labels indicating cell culture chamber, valves, and channel connecting chambers.

Microfluidic devices were fabricated using the protocol described in Lecault et al. (2011). Nature Methods 8, pp. 581-586 or an adapted version of this protocol (e.g., modified baking times or curing protocols) to obtain multiple layers including, from the bottom glass slide to the top: a flow chambers, a control layer, a membrane, and bath layer (FIG. 27). A cross-section of a device and a corresponding 3D-schematic of the chambers, flow channels and control channels are shown in FIG. 61 and FIG. 62, respectively. As described herein, where a control channel crosses a flow channel, a pinch valve is formed, and closed by pressurizing the control channel. A cover layer was added in certain instances to close the bath, or left omitted for an open bath such as the one shown in the device on FIG. 63.

Example 2

Microfluidic Device for Cell Enrichment by Selection and Reinjection

Figure 63:
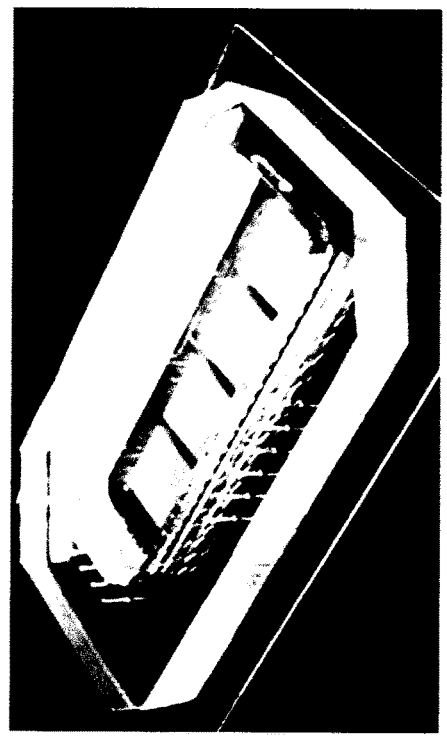
FIG. 63 shows a photograph of a microfluidic device having 8,192 chambers arranged in 4 sub-arrays of 2,048. The microfluidic chamber array is located directly under the osmotic bath reservoir within a 300-micron thick layer of elastomer.
Figure 64:
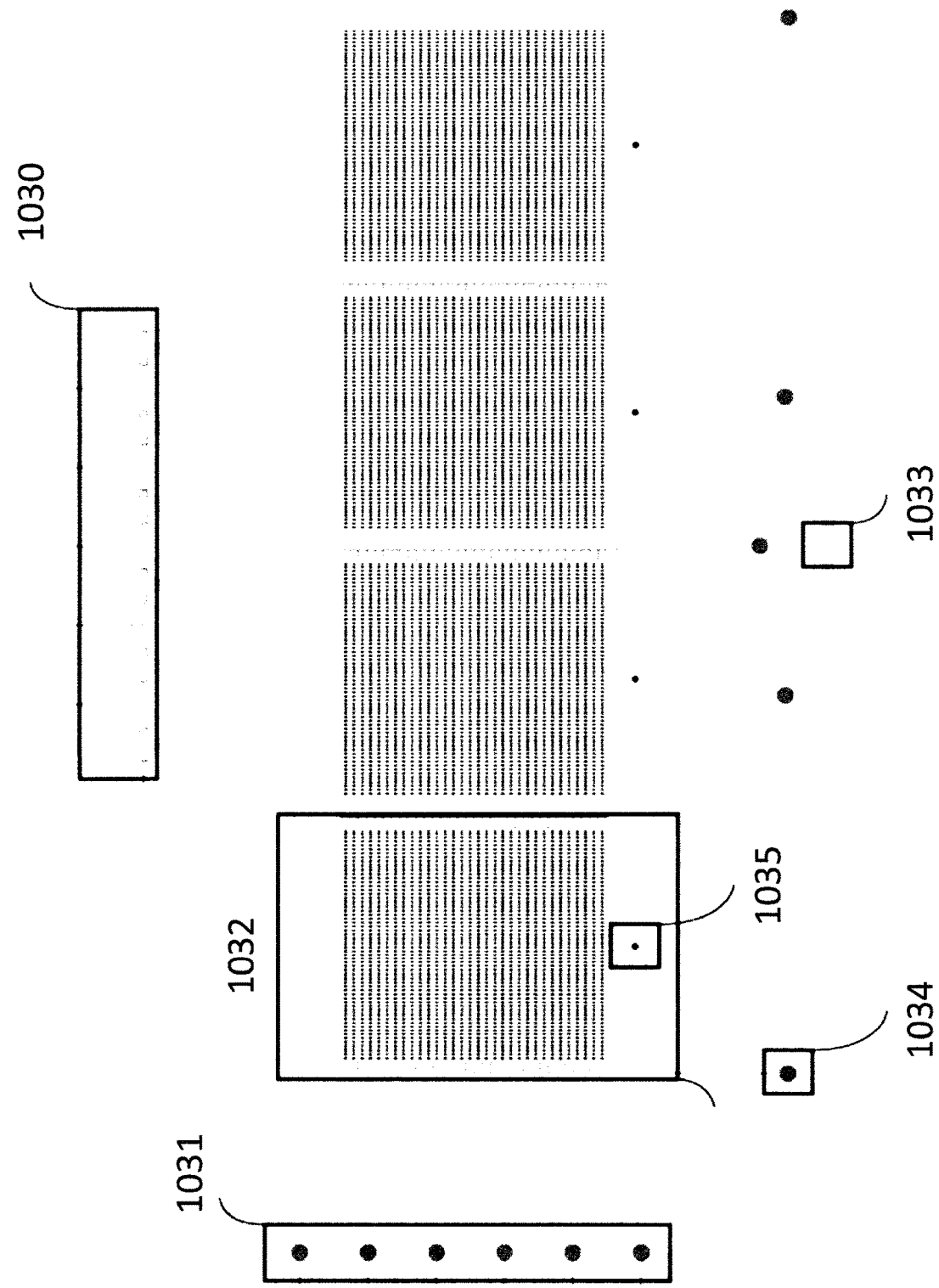
FIG. 64 is a schematic of the microfluidic device shown in FIG. 62.

The microfluidic device shown in FIG. 63 was used to implement an effector cell (antibody secreting cell) selection assay with reinjection capabilities for enrichment. As shown in FIG. 64, the device includes six inlet ports 1030, six control ports 1031 for controlling each inlet, four reinjection ports, one of which is 1032 and a single output port 1033. The device contains an array of 8192 identical unit cells, one of which is depicted in FIG. 2B and FIG. 61. Each unit cell contains a chamber which is 100 µm in width, 160 µm in length and 160 µm in height. Each chamber has a volume of about 2.6 nL. The device is divided into four sub-arrays, one of which is indicated by 1032 (FIG. 64). Each sub-array contains 2048 of the 8192 total unit cells. Each sub-array has its own sub-array valve 1034, which allows each sub-array to be fluidically addressed independently of the other sub-arrays. Each sub-array has a single reinjection port 1035.

The reinjection ports are circular chambers having diameters of about 300 µm, depths of about 160 µm and volumes of about 11.3 nL. The reinjection ports are pierced by a microcapillary in order to inject reagents or particles into one or more of the four sub-arrays.

Example 3

Microfluidic Device for Segregation of Effector and Readout Cells

A microfluidic device was designed to permit readout cells to be kept in separate, isolated chambers from effector cells and to allow the contents of these chambers to be mixed on demand when needed. This configuration is used to implement effector cell assays, for example, cytokine neutralization assays. The architecture is particularly useful to prevent an effector cell's secretion product (e.g., antibody) from being completely washed away when the chamber comprising the effector cell(s) is perfused with a fluid, for example, when provided with fresh culture medium to maintain viability over extended periods of time. This configuration is also amenable if it is useful to limit the time during which the effector cell(s) is exposed to the medium conditions required for the extracellular effect assay (e.g., when a toxic cytokine is used as an accessory particle).

Figure 65:
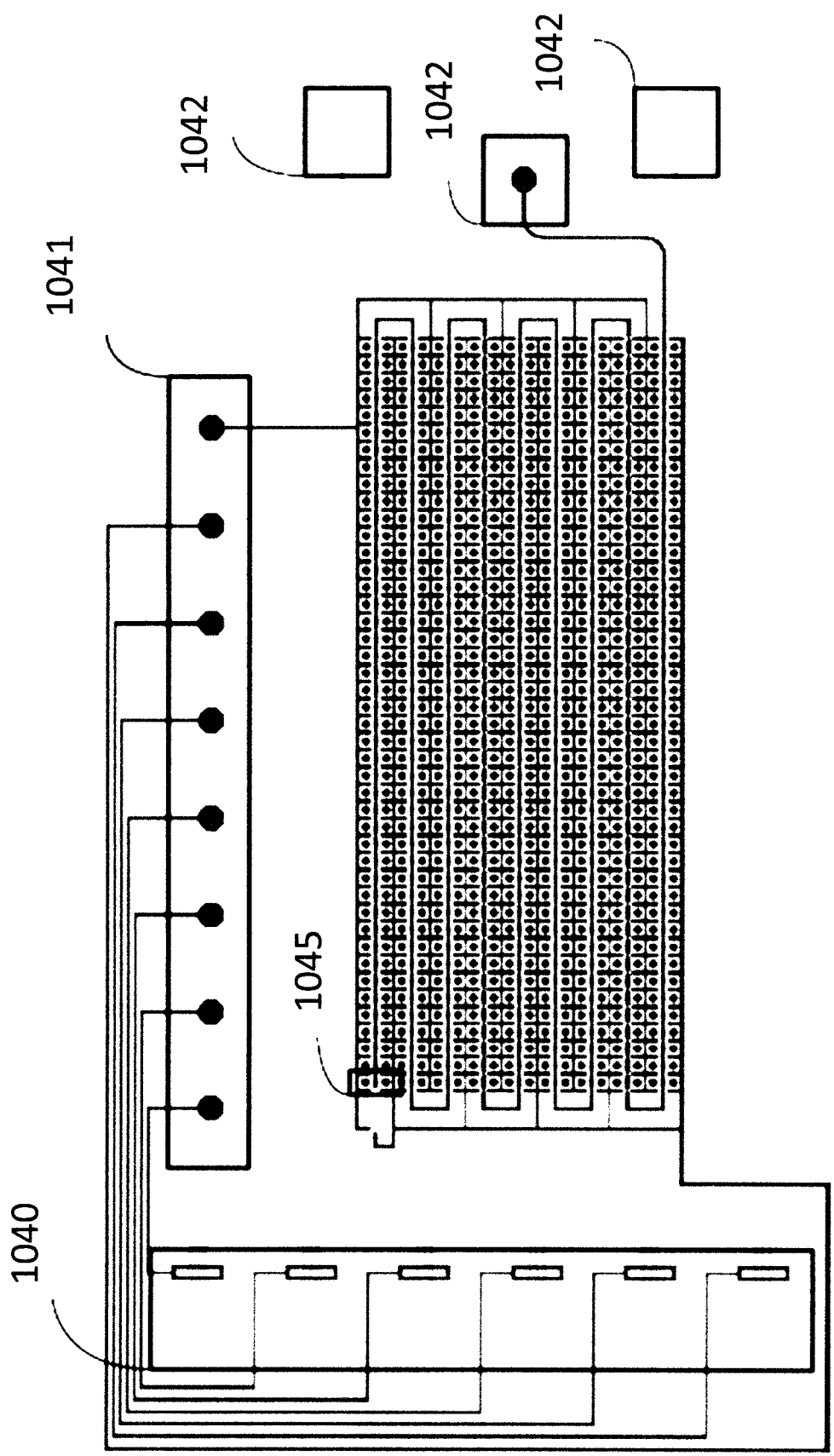
FIG. 65 is a schematic depiction of a microfluidic device that enables the segregation of effector and target cells.
Figure 67:
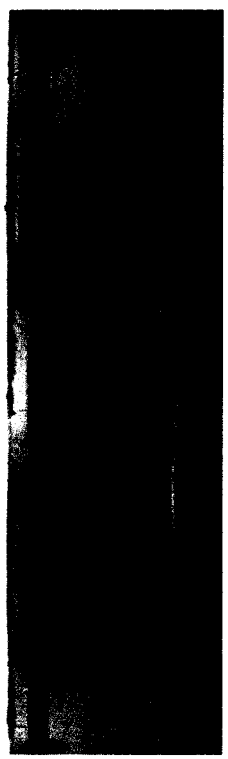
FIG. 67 is a micrograph of a cross-section taken along the vertical dashed line of FIG. 66.
Figure 68:
FIG. 68 is a micrograph of a cross-section taken along the horizontal dashed line of FIG. 66.
Figure 66:
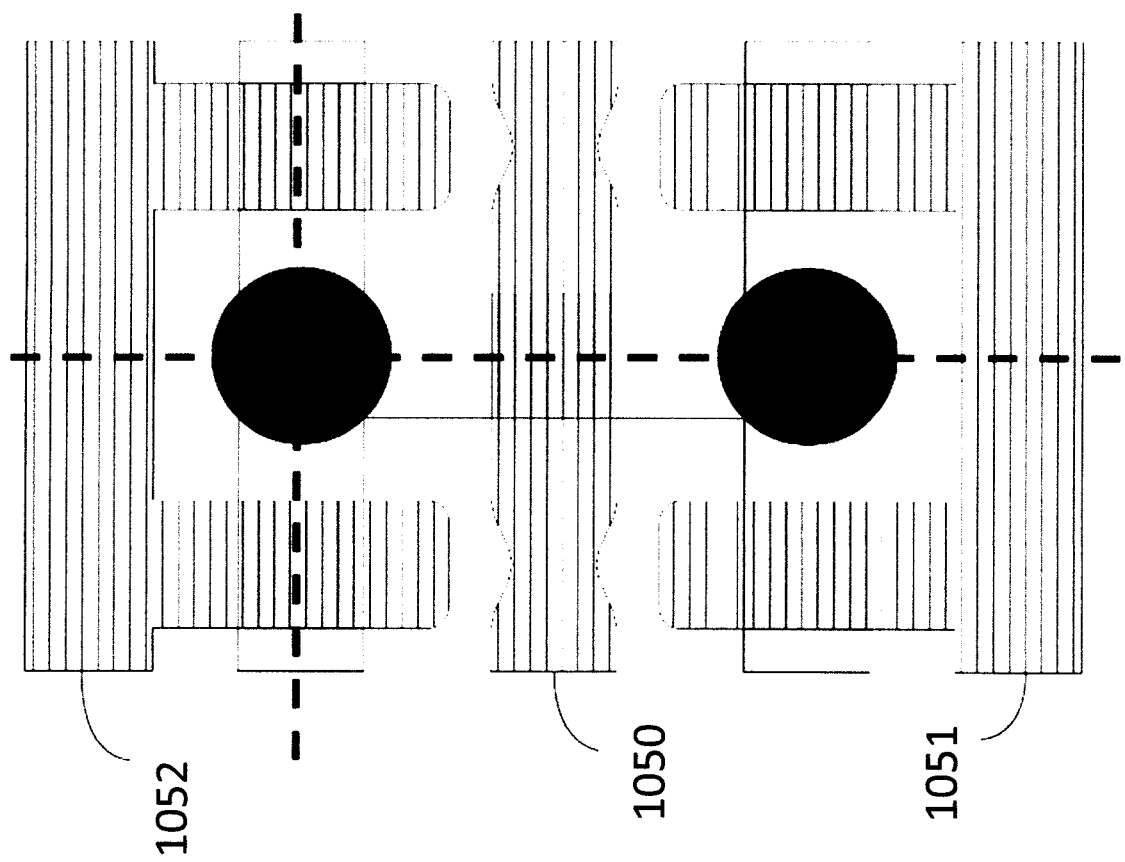
FIG. 66 is a schematic depiction of a single unit cell of the microfluidic device from FIG. 65.

As shown in FIG. 65, this device consists of six inlet ports 1040, nine control ports 1041 and 1042, two outlet ports 1043 and 1044, and an array of 396 unit cells, each identical to 1045 and illustrated in more detail in FIG. 66. Each unit cell contains two circular chambers. Each chamber has a diameter of 210 µm, a height of 180 µm and a volume of 5.6 nL. Typically, one of these chambers holds one or more effector cell and the other chamber holds one or more readout cells. A flow channel connects the two chambers. This flow channel can be closed with the "diffusion valve" 1050. With the diffusion valve 1050 open, the contents of the two chambers mix via diffusion. With the diffusion valve 1050 closed, the chambers are isolated from each other. Two flow channels serially connect each unit cell to each other unit cell in the device. One of these flow channels flows through chamber 1 and the other flows through chamber 2. These two flow channels are closed with "main valve 1" 1051 and "main valve 2" 1052 to isolate the chambers of each unit cell from the chambers of each other unit cell. These two valves are opened and closed independently, permitting independent perfusion of chamber 1 or chamber 2. Cross sections of the device in the vertical and horizontal planes (dotted lines) from FIG. 66 are shown in FIG. 67 and FIG. 68, respectively.

Figure 69:
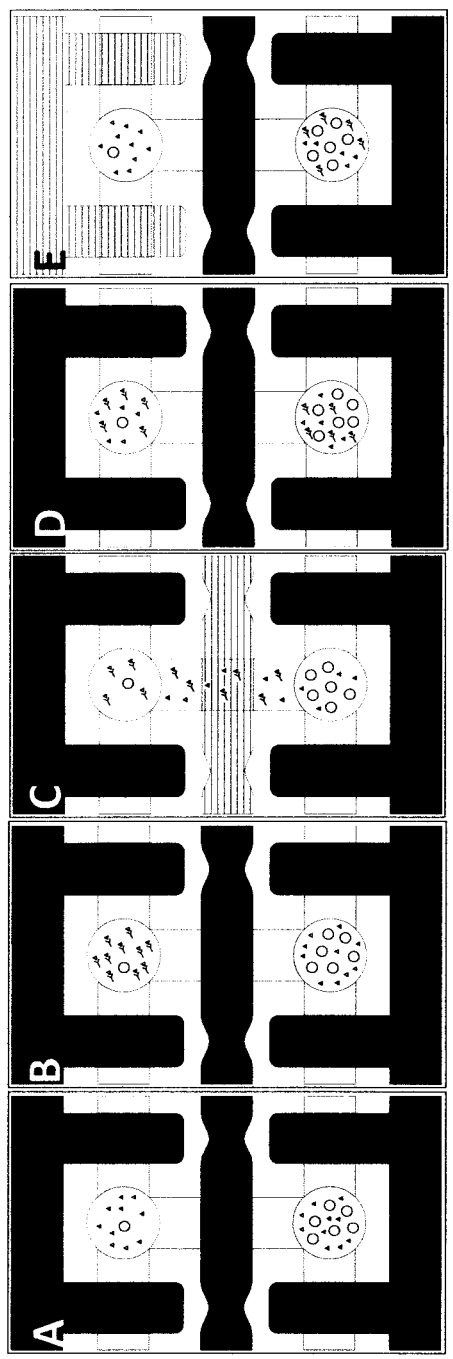
FIG. 69 is a series of schematic diagrams showing an embodiment for a cytokine neutralization assay.

An example of how a cytokine neutralization functional assay which can be implemented with the device is shown in FIG. 69. Panel A shows the top chamber containing at least one effector cell and the bottom chamber containing a plurality of readout cells. Both chambers contain an equal concentration of cytokine, required to maintain the viability of readout cells. All valves are closed. Closed valves are illustrated shaded black and opened valves are illustrated with horizontal hatched lines. Panel B shows that time has passed and the at least one effector cell has secreted antibodies. In the particular case that is illustrated, the antibodies bind to the cytokines in the effector chamber, neutralizing them. Panel C shows that the diffusion valve 1050 has been opened. Free cytokines diffuse from the bottom chamber towards the top chamber. Neutralized cytokines diffuse from the top chamber towards the bottom chamber. Panel D shows that enough time has passed such that the concentration of free and neutralized cytokines in each chamber has substantially equalized. All valves are then actuated and locked. The effective concentration of cytokine in the bottom chambers comprising the readout cells is now about half the initial concentration. Panel E shows that effector cells have been perfused with fresh medium containing additional cytokine. The perfusion has removed the neutralized cytokine from the top chamber. The process is repeated every few hours, eventually leading to a complete depletion of cytokine and death of readout cells. In other cases, the effect of cytokine neutralization on readout cells may include activation or inhibition of a signaling pathway, growth arrest, differentiation, or a change in morphology. The effect on the readout cells is then measured by methods known to those of skill in the art.

Example 4

Integration of Cell Fence Chambers

Devices having cell fences for capture of a single effector cell or a heterogeneous population of cells comprising one or more effector cells were fabricated as follows.

PDMS devices with cell fences were fabricated by molding from a reusable flow channel mold and reusable control channel. The flow channel mold comprised multiple layers of photoresist on a silicon wafer substrate. The bulk of the chambers in the devices utilized herein were defined by an SU-8 100 feature which sits directly on the Si wafer. Cell fences, when fabricated, were defined by a thinner SU-8 2010 feature which sat on top of the SU-8 100 feature. This is depicted schematically in FIG. 31.

The majority of microfluidic chambers were fabricated using SU-8 100 negative photoresist (typically 160 μm in height) following standard protocols, except that the final step, development, was omitted. The wafers were cooled after the post-exposure bake, and then SU-8 2010 was spun on top of the undeveloped SU-8 100, typically at a height 10-20 μm. The thickness of the SU-8 2010 determined the height of the fence. The depth of each chamber was the combined height of both photoresist layers.

In alternative fabrication procedures, the SU-8 100 layer is fully developed, and then the wafer is coated with an additional layer of SU-8 100 which is higher than the first layer, the difference in height becoming the height of the fence.

The molds were then parylene coated (chemical vapor deposited poly(p-xylylene) polymers barrier) to reduce sticking of PDMS during molding, enhance mold durability and enable replication of small features that could not be produced with the aforementioned parylene coating.

A number of prototype devices were fabricated to determine feasible fence width-height combinations. A prototype flow layer mold was fabricated in order to determine dimensions which could successfully be fabricated. This mold consisted of multiple chambers with fences, with the width of the fences being varied across the same mold. Also, the height of the fence and of the chamber could be varied during fabrication (by adjusting spin speeds). The prototype molds contained only chambers for fabrication testing.

Two photolithographic masks were required, one to define the bulk of the chambers (SU-8 100) and the other to define the fences (SU-8 2010). However, one physical mask could be used, containing both sets of features.

A prototype fence chamber was fabricated where the full width W of the chamber and was fixed at 300 μm. The typical width of chambers on most existing devices is 160 μm. Initially, each half of these chambers was made a similar size to allow a separate inlet and outlet for each of the effector and readout zones. L is the length of the chamber. For each unique value of X, there were three chambers with L=160 μm (length) and one more with L=2000 μm. The chamber with extended length was included in order to allow the final PDMS mold to be easily cut perpendicular to the fence, so that the cross-section could be imaged.

Initially a single mold was fabricated, providing data on a single set of chamber and fence heights. Table 5 summarizes the dimensions of the prototype mold:

TABLE 5

| Prototype mold dimension summary | |
|---|---|
| W (design value) | 300 μm |
| L (design value) | 160/2000 μm |
| SU-8 100 Height (measured) | 160 ± 5 μm |
| SU-8 2010 Height (measured) | 17 ± 1 μm |

Table 6 lists the fence widths which were on the mold and which ones were successfully fabricated:

TABLE 6

| X (fence width) [μm] Design Value | X (fence width) [μm] Measured Values | Successful PDMS Fabrication? |
|---|---|---|
| 5.0 | can't measure | No |
| 7.5 | can't measure | No |
| 10 | 18 ± 2 | No |
| 12.5 | 21 ± 2 | No |
| 15 | 25 ± 2 | No |
| 17.5 | 29 ± 2 | Yes |
| 20 | 31 ± 2 | Yes |
| 25 | 37 ± 2 | Yes |
| 30 | 42 ± 2 | Yes |
| 35 | 48 ± 2 | Yes |

The table above shows that the actual fence widths turned out larger than the design values.

Fabrication failures were not obvious until after PDMS molding. For the smaller fence widths, it was difficult to determine the quality of the photoresist mold by viewing it under the microscope. Fences failed because the PDMS making up the fences either stayed in the mold completely or partially ripped away from the bottom of the chambers. For example, a fence having a width of 15 μm failed. The minimum width which could be fabricated using this particular design and the above described methods was 17.5 μM.

It was observed during PDMS molding of the prototype devices that the fence often tore apart from the chamber bottom. This tearing appeared to begin at the 90 degree corner where the fence met the wall of the chamber. This 90 degree corner is a stress concentration. The design was modified to include 45 degree chambers in order to reduce these stress concentrations and thereby improve PMDS molding capability. This design change allowed the fence width to be reduced below the 17.5 μm width, which was the largest size possible on the testing mold. The width of the fence was reduced to a design value of 10 μm. The actual measured value, 12 μm, was much closer to the design value than was achieved on the prototype mold.

Fences in this example run parallel to the flow. However, there is no inherent reason that fences cannot be fabricated to be perpendicular to the flow or diagonal relative to the flow. Similarly, chambers in this example are symmetric. However, the invention is not limited thereto.

Individual microfluidic chambers having a cell fence, an effector zone and a readout zone were loaded with a cell population and readout particles using a tilting method to direct the effector cells to the effector zone or the readout particles to the readout zone.

FIGS. 70A, 70C, and 70E show light microscopy images of microfluidic chambers having cell fences and FIGS. 70B, 70D, and 70F, show the equivalent chambers under fluorescence microscopy. The beads (readout particles) in the readout zone show an aggregation of effector cell product on the beads that is generally uniform despite relative distance from the effector cells and the effector zone.

Example 5

Robust Microfluidic Growth of Antibody-secreting Effector Cells

Figure 71:
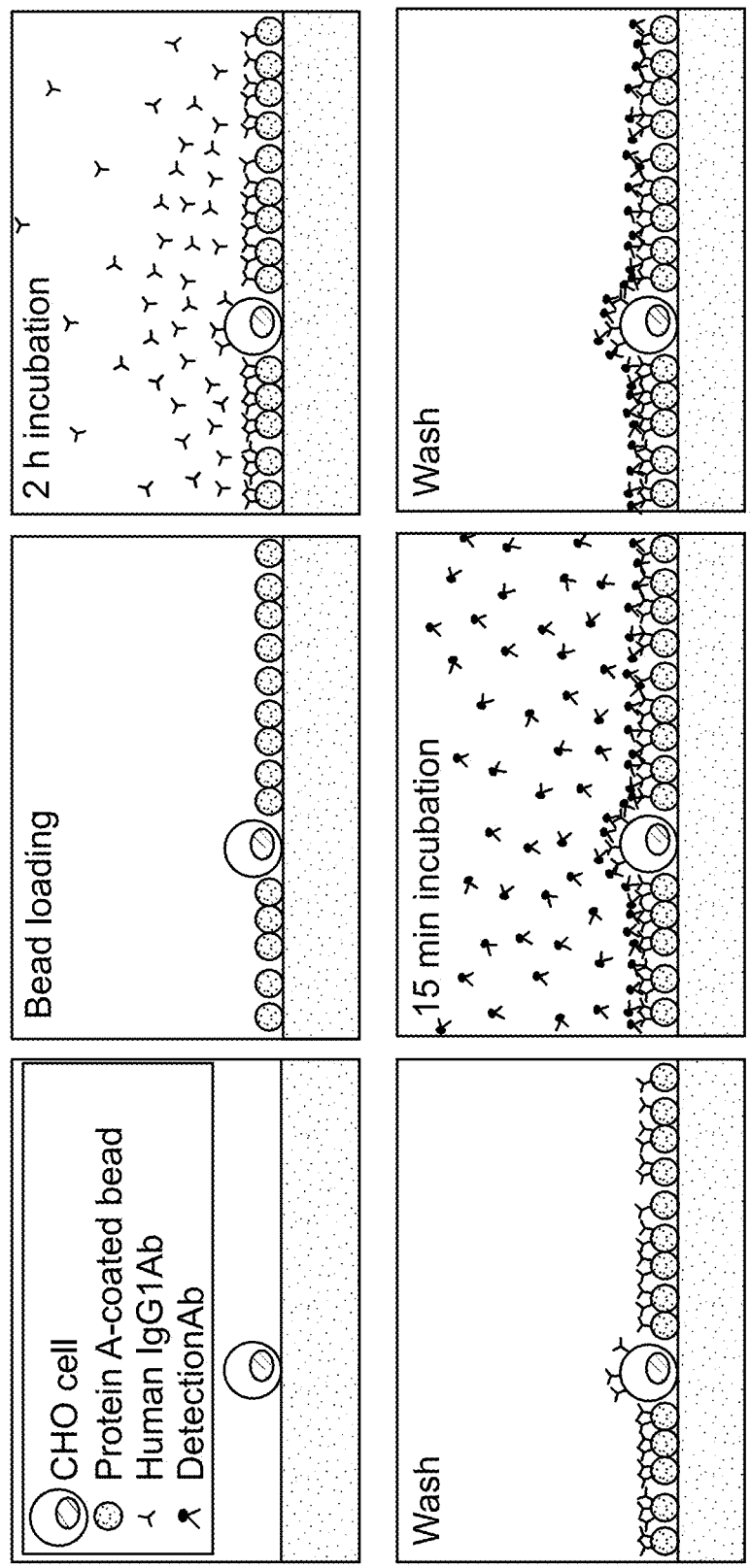
FIG. 71 is a schematic of the workflow for the capture and detection of antibodies from antibody-secreting cells.

A plurality of recombinant Chinese Hamster Ovary (CHO) cells (effector cells) producing a human IgG antibody was loaded in the microfluidic device at a concentration of 2 M cells/mL. Secreted antibodies were captured on protein A-coated beads (average diameter: 4.9 µm) during a 2 hour incubation followed by the addition of Dylight 594-conjugated F(ab')$_2$ fragment of rabbit anti-human IgG (H+L) and washing (FIG. 71). Bright field and fluorescent images were taken to quantify antibody secretion and capture. Cells were subsequently cultured in the device for 4.5 days to generate clonal populations and clones secreting high amounts of antibody were recovered from the device for further expansion.

Figure 72:
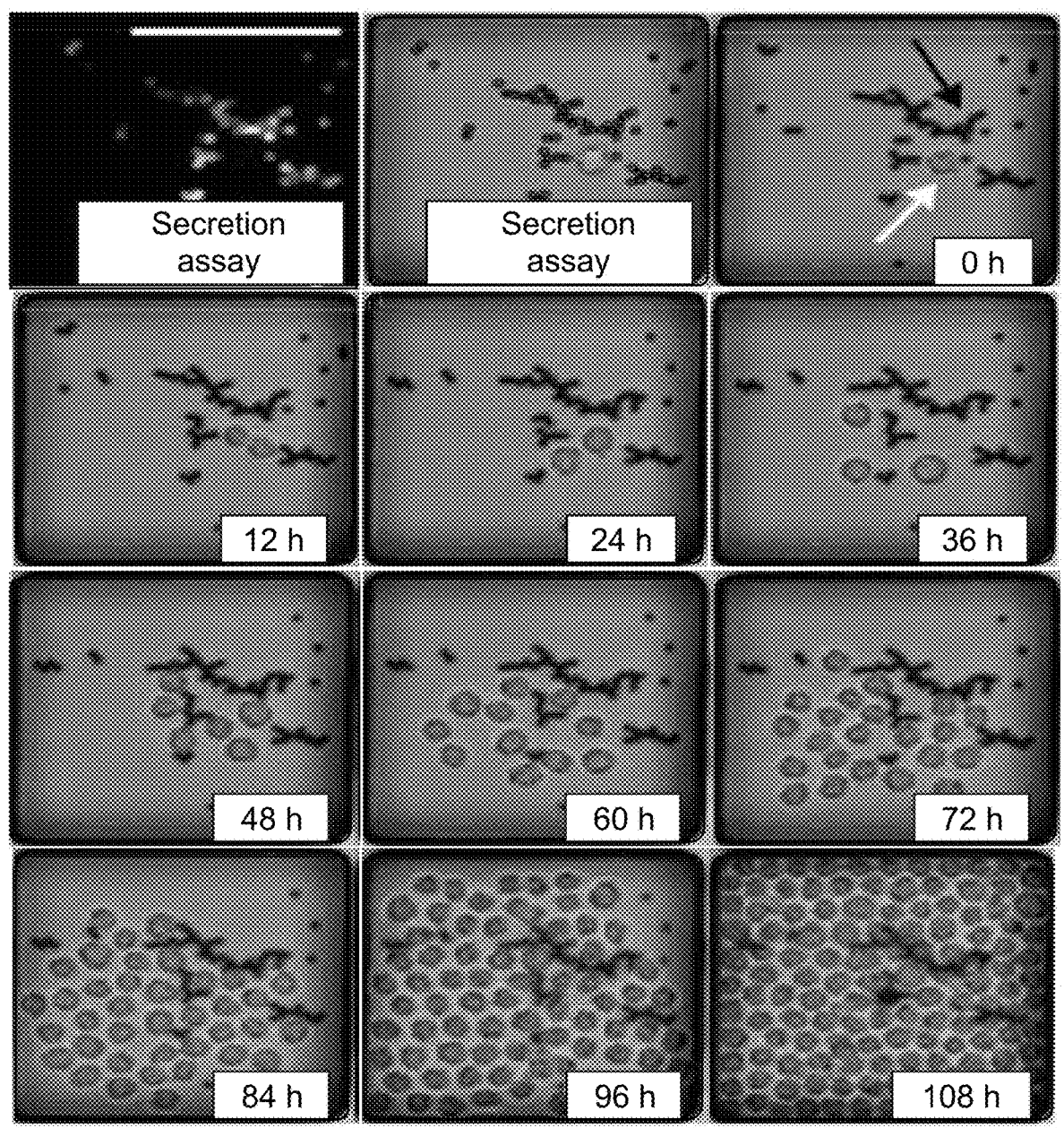
FIG. 72 Example of fluorescent and bright field images from the bead immunocapture assay followed by time-lapse imaging of the clone for 4.5 days.

FIG. 72 shows time-lapse imaging of a CHO clone after the antibody detection effector cell assay was performed. The readout beads are identified by the black arrow while the cells are identified by the white arrow. FIG. 73 shows growth curves (error bars, s.d.) of CHO cells cultivated in shake flasks (n=3 experiments in triplicate seeded at $2.5 \times 10^5$ cells$^{ml-1}$), as single cells in 96 well plates (n=3 experiments; 27-36 clones per plate) or in the microfluidic array (n=3 experiments; 50 clones tracked per experiment). CHO cells expanded in the microfluidic array exhibited growth rates that were comparable to batch shake flask cultures and superior to single cells cultured in 96-multiwell plates (FIG. 73).

Example 6

Sensitivity of Single ASC Detection in the Presence of a Heterogeneous Population of ASCs Mathematical modeling was used to determine the total efficiency of antibody capture on beads within a chamber having a volume of 4.1 nL (160 µM×160 µM×160 µM) as a function of time and as a function of the number of beads. The average secretion rate for this line of CHO cells was measured on bulk samples to be approximately 300 proteins per second. This secretion rate is comparable to the expected secretion rate from primary antibody secreting cells which are estimated to secrete between 100 and 2000 antibodies per second. Thus, based on these measurements it was determined that the beads furthest away from the cell are expected to capture approximately 4000 antibodies during a two hour incubation, and is detected via fluorescence.

Figures 74A, 74B, 74C, 74D, 74E:
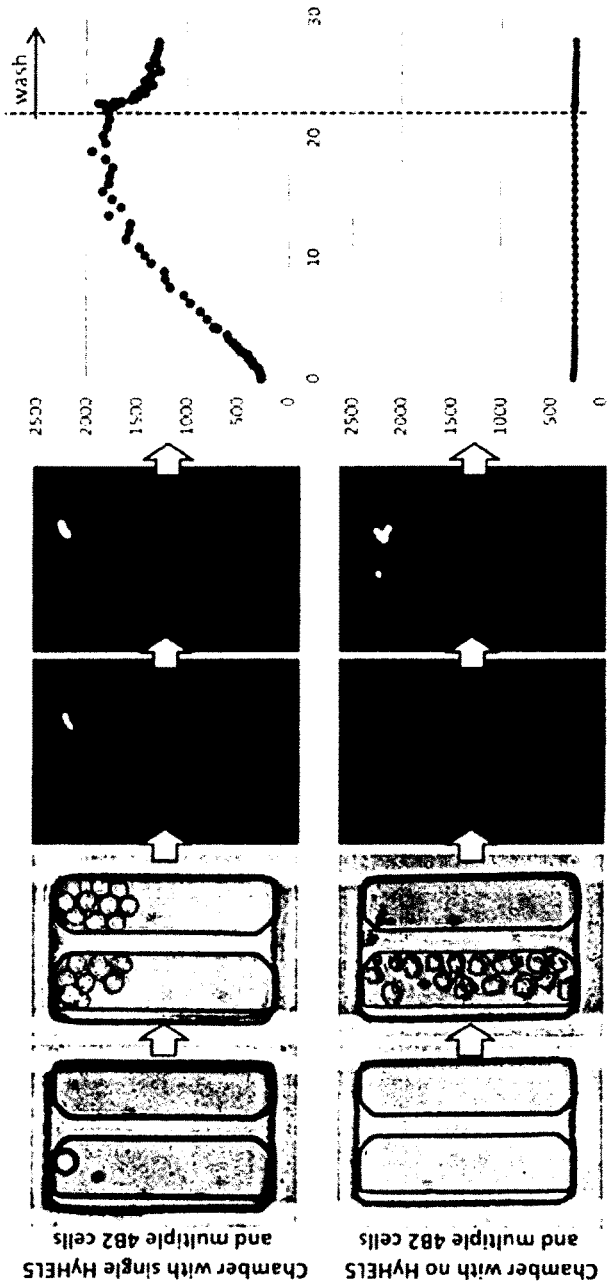
FIG. 74A is a light micrograph of a microfluidic chamber into which a HyHEL5 hybridoma cell secreting an anti-lysozyme antibody has been loaded (top panel) and a microfluidic chamber into which the HyHEL5 hybridoma cell has not been loaded (bottom panel).
FIG. 74B is a light micrograph of the chambers shown in FIG. 74A into which 4B2 hybridoma cells secreting "background" antibodies that do not bind lysozyme have been loaded in addition to HyHEL5 cells.
FIG. 74C is a fluorescence micrograph of the chambers shown in FIG. 74B after incubation with fluorescent lysozyme.
FIG. 74D is a fluorescence micrograph of the chambers shown in FIG. 18C after incubation with fluorescent anti IgG antibodies.
FIG. 74E is a graph showing kinetics of antibody accumulation and release for the chambers depicted in FIG. 74C.

In the example shown in FIG. 74A to 74D, the target of interest (antigen) is hen egg white lysozyme (HEL). A device was loaded with effector cells derived from two hybridoma lines, HyHel5 and 4B2. HyHel5 hybridoma cells secrete a monoclonal antibody that binds HEL and 4B2 hybridoma cells secrete a monoclonal antibody that does not bind HEL. Referring to FIG. 74A, the top panel shows a HyHel5 cell loaded into a chamber of a device having approximately 700 assay chambers. HyHel5 cell were initially loaded at a density that results in an average of approximately 1 cell every 10 chambers. The bottom panel shows a chamber in which no HyHel5 cells are loaded. The locations of the loaded HyHel5 cells were recorded, once loaded into the device. Referring to FIG. 74B, the 4B2 cells were loaded into the chambers at an average ratio of the two cell lines loaded into the device at an average of 25 cells per chamber, corresponding to 250 times the concentration of HyHel5 cells.

Figure 74F:
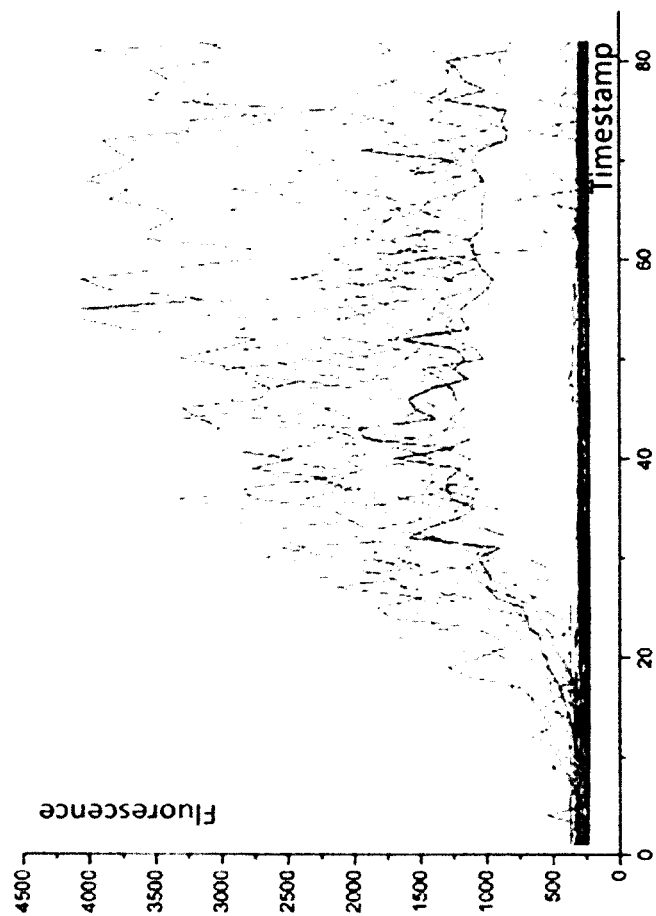
FIG. 74F is a graph of the fluorescence of 600 chambers containing a mix of HyHEL5 and 4B2 hybridoma cells incubated in the presence of Protein A and 10 nM lysozyme in the growth media recorded over time.

The device chambers were then washed and beads functionalized with rabbit polyclonal anti-mouse IgG antibodies (readout particles) were loaded into the chambers. The chambers were then isolated and incubated, resulting in the capture of the antibodies generated by the cells in each chamber on the beads in that chamber. Referring to FIG. 74C, fluorescently labeled HEL (10 nM) was included in the medium during the incubation step and fluorescent images were taken to identify the chambers having beads with bound HyHel5 and to monitor the accumulation of HyHel5 antibodies on the beads. As can be seen in FIG. 74C, fluorescence was only detected in the top panel, indicating that only chambers having HyHel5 cells generate strong fluorescent signal on beads when incubated with the fluorescently labeled HEL antigen. Referring to FIG. 74D, the device was then incubated with fluorescently labeled polyclonal anti-IgG antibodies to identify chambers having beads with bound IgG, either secreted from HyHel5 cells or 4B2 cells. All chambers generated fluorescent signal when exposed to fluorescently labeled anti-IgG antibody, indicating that antibodies from both cell lines were captured in all chambers. Following incubation with fluorescently labeled HEL, the chambers were flushed with medium in the absence of labeled HEL antigen, and images were taken to monitor the dissociation kinetics of the HyHel5-HEL binding in the chambers, as shown in FIG. 74E. FIG. 74F shows the fluorescence over time of 600 chambers containing a mix of HyHEL5 and 4B2 hybridoma cells as described above, incubated in the presence of Protein A beads and 10 nM lysozyme. Chambers containing HyHEL5 cells were easily distinguishable by their fluorescence above the baseline, demonstrating the ability of this system to detect rare cells secreting an antigen-specific mAb.

Figure 75A:
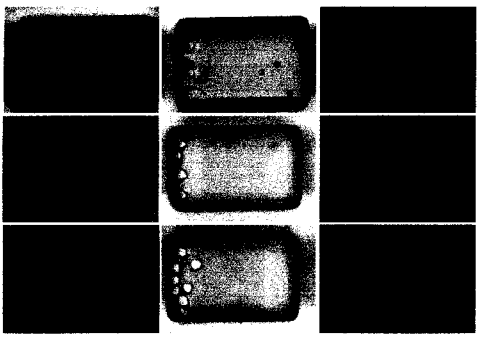
FIG. 75A shows three representative examples of the lack of signal in chambers containing antibody secreting cells but no cell secreting antibodies against an antigen of interest.
Figure 75B:
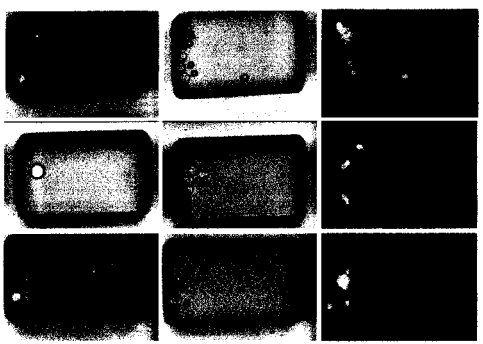
FIG. 75B shows three representative examples of chambers in which a single cell secreting an antibody against an antigen of interest is detected among a background of multiple cells secreting antibodies that are not specific to the antigen of interest.
Figure 75C:
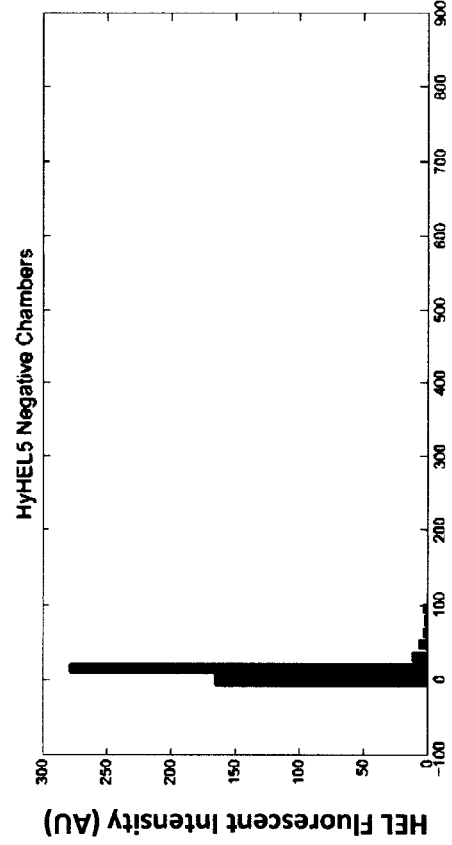
FIG. 75C shows a histogram of the fluorescent signal in all chambers containing only hybridoma cells that do not secrete antibodies against the antigen of interest.
Figure 75D:
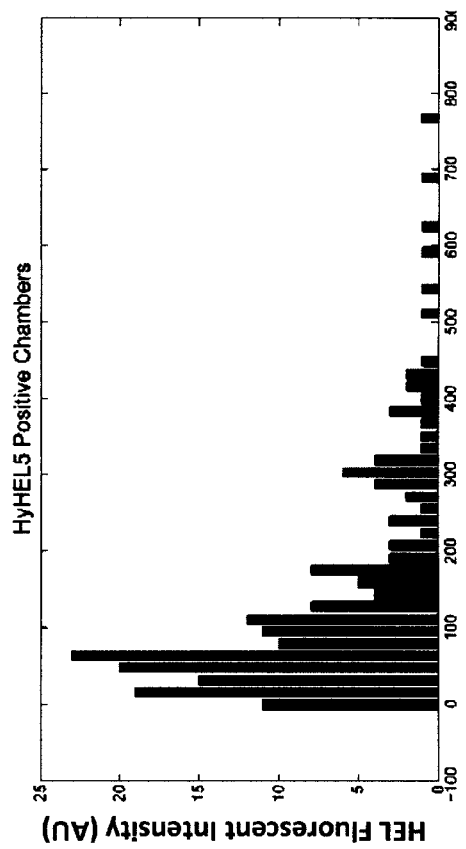
FIG. 75D shows a histogram of the fluorescent signal in chambers containing a mixture of HyHEL5 hybridoma cells producing antibodies against an antigen of interest (hen-egg lysozyme) and DMS-1 hybridoma cells producing an antibody against a different antigen.

In a different example, a population of HyHEL5 hybridoma cells secreting antibodies against hen-egg lysozyme (HEL) was loaded in the microfluidic device at limiting dilution. The device was imaged to determine the presence of HyHEL5 cells in each of the chambers. DMS-1 hybridoma cells secreting antibodies that do not bind HEL were subsequently loaded at an average concentration of approximately 5 cells per chamber in the same array. Cells were incubated in the presence of readout antibody-capture beads (Protein A beads coated with rabbit anti-mouse antibody) and the secretion of lysozyme-specific antibodies was measured by washing with a 1 nM solution of lysozyme labeled with Alexa-488. Bright field images obtained after loading HyHeL5 cells (top), bright field images taken after incubation with DMS-1 cells and beads (middle), and corresponding fluorescent images (bottom) are shown for three representative chambers containing DMS-1 cells only (FIG. 75A) or a mixture consisting of a single HyHEL5 cell and multiple DMS-1 cells (FIG. 75B). The distribution of fluorescence intensity is shown for chambers containing DMS-1 cells only (FIG. 75C) or both HyHEL5 cells and DMS-1 cells (FIG. 75D). Cells secreting antibodies against hen-egg lysozyme in the HyHEL5 population was detected even in the presence of multiple DMS-1 cells secreting non-antigen-specific antibodies.

Example 7

Figure 76A:
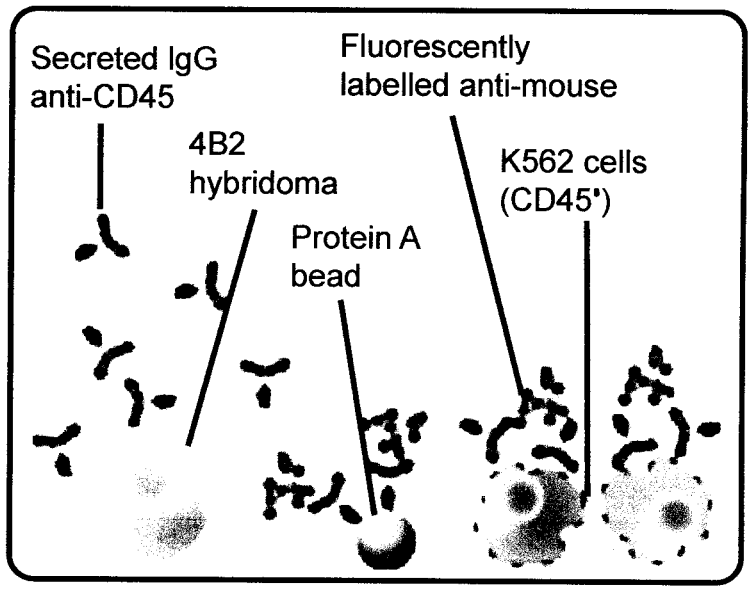
FIG. 76A is a schematic of a single hybridoma cell (4B2) secreting an antibody against human CD45 on fixed K562 cells. Cells and beads are stained with a detection antibody following incubation.
Figure 76B:
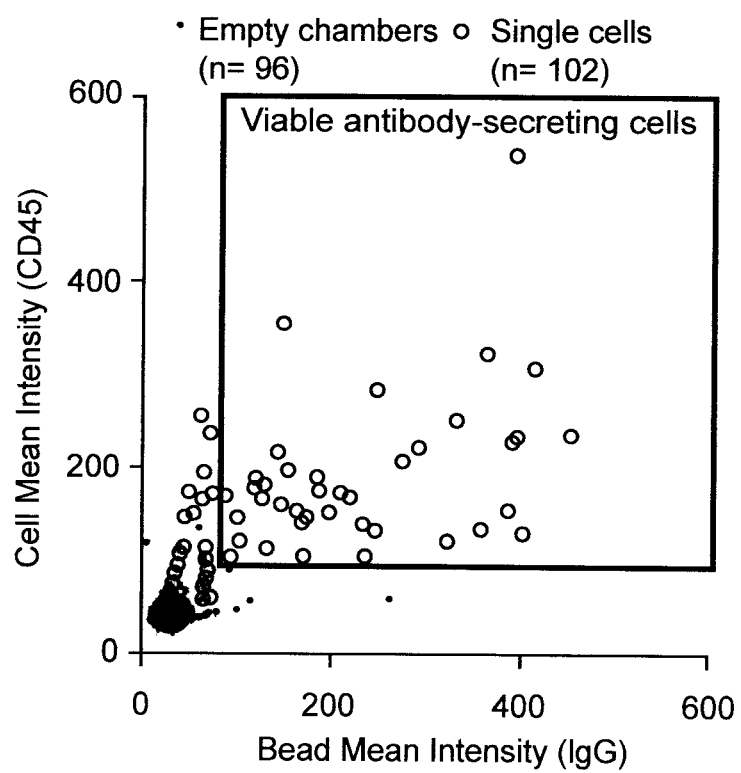
FIG. 76B shows the mean fluorescence intensity of readout cells and beads measured by automated image analysis for empty chambers and chambers containing a single hybridoma.
Figure 76C:
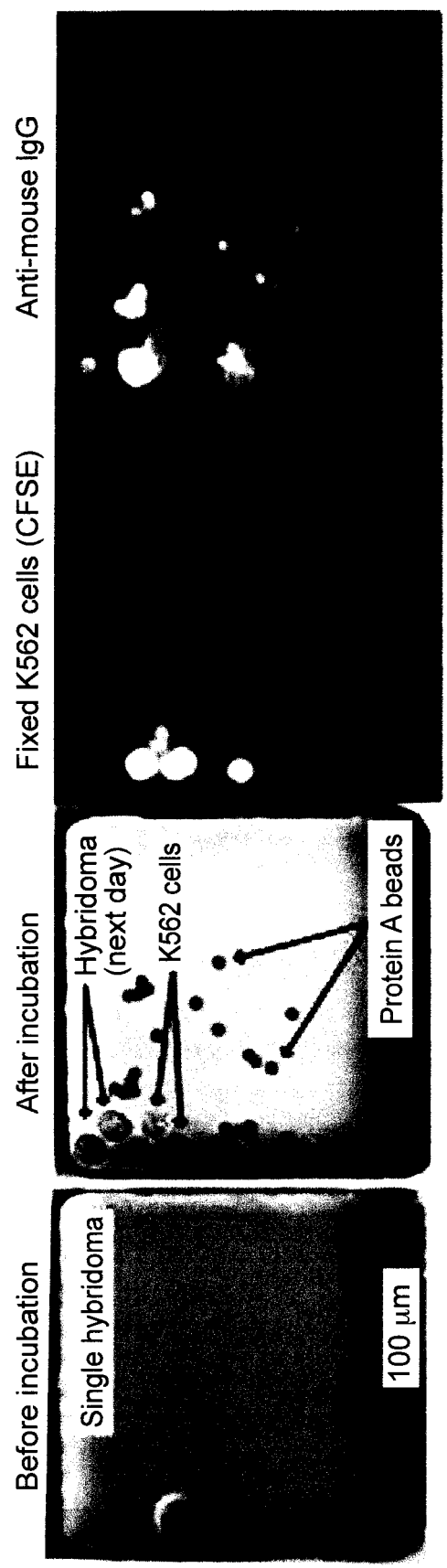
FIG. 76C, from left to right: Chamber with a single hybridoma cell. Bright field, fluorescent and merged images of anti-CD45 antibody staining in the same chamber following an overnight incubation with target fixed K562 cells and a 2-hour incubation period with protein A beads.

Selection of mAbs from Single Cells Using Bead- and Cell-based Binding Assays Single hybridoma effector cells (4B2) were loaded into individual chambers of a microfluidic device and binding of secreted antibodies (IgG against anti-human CD45) was measured using both a bead-based and cell-based readout binding assays. Readout cells in this experiment were K562 cells endogenously expressing the human CD45 membrane receptor and stained with carboxyfluorescein succinimidyl ester (CFSE) prior to fixation so as to distinguish them from the effector cells. Single effector cells were provided to individual chambers of the device and incubated with a plurality of readout K562 cells overnight. Next, the effector cells were incubated with readout Protein A beads for an additional 2 hours and then stained with a detection antibody (fluorescently labeled anti-mouse IgG), which binds the secreted IgG anti-human CD45 antibody. Fluorescence of individual chambers was then measured. A schematic of the experiment is provided in FIG. 76A FIG. 76B is a graph of mean fluorescence intensity of readout cells and readout beads measured by automated image analysis for empty chambers and chambers containing a single hybridoma effector cell. FIG. 76C (left to right) shows a single chamber with a single hybridoma cell (left panel). The hybridoma cell in this example divided overnight. The remaining panels show fluorescent and merged images of anti-CD45 antibody staining in the same chamber following an overnight incubation with target fixed K562 cells and a 2-hour incubation period with protein A beads (labeled with appropriate polyclonal anti-mouse IgG antibodies). A person skilled in the art will understand that this assay can be modified to be performed with live readout cells and/or different species of readout cells.

Example 8

Cell-Based Immunization and Cell Binding Assays

Figure 77A:
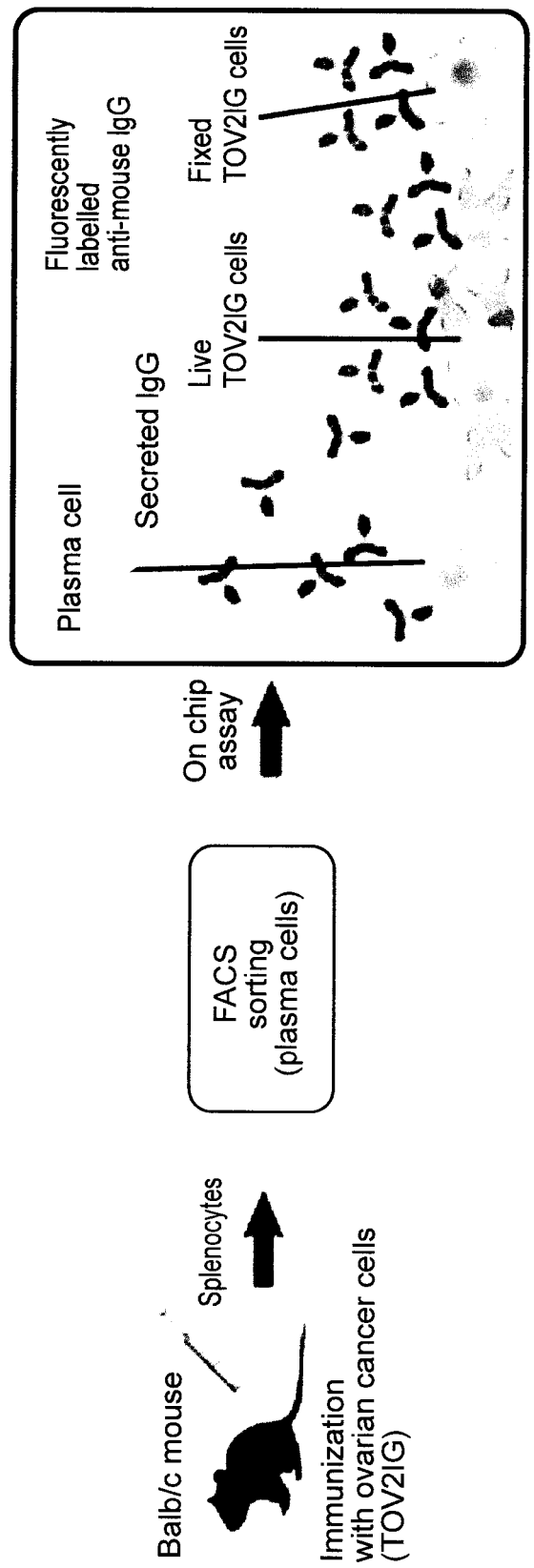
FIG. 77A is a schematic of an immunization and binding assays. Mice were immunized with live cells from an ovarian cancer cells (TOV21G). Antibody-secreting cells were sorted using FACS and were then injected in the microfluidic device and incubated with readout cells (fixed and live TOV21G cells) stained with CFSE. Antibody binding is visualized using a secondary labeled antibody.
Figure 77B:
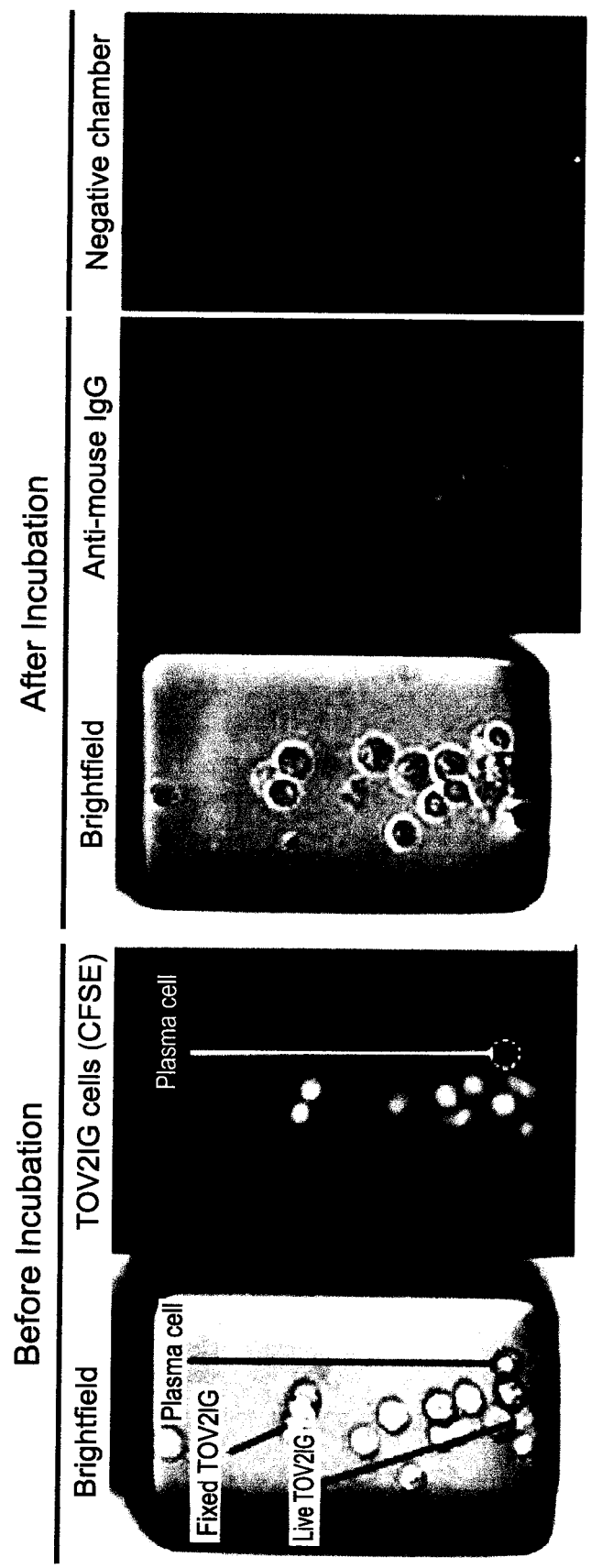
FIG. 77B shows plasma and readout cells (live and fixed) after loading on chip. Readout cells are stained with CFSE for identification. Antibody binding on the cell surface of live and fixed cells is visualized with a secondary labeled antibody. Far right shows a negative chamber with very low signal on the readout cells.

Mice were immunized with fixed cells from a human ovarian cancer cell line (TOV21G) (FIG. 77A). Antibody-secreting effector cells were sorted using FACS and were then injected in the microfluidic device and incubated with readout cells (fixed and live TOV21G cells) stained with CFSE. Antibody binding was visualized using a secondary labeled antibody. FIG. 77B shows the results of this experiment. From left to right: plasma and readout cells (live and fixed) after loading on chip. Readout cells were stained with CFSE for identification. Antibody binding on the cell surface of live and fixed cells was visualized with a secondary labeled antibody (anti-mouse IgG). Far right shows a negative chamber (no effector cells) with very low signal on the readout cells.

Example 9

Maintenance of Cellular Viability and Secretion

Figure 78:
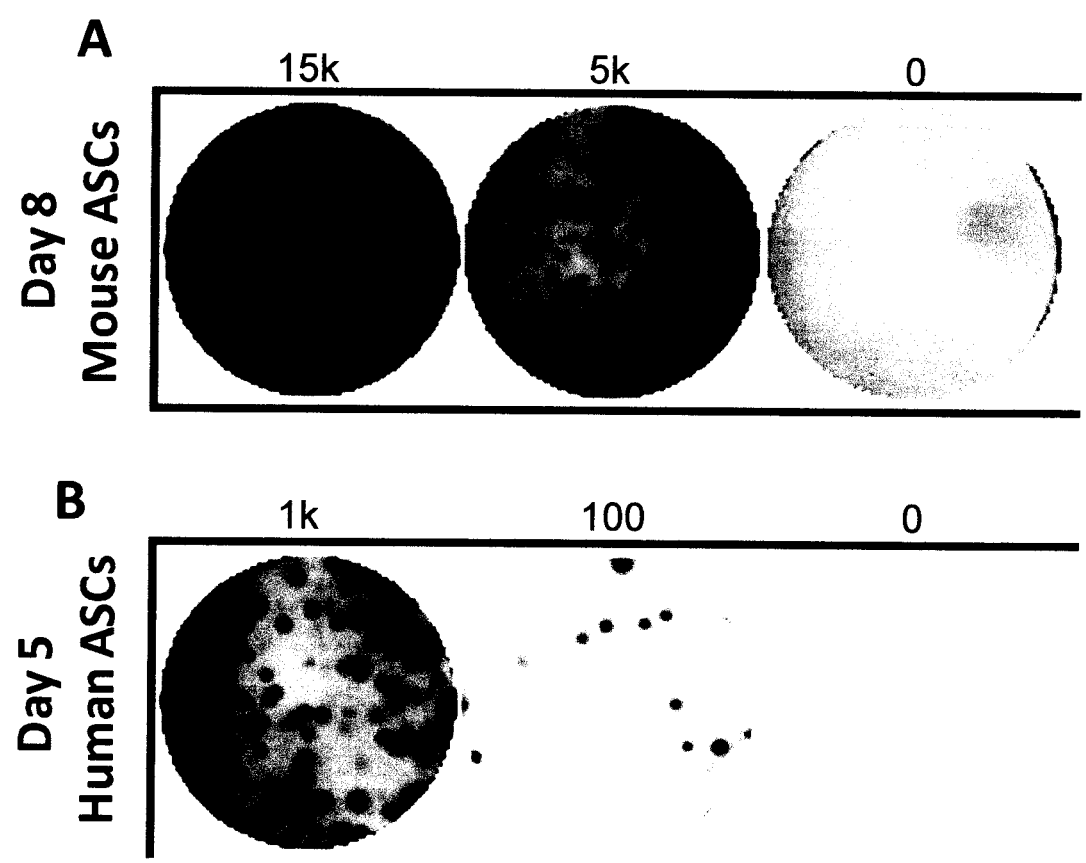
FIG. 78 is an image showing cell survival and antibody-secretion by ELISPOT of (A) mouse ASCs grown for 8 days, and (B) human ASCs grown for 5 days. The number of cells plated per well is indicated.

Conditions were optimized for maintaining cellular viability and secretion of ASC effector cells for 5-8 days. FIG. 78 shows cell survival and antibody-secretion by ELISPOT from mouse ASCs grown for 8 days (FIG. 78A), and human ASCs (FIG. 78B) grown for 5 days in complete RPMI with IL-6 10 ng/mL.

For immunization procedures, mice were subcutaneously injected with hen egg-white lysozyme and Alhydrogel adjuvant (Accurate Chemical & Scientific Corporation) 3 times at 2 week intervals. Humans were immunized with influenza vaccine 1 week prior to blood collection. Immunization procedures were performed in accordance with approved protocols by the University of British Columbia. Mouse spleen cells were isolated and stained with PE anti-mouse CD138 (BD Pharmingen) and sorted by FACS for CD138+ cell population (see Example 10 for a further description). Human peripheral blood mononuclear cells (PBMCs) were isolated and stained with markers as described in Wrammert et al. (2008), *Nature Letters* 453, pp. 667-671, the disclosure of which is incorporated by reference in its entirety for all purposes.

Enzyme-Linked-Immunospot (ELISPOT) assay was performed in polyvinylidene fluoride (PVDF) membrane-lined 96-well microplates (Millipore). The PVDF membrane was pre-wet with 70% ethanol and washed with PBS. Plates were coated overnight with goat anti-mouse IgG (H+L) (Jackson Immunoresearch) or rabbit anti-human IgG (H+L) (Jackson Immunoresearch) antibody (1:1000/100 μL/well) and washed 3-4 times with PBS. Cells were then added and incubated for 20 h at 37° C. Cells were removed by washing 3-4 times with PBS containing 0.1% Tween (PBS-Tween), and plates were incubated with alkaline phosphatase-goat anti-mouse IgG (H+L) (Jackson Immunoresearch) (1:1000/100 uL/well). After washing 3-4 times with PBS-Tween, plates were incubated with BCIP/NBT chromogenic agent (Sigma-Aldrich B6404-100ML). Spots were counted with the aid of an upright microscope and CCD camera.

Example 10

Methods for Enriching Plasma Cells

Figure 79:
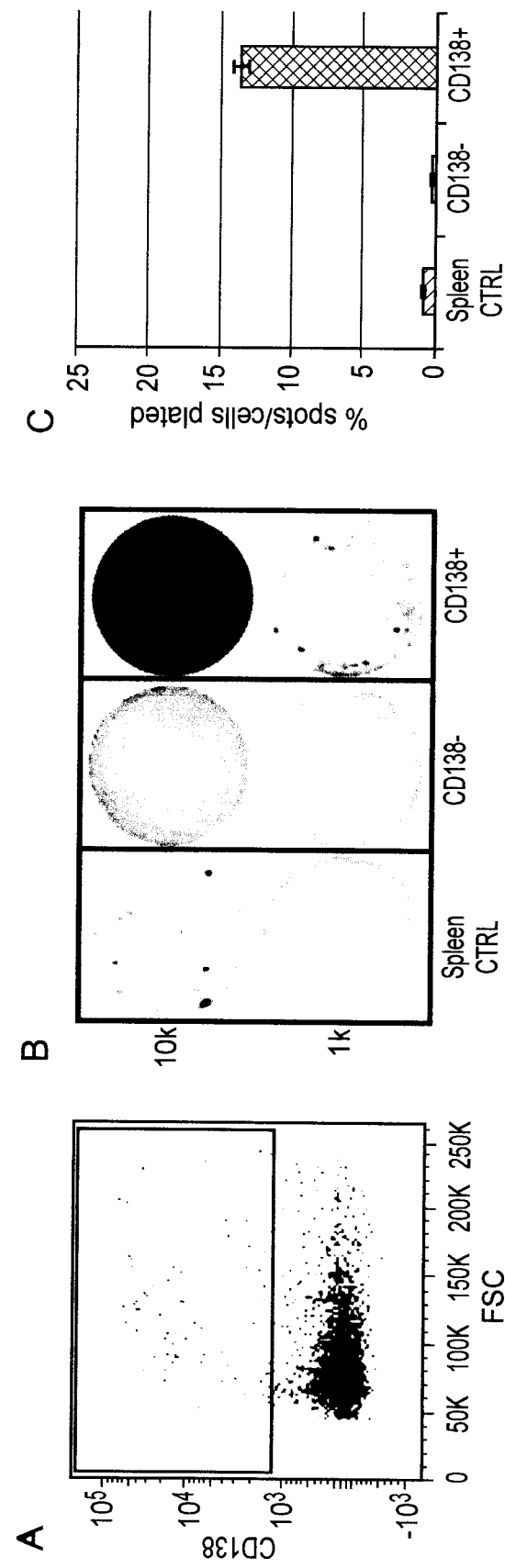
FIG. 79 shows ASC selection from mice immunized with ovarian carcinoma cells. (A) Plot showing fluorescence-activated cell sorting of mouse spleen cells stained with PE anti-mouse CD138. Gating shows CD138+ population. (B) ELISPOT showing antibody secretion from unsorted spleen control, CD138− control, and CD138+ population. The number of cells plated per well is indicated. (C) Graph showing ELISPOT counts as % spots per cells plated for each population.

Antibody-secreting cells were enriched in species with known markers, specifically CD138 plasma cell marker in mice (FIG. 79). First, mice were immunized intraperitoneally with 5×10$^6$ ovarian carcinoma cells (TOV-21G) 3 times at one week intervals, in accordance with approved animal care protocols. Mouse spleen cells were stained with PE anti-mouse CD138 (BD Pharmingen) and sorted by FACS for CD138+, and CD138− as a negative control (FIG. 79A). ELISPOT was performed as described in Example 9 to detect antibody-secretion from the sorted and unsorted cell populations (FIG. 79B). A 20-fold increase in ASCs from the CD138+ population compared to unsorted spleen cells was observed (FIG. 79C). Although not performed here, enrichment can also be done using commercially available magnetic-based enrichment kits (e.g., StemCell Technologies, Miltenyi) alone or in combination with FACS sorting.

Figure 80:
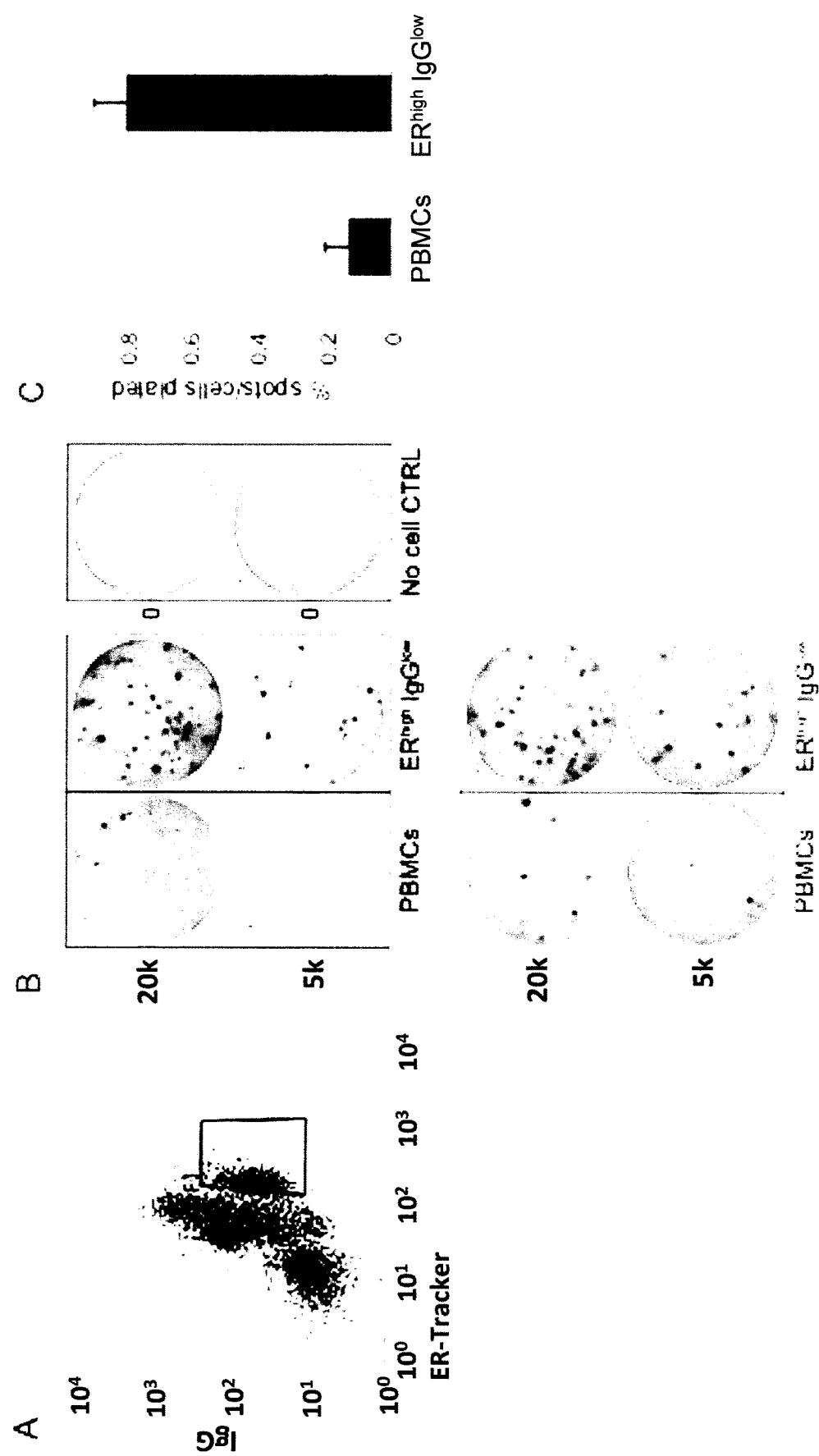
FIG. 80 shows ASC selection from rabbits immunized with influenza. (A) Plot showing fluorescence-activated cell sorting of rabbit PBMCs using ER-Tracker and mouse anti-rabbit IgG. Gating shows selection of $ER^{high}IgG^{low}$ population. (B) ELISPOT showing antibody secretion from unsorted PBMCs control, $ER^{high}IgG^{low}$ population, and no cell control. The number of cells plated per well is indicated. (C) Graph showing ELISPOT counts as % spots per cells plated for unsorted PBMCs control and $ER^{high}IgG^{low}$ population.

Antibody-secreting cells were also enriched from species lacking established markers for plasma cells by using the ER-Tracker™ (Life Technologies) in rabbits (FIG. 80). Rabbits were immunized with influenza vaccine intradermally 4 times at 1 week intervals, followed by boosts 1 week prior to blood collection, in accordance with approved animal care protocols. Rabbit PBMCs were stained with ER-Tracker (Life Technologies) and mouse anti-rabbit IgG (Jackson Immunoresearch), and sorted by FACS for $ER^{high}$-$IgG^{low}$ population (FIG. 80A). ELISPOT was performed as described in Example 9 to detect antibody-secretion from the $ER^{high}IgG^{low}$ population and unsorted PBMCs control (FIG. 80B). A 6-fold increase in antibody secretion from the $ER^{high}IgG^{low}$ population compared to unsorted PBMCs was observed (FIG. 80C).

Example 11

Enrichment Using Influenza Human Systems

Figure 81B:
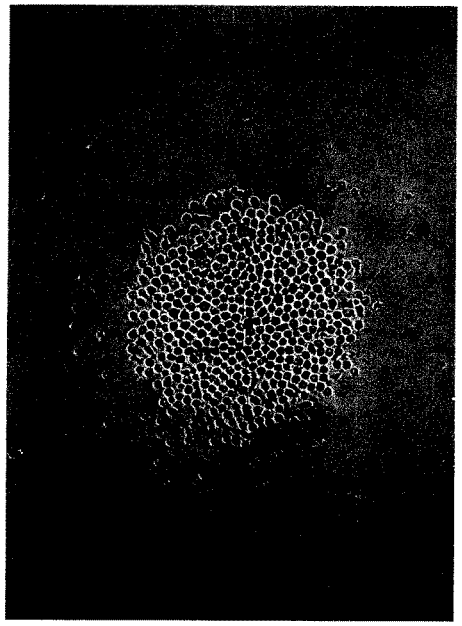
FIG. 81B shows cells in a multiwell plate after culture and recovery overnight.
Figure 81D:
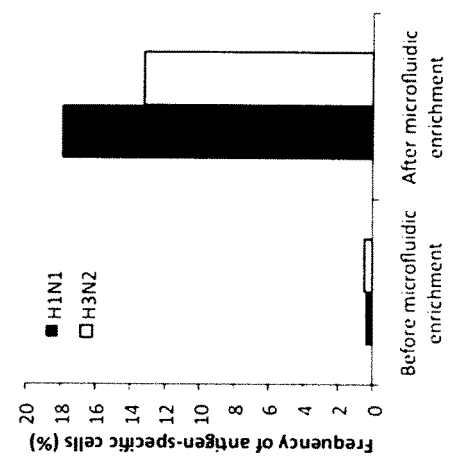
FIG. 81D the frequencies of H1N1- and H3N2-positive chambers before and after enrichment.
Figure 81A:
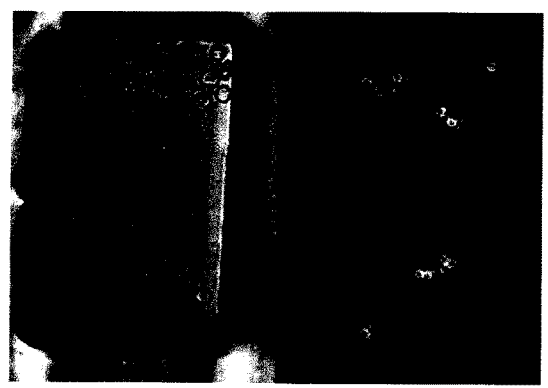
FIG. 81A shows a representative example of bright field (top) and fluorescent (bottom) images from an antigen-specific positive chamber before enrichment.
Figure 81C:
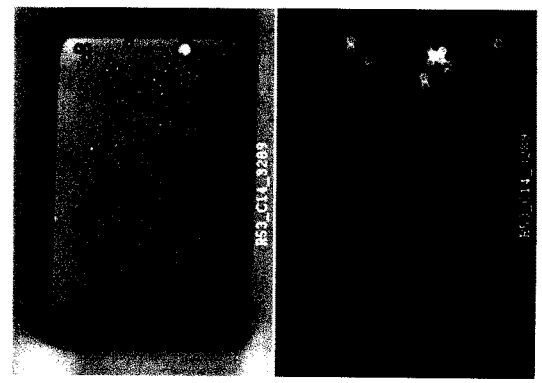
FIG. 81C shows a representative example of bright field (top) and fluorescent (bottom) images of an antigen-specific positive chamber loaded at single-cell dilution after enrichment.

Peripheral blood mononuclear cells (PBMCs) were isolated from the blood of a human patient 7 days following immunization with the influenza trivalent vaccine. Cells were enriched based on CD138 expression using a commercially available bead separation kit (Stem Cell Technologies) and loaded in a microfluidic device at an average density of 11 cells per chamber (i.e., heterogeneous cell populations comprised on average 11 cells) for a total of approximately 44,000 cells. Cells were incubated with Protein A beads for 2 hours, and with fluorescently labeled H1N1 and H3N2 in different colors. A total of 171 H1N1-positive chambers and 199 H3N2-positive chambers (e.g., FIG. 81A) representing antigen-specific frequencies of 0.39% and 0.45%, respectively. The contents of 24 of these chambers were recovered and cultured overnight in a multiwell plate (FIG. 81B) and then introduced in a second microfluidic device the next day. After enrichment, the frequencies of H1N1-positive H3N2-positive chambers (FIG. 81C) were 7% and 6%, respectively, meaning that a 13- to 18-fold enrichment was obtained (FIG. 81D).

Example 12

Bead Aggregation as an Indicator of Antibody Secretion

Chambers of a microfluidic device were loaded with a mixture of cells secreting human antibodies and non-antibody secreting cells. Cells were incubated for 2 hours in the presence of protein-A beads and then stained using secondary labelled antibodies. The beads in chambers that contained antibody-secreting cells formed aggregates (FIG. 82) while beads remained dispersed in the absence of secreted antibodies (FIG. 83).

Example 13

Affinity Measurements for HEL-specific Hybridomas

Figure 84A:
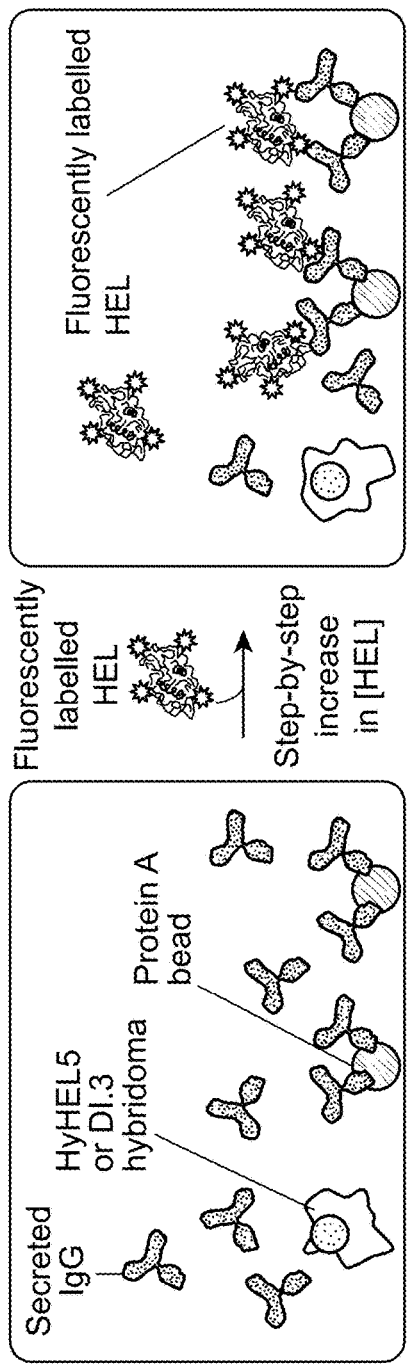
FIG. 84A is a diagram of the experiment depicted in Example 13.
Figure 84B:
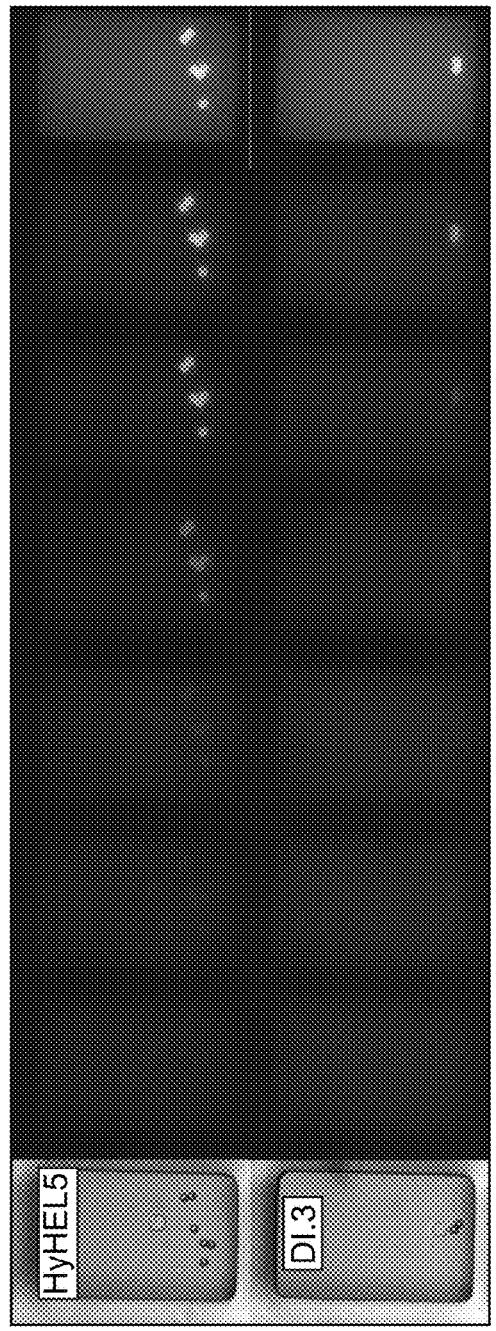
FIG. 84B are optical micrographs of microfluidic chambers having different concentrations of labeled antigen.
Figure 84D:
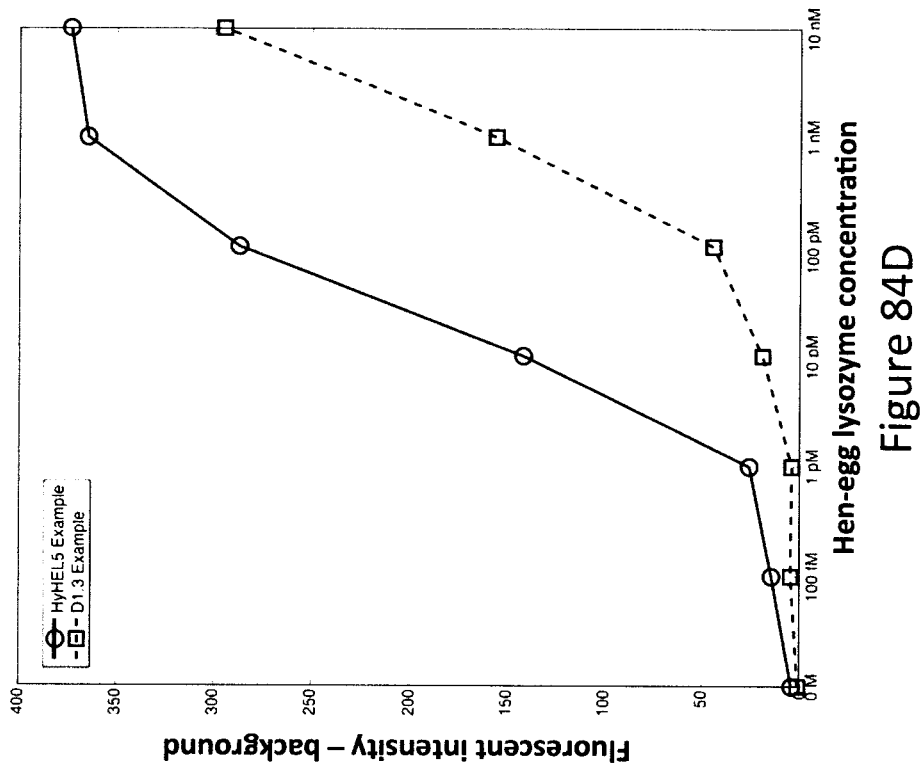
FIG. 84D is a graph showing the bead fluorescent intensities corresponding to images in FIG. 84B after incubation with single D1.3 and HyHEL5 cells secreting antibodies with different affinities and after labeling with different concentrations of antigen (hen egg lysozyme).
Figure 84C:
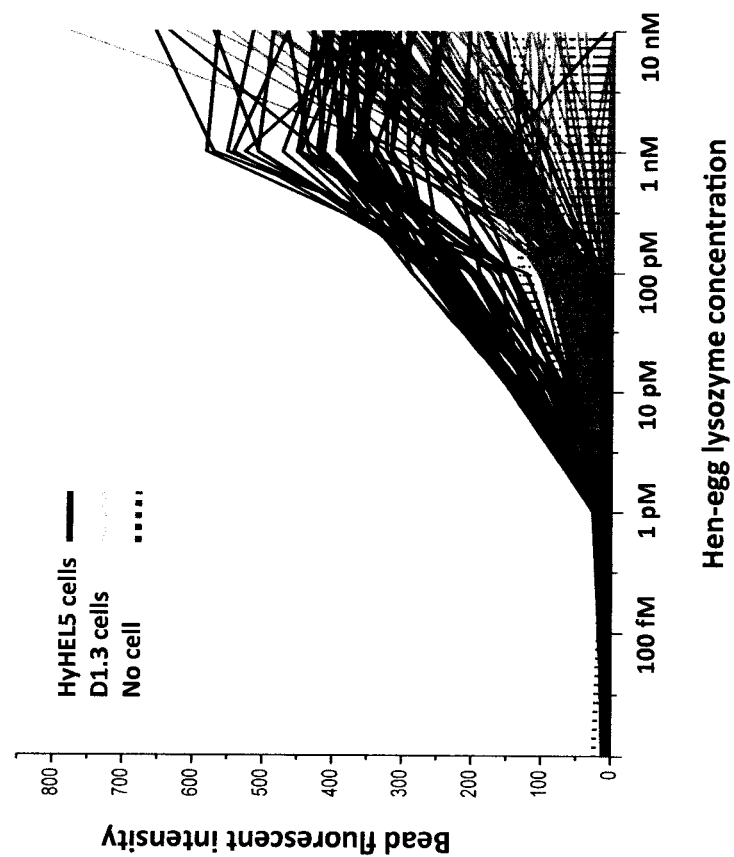
FIG. 84C is a graph of bead fluorescent intensities at different concentrations of labeled antigen (hen-egg lysozyme) after incubation with single hybridoma cells (HyHEL5 and D1.3) secreting antibodies with different affinities.

A population of hybridoma effector cells (HyHEL5) producing an antibody with high affinity for hen-egg lysozyme (HEL) was first introduced in a microfluidic device at limiting dilution. A picture set was taken to identify chambers containing HyHEL 5 cells, and then a second population of hybridoma cells (D1.3) secreting an antibody with low affinity for HEL was loaded in the same device. A second picture set was taken and chambers containing either one HyHEL5 cell or one D1.3 cell were identified. Protein A beads coated with a rabbit anti-mouse antibody were introduced in the chambers and incubated with the cells for 2 hours. At the end of the incubation period, labeled antigen was introduced in the device at increasing concentrations between 100 fM and 10 nM in a step-wise fashion. FIG. 84A shows a diagram of this experiment, and micrographs of the chambers with different concentrations are shown in FIG. 84B. The bead fluorescence intensity was measured at every step, normalized to the background for every chamber. Chambers containing HyHEL5 were distinguished from those containing D1.3 cells based on the affinity measurements (FIG. 84C). Example curves from representative chambers containing single cells HyHEL5 and D1.3 and the images from these same chambers are shown in FIG. 84D and FIG. 84B, respectively. Affinities for HyHel5 and D1.3 antibodies are 30 pM and 1.5 nM, respectively (Singhal et al. (2010), *Anal Chem* 82, pp. 8671-8679, in corporate by reference herein for all purposes).

Example 14

Identification of Antigen-specific Cells with or without Chamber Isolation

Figure 86:
FIG. 86 show a section of a microfluidic array containing human plasma cells secreting antibodies against H3N2 after incubation without using the isolation valve, allowing chambers to remain connected by the flow channels.
Figure 85:
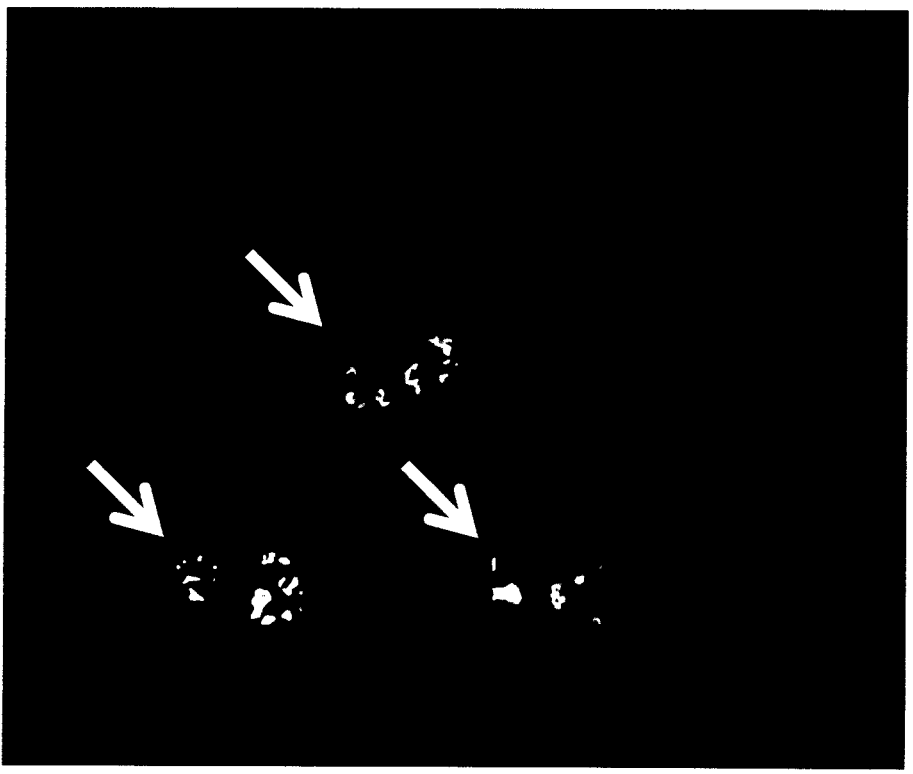
FIG. 85 show a section of a microfluidic array containing human plasma cells secreting antibodies against H3N2 after incubation with a closed valve that maintained each chamber isolated.

Human plasma cells were enriched from PBMCs obtained from the blood of human patients one week after immunization with the trivalent influenza vaccine. Cells were introduced in two different microfluidic devices and incubated in the presence of Protein A beads (readout beads) for 2 hours. In one device (FIG. 85), individual chambers comprising heterogeneous cell populations and readout beads were isolated from one another with a valve during the incubation. In the second device (FIG. 86), the valve was left open. Labeled antigens (H1N1 and H3N2) were introduced in the device at the end of the incubation period for 15 minutes and then the chambers were washed with media. FIG. 85 and FIG. 86 show a plurality of chambers from a section of each array, with H3N2-positive hits identified by white arrow. In the absence of main valve isolation (FIG. 86), the background in surrounding chambers was higher than with the main valve closed (FIG. 85). However antibody-carryover did not prevent clear distinction between negative and positive chambers. The direction of the flow channels is indicated by black arrows.

Example 15

Selection of Novel Mouse Antibody Secreting Cells Based on Affinity Measurements Plasma cells were isolated from the bone marrow of a mouse immunized with hen-egg lysozyme. Approximately 23,800 cells were distributed across 3 sub-arrays containing 6,144 chambers in a microfluidic device (average density: ~4 cells/chamber). Cells were incubated with Protein A beads coated with a rabbit anti-mouse capture antibody for 2 hours, washed with 10 nM of labeled hen-egg lysozyme and imaged. 117 antigen-specific chambers were identified, the contents of which were recovered with a microcapillary and reinjected at limiting dilution in a fourth sub-array containing 2,048 chambers. The reinjected cells were incubated with Protein A beads coated with a rabbit anti-mouse capture antibody for 2 hours, and then exposed to increasing concentrations of labeled antigen. Images were taken at each step and the bead fluorescence intensity was measured. FIG. 87 shows an example of binding curves from 2 single cells (labeled Mm20 and Mm25) secreting antibodies with different affinities. These cells were recovered as follows.

117 chambers containing a total of 882 cells were identified as containing at least one antibody-secreting cell. The contents of all 117 chambers were recovered with a microcapillary, pooled and immediately re-injected into the remaining 2,048 empty chambers of the original device using the recovery robot shown in FIG. 58. FIG. 98 shows a picture of the microcapillary in proximity of the injection port immediately before reinjecting the cells. The recovery process took a total of 1 hour and 35 minutes, or 49 seconds per chamber. After re-injection, a total of 682 cells were present in the analysis chambers, which represented 77% of the initial population recovered (882 cells).

The re-injected cells were immediately assayed again for the presence of one or more antibody secreting cells. 38 chambers were identified as containing at least one antibody-secreting cell (38/117=32%). Of these, 38 chambers, 19 contained single cells (16% of 117). The contents of all 38 chambers, along with 10 control chambers (5 no-cell and 5 non-secreting controls) were recovered for RT-PCR. The recovery process took a total of 2 hours and 15 minutes, or 170 seconds per chamber. In 43 of 48 samples (90%), all cells in the chambers were visually verified to have been recovered by the capillary. In 5 of 48 samples, at least one cell was seen to stick to the chamber bottom and was not recovered.

The following sequences were retrieved.

```
Mm20 (IGHV1-9*01) IGHD2-4*01, IGHD2-4*01, IGHD2-9*02 IGHJ2*01 heavy chain nucleic acid
sequence (SEQ ID NO: 1):
ATGGAATGGACCTGGGTCTTTCTCTTCCTCCTGTCAGTAACTGCAGGTGTCCACTCCCAGGT
TCAGCTGCAGCAGTCTGGACCTGAGCTGATGAAGCCTGGGGCCTCAGTGAAGATATCCTGC
AAGGCAACTGGCTACACATTCAGAAACTACTGGATAGAGTGGATAAAGCAGAGGCCTGGA
CATGCCTTGAGTGGATTGGAGAGATTTTACCTGAAAGTGGTAGTATTAATTACAATGAGA
AATTCAAGGGCAAGGCCACATTCACTGCAGATACATCCTCCAACACAGCCTACTTGCAACT
CCGCAGCCTGACATCTGAGGACTCTGCCGTCTATTATTGTTTTTATGATAATTACGTTTTTGA
CTACTGGGGCCAaggcacCACTctcAC Mm20 light chain amino acid sequence (SEQ ID NO: 2):
MEWTWVFLFLLSVTAGVHSQVQLQQSGPELMKPGASVKISCKATGY
TFRNYWIEWIKQRPGHGLEWIGEILPESGSINYNEKFKGKATFTADT
SSNTAYLQLRSLTSEDSAVYYCFYDNYVFDYWGQGTTL Mm20 (IGKV4-59*01) IGKJ5*01 light chain nucleic acid sequence (SEQ ID NO: 3):
ATGGATTCTCAAGTGCAGATTTTCAGCTTCCTGCTAATCAGTGCCTCGGTCATACTATCCAG
TGGACAAATTGTTCTCATCCAGTCTCCAACAATCATGTCTGCATCTCCAGGGGAGAAGGTC
ACCATGACCTGCAGTGCCAACTCAAGTTTCAGTTACATGCACTGGTACCAGCAGAAGTCAG
GCACCTCCCCCAAAAGATGGATTTATGACACATCCAAACTGGCTTCTGGAGTCCCTGCTCG
CTTCAGTGGCAGTGGGTCTGGGACCTCTTACTCTCTCACAATTAGCAGCATGGAGGCTGAA
GATGCTGCCACTTATTACTGTCAGCAGTGGAGTAGAAACCCCACGTTCGGTGCtggacCaAGCt
Ga Mm20 light chain amino acid sequence (SEQ ID NO: 4):
MDSQVQIFSFLLISASVILSSGQIVLIQSPTIMSASPGEKVTMTCSANS
SFSYMHWYQQKSGTSPKRWIYDTSKLASGVPARFSGSGSGTSYSLTI
SSMEAEDAATYYCQQWSRNPTFGAGTKL >Mm25 (IGHV2-9-1*01) IGHD2-3*01 IGHJ3*01 heavy chain nucleic acid sequence (SEQ ID NO: 5):
ATGCAAGCAGTGGTATCAACGCAGAGTACGGGGAAGGAGTCAGGACCTGGCTTGGTGGCG
CCCTCACAGAGCATGTCCATCATGTGCACTGTCTCTGGGTTTTCATTAAGCAACTATGGTGT
ACACTGGGTTCGCCAGCCTCCAGGAAAGGGTCTGGAGTGGCTGGGAGTAATTTGGGCTGGT
GGAAACACAAATTATAATTCGGCTCTCATGTCCAGACTGAGCATCAGCAAAGACAAGTCCA
AGAGTCAAGTTTTCTTAAAAATGAACCGTCTGGAAACTGATGACACAGCCATGTACTATCT
GTGCCAGTGTAGGATGGTTACCCCTTGCTTACTGGGCCAAGG Mm25 heavy chain amino acid sequence (SEQ ID NO: 6):
MQAVVSTQSTGKESGPGLVAPSQSMSIMCTVSGFSLSNYGVHWVRQ
PPGKGLEWLGVIWAGGNTNYNSALMSRLSISKDKSKSQVFLKMNRL
ETDDTAMYYLCQCRMVTPCLLGQ >Mm25 (IGKV6-17*01) IGKJ4*01 light chain nucleic acid sequence (SEQ ID NO: 7):
ATGGAGTCACAGATTCAGGTCTTTGTATTCGTGTTTCTCTGGTTGTCTGGTGTTGACGGAGA
CATTGTGATGACCCAGTCTCACAAATTCATGTCCACATCAGTAGGAGACAGGGTCAGCATC
ACCTGCAAGGCCAGTCAGGATGTGAGTATTTCTGTAGCCTGGTATCAACAGAAACCAGGAC
AATCTCCTAAACTACTGATTTACTCGGCATCCTACCGGTACACTGGAGTCCCTGATCGCTTC
ACTGGCAGTGGATCTGGGACGGATTTCACTTTCACCATCCGCAGTGTGCAGGCTGAAGACC
TGGCAGTTTATTACTGTCAGCAACATTATAGTACTCCttTCACGTCGGCTCggGaCAAagTG Mm25 light chain amino acid sequence (SEQ ID NO: 8):
MESQIQVFVFVFLWLSGVDGDIVMTQSHKFMSTSVGDRVSITCKAS
QDVSISVAWYQQKPGQSPKLLIYSASYRYTGVPDRFTGSGSGTDFT
TIRSVQAEDLAVYYCQQHYSTPFTSARDKV
```

Example 16

$K_{off}$ Values for HyHEL5 Hybridoma Cells

A mixture of HyHEL5 hybridoma (low $K_{off}$) and a background of D1.3 hybridoma (high $K_{off}$) cells were screened in a microfluidic device according to an embodiment of the invention. Chambers in which HyHEL5 hybridoma were present were detected by fluorescence intensity associated with Ab secretion (i.e., fluorescence accumulation on beads) before and antigen release (for $K_{off}$ measurements) following a wash step for each chamber. FIG. 88 shows a bar graph of the remaining fluorescence level of beads in HyHEL5-positive wells is higher than in the rest of the wells at the end of the wash.

Example 17

Detection of Rare Circulating Antibody-secreting Cells in Humans Against Specific Antigens In one embodiment, the invention is used to screen for extremely rare cells, for instance antigen-specific plasma B cells that occur at basal level, i.e., without recent immunization or infection with the antigen. FIG. 89A shows a population of heterogeneous cells containing enriched B cells and erythrocytes from a healthy patient. The population contained at least one antibody secreting cell as measured by whole IgG staining on readout bead particles (FIGS. 89B and 89C). In addition, this population contained at least one effector cell secreting antibodies specific to H1N1 as measured by the binding of a labeled H1N1 antigen to the readout beads that had captured the antibody (FIGS. 89D and 89E). The entire screen was performed using ~30 cells per chamber in an array of 1,600 chambers for a total population of 48,000 cells. This allowed the detection of one effector cell present at a frequency of 0.000625%. The cells of the chamber were recovered (FIG. 89F) and the heavy and light chains from that effector cell were amplified.

This assay can also be performed to find more abundant cells, for instance after a natural infection or about one week post-immunization with an antigen.

Example 18

Simultaneous Analysis of Extracellular and Intracellular Biomolecules

Figure 90:
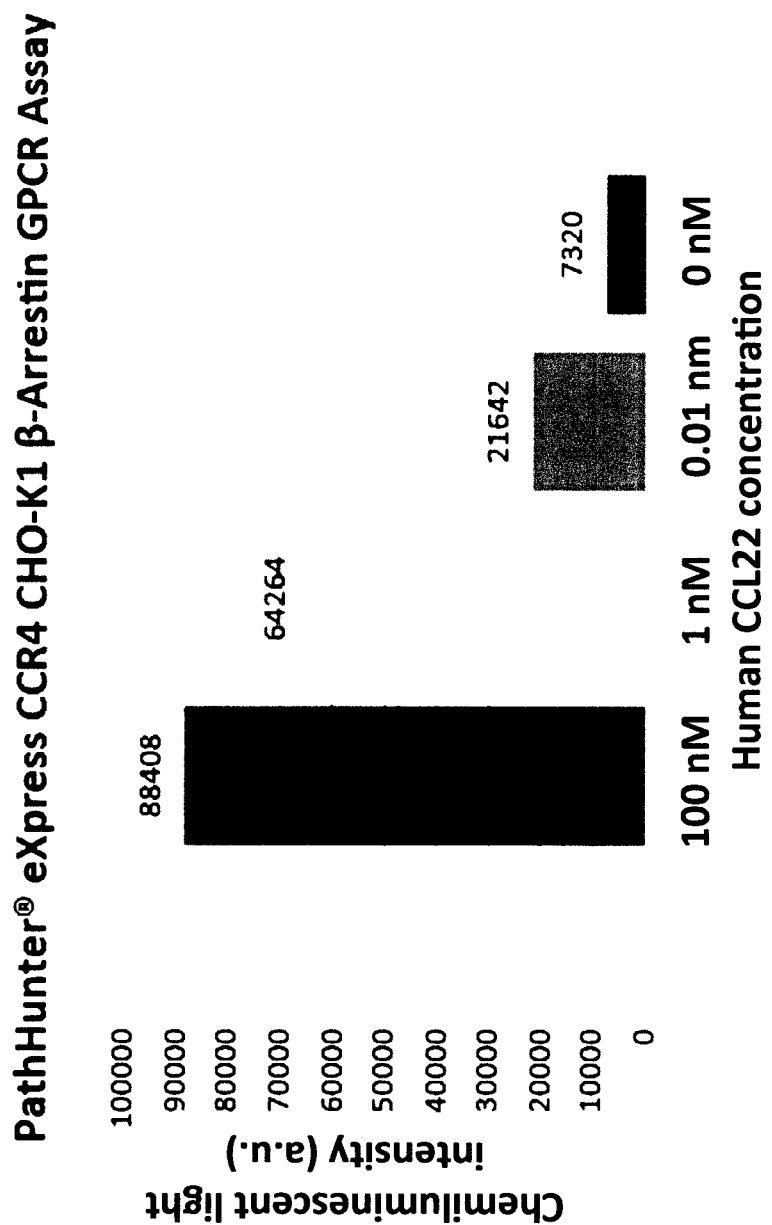
FIG. 90 shows an example of a chemiluminescent signaling assay using PathHunter® eXpress CCR4 CHO-K1 β-Arrestin GPCR Assay in multiwell plates.

The analysis of extracellular and intracellular components was assessed in the context of a cell signaling readout assay. CHO cells engineered to overexpress the GPCR CXCR4 with beta-galactosidase fragment complementation (DiscoverX) were used to quantify the binding of the ligand CCL22 to the receptor. Activation of the receptor by the ligand caused intracellular beta-galactosidate complementation, which was then measured by lysing the cells in the presence of a beta-galactosidate substrate that yields a chemiluminescent signal. An example of this assay performed in multiwell plate is shown in FIG. 90. The assay was performed following the protocol provided by the manufacturer (DiscoverX). Three different concentrations for the agonist/ligand CCL22 (100 nM, 1 nM, 0.01 nM) were incubated with the cells before adding the lysis/chemilumiscent reagents. Light intensity chemiluminescent signal was acquired using a Tecan M200 plate reader from each well corresponding to a particular condition.

This assay can be used in conjunction with a cell binding assay (e.g., the experiment shown at FIG. 77) to find antagonist antibodies specific for a cell surface receptor. Implementation of this lysis assay in the microfluidic chamber requires segregation of the effector cell from the readout cell(s) if it is desired to recover a live, viable effector cell. Such an assay could be implemented in a device such as the one presented in Examples 1 and 2.

Example 19

Antibody Screening and Sequence Recovery from Human Cells

Figure 91:
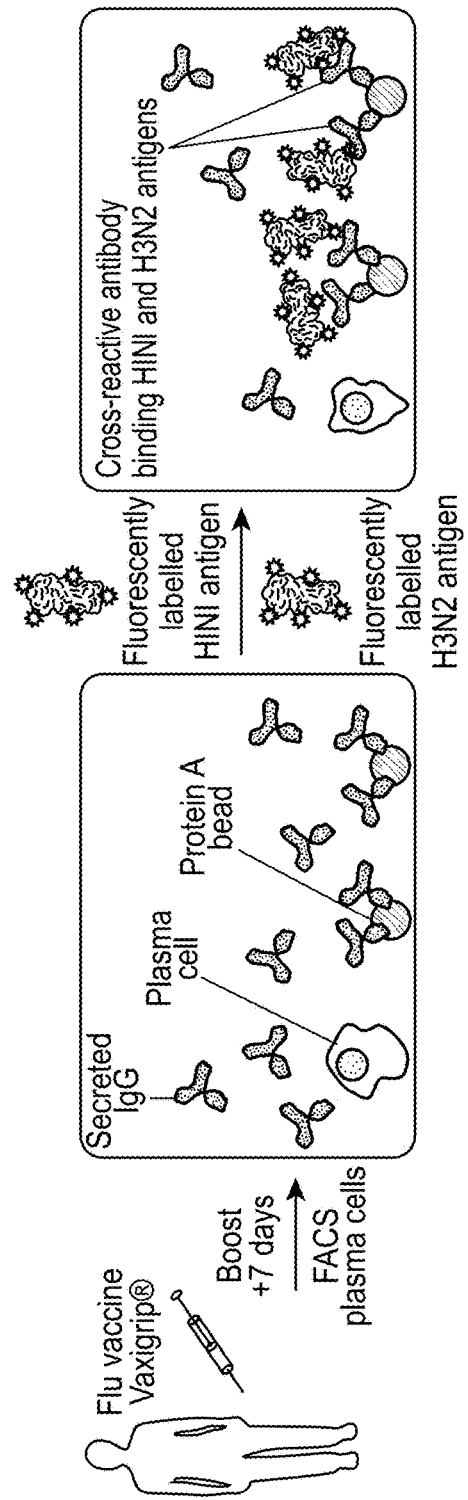
FIG. 91 is a schematic representation of the experiment. Human volunteers were immunized with the seasonal flu vaccine Peripheral blood mononuclear cells (PBMCs) were recovered and sorted with flow cytometry to enrich for plasma cells. The cells were injected in the microfluidic device and assayed for H1N1 and H3N2 specificity.
Figure 92:
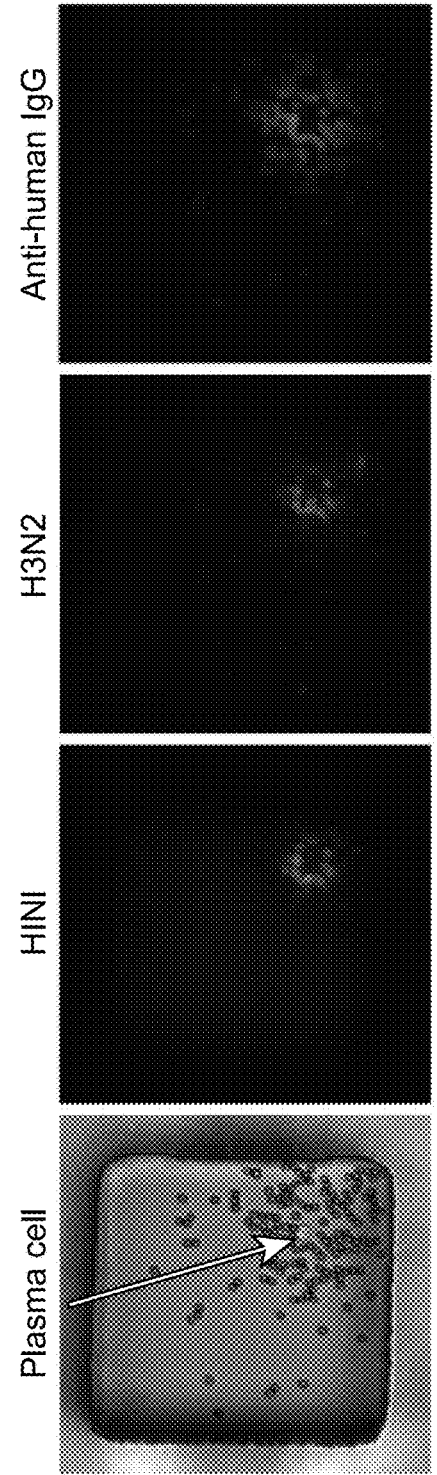
FIG. 92 is an example of a single human plasma cell in a chamber with protein A beads. The secreted antibody captured on the beads binds to both H1N1 and H3N2 labeled antigens and is therefore cross-reactive. Labeled anti-human IgG allows visualization of total IgG secretion.
Figure 93:
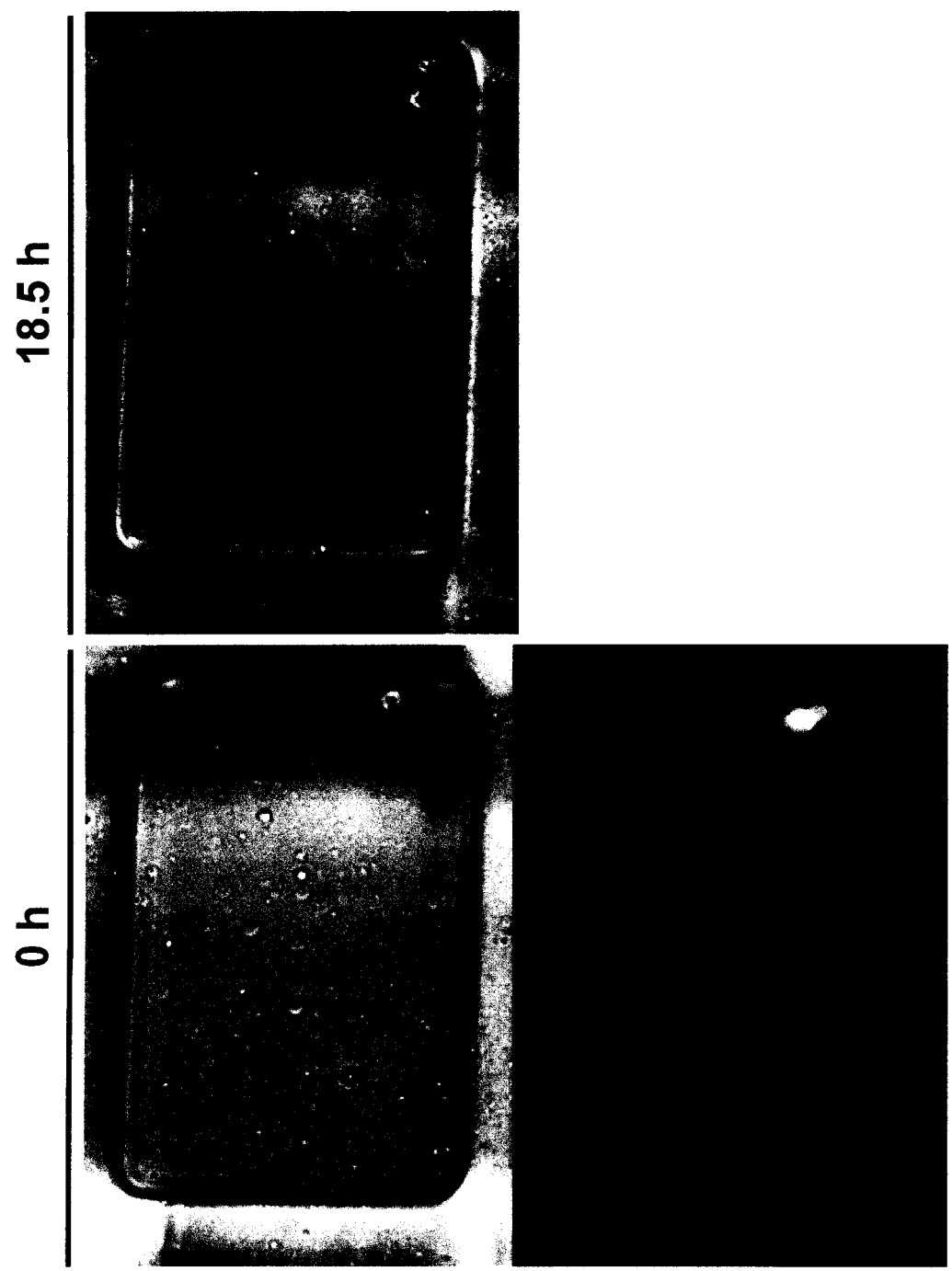
FIG. 93 shows an example of a primary human antibody-secreting cell (top left) identified as producing an antibody against influenza using a bead assay (bottom left) and having divided during an overnight incubation in the microfluidic device (top right).

Blood was collected 7 days after immunization from patients that had received the seasonal flu vaccine (FIG. 91). PBMCs were isolated using a commercially available kit (SepMate, StemCell Technologies) and plasma cells were enriched using FACS based on the markers described in Wrammert et al. (2008), *Nature Letters,* 453:667-671, incorporated by reference herein in its entirety. Cells were then loaded in microfluidic devices at limiting dilution and incubated for 2 hours with Protein A microspheres (4.9 μm in diameter, Bang Laboratories). H1N1 and H3N2 labeled antigens (two different colors: 488 nm and 594 nm emission, respectively) were introduced in the array, incubated for 15 minutes with the plasma cells, and the contents of microfluidic chambers were washed with media before imaging. After detection of chambers containing antigen-specific antibodies, labeled anti-human antibody (Dylight 594) was introduced in the device, incubated for 15 minutes, and then washed to determine the overall frequency of IgG secreting cells. An example of a single plasma cell cross-reactive for both H1N1 and H3N2 is shown in FIG. 92. Antigen-specific cells were either recovered immediately or cultured overnight in the microfluidic devices for next-day recovery. Cells remained viable and in some cases underwent division (e.g., FIG. 93).

Referring to FIG. 94, cells from eight chambers positive for H1N1 and/or H3N2 (flu specific), and IgG (i.e., not antigen-specific) were recovered and lysed. The RNA from the lysed cells was subjected to reverse transcription followed by antibody heavy and light chain (Kappa/lambda) specific PCR. Four samples out of eight provided a positive PCR amplification for both heavy and light chains (50% efficiency with 100% pairing), with an expected product size of ~400 bp, namely samples 3 (H1N1 positive), 4 (H1N1/H3N2 positive), 5 (H1N1/H3N2 positive), and 6 (IgG positive, but not antigen specific). The nucleic acid ladder shows 100 base pair increments. Sanger sequencing from these purified PCR products confirmed that the sequences were specific for heavy, kappa and lambda human immunoglobulin.

Referring to FIG. 95, sequences of two human mAbs (Hs-7 and Hs-15) that were amplified from single cells obtained from patients immunized with seasonal flu vaccine. Cells were selected in a microfluidic assay based on their ability to secrete mAbs having a cross-reactivity to hemagglutinin subtypes H1N1 and H3N2. Antibodies sequences were retrieved by RT-PCR and sequencing as described herein (FIG. 95A). Both mAbs belong to the same clonotype as apparent by shared gene usage, CDR length and junctional sequences. Mutations are shown in lighter grey (FIG. 95B). Antibody sequences were cloned and expressed in HEK293 cells to validate their binding properties. Protein A beads were incubated with the cell supernatant for 3 hours, washed, incubated with either labelled H1N1 or H3N2 at different concentrations and then imaged to measure the bead fluorescent intensity. Both mAbs cross-reacted as expected but, consistent with single cell measurements, had different affinities for H1N1 and H3N2 (FIG. 95C).

Hs7 (IGHV4-39*01) IGHD3-3*02 IGHJ3*02 Heavy chain nucleic acid sequence (SEQ ID NO: 9):
ATGAAGCACCTGTGGTTCTTCCTCCTGCTGGTGGCGGCTCCCAGATGGGTCCTGTCTCAGGT
GCAGCTGCAGGAGTCGGGCCCAGGACTGGTGAAGTCTTCGGAGACCCTGTCCCTCACCTGC
ACTGTCTCTGGTGACTCCATCACCAGCAGTACTTACGACTGGGGCTGGATCCGTCAGCCCC
CCGGGAAGGGCCTGGAGTGGATTGGCAATGTCTATTATAGAGGGAGCACCTACTACAACCC
GTCCCTCAAGAGTCGAGTCACCATATCCGTAGACAGGTCCAGGACCCAGATCTCCCTGAGG
CTGAGCTCTGTGACCGCCGCTGACACGGCTCTGTATTTCTGTGCGAGACACCCGAAACGTC
TAACGGTTTTTGAAGTGGTCAACGCTTTTGATATCTGGGGCCAAGGGACAATGGTCACCGT
CTTTTCAGCCTCCACCAAGGGCCCATCGGTCTTCCCCCTGGCACCCTCCTCCAAGAGCACCT
CTGGGGGCACAGCGGCCCTGGGCTGCCTGGTCTGCTGACGAGGCACTGAGGACTG Hs7 Heavy chain amino acid sequence (SEQ ID NO: 10):
M K H L W F F L L L V A A P R W V L S Q V Q L Q E S G P G L V K S S E T L S L T C T V S G D
S I T S S T Y D W G W I R Q P P G K G L E W I G N V Y Y R G S T Y Y N P S L K S R V T I S V D
R S R T Q I S L R L S S V T A A D T A L Y F C A R H P K R L T V F E V V N A F D I W G Q G Q T
M V T V F S A S T K G P S V F P L A P S S K S T S G G T A Hs7 (IGLV2-14*01) IGLJ3*02 Light chain nucleic acid sequence (SEQ ID NO: 11):
ATGGCCTGGGCTCTGCTACTCCTCACCCTCCTCACTCAGGGCACAGGGTCCTGGGCCCAGT
CTGCCCTGACTCAGCCTGCCTCCGTGTCTGCATCTCCTGGACAGTCGATCACCATCTCCTGC
ACTGGAATCAGCAGTGACATTGGTGGTTATAGCTCTGTCTCCTGGTACCAAGCGCACCCAG
GCAAAGCCCCCAAACTCATGATCTATGATGTCAATAATCGCTCCAGGCATTTCTAATCG
CTTCTCTGGTTCCAAGTCTGGCAACACGGCCTCCCTGGCCATCTCTGGGCTCCAGgctgaGGA
CGAGGCAGATTATTACTGCAGCTTATATACAAGTATCAACGCTTCCATAGTGTTCGGCGGA
GGGACCAAGCTGACCGTCCTAGGTCAGCCCAAGGCTGCCCCCTCGGTCACTCTGTTCCCGC
CCTCCTCTGAGGAGCTTCAAGCCAACAAGGCCACA Hs7 Light chain amino acid sequence (SEQ ID NO: 12):
M A W A L L L L T L L T Q G T G S W A Q S A L T Q P A S V S A S P G Q S I T I S C T G I S S D I
G G Y S S V S W Y Q A H P G K A P K L M I Y D V N N R P S G I S N R F S G S K S G N T A S L
A I S G L Q A E D E A D Y Y C S L Y T S I N A S I V F G G G T K L T V L G Q P K A A P S V T L
F P P S S Hs15 (IGHV4-39*01) IGHD3-3*01 IGHJ3*02 Heavy chain nucleic acid sequence (SEQ ID NO: 13):
ATGAAGCACCTGTGGTTCTTCCTTCTGCTGGTGGCGGCTCCCAGATGGGTCCTGTCCCAGCT
GCAACTGCAGGAGTCGGGCCCAGGACTGGTGAAGCCTTCGGAGACCCTGTCCCTCACCTGC
ACTGTCTCTGGTGACTCCATCAGCAGTAGTACTTACTACTGGGGCTGGATCCGCCAGCCCC
AGGAAAGGGGCTGGAGTGGATTGCCTTTATCTTTTATAGCGGGAGCACCTTCTACAACCCG
TCCCTCAAGAGTCGAGTCACCGTCTCCGTAGACAGGTCCACGAACCAGTTCTCCCTGAGGC
TGAAGTCTGTGACCGCCGCAGACACGTCCAGATATTACTGTGCGAGACACCCAAACGTAT
CTCGATTTTTGAAGTGGTCAACGCTTTTGATATCtGGGGCCAGGGGACAATGGTCACCGTCT
CTTCAGCCTCCACCAAGGGCCCATCGGTCTTCCCCCTGGCACCCTCCTCCAAGAGCACCTCT
GGGGGCACAGCGGCCCTGGGCTGCCTGGTCTGCTGACGAGGCACTGAGGACTG Hs15 Heavy chain amino acid sequence (SEQ ID NO: 14):
M K H L W F F L L L V A A P R W V L S Q L Q L Q E S G P G L V K P S E T L S L T C T V S G D
S I S S S T Y Y W G W I R Q P P G K G L E W I A F I F Y S G S T F Y N P S L K S R V T V S V D R
S T N Q F S L R L K S V T A A D T S R Y Y C A R H P K R I S I F E V V N A F D I W G Q G T M V
T V S S A S T K G P S V F P L A P S S K S T S G G T A >Hs15 (IGLV2-14*01) IGLJ2*01 IGLJ3*01 Light chain nucleic acid sequence (SEQ ID NO: 15):
ATGGCCTGGACTCTGCTATTCCTCACCCTCCTCACTCAGGGCACAGGGTCCTGGGCCCAGT
CTGCCCTGACTCAGCCTGCCTCCGTGTCTGGGTCTCCTGGACAGTCGATCACCATCACCTGC
ACTGGAATCAGCAGTGACGTTGGTGCTTATAATTCTGTCTCCTGGTACCAGCAGTACCCAG
GCAAATCCCCAAGCTCATGATTTATGATGTCAGTAATCGGTCCTCAGGGGTTTCTAATGCC
TTCTCTGGCTCCAAGTCTGACAACACGGCCTCCCTGACCATCTCTGGGCTCCAGGCTGAGG
ACGAGGCTTCTTATTTCTGCAGCTTATATAGAAGCAGCACCACTTCCGTGGTATTCGGCGGA
GGGACCAAGCTGACCGTCCTACGTCAGCCCAAGGCTGCCCCCTCGGTCACTCTGTTCCCGC
CCTCCTCTGAGGAGCTTCAAGCCAACAAGGCCACA Hs15 Light chain nucleic acid sequence (SEQ ID NO: 16):
M A W T L L F L T L L T Q G T G S W A Q S A L T Q P A S V S G S P G Q S I T I T C T G I S S D
V G A Y N S V S W Y Q Q Y P G K S P K L M I Y D V S N R S S G V S N R F S G S K S D N T A S
L T I S G L Q A E D E A S Y F C S L Y R S S T T S V V F G G G T K L T V L R Q P K A A P S V T
L F P P S S

Example 20

Antibody Screening and Sequence Recovery from a Heterogeneous Population of Rabbit Cells Rabbits were immunized with the seasonal flu vaccine. Peripheral blood mononuclear cells (PBMCs) were recovered and either screened directly or sorted with flow cytometry to enrich for plasma cells. The cells were injected in the microfluidic device and assayed for H1N1 and H3N2 specificity. Protein A-coated beads used for fluorescence-based detection were also visible. Cells were incubated with beads for 2 hours, then fluorescently labeled antigen was introduced for 15 minutes and unbound antigen was washed away with media. FIGS. 96A and 96B show examples of H1N1- and H3N2- positive chambers, respectively.

FIG. 97A shows bright field images of several rabbit cells in four microfluidic chambers that have been screened for antigen-specific signal. FIG. 97B shows H1N1 antigen specific antibody screening from rabbit antibody producing cells. The signal was very low and therefore no cell seemed to express H1N1 specific antibodies. FIG. 97C shows H3N2 antigen specific antibody binding from rabbit antibody producing cells. Signal was variable from one chamber to another, however all chambers are positive for H3N2 binding. After cell recovery from the microfluidic chambers using an automated robot and microcapillary, heavy and light chain antibody specific polymerase chain reaction (PCR) products were ran on a 2% Egel (Invitrogen). Bands (~400/500 bp) were visible for 3 out of 4 heavy chains and 4 out of 4 light chains for the 4 samples tested (FIG. 97D). Sanger sequencing revealed that two heavy chain sequences were rabbit heavy chains (www.imgt.org) whereas one contains multiple peaks suggesting that more than one cell in this chamber might have been an antibody-secreting cell. Two light chains out of four were determined to be rabbit light chains while the two others contained multiple peaks. Paired heavy and light chains from chambers 1 and 3 showed that it is possible to determine the sequence of a single effector cell from a heterogeneous cell population. The sequences recovered for the variable regions having single peaks were as follows:

```
Heavy 1 (SEQ ID NO: 17):
GCTAGCCACCATGGAGACTGGGCTGCGCTGGCTTCTCCTGGTCGCTGTGC

TCAAAGGTGTCCAGTGTCAGTCGGTGGAGGAGTCCGGGGGTCGCCTGGTC

ACGCCTGGGACACCCCTGACACTCACCTGCATAGTCTCTGGAATCGACCT

CAGTAGCTATGCAATGGGCTGGGTCCGCCAGGCTCCAGGAAAGGGGCTGG

AATACATCGGAATCATTAGTAGCAGTGGTATCACATACTACGCGAGCTGG

GCGAAAGGCCGATTCACCATCTCCAAAACCTCGTCGACCACGGTGACTCT

GACAATCACCGATCTGCAACCTTCAGACACGGGCACCTATTTCTGTGCCA

GAGGGTCTCGTTATAGTGCTTTTGGTGCTTTTGATACCTGGGGCCCAGGC

ACCCTGGTCACCGTCTCCTCAGCAAGCTTNAN

Heavy 3 (SEQ ID NO: 18):
TTTGGCTAGCCACCATGGAGACTGGGCTGCGCTGGCTTCTCCTGGTCGCT

GTGCTCAAAGGTGTCCAGTGTCAGTCGGTGGAGGAGTCCGGGGGTCGCCT

GGTCACGCCTGGGACACCCCTGACACTCACCTGCACAGTCTCTGGATTCT

CCCTCAGTAGCTATGCAATGGGCTGGGTCCGCCAGGCTCCAGGGAAGGGG

CTGGAATGGATCGGAGTCATTAATAATAATGGTGACACATACTACGCGAG

CTGGCCGAAAGGCCGATTCACCATCTCCAAAACCTCGACCACGGTGGATC

TGAAAATCACCAGTCCGACAACCGAGGACACGGCCACCTATTTCTGTGCC

AGAGATCGTGGTAATAGTTATTACTTTGGATTGGACTACTTTAACTTGTG

GGGCCCAGGCACCCTGGTCACCGTCTCCTCAGCAAGCTTTATAN

Light 1 (SEQ ID NO: 19):
CTCTGCTGCTCTGGCTCCCAGGTGCCAGATGTGCCTTCGAATTGACCCAG

ACTCCATCCTCCGTGGAGGCAGCTGTGGGAGGCACAGTCACCATCAAGTG

CCAGGCCAGTCAGAGTATTAATAGTTGGTTATCCTGGTATCAGCAGAAAC

CAGGGCAGCCTCCCAAGCTCCTGATCTACAAGGCATCCAATCTGGCATCT

GGGGTCCCATCGCGGTTCAGAGGCAGTGGATCTGGGACAGAGTTCACTCT

CACCATCAGCGACCTGGAGTGTGNCGATGCTGCCACTTACTACTGTCAAA

GCNATTATGCTACTAGTAGTGTTGATTATNATGCTTTCGGCGGAAGGACC

GAGGTGGTGGTCAANACTGCGGCNGTANTANTNNN

Light 3 (SEQ ID NO: 20):
TGCAGCTAGCCACCATGGACACGAGGGCCCCCATCAGCTGCTGGGGCTCC

TGCTGCTCTGGCTCCCAGGTGCCAGGTGTGCCCTTGTGATGACCCAGACT

CCAGCCTCTGTGGAGGTAGCTGTGGGAGGCACAGTCACCATCAAGTGCCA

GGCCAGTCAGAGCATTGATAGTTGGTTATCCTGGTATCAGCAGAAACCAG

GGCAGCGTCCCAGGCTCCTGATCTATTATGCATCCAATCTGGCATCTGGG

GTCTCATCGCGGTTCAAAGGCAGTGGATCTGGGACAGAATACACTCTCAC

CATCAGCGGCGTGGAGTGTGCCGATGCTGCCACTTACTACTGTCAAGAGG

GTTATAGTAGTGGTAATGTTGATAATGTTTTCGGCGGAGGGACCGAGGTG

GTGGTCAAAACTGCGNCCGCTATAN
```

Example 21

Expression and Validation of Antibodies from Human Sequences

The expression of a human anti-MCP1 antibody was carried out in HEK293 cells using liposome-based transfection. Expressed antibody was precipitated from growth media on Protein A-coated beads and tested with fluorescently labeled MCP-1 antigen. The affinity of recombinant antibody was compared to the antibody of the same amino-acid sequence produced by the commercially available stable CHO cell line (ATCC® PTA-5308™) (FIG. 99).

Clone Hu-11K2-3f2-H2. Heavy and light chain variable sequences were synthesized and cloned into pFUSEss-CHIg-hG1 and pFUSE2-CLIg-hk expression vectors respectively.

```
aMCP1-Heavy (SEQ ID NO: 21):
GAATTCCATGCAGGTGCAGCTGGTGCAGTCTGGCGCCGAAGTGAAGAAAC

CCGGCAGCAGCGTGAAGGTGTCCTGCAAGGCCAGCGGCCTGACCATCAGC

GACACCTACATGCACTGGGTGCGCCAGGCTCCAGGCCAGGGACTGGAATG

GATGGGCAGAATCGACCCCGCCAACGGCAACACCAAGTTCGACCCCAAGT

TCCAGGGCAGAGTGACCATCACCGCCGACACCAGCACCTCCACCGCCTAC

ATGGAACTGAGCAGCCTGCGGAGCGAGGACACCGCCGTGTACTATTGTGC

CAGAGGCGTGTTCGGCTTCTTCGACTACTGGGGCCAGGGCACCACCGTGA

CCGTGTCATCTGCTAGC aMCP1-Light (SEQ ID NO: 22):
ACCGGTGCCACCATGTACCGGATGCAGCTGCTGAGCTGTATCGCCCTGTC

TCTGGCCCTCGTGACGAATTCAGCCATGGACATCCAGATGACCCAGAGCC

CCAGCAGCCTGTCTGCCAGCGTGGGCGACAGAGTGACCATCACATGCAAG

GCCACCGAGGACATCTACAACCGGCTGGCCTGGTATCAGCAGAAGCCCGG

CAAGGCCCCCAAGCTGCTGATTAGCGGAGCCACCAGCCTGGAAACCGGCG

TGCCAAGCAGATTTTCCGGCAGCGGCTCCGGCAAGGACTACACCCTGACC

ATCAGCTCCCTGCAGCCCGAGGACTTCGCCACCTACTACTGCCAGCAGTT

TTGGAGCGCCCCCTACACCTTTGGCGGAGGCACCAAGGTGGAAATCAAGC

GTACG
```

Example 22

Mouse Sequence Recovery from Single Cells Followed by Cloning and Expression of Antibodies for Validation D1.3 and HyHEL5 were loaded sequentially at limiting dilution in a microfluidic device. A picture set was taken after introducing each cell type in the device to record the position of D1.3 and HyHEL5 cells. Cells were incubated with Protein-A beads coated with rabbit anti-mouse capture antibodies and 10 nM of labeled hen-egg lysozyme for 2 hours. Single antibody-secreting cells were recovered with a microcapillary controlled by a robot, transferred into a tube for RT-PCR, and then the antibody sequences were recovered. Control chambers were recovered between each single cell as negative control. FIG. 100 shows a gel heavy and light chains from 2 single cells, with no signal in the controls. Sequences of variable regions of heavy and light chains of HyHEL5 (high affinity) and D1.3 (low affinity) antibodies were synthesized and cloned into pFUSEss-CHIg-mG1 and pFUSE2ss-CLIg-mk expression vectors. Antibodies were produced in HEK293 cell line, captured on Protein A-coated beads covered with Rabbit anti-mouse antibody. The affinity was tested using increasing concentrations of fluorescently labeled lysozyme (FIG. 101).

D1.3-Heavy (SEQ ID NO: 23):
ATGCAGGTGCAGCTGAAGGAGTCAGGACCTGGCCTGGTGGCGCCCTCACA
GAGCCTGTCCATCACATGCACCGTCTCAGGGTTCTCATTAACCGGCTATG
GTGTAAACTGGGTTCGCCAGCCTCCAGGAAAGGGTCTGGAGTGGCTGGGA
ATGATTTGGGGTGATGGAAACACAGACTATAATTCAGCTCTCAAATCCAG
ACTGAGCATCAGCAAGGACAACTCCAAGAGCCAAGTTTTCTTAAAAATGA
ACAGTCTGCACACTGATGACACAGCCAGGTACTACTGTGCCAGAGAGAGA
GATTATAGGCTTGACTACTGGGGCCAAGGCACCACTCTCACAGTCTCCTC
AGCTAGC D1.3-Light (SEQ ID NO: 24):
ATGGACATCCAGATGACTCAGTCTCCAGCCTCCCTTTCTGCGTCTGTGGG
AGAAACTGTCACCATCACATGTCGAGCAAGTGGGAATATTCACAATTATT
TAGCATGGTATCAGCAGAAACAGGGAAAATCTCCTCAGCTCCTGGTCTAT
TATACAACAACCTTAGCAGATGGTGTGCCATCAAGGTTCAGTGGCAGTGG
ATCAGGAACACAATATTCTCTCAAGATCAACAGCCTGCAGCCTGAAGATT
TTGGGAGTTATTACTGTCAACATTTTTGGAGTACTCCTCGGACGTTCGGT
GGAGGCACCAAGCTCGAG HyHEL5-Heavy (SEQ ID NO: 25):
ATGGAGGTCCAGCTGCAGCAGTCTGGAGCTGAGCTGATGAAGCCAGGGGC
CTCAGTGAAGATATCCTGCAAAGCTTCTGGCTACACATTCAGTGACTACT
GGATAGAGTGGGTAAAGCAGAGGCCTGGACATGGCCTTGAGTGGATTGGA
GAGATTTTACCTGGAAGTGGTAGCACTAATTACCATGAGAGATTCAAGGG
CAAGGCCACATTCACTGCAGATACATCCTCCAGCACAGCCTACATGCAAC
TCAACAGCCTGACATCTGAAGACTCTGGCGTCTATTACTGCCTCCATGGT
AACTACGACTTTGACGGCTGGGGCCAAGGCACCACTCTCACAGTCTCCTC
AGCTAGC HyHEL5-Light (SEQ ID NO: 26):
ATGGATATCGTTCTCACACAGTCTCCAGCAATCATGTCTGCATCTCCAGG
GGAGAAGGTCACCATGACCTGCAGTGCCAGTTCAAGTGTAAATTACATGT
ACTGGTACCAGCAGAAGTCAGGCACTTCCCCCAAAAGATGGATTTATGAC
ACATCCAAACTGGCTTCTGGAGTCCCTGTTCGCTTCAGTGGCAGTGGGTC
TGGGACCTCTTACTCTCTCACAATCAGCAGCATGGAGACTGAAGATGCTG
CCACTTATTACTGCCAACAGTGGGGTCGTAACCCCACGTTCGGAGGGGGG
ACCAAGCTCGAG

Example 23

Validation of Novel Mouse Antibody Sequences Obtained from Microfluidic Screening Splenocytes were isolated from a mouse immunized with hen-egg lysozyme and screened for their antibody secretion in a microfluidic device. The sequence from the antigen-specific cell R05C14 was recovered, cloned and expressed in HEK293 cells. Antigen binding was confirmed by capturing the antibody on Protein A beads coated with rabbit anti-mouse antibody, incubating with 10 nM labeled hen-egg lysozyme and measuring the fluorescence intensity (FIG. 102).

R05C14-Heavy variable (SEQ ID NO: 27):
TGGAAGGTGGTGCACACTGCTGGACAGGGATCCAGAGTTCCAGGTCACTG
TCACTGGCTCAGGGAAATAGCCCTTGACCAGGCATCCCAGGGTCACCATG
GAGTTAGTTTGGGCAGCAGATCCAGGGGCCAGTGGATAGACAGATGGGGG
TGTCGTTTTGGCTGAGGAGACTGTGAGAGTGGTGCCTTGGCCCCAGCAGT
CCCCGTCCCAGTTTGCACAGTAATATGTGGCTGTGTCCTCAGGAGTCACA
GAAATCAACTGCAGGTAGCACTGGTTCTTGGATGTGTCTCGAGTGATAGA
GATTCGACCTTTGAGAGATGGATTGTAGTAAGTGCTACCACTGTAGCTTA
TGTACCCCATATACTCAAGTTTGTTCCCTGGGAATTTCCGGATCCAGCTC
CAGTAATCATTGGTGATGGAGTCGCCAGTGACAGAACAGGTGAGGGACAG
AGTCTGAGAAGGTTTCACGAGGCTAGGTCCAGACTCCTGCAGCTGCACCT
CGAATTCCCA R05C14-Light variable (SEQ ID NO: 28):
TTGGTCCCCCCTCCGAACGTGTACGGCCAGTTGTTACTCTGTTGACAGAA
ATACATTCCAAAATCTTCAGTCTCCACACTGATGATACTGAGAGTGAAAT
CCGTCCCTGATCCACTGCCACTGAACCTGGAGGGGATCCCAGAGATGGAC
TGGGAAGCATACTTGATGAGAAGCCTTGGAGACTCATGTGATTTTTGTTG
ATACCAGTGTAGGTTGTTGCTAATACTTTGGCTGGCCCTGCAGGAAAGAC
TGAGCGCTATCTCCTGGAGTCACAGACAGGGTGTCTGGAGACTGAGTTAGC
ACAATATCACCTCTGGAGGCTGAAATCCAGAAAAGCAAAAAA

Example 24

Sequence Recovery for Amplification of Effector Cell Antibodies

The following protocol and primers was used to recover antibody sequences from mouse, humans or rabbits.

Reagents for reverse transcription (RT) and polymerase chain reaction (PCR) are provided in Table 7.

TABLE 7

| Reverse transcription (RT) reaction | | PCR reaction | |
|---|---|---|---|
| RNAseIn RNAse inhibitor | 2 U/μL | PCR buffer | 1x |
| Betaine | 1M | dNTPs | 200 nM each |
| First strand RT buffer | 1x | MgCl₂ | 1 mM |
| DTT | 2.5 mM | Enzyme (KOD) | 0.008 U/uL |
| MgCl | 29 mM | Universal TS primer | 600 nM |
| RT enzyme (M-MLV) | 1 U/μL | Universal RT primer | 500 nM |
| Template Switching primer | 1.2 μM | Long gene-specific primers | 100 nM |
| RT primers | 40 nM each | | |

The following RT-PCR thermal cycling protocol was followed:

RT: 3 min. at 72° C., 90 min. at 42° C., 10 min at 85° C.

Hot start: 2 min. at 95° C.; Denaturation: 15 sec. at 95° C.; Elongation: 15 sec. at 72° C.; Annealing: 15 sec. at the following temperatures: 72° C. 3 cycles; 70° C. 3 cycles; 68° C. 3 cycles; 66° C. 3 cycles; 64° C. 3 cycles; 62° C. 6 cycles; 60° C. 20-30 cycles.

The primers used in the RT-PCR experiments are provided in Table 8, as follows:

TABLE 8

List of Primers

| Name | Sequence | SEQ ID NO: |
|---|---|---|
| Template switching primer | GCAGTGGTATCAACGCAGAGTACG(r)G(r)G(r) | SEQ ID NO: 29 |
| Universal primer TS | GCAGTGGTATCAACGCAGAGTACG | SEQ ID NO: 30 |
| Universal primer RT | AGACAGTCCTCAGTGCCTCGTCAGCAG | SEQ ID NO: 31 |
| Human RT primer HsRT-01 | gtcctgaggactg | SEQ ID NO: 32 |
| Human RT primer HsRT-02 | tgctctgtgacac | SEQ ID NO: 33 |
| Human RT primer HsRT-03 | ggtgtacaggtcc | SEQ ID NO: 34 |
| Human RT primer HsRT-04 | cagagagcgtgag | SEQ ID NO: 35 |
| Human RT primer HsRT-05 | tcatgtagtagctgtc | SEQ ID NO: 36 |
| Human RT primer HsRT-06 | ctcaggactgatgg | SEQ ID NO: 37 |
| Human RT primer HsRT-07 | gagtcctgagtactg | SEQ ID NO: 38 |
| Human RT primer HsRT-08 | gttgttgctttgtttg | SEQ ID NO: 39 |
| Human RT primer HsRT-09 | ttgttgctctgtttg | SEQ ID NO: 40 |
| Long gene-specific primer HsN2U_01 | AGACAGTCCTCAGTGCCTCGTCAGCAGACCAGGCAGCCCAGGGC | SEQ ID NO: 41 |
| Long gene-specific primer HsN2U_02 | AGACAGTCCTCAGTGCCTCGTCAGCAGCAGTGTGGCCTTGTTGGCTTGAAGCTCC | SEQ ID NO: 42 |
| Long gene-specific primer HsN2U_03 | AGACAGTCCTCAGTGCCTCGTCAGCAGAGCAGGCACACAACAGAGGCAGTTCC | SEQ ID NO: 43 |
| Long gene-specific primer HsN2U_04 | AGACAGTCCTCAGTGCCTCGTCAGCAGGCCCAGAGTCACGGAGGTGGCATTG | SEQ ID NO: 44 |
| Long gene-specific primer HsN2U_05 | AGACAGTCCTCAGTGCCTCGTCAGCAGGCATGCGACGACCACGTTCCCATCTTG | SEQ ID NO: 45 |
| Long gene-specific primer HsN2U_06 | AGACAGTCCTCAGTGCCTCGTCAGCAGGCAGCCAACGGCCACGCTG | SEQ ID NO: 46 |
| Long gene-specific primer HsN2U_07 | AGACAGTCCTCAGTGCCTCGTCAGCAGATGCCAGGACCACAGGGCTGTTATCCTTTG | SEQ ID NO: 47 |
| Long gene-specific primer HsN2U_08 | AGACAGTCCTCAGTGCCTCGTCAGCAGAGTGTGGCCTTGTTGGCTTGGAGCTC | SEQ ID NO: 48 |
| Long gene-specific primer HsN2U_09 | AGACAGTCCTCAGTGCCTCGTCAGCAGACCACGTTCCCATCTGGCTGGGTG | SEQ ID NO: 49 |

TABLE 8-continued

List of Primers

| Name | Sequence | SEQ ID NO: |
|---|---|---|
| RT mouse primer MmRT_01 | acagtcactgagct | SEQ ID NO: 50 |
| RT mouse primer MmRT_02 | ctttgacaaggcatc | SEQ ID NO: 51 |
| RT mouse primer MmRT_03 | ccacttgacattgatg | SEQ ID NO: 52 |
| RT mouse primer MmRT_04 | ctcttctccacagtg | SEQ ID NO: 53 |
| Long gene-specific mouse primer Mmn2_01 | AGACAGTCCTCAGTGCCTCGTCAGCagactgcagg agagctgggaaggtgtg | SEQ ID NO: 54 |
| Long gene-specific mouse primer Mmn2_02 | AGACAGTCCTCAGTGCCTCGTCAGCaggacagctg ggaaggtgtgcacac | SEQ ID NO: 55 |
| Long gene-specific mouse primer Mmn2_03 | AGACAGTCCTCAGTGCCTCGTCAGCtcaagaagcac acgactgaggcacctcc | SEQ ID NO: 56 |
| Long gene-specific mouse primer Mmn2_04 | AGACAGTCCTCAGTGCCTCGTCAGCttgccttccagg ccactgtcacacc | SEQ ID NO: 57 |
| Long gene-specific mouse primer Mmn2_05 | AGACAGTCCTCAGTGCCTCGTCAGCatccagatgtgt cactgcagccagggac | SEQ ID NO: 58 |
| Long gene-specific mouse primer Mmn2_06 | AGACAGTCCTCAGTGCCTCGTCAGCAccttccagtc cactgtcaccacacctg | SEQ ID NO: 59 |
| RT rabbit primer OcRT_01 | TGAAGCTCTGGAC | SEQ ID NO: 60 |
| RT rabbit primer OcRT_02 | CACACTCAGAGGG | SEQ ID NO: 61 |
| RT rabbit primer OcRT_03 | TTCCAGCTCACAC | SEQ ID NO: 62 |
| RT rabbit primer OcRT_04 | AGGAAGCTGCTG | SEQ ID NO: 63 |
| RT rabbit primer OcRT_05 | ACACTGCTCAGC | SEQ ID NO: 64 |
| RT rabbit primer OcRT_06 | TCACATTCAGAGGG | SEQ ID NO: 65 |
| RT rabbit primer OcRT_07 | GTCTTGTCCACTTTG | SEQ ID NO: 66 |
| RT rabbit primer OcRT_08 | CTCTGTTGCTGTTG | SEQ ID NO: 67 |
| Long rabbit gene-specific primer Oc-PCR-IgHA1A7-12 | AGACAGTCCTCAGTGCCTCGTCAGgatcaggcagcc gacgacc | SEQ ID NO: 68 |
| Long rabbit gene-specific primer Oc-PCR-IgKC1 | AGACAGTCCTCAGTGCCTCGTCAGgtgggaagatga ggacagtaggtgc | SEQ ID NO: 69 |
| Long rabbit gene-specific primer Oc-PCR-IgKC1KC2 | AGACAGTCCTCAGTGCCTCGTCAGagatggtgggaa gaggaggacag | SEQ ID NO: 70 |
| Long rabbit gene-specific primer Oc-PCR-IgLC4L5L6 | AGACAGTCCTCAGTGCCTCGTCAGccttgttgtcct tgagttcctcagagg | SEQ ID NO: 71 |
| Long rabbit gene-specific primer Oc-PCR-IgA2A6 | AGACAGTCCTCAGTGCCTCGTCAGcggatcaggcag ccgatgac | SEQ ID NO: 72 |
| Long rabbit gene-specific primer Oc-PCR-IgA4A5 | AGACAGTCCTCAGTGCCTCGTCAGcaggtcagcggg aagatgatcg | SEQ ID NO: 73 |
| Long rabbit gene-specific primer Oc-PCR-IgLC1C2C3 | AGACAGTCCTCAGTGCCTCGTCAGcactgatcagac acaccagggtgg | SEQ ID NO: 74 |
| Long rabbit gene-specific primer Oc-PCR-IgG | AGACAGTCCTCAGTGCCTCGTCAGcaccgtggagct gggtgtg | SEQ ID NO: 75 |
| Long rabbit gene-specific primer Oc-PCR-IgA3A5 | AGACAGTCCTCAGTGCCTCGTCAGgatcaggcagcc ggcgatc | SEQ ID NO: 76 |
| Long rabbit gene-specific primer Oc-PCR-IgM | AGACAGTCCTCAGTGCCTCGTCAGggagacgagcg ggtacagagttg | SEQ ID NO: 77 |
| Long rabbit gene-specific primer Oc-PCR-IgE | AGACAGTCCTCAGTGCCTCGTCAGtctgcagcagga ggccaag | SEQ ID NO: 78 |

FIG. 103A shows a micrograph of PCR amplicons produced as described above and testing a gradient of RT temperatures ranging from 60° C. to 40° C. Template was 200 pg (~ten cell equivalents) of RNA purified from hybridoma cells (D1.3). Far right lane shows optimized condition using KOD polymerase. HV and LV amplicons are expected within 450 to 550 bp where strong bands are observed; this region also includes some non-specific products. Referring to FIG. 103B, band from 400 to 600 bp was extracted and Sanger sequenced using a primer that annealed to a constant region on the heavy chain. The trace showed the junction made by MMLV between template switching oligo and cDNA, joined by CCC that is added by MMLV during cDNA synthesis. The sequence was aligned and confirmed to match the variable region sequence of the heavy chain of D1.3.

Example 25

NGS Sequencing of Single Cells Recovered from Device

A different approach to retrieve antibody sequences combines template-switching and next-generation sequencing. Referring to FIG. 59, single cells are deposited into microfuge tubes and cDNA is generated from multiplexed gene-specific primers targeting the constant region of heavy and light chains. Template-switching activity of MMLV enzyme is used to append the reverse complement of a template-switching oligo onto the 3' end of the resulting cDNA. Semi-nested PCR, using multiplexed primers that anneal to the constant region of heavy and light chain and a universal primer complementary to the copied template switching oligonucleotide, is used to amplify cDNA and introduce indexing sequences that are specific to each single cell amplicon. Amplicons are then pooled and sequenced.

Another approach to recover sequences from heterogeneous populations of cells couples microfluidic single cell antibody analysis with Ig-Seq (FIG. 104A) Following immunization, ASCs are collected from the animal; a fraction are analyzed on microfluidic devices while the remaining are used for construction of a bulk amplicon library for Ig-Seq. From the microfluidic device, a total of 96 indexed single cell (SC) libraries and 96 indexed low diversity (LD) libraries are pooled for sequencing on MiSeq. Analysis of the bulk library is used to determine HV and LV clonotypes present in the immune response, shown as clusters in FIG. 104B. SC libraries provide paired chain HV and LV sequences of mAbs from most abundant clonotypes that are confirmed to be antigen specific. LD libraries provide additional identification of HV and LV sequences that are antigen specific or that are not antigen specific. LD libraries are also used to infer chain pairing by analysis of co-occurrence of HV and LV sequences across LD libraries, illustrated in FIG. 104C. Information on binding status and chain pairing for specific sequences allows interpretation of the bulk sample by assignment of binding status, represented as stars (antigen-specific) and crosses (non-specific) in FIG. 104B, and clonotype pairing.

Example 26

Multiplexed Bead Assay Using Optically Encoded Beads

The multiplexed bead based assay in this example allows the measurement of several different antigen specific antibodies in the same chamber from antibody secreting cells. Fluorescence intensity coded beads (e.g., Starfire Red™ dye beads, Bangs laboratories) can be used to track different antigen specific antibodies by labeling each subset of beads with a different antigen using a traditional sulfo-NHS (N-hydroxysulfosuccinimide)/1-Ethyl-3-[3-dimethylaminopropyl]carbodiimide hydrochloride (EDC) protein coupling strategy (Pierce). Starfire Red™ (excitation from UV to red, emission max at 675 nm) and antigen specific fluorescence signal can then be measured and quantified.

Starfire Red™ dye beads (5.5 μm diameter) containing 3 subsets of fluorescently coded beads were coated with different 2012-2013 seasonal flu specific antigens (FIG. 105A). Beads (from the least intense to the most intense Starfire Red™ intensity respectively) were coupled with H1N1 (A/California/7/2009 (H1N1) pdm09-like strain), H3N2 (A/Victoria/361/2011 (H3N2)-like strain) and B strain (B/Wisconsin/1/2010-like strain) antigens (Protein Science Corp.).

Beads were mixed in a 1:1:1 ratio and were injected in a microfluidic device (FIG. 105B). Starfire Red™ dye fluorescent measurement reveals the positions of each particular subset of beads and allows further subsequent tracking of antigen specific antibody binding (FIG. 105C). Rabbit anti-H1N1 specific antibody (Sino Biological) dissolved in media was then flown in the device at a concentration of 400 pg/mL and incubated for 45 minutes. Anti-rabbit IgG labeled with Dylight 488 (Jackson Immunoresearch) was then sent in the device and fluorescent imaging was performed. Positive signal is clearly visible on the H1N1 coated beads (least bright Starfire Red™ beads represented by arrows) (FIG. 105D) and no unspecific binding is detected on the beads labeled with H3N2 and B strain specific antigens (FIG. 105E).

Example 27

Microfluidic Apoptosis Effector Assay

A functional extracellular effect assay was implemented to find antibodies and effector cells that produce such antibodies, that neutralize TNF-α or that block its receptor. To quantify the effect of TNF-α on target L929 cells (readout cells), the readout cells were stained with $DiOC_{18}$ and incubated in the presence of 1 μg/mL of actinomycin-D and different concentrations of TNF-α in multiwell plates. After 24 hours, cells were counterstained with propidium iodide (PI) and cell viability was measured by counting the fraction of PI-stained cells from DiOC18-stained cells under a microscope. The dose response of TNF-α on L929 cells is shown in FIG. 106A.

In a second experiment, L929 cells were stained with CFSE, loaded in a microfluidic device and incubated in the presence of 10 pg/mL of actinomycin-D and 10 ng/mL of TNF-α and tracked by time-lapse imaging. Cells underwent rapid apoptosis, which was confirmed by PI labeling at 24 hours (FIG. 106B).

Example 28

Microfluidic Cell Signaling Effector Assay

A TNFα functional assay based on nuclear or cytoplasmic fluorescence localization was developed for the function-based selection of antibodies against TNFα. The readout cell line used was previously described in Tay et al. (2010). *Nature* 466, pp. 267-71, incorporated by reference herein in its entirety. Upon TNFα-induced activation, a fluorescently-labeled NF-κB transcription factor subunit is transported from the cytoplasm to the nucleus. FIG. 107A shows time-lapse fluorescence images for the TNFα functional assay. In the absence of TNFα ligand, fluorescence localization is cytoplasmic (FIG. 107A, upper panels). Upon activation by TNFα ligand (10 ng/mL), a change in fluorescence from cytoplasmic to nuclear is observed (FIG. 107A, middle panels). In the presence of cell supernatant containing an antibody that neutralizes TNFα ligand in addition to TNFα ligand (10 ng/mL), the fluorescence localization remains cytoplasmic (FIG. 107A, lower panels), indicating that TNFα ligand has been effectively neutralized by the antibody thus preventing NFκB signaling. The fraction of activated cells for each condition is shown in FIG. 107B.

Example 29

Microfluidic Proliferation and Autophagy Effector Cell Assay

A human breast cancer cell line (SKBR3) overexpressing HER2 and engineered with an LC3-GFP autophagy reporter was loaded in a microfluidic device and cultured for 3 days to determine the feasibility of using this cell line as readout cells. (FIG. 108). Individual SKBR3 cell populations were provided to individual microfluidic chambers. Time-lapse imaging in bright field and fluorescence showed an increase in the number of cells over time (FIG. 108). The results indicated that the SKBR3 cells are suitable to use as readout cells in extracellular effect assays that measure an effector cell's ability/propensity to block the proliferation of SKBR3 cells. Using the SKBR3cell line it is also possible to screen for antibodies that modulate autophagy.

Example 30

Detection and Recovery of Antigen Specific T Cells

Referring to FIG. 109, peripheral blood mononuclear cells (PBMCs) from a human patient were loaded in a microfluidic device and stimulated with a pool of viral antigens derived from Cytomegalovirus, Epstein-Barr Virus and Influenza Virus (CEF) peptides at 10 µg/mL overnight. FIG. 109A shows a bright field image of a microfluidic chamber loaded with PBMCs and interferon-γ (IFNγ) capture beads. Upon stimulation with CEF peptides, IFNγ secreted by activated antigen-specific T cells was captured on functionalized beads coated with anti-IFNγ antibody and detected with a fluorescently labeled secondary antibody. FIG. 109B is a fluorescent image of the positive chamber from FIG. 109A containing an activated antigen-specific T cell. Activated cells were expanded with 100 U/mL of interleukin-2 (IL-2) for 5 days (FIG. 109C) and were subsequently recovered. The frequency of CEF-specific T cells in peripheral blood mononuclear cells from the same patient was measured by ELISPOT and the microfluidic bead assay for comparison. The sensitivity of the microfluidic assay allowed for the detection of higher frequencies of antigen-specific T cells than ELISPOT (FIG. 109D).

Example 31

BAF3 PDGFRα Assay for Signaling

A cell survival assay was generated for the function-based selection of antibodies against PDGFRα. A BaF3 suspension cell line, dependent on the cytokine IL-3 for survival and growth, was electroporated with human PDGFRα driven by a CMV promoter (Origene) and stably expressing clones were generated. The PDGFRα overexpressed in Ba/F3 cells substitutes for the requirement of IL-3 signaling; in the absence of IL-3 BaF3 cells arrest and die, but in the presence of PDGF ligand PDGFRα signaling rescues these cells, giving a cell survival and mitogenic response that is easily detected by microscopy, including proliferation, morphological changes, and increased motility/chemotaxis. As a fluorescence readout, BaF3 cells were also stably expressing histone 2B fused to a yellow fluorescent protein (YFP) to label cell nuclei. FIG. 110 shows validation of cell survival PDGFRα functional assay, showing a BaF3 clone expressing PDGFRα and histone 2B-YFP in the presence of no ligand or PDGF-AA 25 ng/mL for T=48 hours. In the absence of ligand, BaF3 cells undergo apoptosis and loss of YFP fluorescence (likely a result of protein degradation upon apoptosis) (FIG. 110A). In the presence of PDGF-AA ligand, cell survival and growth are rescued as shown by YFP fluorescence readout (FIG. 110B).

To test whether antibody-secreting cells could be kept viable for the length of such an assay, mouse splenocytes were enriched for plasma cells and co-incubated with BaF3 cells overexpressing PDFGRα in a microfluidic device. Bright field and fluorescent images were taken at the beginning of the experiment to distinguish the effector cell population from the readout cell population (containing H2B-YFP). Cells were cultured in the presence of IL-3 and tracked by time-lapse imaging for 48 hours, at which point anti-mouse antibody capture beads were introduced in the device for a 2-hour incubation. Chambers containing antibody-secreting cells were identified using a Dylight-594 labeled antibody. FIG. 110C shows an example of a microfluidic chamber containing 2 splenocytes (black arrows) and 2 readout cells (white arrows) at the beginning of the experiment. Readout cells proliferated to 22 cells while the effector cell population kept secreting antibodies after 48 hours of culture.

Example 32

GPCR Response to Ligand Using DiscoveRx Cells

In the PathHunter® β-Arrestin system from DiscoveRx (www.discoverx.com), a small peptide is fused to the intracellular sequence of a GPCR target of interest, and a complementing peptide fragment is fused to another intracellular protein (β-arrestin). After binding to its specific ligand, the GPCR recruits β-arrestin, forcing the complementation of the two peptides to produce a functional β-galactosidase enzyme. In the conventional non-microfluidic assay, the enzyme activity, and thus the amount of ligand bound to the GPCR, is detected with a single addition of a reagent cocktail to lyse the cells and produce a chemiluminescent before being analyzed using a traditional plate reader.

This assay was modified to adapt it to the microfluidic format described herein by using a fluorescent based substrate. 5-Dodecanoylaminofluorescein Di-β-D-Galactopyranoside ($C_{12}FDG$) is a chemically modified and non-fluorescent β-galactosidase substrate that becomes fluorescent after enzyme cleavage. It also includes a lipophilic tail that allows the substrate to diffuse inside the cell membrane and also promotes the retention inside the cells after cleavage.

The CCR4/CCL22 GPCR-agonist pair (PathHunter® eXpress CCR4 CHO-K1 β-Arrestin GPCR Assay) was used as an example to adapt the assay with the C12FDG substrate. Cells were incubated with various concentrations of substrate and ligand before being imaged using fluorescence.

The adapted assay was first tested in multiwell plates. Cells were incubated in media for 90 minutes with various concentrations of $C_{12}$FDG substrate. The substrate diffused in the cells and remained non fluorescent until it was cleaved. Then, the ligand/agonist CCL22 was added at different concentrations and incubated for 60 minutes for the complementation to occur inside the cells, leading to the formation of β-galactosidase and cleavage of the substrate, producing a fluorescent product inside the cells. Fluorescence-based microscopy was then used to image each well corresponding to a particular condition (FIG. 111).

Cells were then loaded in a microfluidic device and incubated with 33 μM $C_{12}$FDG substrate in cell culture media. The substrate and the cells were incubated for 90 minutes in order to allow diffusion and accumulation of the non-fluorescent substrate inside the cells. Cells were washed with media for 10 minutes at the end of the incubation. CCL22 agonist/ligand was then loaded at 4 different concentrations in 4 different sub-arrays of the device (sub-array 1: 0.01 nM, sub-array 2: 1 nM, sub-array 3: 100 nM, sub array 4: no agonist). Fluorescence-based microscopy was then used to image each chamber corresponding to a particular condition (FIG. 112A). Image analysis was performed for each chamber and average intensity was measured in the chambers. Background subtraction was performed and the results were plotted in FIG. 112B.

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

---

What is claimed is:

1. A method of identifying a heterologous cell population comprising an antibody secreting cell (ASC) that secretes an antibody that binds to a target epitope, comprising:
   retaining, in each of a plurality of microreactors, one of a plurality of heterogeneous cell populations, each population comprising 10 to 500 cells, wherein each heterogeneous cell population comprises one or more ASCs, wherein the contents of each microreactor further comprise a readout particle population comprising one or more readout beads, readout cells, or a combination thereof displaying the target epitope on their surfaces, and wherein individual heterogenous cell populations are retained in individual microreactors,
   incubating the heterogeneous cell populations and the readout particle population within the plurality of microreactors to allow for secreted antibody binding to the readout particle population via the target epitope,
   introducing a fluorescently labeled secondary antibody into the plurality of microreactors, wherein the fluorescently labeled secondary antibody binds to the secreted antibody,
   washing the plurality of microreactors to remove unbound secreted antibody and unbound fluorescently labeled secondary antibody,
   assaying the individual microreactors for the presence of a binding interaction between secreted antibody and the target epitope via detection of the fluorescent label, and
   determining, based on the results of the assaying step, whether one or more of the heterogenous cell populations includes an ASC that secretes an antibody that binds to the target epitope.

2. The method of claim 1, wherein the readout particle population is a homogeneous population or a heterogeneous population of readout particles.

3. The method of claim 1, wherein the readout particle population is immobilized on a surface of the individual microreactors.

4. The method of claim 1, wherein the binding interaction is an antigen-antibody binding specificity interaction, antigen-antibody binding affinity interaction or antigen-antibody binding kinetic interaction.

5. The method of claims 1, further comprising maintaining the heterogeneous cell populations in substantially a single plane.

6. The method of claim 1, further comprising maintaining the readout particle population in substantially a single plane.

7. The method of claim 1, wherein if a heterogenous cell population includes an ASC that secretes an antibody that binds to the target epitope, the method further comprises recovering the heterogenous cell population or a portion thereof to obtain a recovered cell population.

8. The method of claim 7, wherein the recovering step comprises positioning the open end of a microcapillary in a microreactor comprising the heterogeneous cell population that includes an ASC that secretes an antibody that binds to the target epitope and aspirating the microreactor's contents or a portion thereof to obtain a recovered aspirated cell population.

9. The method of claim 8, wherein the microcapillary is mounted on a robotic micromanipulation system on a microscope or the microcapillary is controlled robotically.

10. The method of claim 7, further comprising,
retaining a plurality of cell subpopulations originating from the recovered cell population in a plurality of vessels, wherein each cell subpopulation is present in an individual vessel,
lysing the individual cell subpopulations to provide lysed cell subpopulations, and
amplifying one or more nucleic acids within each of the lysed cell populations.

* * * * *

SEQUENCE LISTING

```
<160> NUMBER OF SEQ ID NOS: 86

<210> SEQ ID NO 1
<211> LENGTH: 395
<212> TYPE: DNA
<213> ORGANISM: Mus sp.

<400> SEQUENCE: 1
atggaatgga cctgggtctt tctcttcctc ctgtcagtaa ctgcaggtgt ccactcccag      60
gttcagctgc agcagtctgg acctgagctg atgaagcctg gggcctcagt gaagatatcc     120
tgcaaggcaa ctggctacac attcagaaac tactggatag agtggataaa gcagaggcct    180
ggacatggcc ttgagtggat tggagagatt ttacctgaaa gtggtagtat taattacaat    240
gagaaattca agggcaaggc cacattcact gcagatacat cctccaacac agcctacttg    300
caactccgca gcctgacatc tgaggactct gccgtctatt attgttttta tgataattac    360 gttttttgact actggggcca aggcaccact ctcac                              395

<210> SEQ ID NO 2
<211> LENGTH: 131
<212> TYPE: PRT
<213> ORGANISM: Mus sp.

<400> SEQUENCE: 2

Met Glu Trp Thr Trp Val Phe Leu Phe Leu Leu Ser Val Thr Ala Gly
1               5                   10                  15

Val His Ser Gln Val Gln Leu Gln Gln Ser Gly Pro Glu Leu Met Lys
            20                  25                  30

Pro Gly Ala Ser Val Lys Ile Ser Cys Lys Ala Thr Gly Tyr Thr Phe
        35                  40                  45

Arg Asn Tyr Trp Ile Glu Trp Ile Lys Gln Arg Pro Gly His Gly Leu
    50                  55                  60

Glu Trp Ile Gly Glu Ile Leu Pro Glu Ser Gly Ser Ile Asn Tyr Asn
65                  70                  75                  80

Glu Lys Phe Lys Gly Lys Ala Thr Phe Thr Ala Asp Thr Ser Ser Asn
                85                  90                  95

Thr Ala Tyr Leu Gln Leu Arg Ser Leu Thr Ser Glu Asp Ser Ala Val
```

```
                100              105              110
Tyr Tyr Cys Phe Tyr Asp Asn Tyr Val Phe Asp Tyr Trp Gly Gln Gly
        115                  120                  125

Thr Thr Leu
    130

<210> SEQ ID NO 3
<211> LENGTH: 372
<212> TYPE: DNA
<213> ORGANISM: Mus sp.

<400> SEQUENCE: 3
atggattctc aagtgcagat tttcagcttc ctgctaatca gtgcctcggt catactatcc     60
agtggacaaa ttgttctcat ccagtctcca acaatcatgt ctgcatctcc aggggagaag    120
gtcaccatga cctgcagtgc caactcaagt ttcagttaca tgcactggta ccagcagaag    180
tcaggcacct cccccaaaag atggatttat gacacatcca aactggcttc tggagtccct    240
gctcgcttca gtggcagtgg gtctgggacc tcttactctc tcacaattag cagcatggag    300
gctgaagatg ctgccactta ttactgtcag cagtggagta aaacccccac gttcggtgct    360
ggaccaagct ga                                                         372

<210> SEQ ID NO 4
<211> LENGTH: 124
<212> TYPE: PRT
<213> ORGANISM: Mus sp.

<400> SEQUENCE: 4

Met Asp Ser Gln Val Gln Ile Phe Ser Phe Leu Leu Ile Ser Ala Ser
1               5                   10                  15

Val Ile Leu Ser Ser Gly Gln Ile Val Leu Ile Gln Ser Pro Thr Ile
            20                  25                  30

Met Ser Ala Ser Pro Gly Glu Lys Val Thr Met Thr Cys Ser Ala Asn
        35                  40                  45

Ser Ser Phe Ser Tyr Met His Trp Tyr Gln Gln Lys Ser Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Trp
            100                 105                 110

Ser Arg Asn Pro Thr Phe Gly Ala Gly Thr Lys Leu
        115                 120

<210> SEQ ID NO 5
<211> LENGTH: 347
<212> TYPE: DNA
<213> ORGANISM: Mus sp.

<400> SEQUENCE: 5
atgcaagcag tggtatcaac gcagagtacg gggaaggagt caggacctgg cttggtggcg     60
ccctcacaga gcatgtccat catgtgcact gtctctgggt tttcattaag caactatggt    120
gtacactggg ttcgccagcc tccaggaaag ggtctggagt ggctgggagt aatttgggct    180
ggtggaaaca caaattataa ttcggctctc atgtccagac tgagcatcag caaagacaag    240
tccaagagtc aagttttctt aaaaatgaac cgtctggaaa ctgatgacac agccatgtac    300
```
tatctgtgcc agtgtaggat ggttacccct tgcttactgg gccaagg         347

<210> SEQ ID NO 6
<211> LENGTH: 115
<212> TYPE: PRT
<213> ORGANISM: Mus sp.

<400> SEQUENCE: 6

Met Gln Ala Val Val Ser Thr Gln Ser Thr Gly Lys Glu Ser Gly Pro
1               5                   10                  15

Gly Leu Val Ala Pro Ser Gln Ser Met Ser Ile Met Cys Thr Val Ser
                20                  25                  30

Gly Phe Ser Leu Ser Asn Tyr Gly Val His Trp Val Arg Gln Pro Pro
            35                  40                  45

Gly Lys Gly Leu Glu Trp Leu Gly Val Ile Trp Ala Gly Gly Asn Thr
        50                  55                  60

Asn Tyr Asn Ser Ala Leu Met Ser Arg Leu Ser Ile Ser Lys Asp Lys
65                  70                  75                  80

Ser Lys Ser Gln Val Phe Leu Lys Met Asn Arg Leu Glu Thr Asp Asp
                85                  90                  95

Thr Ala Met Tyr Tyr Leu Cys Gln Cys Arg Met Val Thr Pro Cys Leu
            100                 105                 110

Leu Gly Gln
        115

<210> SEQ ID NO 7
<211> LENGTH: 369
<212> TYPE: DNA
<213> ORGANISM: Mus sp.

<400> SEQUENCE: 7
atggagtcac agattcaggt ctttgtattc gtgtttctct ggttgtctgg tgttgacgga      60
gacattgtga tgacccagtc tcacaaattc atgtccacat cagtaggaga cagggtcagc     120
atcacctgca aggccagtca ggatgtgagt atttctgtag cctggtatca acagaaacca     180
ggacaatctc ctaaactact gatttactcg gcatcctacc ggtacactgg agtccctgat     240
cgcttcactg gcagtggatc tgggacggat ttcactttca ccatccgcag tgtgcaggct     300
gaagacctgg cagtttatta ctgtcagcaa cattatagta ctccttttac gtcggctcgg     360
gacaaagtg                                                              369

<210> SEQ ID NO 8
<211> LENGTH: 123
<212> TYPE: PRT
<213> ORGANISM: Mus sp.

<400> SEQUENCE: 8

Met Glu Ser Gln Ile Gln Val Phe Val Phe Val Phe Leu Trp Leu Ser
1               5                   10                  15

Gly Val Asp Gly Asp Ile Val Met Thr Gln Ser His Lys Phe Met Ser
                20                  25                  30

Thr Ser Val Gly Asp Arg Val Ser Ile Thr Cys Lys Ala Ser Gln Asp
            35                  40                  45

Val Ser Ile Ser Val Ala Trp Tyr Gln Gln Lys Pro Gly Gln Ser Pro
        50                  55                  60

Lys Leu Leu Ile Tyr Ser Ala Ser Tyr Arg Tyr Thr Gly Val Pro Asp
65                  70                  75                  80

```
Arg Phe Thr Gly Ser Gly Ser Gly Thr Asp Phe Thr Phe Thr Ile Arg
                85                  90                  95

Ser Val Gln Ala Glu Asp Leu Ala Val Tyr Tyr Cys Gln Gln His Tyr
                100                 105                 110

Ser Thr Pro Phe Thr Ser Ala Arg Asp Lys Val
            115                 120
```

<210> SEQ ID NO 9
<211> LENGTH: 545
<212> TYPE: DNA
<213> ORGANISM: Homo sapiens

<400> SEQUENCE: 9

```
atgaagcacc tgtggttctt cctcctgctg gtggcggctc ccagatgggt cctgtctcag     60
gtgcagctgc aggagtcggg cccaggactg gtgaagtctt cggagaccct gtccctcacc    120
tgcactgtct ctggtgactc catcaccagc agtacttacg actggggctg gatccgtcag    180
ccccccggga agggcctgga gtggattggc aatgtctatt atagagggag cacctactac    240
aacccgtccc tcaagagtcg agtcaccata tccgtagaca ggtccaggac ccagatctcc    300
ctgaggctga gctctgtgac cgccgctgac acggctctgt atttctgtgc gagacacccg    360
aaacgtctaa cggttttttga agtggtcaac gcttttgata tctggggcca agggacaatg    420
gtcaccgtct tttcagcctc caccaagggc ccatcggtct tccccctggc accctcctcc    480
aagagcacct ctgggggcac agcggccctg ggctgcctgg tctgctgacg aggcactgag    540
gactg                                                                545
```

<210> SEQ ID NO 10
<211> LENGTH: 169
<212> TYPE: PRT
<213> ORGANISM: Homo sapiens

<400> SEQUENCE: 10

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Ser Ser Glu Thr Leu Ser Leu Thr Cys Thr Val Ser Gly Asp Ser Ile
        35                  40                  45

Thr Ser Ser Thr Tyr Asp Trp Gly Trp Ile Arg Gln Pro Pro Gly Lys
    50                  55                  60

Gly Leu Glu Trp Ile Gly Asn Val Tyr Tyr Arg Gly Ser Thr Tyr Tyr
65                  70                  75                  80

Asn Pro Ser Leu Lys Ser Arg Val Thr Ile Ser Val Asp Arg Ser Arg
                85                  90                  95

Thr Gln Ile Ser Leu Arg Leu Ser Ser Val Thr Ala Ala Asp Thr Ala
            100                 105                 110

Leu Tyr Phe Cys Ala Arg His Pro Lys Arg Leu Thr Val Phe Glu Val
        115                 120                 125

Val Asn Ala Phe Asp Ile Trp Gly Gln Gly Gln Thr Met Val Thr Val
    130                 135                 140

Phe Ser Ala Ser Thr Lys Gly Pro Ser Val Phe Pro Leu Ala Pro Ser
145                 150                 155                 160

Ser Lys Thr Ser Gly Gly Thr Ala
                165
```

<210> SEQ ID NO 11
<211> LENGTH: 465
<212> TYPE: DNA
<213> ORGANISM: Homo sapiens

<400> SEQUENCE: 11

| | | | | | |
|---|---|---|---|---|---|
| atggcctggg | ctctgctact | cctcaccctc | ctcactcagg | gcacagggtc | ctgggcccag | 60 |
| tctgccctga | ctcagcctgc | ctccgtgtct | gcatctcctg | gacagtcgat | caccatctcc | 120 |
| tgcactggaa | tcagcagtga | cattggtggt | tatagctctg | tctcctggta | ccaagcgcac | 180 |
| ccaggcaaag | cccccaaact | catgatctat | gatgtcaata | atcggccctc | aggcatttct | 240 |
| aatcgcttct | ctggttccaa | gtctggcaac | acggcctccc | tggccatctc | tgggctccag | 300 |
| gctgaggacg | aggcagatta | ttactgcagc | ttatatacaa | gtatcaacgc | ttccatagtg | 360 |
| ttcggcggag | ggaccaagct | gaccgtccta | ggtcagccca | aggctgcccc | ctcggtcact | 420 |
| ctgttcccgc | cctcctctga | ggagcttcaa | gccaacaagg | ccaca | | 465 |

<210> SEQ ID NO 12
<211> LENGTH: 146
<212> TYPE: PRT
<213> ORGANISM: Homo sapiens

<400> SEQUENCE: 12

Met Ala Trp Ala Leu Leu Leu Thr Leu Leu Thr Gln Gly Thr Gly
1               5                   10                  15

Ser Trp Ala Gln Ser Ala Leu Thr Gln Pro Ala Ser Val Ser Ala Ser
            20                  25                  30

Pro Gly Gln Ser Ile Thr Ile Ser Cys Thr Gly Ile Ser Ser Asp Ile
        35                  40                  45

Gly Gly Tyr Ser Ser Val Ser Trp Tyr Gln Ala His Pro Gly Lys Ala
    50                  55                  60

Pro Lys Leu Met Ile Tyr Asp Val Asn Asn Arg Pro Ser Gly Ile Ser
65                  70                  75                  80

Asn Arg Phe Ser Gly Ser Lys Ser Gly Asn Thr Ala Ser Leu Ala Ile
                85                  90                  95

Ser Gly Leu Gln Ala Glu Asp Glu Ala Asp Tyr Tyr Cys Ser Leu Tyr
            100                 105                 110

Thr Ser Ile Asn Ala Ser Ile Val Phe Gly Gly Gly Thr Lys Leu Thr
        115                 120                 125

Val Leu Gly Gln Pro Lys Ala Ala Pro Ser Val Thr Leu Phe Pro Pro
    130                 135                 140

Ser Ser
145

<210> SEQ ID NO 13
<211> LENGTH: 545
<212> TYPE: DNA
<213> ORGANISM: Homo sapiens

<400> SEQUENCE: 13

| | | | | | |
|---|---|---|---|---|---|
| atgaagcacc | tgtggttctt | ccttctgctg | gtggcggctc | ccagatgggt | cctgtcccag | 60 |
| ctgcaactgc | aggagtcggg | cccaggactg | gtgaagcctt | cggagaccct | gtccctcacc | 120 |
| tgcactgtct | ctggtgactc | catcagcagt | agtacttact | actggggctg | gatccgccag | 180 |
| cccccaggaa | aggggctgga | gtggattgcc | tttatctttt | atagcgggag | caccttctac | 240 |
| aacccgtccc | tcaagagtcg | agtcaccgtc | tccgtagaca | ggtccacgaa | ccagttctcc | 300 |

```
ctgaggctga agtctgtgac cgccgcagac acgtccagat attactgtgc gagacaccca    360
aaacgtatct cgattttgta agtggtcaac gcttttgata tctggggcca ggggacaatg    420
gtcaccgtct cttcagcctc caccaagggc ccatcggtct ccccctggc acctcctcc      480 aagagcacct ctgggggcac agcggccctg gctgcctgg tctgctgacg aggcactgag     540
gactg                                                                 545
```

<210> SEQ ID NO 14
<211> LENGTH: 168
<212> TYPE: PRT
<213> ORGANISM: Homo sapiens

<400> SEQUENCE: 14

```
Met Lys His Leu Trp Phe Phe Leu Leu Leu Val Ala Ala Pro Arg Trp
1               5                   10                  15

Val Leu Ser Gln Leu Gln Leu Gln Glu Ser Gly Pro Gly Leu Val Lys
            20                  25                  30

Pro Ser Glu Thr Leu Ser Leu Thr Cys Thr Val Ser Gly Asp Ser Ile
        35                  40                  45

Ser Ser Ser Thr Tyr Tyr Trp Gly Trp Ile Arg Gln Pro Pro Gly Lys
    50                  55                  60

Gly Leu Glu Trp Ile Ala Phe Ile Phe Tyr Ser Gly Ser Thr Phe Tyr
65                  70                  75                  80

Asn Pro Ser Leu Lys Ser Arg Val Thr Val Ser Val Asp Arg Ser Thr
                85                  90                  95

Asn Gln Phe Ser Leu Arg Leu Lys Ser Val Thr Ala Ala Asp Thr Ser
            100                 105                 110

Arg Tyr Tyr Cys Ala Arg His Pro Lys Arg Ile Ser Ile Phe Glu Val
        115                 120                 125

Val Asn Ala Phe Asp Ile Trp Gly Gln Gly Thr Met Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala
                165
```

<210> SEQ ID NO 15
<211> LENGTH: 465
<212> TYPE: DNA
<213> ORGANISM: Homo sapiens

<400> SEQUENCE: 15

```
atggcctgga ctctgctatt cctcaccctc ctcactcagg gcacagggtc ctgggcccag    60
tctgccctga ctcagcctgc ctccgtgtct gggtctcctg gacagtcgat caccatcacc   120
tgcactggaa tcagcagtga cgttggtgct tataattctg tctcctggta ccagcagtac   180
ccaggcaaat cccccaagct catgatttat gatgtcagta tcggtcctc agggtttct    240 aatcgcttct ctggctccaa gtctgacaac acggcctccc tgaccatctc tgggctccag   300
gctgaggacg aggcttctta tttctgcagc ttatatagaa gcagcaccac ttccgtggta   360
ttcggcggag ggaccaagct gaccgtccta cgtcagccca aggctgcccc ctcggtcact   420
ctgttcccgc cctcctctga ggagcttcaa gccaacaagg ccaca                   465
```

<210> SEQ ID NO 16
<211> LENGTH: 146

-continued

```
<212> TYPE: PRT
<213> ORGANISM: Homo sapiens

<400> SEQUENCE: 16

Met Ala Trp Thr Leu Leu Phe Leu Thr Leu Thr Gln Gly Thr Gly
1               5                   10                  15

Ser Trp Ala Gln Ser Ala Leu Thr Gln Pro Ala Ser Val Ser Gly
            20                  25                  30

Pro Gly Gln Ser Ile Thr Ile Thr Cys Thr Gly Ile Ser Ser Asp Val
        35                  40                  45

Gly Ala Tyr Asn Ser Val Ser Trp Tyr Gln Gln Tyr Pro Gly Lys Ser
    50                  55                  60

Pro Lys Leu Met Ile Tyr Asp Val Ser Asn Arg Ser Ser Gly Val Ser
65                  70                  75                  80

Asn Arg Phe Ser Gly Ser Lys Ser Asp Asn Thr Ala Ser Leu Thr Ile
                85                  90                  95

Ser Gly Leu Gln Ala Glu Asp Glu Ala Ser Tyr Phe Cys Ser Leu Tyr
            100                 105                 110

Arg Ser Ser Thr Thr Ser Val Val Phe Gly Gly Gly Thr Lys Leu Thr
        115                 120                 125

Val Leu Arg Gln Pro Lys Ala Ala Pro Ser Val Thr Leu Phe Pro Pro
    130                 135                 140

Ser Ser
145

<210> SEQ ID NO 17
<211> LENGTH: 432
<212> TYPE: DNA
<213> ORGANISM: Oryctolagus sp.
<220> FEATURE:
<221> NAME/KEY: misc_feature
<222> LOCATION: (430)..(430)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t

<400> SEQUENCE: 17
gctagccacc atggagactg ggctgcgctg gcttctcctg gtcgctgtgc tcaaaggtgt     60
ccagtgtcag tcggtggagg agtccggggg tcgcctggtc acgcctggga cacccctgac    120
actcacctgc atagtctctg gaatcgacct cagtagctat gcaatgggct gggtccgcca    180
ggctccagga aagggctgg aatacatcgg aatcattagt agcagtggta tcacatacta    240
cgcgagctgg gcgaaaggcc gattcaccat ctccaaaacc tcgtcgacca cggtgactct    300
gacaatcacc gatctgcaac ttcagacac gggcacctat ttctgtgcca gagggtctcg    360
ttatagtgct tttggtgctt ttgatacctg ggcccaggc accctggtca ccgtctcctc    420
agcaagcttn an                                                        432

<210> SEQ ID NO 18
<211> LENGTH: 444
<212> TYPE: DNA
<213> ORGANISM: Oryctolagus sp.
<220> FEATURE:
<221> NAME/KEY: misc_feature
<222> LOCATION: (444)..(444)
<223> OTHER INFORMATION: n is a, c, g, or t

<400> SEQUENCE: 18
```

```
tttggctagc caccatggag actgggctgc gctggcttct cctggtcgct gtgctcaaag    60
gtgtccagtg tcagtcggtg gaggagtccg ggggtcgcct ggtcacgcct gggacacccc   120
tgacactcac ctgcacagtc tctggattct ccctcagtag ctatgcaatg ggctgggtcc   180
gccaggctcc agggaagggg ctggaatgga tcggagtcat taataataat ggtgacacat   240
actacgcgag ctggccgaaa ggccgattca ccatctccaa aacctcgacc acggtggatc   300
tgaaaatcac cagtccgaca accgaggaca cggccaccta tttctgtgcc agagatcgtg   360
gtaatagtta ttactttgga ttggactact ttaacttgtg gggcccaggc accctggtca   420
ccgtctcctc agcaagcttt atan                                          444
```

<210> SEQ ID NO 19
<211> LENGTH: 385
<212> TYPE: DNA
<213> ORGANISM: Oryctolagus sp.
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (383)..(385)
<223> OTHER INFORMATION: n is a, c, g, or t
<400> SEQUENCE: 19

```
ctctgctgct ctggctccca ggtgccagat gtgccttcga attgacccag actccatcct    60
ccgtggaggc agctgtggga ggcacagtca ccatcaagtg ccaggccagt cagagtatta   120
atagttggtt atcctggtat cagcagaaac agggcagcc tcccaagctc ctgatctaca   180
aggcatccaa tctggcatct ggggtcccat cgcggttcag aggcagtgga tctgggacag   240
agttcactct caccatcagc gacctggagt gtgncgatgc tgccacttac tactgtcaaa   300
gcnattatgc tactagtagt gttgattatn atgctttcgg cggaaggacc gaggtggtgg   360
tcaanactgc ggcngtanta ntnnn                                         385
```

<210> SEQ ID NO 20
<211> LENGTH: 425
<212> TYPE: DNA
<213> ORGANISM: Oryctolagus sp.
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t

<400> SEQUENCE: 20

| | | | | | |
|---|---|---|---|---|---|
| tgcagctagc | caccatggac | acgagggccc | ccatcagctg | ctggggctcc | tgctgctctg | 60 |
| gctcccaggt | gccaggtgtg | cccttgtgat | gacccagact | ccagcctctg | tggaggtagc | 120 |
| tgtgggaggc | acagtcacca | tcaagtgcca | ggccagtcag | agcattgata | gttggttatc | 180 |
| ctggtatcag | cagaaaccag | ggcagcgtcc | caggctcctg | atctattatg | catccaatct | 240 |
| ggcatctggg | gtctcatcgc | ggttcaaagg | cagtggatct | gggacagaat | acactctcac | 300 |
| catcagcggc | gtggagtgtg | ccgatgctgc | cacttactac | tgtcaagagg | ttatagtag | 360 |
| tggtaatgtt | gataatgttt | tcggcggagg | gaccgaggtg | gtggtcaaaa | ctgcgnccgc | 420 |
| tatan | | | | | | 425 |

<210> SEQ ID NO 21
<211> LENGTH: 367
<212> TYPE: DNA
<213> ORGANISM: Homo sapiens

<400> SEQUENCE: 21

| | | | | | |
|---|---|---|---|---|---|
| gaattccatg | caggtgcagc | tggtgcagtc | tggcgccgaa | gtgaagaaac | ccggcagcag | 60 |
| cgtgaaggtg | tcctgcaagg | ccagcggcct | gaccatcagc | gacacctaca | tgcactgggt | 120 |
| gcgccaggct | ccaggccagg | gactggaatg | gatgggcaga | atcgaccccg | ccaacggcaa | 180 |
| caccaagttc | gaccccaagt | tccagggcag | agtgaccatc | accgccgaca | ccagcaccte | 240 |
| caccgcctac | atggaactga | gcagcctgcg | gagcgaggac | accgccgtgt | actattgtgc | 300 |
| cagaggcgtg | ttcggcttct | tcgactactg | gggccagggc | accaccgtga | ccgtgtcatc | 360 |
| tgctagc | | | | | | 367 |

<210> SEQ ID NO 22
<211> LENGTH: 405
<212> TYPE: DNA
<213> ORGANISM: Homo sapiens

<400> SEQUENCE: 22

| | | | | | |
|---|---|---|---|---|---|
| accggtgcca | ccatgtaccg | gatgcagctg | ctgagctgta | tcgccctgtc | tctggccctc | 60 |
| gtgacgaatt | cagccatgga | catccagatg | acccagagcc | ccagcagcct | gtctgccagc | 120 |
| gtgggcgaca | gagtgaccat | cacatgcaag | gccaccgagg | acatctacaa | ccggctggcc | 180 |
| tggtatcagc | agaagcccgg | caaggccccc | aagctgctga | ttagcggagc | caccagcctg | 240 |
| gaaaccggcg | tgccaagcag | attttccggc | agcggctccg | gcaaggacta | caccctgacc | 300 |
| atcagctccc | tgcagcccga | ggacttcgcc | acctactact | gccagcagtt | ttggagcgcc | 360 |
| ccctacacct | ttggcggagg | caccaaggtg | gaaatcaagc | gtacg | | 405 |

<210> SEQ ID NO 23
<211> LENGTH: 357
<212> TYPE: DNA
<213> ORGANISM: Mus sp.

<400> SEQUENCE: 23

| | | | | | |
|---|---|---|---|---|---|
| atgcaggtgc | agctgaagga | gtcaggacct | ggcctggtgg | cgccctcaca | gagcctgtcc | 60 |
| atcacatgca | ccgtctcagg | gttctcatta | accggctatg | gtgtaaactg | ggttcgccag | 120 |

```
cctccaggaa agggtctgga gtggctggga atgatttggg gtgatggaaa cacagactat    180
aattcagctc tcaaatccag actgagcatc agcaaggaca actccaagag ccaagttttc    240
ttaaaaatga acagtctgca cactgatgac acagccaggt actactgtgc cagagagaga    300
gattataggc ttgactactg gggccaaggc accactctca cagtctcctc agctagc      357

<210> SEQ ID NO 24
<211> LENGTH: 318
<212> TYPE: DNA
<213> ORGANISM: Mus sp.

<400> SEQUENCE: 24
atggacatcc agatgactca gtctccagcc tcccttyctg cgtctgtggg agaaactgtc    60
accatcacat gtcgagcaag tgggaatatt cacaattatt tagcatggta tcagcagaaa    120
cagggaaaat ctcctcagct cctggtctat tatacaacaa ccttagcaga tggtgtgcca    180
tcaaggttca gtggcagtgg atcaggaaca caatattctc tcaagatcaa cagcctgcag    240
cctgaagatt ttgggagtta ttactgtcaa cattttggaa gtactcctcg gacgttcggt    300
ggaggcacca agctcgag                                                 318

<210> SEQ ID NO 25
<211> LENGTH: 357
<212> TYPE: DNA
<213> ORGANISM: Mus sp.

<400> SEQUENCE: 25
atggaggtcc agctgcagca gtctggagct gagctgatga gccaggggc ctcagtgaag     60 atatcctgca agcttctgg ctacacattc agtgactact ggatagagtg ggtaaagcag    120
aggcctggac atggccttga gtggattgga gagattttac ctggaagtgg tagcactaat    180
taccatgaga gattcaaggg caaggccaca ttcactgcag atacatcctc cagcacagcc    240
tacatgcaac tcaacagcct gacatctgaa gactctggcg tctattactg cctccatggt    300
aactacgact ttgacggctg gggccaaggc accactctca cagtctcctc agctagc      357

<210> SEQ ID NO 26
<211> LENGTH: 312
<212> TYPE: DNA
<213> ORGANISM: Mus sp.

<400> SEQUENCE: 26
atggatatcg ttctcacaca gtctccagca atcatgtctg catctccagg ggagaaggtc    60
accatgacct gcagtgccag ttcaagtgta aattacatgt actggtacca gcagaagtca    120
ggcacttccc ccaaaagatg gatttatgac acatccaaac tggcttctgg agtccctgtt    180
cgcttcagtg gcagtgggtc tgggacctct tactctctca caatcagcag catggagact    240
gaagatgctg ccacttatta ctgccaacag tggggtcgta accccacgtt cggagggggg    300
accaagctcg ag                                                       312

<210> SEQ ID NO 27
<211> LENGTH: 510
<212> TYPE: DNA
<213> ORGANISM: Mus sp.

<400> SEQUENCE: 27
tggaaggtgg tgcacactgc tggacaggga tccagagttc caggtcactg tcactggctc    60
agggaaatag cccttgacca ggcatcccag ggtcaccatg gagttagttt gggcagcaga    120
```

```
tccaggggcc agtggataga cagatggggg tgtcgttttg gctgaggaga ctgtgagagt    180
ggtgccttgg ccccagcagt ccccgtccca gtttgcacag taatatgtgg ctgtgtcctc    240
aggagtcaca gaaatcaact gcaggtagca ctggttcttg gatgtgtctc gagtgataga    300
gattcgacct tgagagatg gattgtagta agtgctacca ctgtagctta tgtaccccat     360
atactcaagt tgttccctg ggaatttccg gatccagctc cagtaatcat tggtgatgga     420
gtcgccagtg acagaacagg tgagggacag agtctgagaa ggtttcacga ggctaggtcc    480
agactcctgc agctgcacct cgaattccca                                     510

<210> SEQ ID NO 28
<211> LENGTH: 342
<212> TYPE: DNA
<213> ORGANISM: Mus sp.

<400> SEQUENCE: 28
ttggtccccc ctccgaacgt gtacggccag ttgttactct gttgacagaa atacattcca     60
aaatcttcag tctccacact gatgatactg agagtgaaat ccgtccctga tccactgcca    120
ctgaacctgg aggggatccc agagatggac tgggaagcat acttgatgag aagccttgga    180
gactcatgtg attttttgttg ataccagtgt aggttgttgc taatactttg gctggccctg    240 caggaaaagac tgacgctatc tcctggagtc acagacaggg tgtctggaga ctgagttagc    300
acaatatcac ctctggaggc tgaaatccag aaaagcaaaa aa                       342

<210> SEQ ID NO 29
<211> LENGTH: 26
<212> TYPE: DNA
<213> ORGANISM: Artificial Sequence
<220> FEATURE:
<223> OTHER INFORMATION: Template switching primer
<220> FEATURE:
<221> NAME/KEY: misc_feature
<222> LOCATION: (24)..(26)
<223> OTHER INFORMATION: May be ribonucleic acid residues

<400> SEQUENCE: 29
gcagtggtat caacgcagag tacggg                                          26

<210> SEQ ID NO 30
<211> LENGTH: 24
<212> TYPE: DNA
<213> ORGANISM: Artificial Sequence
<220> FEATURE:
<223> OTHER INFORMATION: Universal primer TS

<400> SEQUENCE: 30
gcagtggtat caacgcagag tacg                                            24

<210> SEQ ID NO 31
<211> LENGTH: 27
<212> TYPE: DNA
<213> ORGANISM: Artificial Sequence
<220> FEATURE:
<223> OTHER INFORMATION: Universal primer RT

<400> SEQUENCE: 31
agacagtcct cagtgcctcg tcagcag                                         27

<210> SEQ ID NO 32
<211> LENGTH: 13
<212> TYPE: DNA
```

-continued

<213> ORGANISM: Artificial Sequence
<220> FEATURE:
<223> OTHER INFORMATION: Human RT primer HsRT-01

<400> SEQUENCE: 32
gtcctgagga ctg                                                    13

<210> SEQ ID NO 33
<211> LENGTH: 13
<212> TYPE: DNA
<213> ORGANISM: Artificial Sequence
<220> FEATURE:
<223> OTHER INFORMATION: Human RT primer HsRT-02

<400> SEQUENCE: 33
tgctctgtga cac                                                    13

<210> SEQ ID NO 34
<211> LENGTH: 13
<212> TYPE: DNA
<213> ORGANISM: Artificial Sequence
<220> FEATURE:
<223> OTHER INFORMATION: Human RT primer HsRT-03

<400> SEQUENCE: 34
ggtgtacagg tcc                                                    13

<210> SEQ ID NO 35
<211> LENGTH: 13
<212> TYPE: DNA
<213> ORGANISM: Artificial Sequence
<220> FEATURE:
<223> OTHER INFORMATION: Human RT primer HsRT-04

<400> SEQUENCE: 35
cagagagcgt gag                                                    13

<210> SEQ ID NO 36
<211> LENGTH: 16
<212> TYPE: DNA
<213> ORGANISM: Artificial Sequence
<220> FEATURE:
<223> OTHER INFORMATION: Human RT primer HsRT-05

<400> SEQUENCE: 36
tcatgtagta gctgtc                                                 16

<210> SEQ ID NO 37
<211> LENGTH: 14
<212> TYPE: DNA
<213> ORGANISM: Artificial Sequence
<220> FEATURE:
<223> OTHER INFORMATION: Human RT primer HsRT-06

<400> SEQUENCE: 37
ctcaggactg atgg                                                   14

<210> SEQ ID NO 38
<211> LENGTH: 15
<212> TYPE: DNA
<213> ORGANISM: Artificial Sequence
<220> FEATURE:
<223> OTHER INFORMATION: Human RT primer HsRT-07

<400> SEQUENCE: 38
gagtcctgag tactg                                                  15

<210> SEQ ID NO 39
<211> LENGTH: 16
<212> TYPE: DNA
<213> ORGANISM: Artificial Sequence
<220> FEATURE:
<223> OTHER INFORMATION: Human RT primer HsRT-08

<400> SEQUENCE: 39
gttgttgctt tgtttg                                              16

<210> SEQ ID NO 40
<211> LENGTH: 15
<212> TYPE: DNA
<213> ORGANISM: Artificial Sequence
<220> FEATURE:
<223> OTHER INFORMATION: Human RT primer HsRT-09

<400> SEQUENCE: 40
ttgttgctct gtttg                                               15

<210> SEQ ID NO 41
<211> LENGTH: 44
<212> TYPE: DNA
<213> ORGANISM: Artificial Sequence
<220> FEATURE:
<223> OTHER INFORMATION: Long gene-specific primer HsN2U_01

<400> SEQUENCE: 41
agacagtcct cagtgcctcg tcagcagacc aggcagccca gggc                44

<210> SEQ ID NO 42
<211> LENGTH: 55
<212> TYPE: DNA
<213> ORGANISM: Artificial Sequence
<220> FEATURE:
<223> OTHER INFORMATION: Long gene-specific primer HsN2U_02

<400> SEQUENCE: 42
agacagtcct cagtgcctcg tcagcagcag tgtggccttg ttggcttgaa gctcc    55

<210> SEQ ID NO 43
<211> LENGTH: 53
<212> TYPE: DNA
<213> ORGANISM: Artificial Sequence
<220> FEATURE:
<223> OTHER INFORMATION: Long gene-specific primer HsN2U_03

<400> SEQUENCE: 43
agacagtcct cagtgcctcg tcagcagagc aggcacacaa cagaggcagt tcc      53

<210> SEQ ID NO 44
<211> LENGTH: 52
<212> TYPE: DNA
<213> ORGANISM: Artificial Sequence
<220> FEATURE:
<223> OTHER INFORMATION: Long gene-specific primer HsN2U_04

<400> SEQUENCE: 44
agacagtcct cagtgcctcg tcagcaggcc cagagtcacg gaggtggcat tg       52

<210> SEQ ID NO 45
<211> LENGTH: 54
<212> TYPE: DNA
<213> ORGANISM: Artificial Sequence
<220> FEATURE:

<223> OTHER INFORMATION: Long gene-specific primer HsN2U_05

<400> SEQUENCE: 45
agacagtcct cagtgcctcg tcagcaggca tgcgacgacc acgttcccat cttg    54

<210> SEQ ID NO 46
<211> LENGTH: 46
<212> TYPE: DNA
<213> ORGANISM: Artificial Sequence
<220> FEATURE:
<223> OTHER INFORMATION: Long gene-specific primer HsN2U_06

<400> SEQUENCE: 46
agacagtcct cagtgcctcg tcagcaggca gccaacggcc acgctg    46

<210> SEQ ID NO 47
<211> LENGTH: 57
<212> TYPE: DNA
<213> ORGANISM: Artificial Sequence
<220> FEATURE:
<223> OTHER INFORMATION: Long gene-specific primer HsN2U_07

<400> SEQUENCE: 47
agacagtcct cagtgcctcg tcagcagatg ccaggaccac agggctgtta tcctttg    57

<210> SEQ ID NO 48
<211> LENGTH: 53
<212> TYPE: DNA
<213> ORGANISM: Artificial Sequence
<220> FEATURE:
<223> OTHER INFORMATION: Long gene-specific primer HsN2U_08

<400> SEQUENCE: 48
agacagtcct cagtgcctcg tcagcagagt gtggccttgt tggcttggag ctc    53

<210> SEQ ID NO 49
<211> LENGTH: 51
<212> TYPE: DNA
<213> ORGANISM: Artificial Sequence
<220> FEATURE:
<223> OTHER INFORMATION: Long gene-specific primer HsN2U_09

<400> SEQUENCE: 49
agacagtcct cagtgcctcg tcagcagacc acgttcccat ctggctgggt g    51

<210> SEQ ID NO 50
<211> LENGTH: 14
<212> TYPE: DNA
<213> ORGANISM: Artificial Sequence
<220> FEATURE:
<223> OTHER INFORMATION: RT mouse primer MmRT_01

<400> SEQUENCE: 50
acagtcactg agct    14

<210> SEQ ID NO 51
<211> LENGTH: 15
<212> TYPE: DNA
<213> ORGANISM: Artificial Sequence
<220> FEATURE:
<223> OTHER INFORMATION: RT mouse primer MmRT_02

<400> SEQUENCE: 51
ctttgacaag gcatc    15

```
<210> SEQ ID NO 52
<211> LENGTH: 16
<212> TYPE: DNA
<213> ORGANISM: Artificial Sequence
<220> FEATURE:
<223> OTHER INFORMATION: RT mouse primer MmRT_03

<400> SEQUENCE: 52
ccacttgaca ttgatg                                                    16

<210> SEQ ID NO 53
<211> LENGTH: 15
<212> TYPE: DNA
<213> ORGANISM: Artificial Sequence
<220> FEATURE:
<223> OTHER INFORMATION: RT mouse primer MmRT_04

<400> SEQUENCE: 53
ctcttctcca cagtg                                                     15

<210> SEQ ID NO 54
<211> LENGTH: 52
<212> TYPE: DNA
<213> ORGANISM: Artificial Sequence
<220> FEATURE:
<223> OTHER INFORMATION: Long gene-specific mouse primer Mmn2_01

<400> SEQUENCE: 54
agacagtcct cagtgcctcg tcagcagact gcaggagagc tgggaaggtg tg            52

<210> SEQ ID NO 55
<211> LENGTH: 50
<212> TYPE: DNA
<213> ORGANISM: Artificial Sequence
<220> FEATURE:
<223> OTHER INFORMATION: Long gene-specific mouse primer Mmn2_02

<400> SEQUENCE: 55
agacagtcct cagtgcctcg tcagcaggac agctgggaag gtgtgcacac               50

<210> SEQ ID NO 56
<211> LENGTH: 53
<212> TYPE: DNA
<213> ORGANISM: Artificial Sequence
<220> FEATURE:
<223> OTHER INFORMATION: Long gene-specific mouse primer Mmn2_03

<400> SEQUENCE: 56
agacagtcct cagtgcctcg tcagctcaag aagcacacga ctgaggcacc tcc           53

<210> SEQ ID NO 57
<211> LENGTH: 50
<212> TYPE: DNA
<213> ORGANISM: Artificial Sequence
<220> FEATURE:
<223> OTHER INFORMATION: Long gene-specific mouse primer Mmn2_04

<400> SEQUENCE: 57
agacagtcct cagtgcctcg tcagcttgcc ttccaggcca ctgtcacacc               50

<210> SEQ ID NO 58
<211> LENGTH: 53
<212> TYPE: DNA
<213> ORGANISM: Artificial Sequence
<220> FEATURE:
<223> OTHER INFORMATION: Long gene-specific mouse primer Mmn2_05
```

```
<400> SEQUENCE: 58
agacagtcct cagtgcctcg tcagcatcca gatgtgtcac tgcagccagg gac          53

<210> SEQ ID NO 59
<211> LENGTH: 53
<212> TYPE: DNA
<213> ORGANISM: Artificial Sequence
<220> FEATURE:
<223> OTHER INFORMATION: Long gene-specific mouse primer Mmn2_06

<400> SEQUENCE: 59
agacagtcct cagtgcctcg tcagcacctt ccagtccact gtcaccacac ctg          53

<210> SEQ ID NO 60
<211> LENGTH: 13
<212> TYPE: DNA
<213> ORGANISM: Artificial Sequence
<220> FEATURE:
<223> OTHER INFORMATION: RT rabbit primer OcRT_01

<400> SEQUENCE: 60
tgaagctctg gac                                                      13

<210> SEQ ID NO 61
<211> LENGTH: 13
<212> TYPE: DNA
<213> ORGANISM: Artificial Sequence
<220> FEATURE:
<223> OTHER INFORMATION: RT rabbit primer OcRT_02

<400> SEQUENCE: 61
cacactcaga ggg                                                      13

<210> SEQ ID NO 62
<211> LENGTH: 13
<212> TYPE: DNA
<213> ORGANISM: Artificial Sequence
<220> FEATURE:
<223> OTHER INFORMATION: RT rabbit primer OcRT_03

<400> SEQUENCE: 62
ttccagctca cac                                                      13

<210> SEQ ID NO 63
<211> LENGTH: 12
<212> TYPE: DNA
<213> ORGANISM: Artificial Sequence
<220> FEATURE:
<223> OTHER INFORMATION: RT rabbit primer OcRT_04

<400> SEQUENCE: 63
aggaagctgc tg                                                       12

<210> SEQ ID NO 64
<211> LENGTH: 12
<212> TYPE: DNA
<213> ORGANISM: Artificial Sequence
<220> FEATURE:
<223> OTHER INFORMATION: RT rabbit primer OcRT_05

<400> SEQUENCE: 64
acactgctca gc                                                       12

<210> SEQ ID NO 65
<211> LENGTH: 14
```

```
<212> TYPE: DNA
<213> ORGANISM: Artificial Sequence
<220> FEATURE:
<223> OTHER INFORMATION: RT rabbit primer OcRT_06

<400> SEQUENCE: 65
tcacattcag aggg                                                    14

<210> SEQ ID NO 66
<211> LENGTH: 15
<212> TYPE: DNA
<213> ORGANISM: Artificial Sequence
<220> FEATURE:
<223> OTHER INFORMATION: RT rabbit primer OcRT_07

<400> SEQUENCE: 66
gtcttgtcca ctttg                                                   15

<210> SEQ ID NO 67
<211> LENGTH: 14
<212> TYPE: DNA
<213> ORGANISM: Artificial Sequence
<220> FEATURE:
<223> OTHER INFORMATION: RT rabbit primer OcRT_08

<400> SEQUENCE: 67
ctctgttgct gttg                                                    14

<210> SEQ ID NO 68
<211> LENGTH: 43
<212> TYPE: DNA
<213> ORGANISM: Artificial Sequence
<220> FEATURE:
<223> OTHER INFORMATION: Long rabbit gene-specific primer Oc-PCR-
     IgHA1A7-12

<400> SEQUENCE: 68
agacagtcct cagtgcctcg tcaggatcag gcagccgacg acc                    43

<210> SEQ ID NO 69
<211> LENGTH: 49
<212> TYPE: DNA
<213> ORGANISM: Artificial Sequence
<220> FEATURE:
<223> OTHER INFORMATION: Long rabbit gene-specific primer Oc-PCR-IgKC1

<400> SEQUENCE: 69
agacagtcct cagtgcctcg tcaggtggga agatgaggac agtaggtgc              49

<210> SEQ ID NO 70
<211> LENGTH: 47
<212> TYPE: DNA
<213> ORGANISM: Artificial Sequence
<220> FEATURE:
<223> OTHER INFORMATION: Long rabbit gene-specific primer Oc-PCR-
     IgKC1KC2

<400> SEQUENCE: 70
agacagtcct cagtgcctcg tcagagatgg tgggaagagg aggacag                47

<210> SEQ ID NO 71
<211> LENGTH: 51
<212> TYPE: DNA
<213> ORGANISM: Artificial Sequence
<220> FEATURE:
<223> OTHER INFORMATION: Long rabbit gene-specific primer Oc-PCR-
     IgLC4L5L6
```

<400> SEQUENCE: 71
agacagtcct cagtgcctcg tcagccttgt tgtccttgag ttcctcagag g        51

<210> SEQ ID NO 72
<211> LENGTH: 44
<212> TYPE: DNA
<213> ORGANISM: Artificial Sequence
<220> FEATURE:
<223> OTHER INFORMATION: Long rabbit gene-specific primer Oc-PCR-IgA2A6

<400> SEQUENCE: 72
agacagtcct cagtgcctcg tcagcggatc aggcagccga tgac        44

<210> SEQ ID NO 73
<211> LENGTH: 46
<212> TYPE: DNA
<213> ORGANISM: Artificial Sequence
<220> FEATURE:
<223> OTHER INFORMATION: Long rabbit gene-specific primer Oc-PCR-IgA4A5

<400> SEQUENCE: 73
agacagtcct cagtgcctcg tcagcaggtc agcgggaaga tgatcg        46

<210> SEQ ID NO 74
<211> LENGTH: 48
<212> TYPE: DNA
<213> ORGANISM: Artificial Sequence
<220> FEATURE:
<223> OTHER INFORMATION: Long rabbit gene-specific primer Oc-PCR-
      IgLC1C2C3

<400> SEQUENCE: 74
agacagtcct cagtgcctcg tcagcactga tcagacacac cagggtgg        48

<210> SEQ ID NO 75
<211> LENGTH: 43
<212> TYPE: DNA
<213> ORGANISM: Artificial Sequence
<220> FEATURE:
<223> OTHER INFORMATION: Long rabbit gene-specific primer Oc-PCR-IgG

<400> SEQUENCE: 75
agacagtcct cagtgcctcg tcagcaccgt ggagctgggt gtg        43

<210> SEQ ID NO 76
<211> LENGTH: 43
<212> TYPE: DNA
<213> ORGANISM: Artificial Sequence
<220> FEATURE:
<223> OTHER INFORMATION: Long rabbit gene-specific primer Oc-PCR-IgA3A5

<400> SEQUENCE: 76
agacagtcct cagtgcctcg tcaggatcag gcagccggcg atc        43

<210> SEQ ID NO 77
<211> LENGTH: 47
<212> TYPE: DNA
<213> ORGANISM: Artificial Sequence
<220> FEATURE:
<223> OTHER INFORMATION: Long rabbit gene-specific primer Oc-PCR-IgM

<400> SEQUENCE: 77
agacagtcct cagtgcctcg tcagggagac gagcgggtac agagttg        47

<210> SEQ ID NO 78
<211> LENGTH: 43
<212> TYPE: DNA
<213> ORGANISM: Artificial Sequence
<220> FEATURE:
<223> OTHER INFORMATION: Long rabbit gene-specific primer Oc-PCR-IgE

<400> SEQUENCE: 78
agacagtcct cagtgcctcg tcagtctgca gcaggaggcc aag    43

<210> SEQ ID NO 79
<211> LENGTH: 528
<212> TYPE: PRT
<213> ORGANISM: Homo sapiens

<400> SEQUENCE: 79

```
Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
                245                 250                 255

Gly Ile Thr Met Leu Glu Glu Ile Lys Val Pro Ser Ile Lys Leu Val
            260                 265                 270

Tyr Thr Leu Thr Val Pro Glu Ala Thr Val Lys Asp Ser Gly Asp Tyr
        275                 280                 285

Glu Cys Ala Ala Arg Gln Ala Thr Arg Glu Val Lys Glu Met Lys Lys
    290                 295                 300

Val Thr Ile Ser Val His Glu Lys Gly Phe Ile Glu Ile Lys Pro Thr
305                 310                 315                 320
```

-continued

Phe Ser Gln Leu Glu Ala Val Asn Leu His Glu Val Lys His Phe Val
             325                 330                 335

Val Glu Val Arg Ala Tyr Pro Pro Arg Ile Ser Trp Leu Lys Asn
         340                 345                 350

Asn Leu Thr Leu Ile Glu Asn Leu Thr Glu Ile Thr Thr Asp Val Glu
             355                 360                 365

Lys Ile Gln Glu Ile Arg Tyr Arg Ser Lys Leu Lys Leu Ile Arg Ala
370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                 405                 410                 415

Ile Leu Asp Leu Val Asp Asp His His Gly Ser Thr Gly Gly Gln Thr
             420                 425                 430

Val Arg Cys Thr Ala Glu Gly Thr Pro Leu Pro Asp Ile Glu Trp Met
         435                 440                 445

Ile Cys Lys Asp Ile Lys Lys Cys Asn Asn Glu Thr Ser Trp Thr Ile
450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                 485                 490                 495

Ile Ala Val Arg Cys Leu Ala Lys Asn Leu Leu Gly Ala Glu Asn Arg
             500                 505                 510

Glu Leu Lys Leu Val Ala Pro Thr Leu Arg Ser Glu Leu Thr Val Ala
         515                 520                 525

<210> SEQ ID NO 80
<211> LENGTH: 528
<212> TYPE: PRT
<213> ORGANISM: Mus musculus

<400> SEQUENCE: 80

Met Gly Thr Ser His Gln Val Phe Leu Val Leu Ser Cys Leu Leu Thr
1               5                   10                  15

Gly Pro Gly Leu Ile Ser Cys Gln Leu Leu Pro Ser Ile Leu Pro
             20                  25                  30

Asn Glu Asn Glu Lys Ile Val Gln Leu Asn Ser Ser Phe Ser Leu Arg
             35                  40                  45

Cys Val Gly Glu Ser Glu Val Ser Trp Gln His Pro Met Ser Glu Glu
         50                  55                  60

Asp Asp Pro Asn Val Glu Ile Arg Ser Glu Glu Asn Asn Ser Gly Leu
65                  70                  75                  80

Phe Val Thr Val Leu Glu Val Val Asn Ala Ser Ala His Thr Gly
                 85                  90                  95

Trp Tyr Thr Cys Tyr Tyr Asn His Thr Gln Thr Asp Glu Ser Glu Ile
             100                 105                 110

Glu Gly Arg His Ile Tyr Ile Tyr Val Pro Asp Pro Asp Met Ala Phe
         115                 120                 125

Val Pro Leu Gly Met Thr Asp Ser Leu Val Ile Glu Glu Asp Asp
         130                 135                 140

Ser Ala Ile Ile Pro Cys Arg Thr Thr Asp Pro Glu Thr Gln Val Thr
145                 150                 155                 160

Leu His Asn Asn Gly Arg Leu Val Pro Ala Ser Tyr Asp Ser Arg Gln
                 165                 170                 175

Gly Phe Asn Gly Thr Phe Ser Val Gly Pro Tyr Ile Cys Glu Ala Thr
            180                 185                 190

Val Lys Gly Arg Thr Phe Lys Thr Ser Glu Phe Asn Val Tyr Ala Leu
        195                 200                 205

Lys Ala Thr Ser Glu Leu Asn Leu Glu Met Asp Ala Arg Gln Thr Val
    210                 215                 220

Tyr Lys Ala Gly Glu Thr Ile Val Val Thr Cys Ala Val Phe Asn Asn
225                 230                 235                 240

Glu Val Val Asp Leu Gln Trp Thr Tyr Pro Gly Glu Val Arg Asn Lys
                245                 250                 255

Gly Ile Thr Met Leu Glu Glu Ile Lys Leu Pro Ser Ile Lys Leu Val
            260                 265                 270

Tyr Thr Leu Thr Val Pro Lys Ala Thr Val Lys Asp Ser Gly Glu Tyr
        275                 280                 285

Glu Cys Ala Ala Arg Gln Ala Thr Lys Glu Val Lys Glu Met Lys Arg
    290                 295                 300

Val Thr Ile Ser Val His Glu Lys Gly Phe Val Glu Ile Glu Pro Thr
305                 310                 315                 320

Phe Gly Gln Leu Glu Ala Val Asn Leu His Glu Val Arg Glu Phe Val
                325                 330                 335

Val Glu Val Gln Ala Tyr Pro Thr Pro Arg Ile Ser Trp Leu Lys Asp
            340                 345                 350

Asn Leu Thr Leu Ile Glu Asn Leu Thr Glu Ile Thr Thr Asp Val Gln
        355                 360                 365

Lys Ser Gln Glu Thr Arg Tyr Gln Ser Lys Leu Lys Leu Ile Arg Ala
    370                 375                 380

Lys Glu Glu Asp Ser Gly His Tyr Thr Ile Ile Val Gln Asn Glu Asp
385                 390                 395                 400

Asp Val Lys Ser Tyr Thr Phe Glu Leu Ser Thr Leu Val Pro Ala Ser
                405                 410                 415

Ile Leu Asp Leu Val Asp Asp His Gly Ser Gly Gly Gln Thr
            420                 425                 430

Val Arg Cys Thr Ala Glu Gly Thr Pro Leu Pro Glu Ile Asp Trp Met
        435                 440                 445

Ile Cys Lys His Ile Lys Lys Cys Asn Asn Asp Thr Ser Trp Thr Val
    450                 455                 460

Leu Ala Ser Asn Val Ser Asn Ile Ile Thr Glu Leu Pro Arg Arg Gly
465                 470                 475                 480

Arg Ser Thr Val Glu Gly Arg Val Ser Phe Ala Lys Val Glu Glu Thr
                485                 490                 495

Ile Ala Val Arg Cys Leu Ala Lys Asn Asn Leu Ser Val Ala Arg
            500                 505                 510

Glu Leu Lys Leu Val Ala Pro Thr Leu Arg Ser Glu Leu Thr Val Ala
        515                 520                 525

<210> SEQ ID NO 81
<211> LENGTH: 525
<212> TYPE: PRT
<213> ORGANISM: Oryctolagus cuniculus

<400> SEQUENCE: 81

Met Gly Pro Ser Pro Ala Phe Leu Val Leu Val Leu Gly Trp Leu
1               5                   10                  15

Leu Ala Gly Pro Ser Leu Thr Arg Cys Gln Leu Pro Leu Pro Ser Ile

```
                20                  25                  30
Ser Pro Gly Asp Ser Glu Arg Val Val Pro Leu Asn Ser Ser Phe Thr
            35                  40                  45
Leu Arg Cys Ser Gly Glu Ser Glu Val Ser Trp Gln Tyr Pro Val Ser
        50                  55                  60
Glu Asp Glu Gly Pro Arg Val Asp Val Arg Ser Glu Glu Asn Asn Thr
65                  70                  75                  80
Gly Tyr Phe Val Ala Val Leu Glu Val Gly Ser Ala Thr Ala Ala His
                85                  90                  95
Thr Gly Leu Tyr Thr Cys Tyr Tyr Asn His Thr Gln Thr Glu Asp Ser
            100                 105                 110
Asp Val Glu Gly Ser His Val Tyr Ile Tyr Val Pro Asp Pro Asp Val
        115                 120                 125
Ala Phe Val Pro Leu Gly Met Thr Asp Tyr Leu Val Ile Val Glu Asp
    130                 135                 140
Asp Asp Ser Ala Ile Ile Pro Cys Arg Thr Thr Asp Pro Glu Thr Pro
145                 150                 155                 160
Val Thr Leu Arg Asn Ser Gln Gly Leu Val Pro Ala Ser Tyr Asp Ser
                165                 170                 175
Arg His Gly Phe Asn Gly Thr Phe Thr Met Gly Pro Tyr Val Cys Glu
            180                 185                 190
Ala Thr Val Arg Gly Lys Thr Val Gln Thr Ile Pro Phe Asn Ile Tyr
        195                 200                 205
Ala Leu Lys Ala Thr Ser Glu Leu Asp Leu Glu Met Glu Ala Leu Gln
    210                 215                 220
Thr Val Tyr Lys Ala Gly Glu Thr Ile Val Val Thr Cys Ala Val Phe
225                 230                 235                 240
Asn Asn Glu Val Val Asp Leu Gln Trp Thr Tyr Pro Gly Glu Met Lys
                245                 250                 255
Gly Lys Gly Val Thr Met Leu Glu Glu Ile Lys Val Pro Thr Leu Lys
            260                 265                 270
Leu Val Tyr Thr Leu Thr Val Pro Arg Ala Thr Val Lys Asp Ser Gly
        275                 280                 285
Asp Tyr Glu Cys Ala Ala Arg Gln Ala Thr Val Lys Glu Met Lys Lys
    290                 295                 300
Val Thr Ile Ala Val His Glu Lys Gly Phe Val Glu Ile Lys Pro Thr
305                 310                 315                 320
Phe Asn Gln Ser Glu Ala Val Asn Leu His Glu Val Lys His Phe Val
                325                 330                 335
Val Glu Val Arg Ala Tyr Pro Pro Pro Arg Ile Ser Trp Leu Lys Asp
            340                 345                 350
Ser Arg Thr Leu Ile Glu Asn Leu Thr Glu Ile Thr Thr Asp Val Glu
        355                 360                 365
Gln Val Gln Glu Thr Arg Leu Ser Ser Met Cys Asn Arg Ser Ala Ala
    370                 375                 380
Cys Gly Lys Trp Asn Phe Leu Thr Ser Val Glu Gln Gly Trp Gln Ile
385                 390                 395                 400
Val Gln Cys Ser Ala Trp Lys Ala Pro Leu Ala Val Pro Ala Thr Ile
                405                 410                 415
Leu Asp Leu Val Asp His His Pro Pro Gly Glu Lys Arg Val Arg
            420                 425                 430
Cys Thr Ala Ala Gly Thr Pro Pro Asp Val Glu Trp Met Ile Cys Lys
        435                 440                 445
```

```
Asp Ile Lys Arg Cys Asn Asn Glu Thr Ser Trp Thr Leu Leu Ala Asn
        450                 455                 460

Asn Val Ser Asn Ile Val Thr Glu Thr His Pro Arg Gly Gly Gly Ala
465                 470                 475                 480

Val Glu Gly Arg Val Thr Phe Ala Lys Val Glu Glu Thr Leu Ala Val
                485                 490                 495

Arg Cys Leu Ala Arg Asn Pro Leu Gly Thr Glu Asn Arg Glu Leu Lys
                500                 505                 510

Leu Val Ala Pro Thr Leu Arg Ser Glu Leu Thr Val Ala
            515                 520                 525

<210> SEQ ID NO 82
<211> LENGTH: 527
<212> TYPE: PRT
<213> ORGANISM: Rattus norvegicus

<400> SEQUENCE: 82

Met Gly Thr Ser Gln Ala Phe Leu Val Leu Ser Cys Leu Leu Thr Gly
1               5                   10                  15

Pro Ser Leu Ile Val Cys Gln Leu Leu Leu Pro Ser Ile Leu Pro Asn
            20                  25                  30

Glu Asn Glu Lys Ile Val Pro Leu Ser Ser Ser Phe Ser Leu Arg Cys
        35                  40                  45

Phe Gly Glu Ser Glu Val Ser Trp Gln His Pro Met Ser Glu Glu Glu
    50                  55                  60

Asp Pro Asn Val Glu Ile Arg Thr Glu Glu Asn Asn Ser Ser Leu Phe
65                  70                  75                  80

Val Thr Val Leu Glu Val Val Asn Ala Ser Ala Ala His Thr Gly Trp
                85                  90                  95

Tyr Thr Cys Tyr Tyr Asn His Thr Gln Thr Glu Glu Ser Glu Ile Glu
            100                 105                 110

Gly Arg His Ile Tyr Ile Tyr Val Pro Asp Pro Asp Met Ala Phe Val
        115                 120                 125

Pro Leu Gly Met Thr Asp Ser Leu Val Ile Val Glu Glu Asp Asp Ser
    130                 135                 140

Ala Ile Ile Pro Cys Leu Thr Thr Asp Pro Asp Thr Glu Val Thr Leu
145                 150                 155                 160

His Asn Asn Gly Arg Leu Val Pro Ala Ser Tyr Asp Ser Arg Gln Gly
                165                 170                 175

Phe Asn Gly Thr Phe Ser Val Gly Pro Tyr Ile Cys Glu Ala Thr Val
            180                 185                 190

Arg Gly Arg Thr Phe Lys Thr Ser Glu Phe Asn Val Tyr Ala Leu Lys
        195                 200                 205

Ala Thr Ser Glu Leu Asn Leu Glu Met Asp Thr Arg Gln Thr Val Tyr
    210                 215                 220

Lys Ala Gly Glu Thr Ile Val Val Thr Cys Ala Val Phe Asn Asn Glu
225                 230                 235                 240

Val Val Asp Leu Gln Trp Thr Tyr Pro Gly Glu Val Arg Asn Lys Gly
                245                 250                 255

Ile Thr Met Leu Glu Glu Ile Lys Leu Pro Ser Ile Lys Leu Val Tyr
            260                 265                 270

Thr Leu Thr Val Pro Lys Ala Thr Val Lys Asp Ser Gly Asp Tyr Glu
        275                 280                 285

Cys Ala Ala Arg Gln Ala Thr Lys Glu Val Lys Glu Met Lys Thr Val
```

```
                290                 295                 300
Thr Ile Ser Val His Glu Lys Gly Phe Val Gln Ile Arg Pro Thr Phe
305                 310                 315                 320

Gly His Leu Glu Thr Val Asn Leu His Gln Val Arg Glu Phe Val Val
                325                 330                 335

Glu Val Gln Ala Tyr Pro Thr Pro Arg Ile Ser Trp Leu Lys Asp Asn
                340                 345                 350

Leu Thr Leu Ile Glu Asn Leu Thr Glu Ile Thr Thr Asp Val Gln Arg
                355                 360                 365

Ser Gln Glu Thr Arg Tyr Gln Ser Lys Leu Lys Leu Ile Arg Ala Lys
                370                 375                 380

Glu Glu Asp Ser Gly His Tyr Thr Ile Ile Val Gln Asn Asp Asp Asp
385                 390                 395                 400

Met Lys Ser Tyr Thr Phe Glu Leu Ser Thr Leu Val Pro Ala Ser Ile
                405                 410                 415

Leu Glu Leu Val Asp Asp His His Gly Ser Gly Gly Gln Thr Val
                420                 425                 430

Arg Cys Thr Ala Glu Gly Thr Pro Leu Pro Asn Ile Glu Trp Met Ile
                435                 440                 445

Cys Lys Asp Ile Lys Lys Cys Asn Asn Asp Thr Ser Trp Thr Val Leu
                450                 455                 460

Ala Ser Asn Val Ser Asn Ile Ile Thr Glu Phe His Gln Arg Gly Arg
465                 470                 475                 480

Ser Thr Val Glu Gly Arg Val Ser Phe Ala Lys Val Glu Glu Thr Ile
                485                 490                 495

Ala Val Arg Cys Leu Ala Lys Asn Asp Leu Gly Ile Gly Asn Arg Glu
                500                 505                 510

Leu Lys Leu Val Ala Pro Ser Leu Arg Ser Glu Leu Thr Val Ala
                515                 520                 525

<210> SEQ ID NO 83
<211> LENGTH: 168
<212> TYPE: PRT
<213> ORGANISM: Homo sapiens

<400> SEQUENCE: 83

Met Lys His Leu Trp Phe Phe Leu Leu Leu Val Ala Ala Pro Arg Trp
1               5                   10                  15

Val Leu Ser Gln Leu Gln Leu Gln Glu Ser Gly Pro Gly Leu Val Lys
                20                  25                  30

Pro Ser Glu Thr Leu Ser Leu Thr Cys Thr Val Ser Gly Asp Ser Ile
            35                  40                  45

Ser Ser Ser Thr Tyr Tyr Trp Gly Trp Ile Arg Gln Pro Pro Gly Lys
50                  55                  60

Gly Leu Glu Trp Ile Ala Phe Ile Phe Tyr Ser Gly Ser Thr Phe Tyr
65                  70                  75                  80

Asn Pro Ser Leu Lys Ser Arg Val Thr Val Ser Val Asp Arg Ser Thr
                85                  90                  95

Asn Gln Phe Ser Leu Arg Leu Lys Ser Val Thr Ala Ala Asp Thr Ser
            100                 105                 110

Arg Tyr Tyr Cys Ala Arg His Pro Lys Arg Ile Ser Ile Phe Glu Val
        115                 120                 125

Val Asn Ala Phe Asp Ile Trp Gly Gln Gly Thr Met Val Thr Val Ser
    130                 135                 140
```

```
Ser Ala Ser Thr Lys Gly Pro Ser Val Phe Pro Leu Ala Pro Ser Ser
145                 150                 155                 160

Lys Ser Thr Ser Gly Gly Thr Ala
                165
```

<210> SEQ ID NO 84
<211> LENGTH: 169
<212> TYPE: PRT
<213> ORGANISM: Homo sapiens

<400> SEQUENCE: 84

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
                20                  25                  30

Ser Ser Glu Thr Leu Ser Leu Thr Cys Thr Val Ser Gly Asp Ser Ile
            35                  40                  45

Thr Ser Thr Tyr Asp Trp Gly Trp Ile Arg Gln Pro Pro Gly Lys
        50                  55                  60

Gly Leu Glu Trp Ile Gly Asn Val Tyr Tyr Arg Gly Ser Thr Tyr Tyr
65                  70                  75                  80

Asn Pro Ser Leu Lys Ser Arg Val Thr Ile Ser Val Asp Arg Ser Arg
                85                  90                  95

Thr Gln Ile Ser Leu Arg Leu Ser Val Thr Ala Ala Asp Thr Ala
            100                 105                 110

Leu Tyr Phe Cys Ala Arg His Pro Lys Arg Leu Thr Val Phe Glu Val
        115                 120                 125

Val Asn Ala Phe Asp Ile Trp Gly Gln Gly Gln Thr Met Val Thr Val
    130                 135                 140

Phe Ser Ala Ser Thr Lys Gly Pro Ser Val Phe Pro Leu Ala Pro Ser
145                 150                 155                 160

Ser Lys Ser Thr Ser Gly Gly Thr Ala
                165
```

<210> SEQ ID NO 85
<211> LENGTH: 146
<212> TYPE: PRT
<213> ORGANISM: Homo sapiens

<400> SEQUENCE: 85

```
Met Ala Trp Thr Leu Leu Phe Leu Thr Leu Thr Gln Gly Thr Gly
1               5                   10                  15

Ser Trp Ala Gln Ser Ala Leu Thr Gln Pro Ala Ser Val Ser Gly Ser
                20                  25                  30

Pro Gly Gln Ser Ile Thr Ile Thr Cys Thr Gly Ile Ser Ser Asp Val
            35                  40                  45

Gly Ala Tyr Asn Ser Val Ser Trp Tyr Gln Gln Tyr Pro Gly Lys Ser
        50                  55                  60

Pro Lys Leu Met Ile Tyr Asp Val Ser Asn Arg Ser Ser Gly Val Ser
65                  70                  75                  80

Asn Arg Phe Ser Gly Ser Lys Ser Asp Asn Thr Ala Ser Leu Thr Ile
                85                  90                  95

Ser Gly Leu Gln Ala Glu Asp Glu Ala Ser Tyr Phe Cys Ser Leu Tyr
            100                 105                 110

Arg Ser Ser Thr Thr Ser Val Val Phe Gly Gly Gly Thr Lys Leu Thr
        115                 120                 125
```

-continued

```
Val Leu Arg Gln Pro Lys Ala Ala Pro Ser Val Thr Leu Phe Pro Pro
    130                 135                 140

Ser Ser
145

<210> SEQ ID NO 86
<211> LENGTH: 146
<212> TYPE: PRT
<213> ORGANISM: Homo sapiens

<400> SEQUENCE: 86

Met Ala Trp Ala Leu Leu Leu Thr Leu Leu Thr Gln Gly Thr Gly
1               5                   10                  15

Ser Trp Ala Gln Ser Ala Leu Thr Gln Pro Ala Ser Val Ser Ala Ser
                20                  25                  30

Pro Gly Gln Ser Ile Thr Ile Ser Cys Thr Gly Ile Ser Ser Asp Ile
            35                  40                  45

Gly Gly Tyr Ser Ser Val Ser Trp Tyr Gln Ala His Pro Gly Lys Ala
        50                  55                  60

Pro Lys Leu Met Ile Tyr Pro Val Asn Asn Arg Pro Ser Gly Ile Ser
65                  70                  75                  80

Asn Arg Phe Ser Gly Ser Lys Ser Gly Asn Thr Ala Ser Leu Ala Ile
                85                  90                  95

Ser Gly Leu Gln Ala Glu Asp Glu Ala Asp Tyr Tyr Cys Ser Leu Tyr
            100                 105                 110

Thr Ser Ile Asn Ala Ser Ile Val Phe Gly Gly Gly Thr Lys Leu Thr
        115                 120                 125

Val Leu Gly Gln Pro Lys Ala Ala Pro Ser Val Thr Leu Phe Pro Pro
    130                 135                 140

Ser Ser
145
```

UNITED STATES PATENT AND TRADEMARK OFFICE
CERTIFICATE OF CORRECTION

PATENT NO. : 10,725,024 B2
APPLICATION NO. : 14/773244
DATED : July 28, 2020
INVENTOR(S) : Marketa Ricicova et al.

It is certified that error appears in the above-identified patent and that said Letters Patent is hereby corrected as shown below:

In the Claims

At Column 185, Claim 1, Line 1, the text "heterologous" should be changed to --heterogeneous--

Signed and Sealed this
Twenty-fifth Day of August, 2020

Andrei Iancu
*Director of the United States Patent and Trademark Office*